(12) United States Patent
Barthelemy et al.

(10) Patent No.: US 11,635,440 B2
(45) Date of Patent: *Apr. 25, 2023

(54) METHODS OF TREATING BASED ON SITE-SPECIFIC TAU PHOSPHORYLATION

(71) Applicant: Washington University, St. Louis, MO (US)

(72) Inventors: Nicolas Barthelemy, St. Louis, MO (US); Randall Bateman, St. Louis, MO (US); Eric McDade, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/843,470

(22) Filed: Jun. 17, 2022

(65) Prior Publication Data

US 2022/0317136 A1 Oct. 6, 2022

Related U.S. Application Data

(63) Continuation of application No. 17/368,403, filed on Jul. 6, 2021, now Pat. No. 11,402,392, which is a continuation of application No. 17/015,985, filed on Sep. 9, 2020, now Pat. No. 11,085,935, which is a continuation-in-part of application No. PCT/US2019/030725, filed on May 3, 2019.

(60) Provisional application No. 62/898,407, filed on Sep. 10, 2019, provisional application No. 62/666,509, filed on May 3, 2018, provisional application No. 62/666,504, filed on May 3, 2018.

(51) Int. Cl.
*G01N 33/68* (2006.01)
*A61P 25/00* (2006.01)

(52) U.S. Cl.
CPC .............................. *G01N 33/6896* (2013.01)

(58) Field of Classification Search
CPC ........................... G01N 33/6896; A61P 25/00
See application file for complete search history.

(56) References Cited

PUBLICATIONS

Ittner et al. "Site-specific phosphorylation of tau inhibits amyloid-beta toxicity in Alzheimer's mice" Science, Nov. 18, 2016, vol. 35, 2016 (Year: 2016).*

\* cited by examiner

*Primary Examiner* — Daniel E Kolker
*Assistant Examiner* — James L Rogers
(74) *Attorney, Agent, or Firm* — Polsinelli PC

(57) ABSTRACT

The present disclosure provides methods to quantify tau phosphorylation at specific amino acid residues to predict time to onset of mild cognitive impairment due to Alzheimer's disease, stage Alzheimer's disease, guide treatment decisions, select subjects for clinical trials, and evaluate the clinical efficacy of certain therapeutic interventions.

30 Claims, 66 Drawing Sheets
Specification includes a Sequence Listing.

R.IPAKTPPAPK.T (SEQ ID NO: 57)

SEQUENCE LISTING

```
<160> NUMBER OF SEQ ID NOS: 72

<210> SEQ ID NO 1
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 1

Lys Ala Glu Glu Ala Gly Ile Gly Asp Thr Pro Ser Leu Glu Asp Glu
1               5                   10                  15

Ala Ala Gly His Val Thr Gln Ala Arg Met
            20                  25

<210> SEQ ID NO 2
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 2

Ala Glu Glu Ala Gly Ile Gly Asp Thr Pro Ser Leu Glu Asp Glu Ala
1               5                   10                  15
```

Ala Gly His Val Thr Gln Ala Arg
            20

<210> SEQ ID NO 3
<211> LENGTH: 24
<212> TYPE: PRT
<213> ORGANISM: Artificial Sequence
<220> FEATURE:
<223> OTHER INFORMATION: SYNTEHSIZED
<220> FEATURE:
<221> NAME/KEY: MOD_RES
<222> LOCATION: (8)..(8)
<223> OTHER INFORMATION: PHOSPHORYLATION

<400> SEQUENCE: 3

Ala Glu Glu Ala Gly Ile Gly Asp Thr Pro Ser Leu Glu Asp Glu Ala
1               5                   10                  15

Ala Gly His Val Thr Gln Ala Arg
            20

<210> SEQ ID NO 4
<211> LENGTH: 24
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (10)..(10)
<223> OTHER INFORMATION: PHOSPHORYLATION

<400> SEQUENCE: 4

Ala Glu Glu Ala Gly Ile Gly Asp Thr Pro Ser Leu Glu Asp Glu Ala
1               5                   10                  15

Ala Gly His Val Thr Gln Ala Arg
            20

<210> SEQ ID NO 5
<211> LENGTH: 24
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (20)..(20)
<223> OTHER INFORMATION: PHOSPHORYLATION

<400> SEQUENCE: 5

Ala Glu Glu Ala Gly Ile Gly Asp Thr Pro Ser Leu Glu Asp Glu Ala
1               5                   10                  15

Ala Gly His Val Thr Gln Ala Arg
            20

<210> SEQ ID NO 6
<211> LENGTH: 32
<212> TYPE: PRT
<213> ORGANISM: Artificial Sequence
<220> FEATURE:
<223> OTHER INFORMATION: SYNTHESIZED

<400> SEQUENCE: 6

Lys Ser Thr Pro Thr Ala Glu Ala Glu Glu Ala Gly Ile Gly Asp Thr
1               5                   10                  15

Pro Ser Leu Glu Asp Glu Ala Ala Gly His Val Thr Gln Ala Arg Met
            20                  25                  30

```
<210> SEQ ID NO 7
<211> LENGTH: 30
<212> TYPE: PRT
<213> ORGANISM: Artificial Sequence
<220> FEATURE:
<223> OTHER INFORMATION: SYNTHESIZED

<400> SEQUENCE: 7

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (15)..(15)
<223> OTHER INFORMATION: PHOSPHORYLATION

<400> SEQUENCE: 8

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (17)..(17)
<223> OTHER INFORMATION: PHOSPHORYLATION

<400> SEQUENCE: 9

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (27)..(27)
<223> OTHER INFORMATION: PHOSPHORYLATION

<400> SEQUENCE: 10

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 11
```

```
<211> LENGTH: 30
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (2)..(2)
<223> OTHER INFORMATION: PHOSPHORYLATION

<400> SEQUENCE: 11

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (1)..(1)
<223> OTHER INFORMATION: PHOSPHORYLATION

<400> SEQUENCE: 12

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (4)..(4)
<223> OTHER INFORMATION: PHOSPHORYLATION

<400> SEQUENCE: 13

Ser Thr Pro Thr Ala Glu Ala Glu Glu Ala Gly Ile Gly Asp Thr Pro
1               5                   10                  15

Ser Leu Glu Asp Glu Ala Ala Gly His Val Thr Gln Ala Arg
            20                  25                  30

<210> SEQ ID NO 14
<211> LENGTH: 25
<212> TYPE: PRT
<213> ORGANISM: Artificial Sequence
<220> FEATURE:
<223> OTHER INFORMATION: SYNTHESIZED

<400> SEQUENCE: 14

Lys Glu Ser Pro Leu Gln Thr Pro Thr Glu Asp Gly Ser Glu Glu Pro
1               5                   10                  15

Gly Ser Glu Thr Ser Asp Ala Lys Ser
            20                  25

<210> SEQ ID NO 15
<211> LENGTH: 23
<212> TYPE: PRT
<213> ORGANISM: Artificial Sequence
```

<220> FEATURE:
<223> OTHER INFORMATION: SYNTHESIZED

<400> SEQUENCE: 15

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 16
<211> LENGTH: 23
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (6)..(6)
<223> OTHER INFORMATION: PHOSPHORYLATION

<400> SEQUENCE: 16

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 17
<211> LENGTH: 23
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (8)..(8)
<223> OTHER INFORMATION: PHOSPHORYLATION

<400> SEQUENCE: 17

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 18
<211> LENGTH: 23
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (17)..(17)
<223> OTHER INFORMATION: PHOSPHORYLATION

<400> SEQUENCE: 18

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 19
<211> LENGTH: 23
<212> TYPE: PRT
<213> ORGANISM: Artificial Sequence
<220> FEATURE:
<223> OTHER INFORMATION: SYNTHESIZED
<220> FEATURE:

```
<221> NAME/KEY: MOD_RES
<222> LOCATION: (2)..(2)
<223> OTHER INFORMATION: PHOSPHORYLATION

<400> SEQUENCE: 19

Glu Ser Pro Leu Gln Thr Pro Thr Glu Asp Gly Ser Glu Pro Gly
1               5                   10                  15

Ser Glu Thr Ser Asp Ala Lys
            20

<210> SEQ ID NO 20
<211> LENGTH: 41
<212> TYPE: PRT
<213> ORGANISM: Artificial Sequence
<220> FEATURE:
<223> OTHER INFORMATION: SYNTHESIZED

<400> SEQUENCE: 20

Lys Gln Ala Ala Ala Gln Pro His Thr Glu Ile Pro Glu Gly Thr Thr
1               5                   10                  15

Ala Glu Glu Ala Gly Ile Gly Asp Thr Pro Ser Leu Glu Asp Glu Ala
                20                  25                  30

Ala Gly His Val Thr Gln Ala Arg Met
        35                  40

<210> SEQ ID NO 21
<211> LENGTH: 39
<212> TYPE: PRT
<213> ORGANISM: Artificial Sequence
<220> FEATURE:
<223> OTHER INFORMATION: SYNTHESIZED

<400> SEQUENCE: 21

Gln Ala Ala Ala Gln Pro His Thr Glu Ile Pro Glu Gly Thr Thr Ala
1               5                   10                  15

Glu Glu Ala Gly Ile Gly Asp Thr Pro Ser Leu Glu Asp Glu Ala Ala
                20                  25                  30

Gly His Val Thr Gln Ala Arg
        35

<210> SEQ ID NO 22
<211> LENGTH: 39
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (24)..(24)
<223> OTHER INFORMATION: PHOSPHORYLATION

<400> SEQUENCE: 22

Gln Ala Ala Ala Gln Pro His Thr Glu Ile Pro Glu Gly Thr Thr Ala
1               5                   10                  15

Glu Glu Ala Gly Ile Gly Asp Thr Pro Ser Leu Glu Asp Glu Ala Ala
                20                  25                  30

Gly His Val Thr Gln Ala Arg
        35

<210> SEQ ID NO 23
<211> LENGTH: 39
<212> TYPE: PRT
<213> ORGANISM: Artificial Sequence
<220> FEATURE:
```

```
<223> OTHER INFORMATION: SYNTHESIZED
<220> FEATURE:
<221> NAME/KEY: MOD_RES
<222> LOCATION: (26)..(26)
<223> OTHER INFORMATION: PHOSPHORYLATION

<400> SEQUENCE: 23

Gln Ala Ala Ala Gln Pro His Thr Glu Ile Pro Glu Gly Thr Thr Ala
1               5                   10                  15
Glu Glu Ala Gly Ile Gly Asp Thr Pro Ser Leu Glu Asp Glu Ala Ala
            20                  25                  30
Gly His Val Thr Gln Ala Arg
        35

<210> SEQ ID NO 24
<211> LENGTH: 39
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (14)..(14)
<223> OTHER INFORMATION: PHOSPHORYLATION

<400> SEQUENCE: 24

Gln Ala Ala Ala Gln Pro His Thr Glu Ile Pro Glu Gly Thr Thr Ala
1               5                   10                  15
Glu Glu Ala Gly Ile Gly Asp Thr Pro Ser Leu Glu Asp Glu Ala Ala
            20                  25                  30
Gly His Val Thr Gln Ala Arg
        35

<210> SEQ ID NO 25
<211> LENGTH: 39
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (8)..(8)
<223> OTHER INFORMATION: PHOSPHORYLATION

<400> SEQUENCE: 25

Gln Ala Ala Ala Gln Pro His Thr Glu Ile Pro Glu Gly Thr Thr Ala
1               5                   10                  15
Glu Glu Ala Gly Ile Gly Asp Thr Pro Ser Leu Glu Asp Glu Ala Ala
            20                  25                  30
Gly His Val Thr Gln Ala Arg
        35

<210> SEQ ID NO 26
<211> LENGTH: 22
<212> TYPE: PRT
<213> ORGANISM: Artificial Sequence
<220> FEATURE:
<223> OTHER INFORMATION: SYNTHESIZED

<400> SEQUENCE: 26

Lys Ser Thr Pro Thr Ala Glu Asp Val Thr Ala Pro Leu Val Asp Glu
1               5                   10                  15
Gly Ala Pro Gly Lys Gln
            20
```

```
<210> SEQ ID NO 27
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 27

Ser Thr Pro Thr Ala Glu Asp Val Thr Ala Pro Leu Val Asp Glu Gly
1               5                   10                  15

Ala Pro Gly Lys
            20

<210> SEQ ID NO 28
<211> LENGTH: 20
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (4)..(4)
<223> OTHER INFORMATION: PHOSPHORYLATION

<400> SEQUENCE: 28

Ser Thr Pro Thr Ala Glu Asp Val Thr Ala Pro Leu Val Asp Glu Gly
1               5                   10                  15

Ala Pro Gly Lys
            20

<210> SEQ ID NO 29
<211> LENGTH: 20
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (9)..(9)
<223> OTHER INFORMATION: PHOSPHORYLATION

<400> SEQUENCE: 29

Ser Thr Pro Thr Ala Glu Asp Val Thr Ala Pro Leu Val Asp Glu Gly
1               5                   10                  15

Ala Pro Gly Lys
            20

<210> SEQ ID NO 30
<211> LENGTH: 20
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (2)..(2)
<223> OTHER INFORMATION: PHOSPHORYLATION

<400> SEQUENCE: 30

Ser Thr Pro Thr Ala Glu Asp Val Thr Ala Pro Leu Val Asp Glu Gly
1               5                   10                  15

Ala Pro Gly Lys
            20

<210> SEQ ID NO 31
<211> LENGTH: 20
```

```
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (1)..(1)
<223> OTHER INFORMATION: PHOSPHORYLATION

<400> SEQUENCE: 31

Ser Thr Pro Thr Ala Glu Asp Val Thr Ala Pro Leu Val Asp Glu Gly
1               5                   10                  15

Ala Pro Gly Lys
            20

<210> SEQ ID NO 32
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 32

Arg Ile Pro Ala Lys Thr Pro Pro Ala Pro Lys Thr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (6)..(6)
<223> OTHER INFORMATION: PHOSPHORYLATION

<400> SEQUENCE: 33

Arg Ile Pro Ala Lys Thr Pro Pro Ala Pro Lys Thr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (2)..(2)
<223> OTHER INFORMATION: PHOSPHORYLATION

<400> SEQUENCE: 34

Lys Thr Pro Pro Ser Ser Gly Glu Pro Pro Lys Ser
1               5                   10

<210> SEQ ID NO 35
<211> LENGTH: 18
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (8)..(8)
<223> OTHER INFORMATION: PHOSPHORYLATION

<400> SEQUENCE: 35

Lys Thr Pro Pro Ala Pro Lys Thr Pro Pro Ser Ser Gly Glu Pro Pro
```

```
1               5                  10                 15
Lys Ser

<210> SEQ ID NO 36
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 36

Arg Ser Gly Tyr Ser Ser Pro Gly Ser Pro Gly Thr Pro Gly Ser Arg
1               5                  10                 15
Ser

<210> SEQ ID NO 37
<211> LENGTH: 17
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (6)..(6)
<223> OTHER INFORMATION: PHOSPHORYLATION

<400> SEQUENCE: 37

Arg Ser Gly Tyr Ser Ser Pro Gly Ser Pro Gly Thr Pro Gly Ser Arg
1               5                  10                 15
Ser

<210> SEQ ID NO 38
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 38

Ser Gly Tyr Ser Ser Pro Gly Ser Pro Gly Thr Pro Gly Ser Arg
1               5                  10                 15

<210> SEQ ID NO 39
<211> LENGTH: 15
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 39

Ser Gly Tyr Ser Ser Pro Gly Ser Pro Gly Thr Pro Gly Ser Arg
1               5                  10                 15

<210> SEQ ID NO 40
<211> LENGTH: 15
<212> TYPE: PRT
<213> ORGANISM: Artificial Sequence
<220> FEATURE:
<223> OTHER INFORMATION: SYNTHESIZED
```

```
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 40

Ser Gly Tyr Ser Ser Pro Gly Ser Pro Gly Thr Pro Gly Ser Arg
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 41

Ser Gly Tyr Ser Ser Pro Gly Ser Pro Gly Thr Pro Gly Ser Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (11)..(11)
<223> OTHER INFORMATION: PHOSPHORYLATION

<400> SEQUENCE: 42

Ser Gly Tyr Ser Ser Pro Gly Ser Pro Gly Thr Pro Gly Ser Arg
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (14)..(14)
<223> OTHER INFORMATION: PHOSPHORYLATION

<400> SEQUENCE: 43

Ser Gly Tyr Ser Ser Pro Gly Ser Pro Gly Thr Pro Gly Ser Arg
1               5                   10                  15

<210> SEQ ID NO 44
<211> LENGTH: 12
<212> TYPE: PRT
<213> ORGANISM: Artificial Sequence
<220> FEATURE:
```

```
<223> OTHER INFORMATION: SYNTHESIZED
<220> FEATURE:
<221> NAME/KEY: MOD_RES
<222> LOCATION: (7)..(7)
<223> OTHER INFORMATION: PHOSPHORYLATION

<400> SEQUENCE: 44

Arg Thr Pro Ser Leu Pro Thr Pro Pro Thr Arg Glu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (4)..(4)
<223> OTHER INFORMATION: PHOSPHORYLATION

<400> SEQUENCE: 45

Arg Thr Pro Ser Leu Pro Thr Pro Pro Thr Arg Glu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (2)..(2)
<223> OTHER INFORMATION: PHOSPHORYLATION

<400> SEQUENCE: 46

Arg Ser Arg Thr Pro Ser Leu Pro Thr Pro Pro Thr Arg Glu
1               5                   10

<210> SEQ ID NO 47
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (7)..(7)
<223> OTHER INFORMATION: PHOSPHORYLATION

<400> SEQUENCE: 47

Lys Val Ala Val Val Arg Thr Pro Pro Lys Ser
1               5                   10

<210> SEQ ID NO 48
<211> LENGTH: 13
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (10)..(10)
<223> OTHER INFORMATION: PHOSPHORYLATION

<400> SEQUENCE: 48

Lys Ser Pro Val Val Ser Gly Asp Thr Ser Pro Arg His
1               5                   10
```

```
<210> SEQ ID NO 49
<211> LENGTH: 13
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (2)..(2)
<223> OTHER INFORMATION: PHOSPHORYLATION

<400> SEQUENCE: 49

Lys Ser Pro Val Val Ser Gly Asp Thr Ser Pro Arg His
1               5                   10

<210> SEQ ID NO 50
<211> LENGTH: 23
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (12)..(12)
<223> OTHER INFORMATION: PHOSPHORYLATION

<400> SEQUENCE: 50

Lys Thr Asp His Gly Ala Glu Ile Val Tyr Lys Ser Pro Val Val Ser
1               5                   10                  15

Gly Asp Thr Ser Pro Arg His
            20

<210> SEQ ID NO 51
<211> LENGTH: 23
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION

<400> SEQUENCE: 51

Lys Thr Asp His Gly Ala Glu Ile Val Tyr Lys Ser Pro Val Val Ser
1               5                   10                  15

Gly Asp Thr Ser Pro Arg His
            20

<210> SEQ ID NO 52
<211> LENGTH: 34
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (11)..(11)
<223> OTHER INFORMATION: PHOSPHORYLATION

<400> SEQUENCE: 52

Arg His Leu Ser Asn Val Ser Ser Thr Gly Ser Ile Asp Met Val Asp
1               5                   10                  15

Ser Pro Gln Leu Ala Thr Leu Ala Asp Glu Val Ser Ala Ser Leu Ala
```

<210> SEQ ID NO 53
<211> LENGTH: 34
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (7)..(7)
<223> OTHER INFORMATION: PHOSPHORYLATION

<400> SEQUENCE: 53

Arg His Leu Ser Asn Val Ser Ser Thr Gly Ser Ile Asp Met Val Asp
1               5                   10                  15

Ser Pro Gln Leu Ala Thr Leu Ala Asp Glu Val Ser Ala Ser Leu Ala
            20                  25                  30

Lys Gln

<210> SEQ ID NO 54
<211> LENGTH: 34
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (4)..(4)
<223> OTHER INFORMATION: PHOSPHORYLATION

<400> SEQUENCE: 54

Arg His Leu Ser Asn Val Ser Ser Thr Gly Ser Ile Asp Met Val Asp
1               5                   10                  15

Ser Pro Gln Leu Ala Thr Leu Ala Asp Glu Val Ser Ala Ser Leu Ala
            20                  25                  30

Lys Gln

<210> SEQ ID NO 55
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 55

Ile Ala Thr Pro Arg
1               5

<210> SEQ ID NO 56
<211> LENGTH: 5
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (3)..(3)
<223> OTHER INFORMATION: PHOSPHORYLATION

<400> SEQUENCE: 56

Ile Ala Thr Pro Arg
1               5

```
<210> SEQ ID NO 57
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 57

Arg Ile Pro Ala Lys Thr Pro Pro Ala Pro Lys Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 58

Ile Pro Ala Lys Thr Pro Pro Ala Pro Lys
1               5                   10

<210> SEQ ID NO 59
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 59

Lys Val Ala Val Val Arg Thr Pro Pro Lys Ser
1               5                   10

<210> SEQ ID NO 60
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 60

Thr Pro Pro Ala Pro Lys
1               5

<210> SEQ ID NO 61
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 61

Thr Pro Pro Ser Ser Gly Glu Pro Pro Lys
1               5                   10

<210> SEQ ID NO 62
<211> LENGTH: 16
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (7)..(7)
<223> OTHER INFORMATION: PHOSPHORYLATION

<400> SEQUENCE: 62

Thr Pro Pro Ala Pro Lys Thr Pro Pro Ser Ser Gly Glu Pro Pro Lys
```

```
                1               5                  10                  15
```

\<210\> SEQ ID NO 63
\<211\> LENGTH: 13
\<212\> TYPE: PRT
\<213\> ORGANISM: Artificial Sequence
\<220\> FEATURE:
\<223\> OTHER INFORMATION: SYNTHESIZED

\<400\> SEQUENCE: 63

Thr Pro Ser Leu Pro Thr Pro Pro Thr Arg Glu Pro Lys
1               5                   10

\<210\> SEQ ID NO 64
\<211\> LENGTH: 13
\<212\> TYPE: PRT
\<213\> ORGANISM: Artificial Sequence
\<220\> FEATURE:
\<223\> OTHER INFORMATION: SYNTHESIZED
\<220\> FEATURE:
\<221\> NAME/KEY: MOD_RES
\<222\> LOCATION: (6)..(6)
\<223\> OTHER INFORMATION: PHOSPHORYLATION

\<400\> SEQUENCE: 64

Thr Pro Ser Leu Pro Thr Pro Pro Thr Arg Glu Pro Lys
1               5                   10

\<210\> SEQ ID NO 65
\<211\> LENGTH: 10
\<212\> TYPE: PRT
\<213\> ORGANISM: Artificial Sequence
\<220\> FEATURE:
\<223\> OTHER INFORMATION: SYNTHESIZED

\<400\> SEQUENCE: 65

Thr Pro Ser Leu Pro Thr Pro Pro Thr Arg
1               5                   10

\<210\> SEQ ID NO 66
\<211\> LENGTH: 10
\<212\> TYPE: PRT
\<213\> ORGANISM: Artificial Sequence
\<220\> FEATURE:
\<223\> OTHER INFORMATION: SYNTHESIZED
\<220\> FEATURE:
\<221\> NAME/KEY: MOD_RES
\<222\> LOCATION: (6)..(6)
\<223\> OTHER INFORMATION: PHOSPHORYLATION

\<400\> SEQUENCE: 66

Thr Pro Ser Leu Pro Thr Pro Pro Thr Arg
1               5                   10

\<210\> SEQ ID NO 67
\<211\> LENGTH: 10
\<212\> TYPE: PRT
\<213\> ORGANISM: Artificial Sequence
\<220\> FEATURE:
\<223\> OTHER INFORMATION: SYNTHESIZED
\<220\> FEATURE:
\<221\> NAME/KEY: MOD_RES
\<222\> LOCATION: (3)..(3)
\<223\> OTHER INFORMATION: PHOSPHORYLATION

\<400\> SEQUENCE: 67

Thr Pro Ser Leu Pro Thr Pro Pro Thr Arg
1               5                   10

<210> SEQ ID NO 68
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (1)..(1)
<223> OTHER INFORMATION: PHOSPHORYLATION

<400> SEQUENCE: 68

Thr Pro Pro Ser Ser Gly Glu Pro Pro Lys
1               5                   10

<210> SEQ ID NO 69
<211> LENGTH: 23
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (12)..(12)
<223> OTHER INFORMATION: PHOSPHORYLATION

<400> SEQUENCE: 69

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 70
<211> LENGTH: 12
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (5)..(5)
<223> OTHER INFORMATION: PHOSPHORYLATION

<400> SEQUENCE: 70

Lys Thr Pro Pro Ser Ser Gly Glu Pro Pro Lys Ser
1               5                   10

<210> SEQ ID NO 71
<211> LENGTH: 17
<212> TYPE: PRT
<213> ORGANISM: Artificial Sequence
<220> FEATURE:
<223> OTHER INFORMATION: SYNTHESIZED
<220> FEATURE:
<221> NAME/KEY: MOD_RES
<222> LOCATION: (9)..(9)
<223> OTHER INFORMATION: PHOSPHORYLATION

<400> SEQUENCE: 71

Arg Ser Gly Tyr Ser Ser Pro Gly Ser Pro Gly Thr Pro Gly Ser Arg
1               5                   10                  15

Ser

<210> SEQ ID NO 72
<211> LENGTH: 12
<212> TYPE: PRT
<213> ORGANISM: Artificial Sequence
<220> FEATURE:

<223> OTHER INFORMATION: SYNTHESIZED

<400> SEQUENCE: 72

Arg Thr Pro Ser Leu Pro Thr Pro Pro Thr Arg Glu
1               5                   10

METHODS OF TREATING BASED ON SITE-SPECIFIC TAU PHOSPHORYLATION

CROSS REFERENCE TO RELATED APPLICATIONS

This application claims priority to U.S. Application Ser. No. 17/368,403, filed Jul. 6, 2021, U.S. Pat. No. 11,085,935, filed Sep. 9, 2020, which claims priority to U.S. Provisional Application No. 62/898,407, filed Sep. 10, 2019, and to PCT Application No. PCT/US2019/030725, filed May 3, 2019, which claims priority to U.S. Provisional Application No. 62/666,504, filed May 3, 2018, and U.S. Provisional Application No. 62/666,509, filed May 3, 2018, the disclosures of which are incorporated herein by reference.

GOVERNMENTAL RIGHTS

This invention was made with government support under NS065667, AG061900, and NS095773 awarded by the National Institutes of Health. The government has certain rights in the invention.

REFERENCE TO SEQUENCE LISTING

This application contains a Sequence Listing that has been submitted in ASCII format via EFS-Web and is hereby incorporated by reference in its entirety. The ASCII copy, created on Sep. 11, 2020, is named 665868_ST25.txt, and is 24 KB bytes in size.

BACKGROUND OF THE INVENTION

The microtubule-associated protein tau (MAPT or tau) plays an essential role in the morphology and physiology of neurons. Tau has six different isoforms of the full-length protein and undergoes a number of possible post-translational modifications including acetylation, glycosylation and phosphorylation. Phosphorylation is important for regulating the normal function of tau in axonal stabilization and can occur at over 80 different residues. However, excessive phosphorylation of tau appears to increase the probability of tau aggregating into intracellular insoluble paired helical filaments (PHF) and neurofibrillary tangles (NFT), which are primarily composed of hyperphosphorylated tau.

Intracellular neurofibrillary tangles in the cerebral cortex are a defining pathological feature of Alzheimer disease (AD) and correlate with the onset of clinical symptoms long after the appearance of extracellular amyloid-β (Aβ) plaques, which begin to develop up two decades before symptom onset. In AD, soluble p-tau and unphosphorylated tau are increased by two-fold in the cerebrospinal fluid (CSF). It has been proposed that these changes reflect the effects of neuronal death (neurodegeneration) passively releasing tau and NFT into the CSF. However, in other tauopathies with significant NFT pathology and neurodegeneration (e.g. progressive supranuclear palsy, frontotemporal lobar degeneration-tau), CSF levels of soluble p-tau and total tau do not increase. These observations suggest that Aβ may trigger a process that leads to the unique tauopathy of AD, an idea that is supported by cellular and animal models. This concept is further supported by an increase in the active production of soluble tau in the presence of amyloid plaques in humans.

Although tau comprises a hallmark AD pathology and can be measured in aggregated or soluble forms, important gaps remain in our understanding of how the post-translational modifications of this critical neuronal protein lead to the development of NFT and neurodegeneration in humans. For instance, the relationship of tau to amyloid-β plaques is unknown. Similarly, it is unknown what, if any, pathophysiologic changes occur to tau during the preclinical and clinical stages of AD. As such, it is unclear to what extent, if any, tau can be used to stage subjects prior to the onset of symptoms associated with AD and guide treatment decisions.

Accordingly, there remains a need in the art for improved methods to quantify tau phosphorylation.

SUMMARY OF THE INVENTION

In an aspect, the present disclosure encompasses a method to diagnose a subject as having an increased risk for conversion to mild cognitive impairment (MCI) due to Alzheimer's disease (AD). The method comprises (a) providing an isolated tau sample obtained from a subject and measuring, in the isolated tau sample, tau phosphorylation at one or more amino acid residue chosen from T181, T205 and T217 and optionally measuring total tau; and (b) diagnosing the subject as having an increased risk for conversion to MCI due to AD when the measured phosphorylation level(s) significantly deviate from the mean in a control population without brain amyloid plaques as measured by PET imaging and/or Aβ42/40 measurement in CSF. Alternatively, or in addition to, using a measurement of tau phosphorylation at T181, T205 and/or T217, optionally with a measurement of total tau, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau. Mathematical operations other than a ratio may also be used.

In another aspect, the present disclosure encompasses a method to stage a subject prior to the onset of mild cognitive impairment (MCI) due to Alzheimer's disease (AD). The method comprises (a) providing an isolated tau sample obtained from a subject and measuring, in the isolated tau sample, tau phosphorylation at one or more amino acid residue chosen from T181, T205 and T217 and optionally measuring total tau; and (b) diagnosing the subject as being a certain number of years from onset of MCI due to AD when the measured phosphorylation level(s) significantly deviate from the mean in a control population without brain amyloid plaques as measured by PET imaging and/or Aβ42/40 measurement in CSF. Alternatively, or in addition to, using a measurement of tau phosphorylation at T181, T205 and/or T217, optionally with a measurement of total tau, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau. Mathematical operations other than a ratio may also be used.

In another aspect, the present disclosure encompasses a method to stage a subject after onset of Alzheimer's disease (AD) symptoms. The method comprises (a) providing an isolated tau sample obtained from a subject and measuring, in the isolated tau sample, tau phosphorylation at one or more amino acid residue chosen from T181, T205 and T217 and optionally measuring total tau; and (b) diagnosing the subject as being a certain number of years after onset of MCI due to AD when the measured phosphorylation level(s) significantly deviate from the mean in a control population without brain amyloid plaques as measured by PET imaging and/or Aβ42/40 measurement in CSF. Alternatively, or in addition to, using a measurement of tau phosphorylation at T181, T205 and/or T217, optionally with a measurement of total tau, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau. Mathematical operations other than a ratio may also be used.

In another aspect, the present disclosure encompasses a method for treating a subject in need thereof. The method comprises (a) providing an isolated tau sample obtained from a subject and measuring, in the isolated tau sample, tau phosphorylation at one or more amino acid residue chosen from T181, T205 and T217 and optionally measuring total tau; and (b) administering a pharmaceutical composition to the subject when the measured phosphorylation level(s) significantly deviate from the mean in a control population without brain amyloid plaques as measured by PET imaging and/or Aβ42/40 measurement in CSF. Alternatively, or in addition to, using a measurement of tau phosphorylation at T181, T205 and/or T217, optionally with a measurement of total tau, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau. Mathematical operations other than a ratio may also be used.

In another aspect, present disclosure encompasses a method for enrolling a subject into a clinical trial. The method comprises (a) providing an isolated tau sample obtained from a subject and measuring, in the isolated tau sample, tau phosphorylation at one or more amino acid residue chosen from T181, T205 and T217 and optionally measuring total tau; and (b) enrolling the subject into a clinical trial when the measured phosphorylation level(s) significantly deviate from the mean in a control population without brain amyloid plaques as measured by PET imaging and/or Aβ42/40 measurement in CSF. Alternatively, or in addition to, using a measurement of tau phosphorylation at T181, T205 and/or T217, optionally with a measurement of total tau, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau. Mathematical operations other than a ratio may also be used.

Other aspects and iterations of the invention are described more thoroughly below.

BRIEF DESCRIPTION OF THE FIGURES

The application file contains at least one photograph executed in color. Copies of this patent application publication with color photographs will be provided by the Office upon request and payment of the necessary fee.

(FIG. 14A) Tau phosphorylation ratio measurements on pT181/T181, pT231/T231 are consistent across antibodies tested. PS199/S199 is decreased by using Tau1 or Tau1+HJ8.5 in comparison to other antibodies. (FIG. 14B) Low recovery of pS199 by Tau1 or Tau1+HJ8.5 IP underestimate pS199/S199 ratio measurements compared to other antibodies. Tau13, HJ8.5, and HJ8.7 antibodies indicate no significant changes of pS199 phosphorylation ratio between brain and CSF. Compared to brain, pS202/S202 CSF hypophosphorylation (FIG. 14C) and pT217/pT217 hyperphosphorylation (FIG. 14D) are evidenced independently of the antibody used for IP-MS. The legend for FIG. 14B-D is the same and shown in FIG. 14C—Brain (blue), nonAD CSF (green), and AD CSF (red).

FIG. 16A Receiver operating characteristics for total tau (blue line, AUC=0.62) and site-specific phosphorylation ratios in classifying participants as having Aβ pathology based on Aβ PiB-PET (SUVR cutoff of 1.25), p-T217 (yellow line) demonstrates a near perfect association with Aβ pathology (AUC=0.97), followed by p-T181 (AUC=0.89) and p-T205 (AUC=0.74). Standardized (z-score) phosphorylation ratios are shown for p-T217 (FIG. 16B), p-T181, (FIG. 16C), p-S202 (FIG. 16D), p-T205 (FIG. 16E) and total tau (FIG. 16F) levels by AβPiB-PET quartiles (n=45, 47, 28, 30) for mutation carriers highlights site-specific differences in phosphorylation with increasing AβPiB-PET levels: p-T217 and p-T181 increase greatest with the initial increase in AβPiB-PET amount and slow with the highest levels of AB PiB-PET, while p-T205 and total tau demonstrate a continued increase. For p-S202, there was a significant decrease in phosphorylation at the highest AβPiB-PET quartiles relative to the lowest; *—p-value<0.001, —p-value<0.01 based on Wilcoxon two sample test; the middle line represents the median, and the upper and lower notch=median+/−1.58*interquartile range/square root(n-observations), the upper and lower whisker=largest observation greater/less than or equal to upper/lower hinge+1.58*IQR. FIG. 16G Bivariate correlations between cortical and sub-cortical AβPiB-PET SUVR and site-specific phosphorylation for asymptomatic mutation carriers (n=139). The colors represent the correlation with positive correlations (yellow-red) and negative correlations (blue); all correlations represent statistically significant values surviving a false discovery rate (p<0.05) and are arranged by the strength of the correlations from top to bottom.

(FIG. 17F) Model estimated, longitudinal rates of change for each site of phosphorylation where standardized to the rates of non-carriers and plotted over EYO along with amyloid PET (red) and cognitive decline (yellow); the solid circles represent the point when the rate of change for each variable first becomes different for mutation carriers compared to non-carriers. This highlights the pattern of change for p-tau isoforms over the course of the AD spectrum and the close association between amyloid plaque growth and the increase in p-T217 with plaques beginning to increase at −21 EYO and the hyperphosphorylation of p-T217 (black) beginning at −21 EYO and the decline in phosphorylation rate of these two sites with a decline in cognition (yellow line). In contrast, p-T205 (purple) continues increasing throughout disease progression and total tau levels (grey) increase at an increased rate near the time of symptom onset.

FIG. 18A. Bivariate correlations between cortical and sub-cortical atrophy and site-specific phosphorylation ratios in asymptomatic mutation carriers (n=152) demonstrates increases in phosphorylation of p-T205 and p-T217, with smaller associations for p-T181. Total tau levels are associated with greater atrophy in multiple cortical and subcortical regions.

FIG. 18B. Bivariate correlations between cortical and sub-cortical brain metabolism measured by FDG-PET and site-specific phosphorylation ratios in asymptomatic mutation carriers (n=143) demonstrates an increase in phosphorylation of p-T205 is associated with a decrease in most cortical and sub-cortical regions but not for other p-tau sites or tau.

FIG. 23A, T181 monitoring using a microLC system. FIG. 23B, S199, S202, T205 (coeluted in framed signal) and T217 monitoring using a nanoLC system. Endogenous signals (full blue line), 15N labeled peptides (red dotted line), AQUA peptides (green dotted line). FIG. 23C shows specific PRM transitions, according to Biemann nomenclature for peptide fragmentation, which allowed identification of the three co-eluted monophosphorylated peptides carrying pS199, pS202 or pT205. Cps=Count per second.

FIG. 24A: T217 phosphorylation significantly increases in participants having amyloidosis (PiB-PET and CSF Aβ42/40 ratio positive) compared to amyloid-negative controls with no or mild cognitive decline. FIG. 24B: ROC curves for the diagnosis of amyloid-positive from amyloid-negative participants using phosphorylation rate of T217, T181 by MS and T181 by ELISA. FIG. 24C: pT217/T217 ratio comparison demonstrates the specific phosphorylation on T217 in participants with amyloidosis. FIG. 24D: Comparison of T217 phosphorylation with CSF Aβ42/40 changes measured by MS and to amyloid plaque deposition measured by PiB-PET. FIG. 24D: The extent of T217 hyperphosphorylation is not correlated with the decrease of CSF Aβ42 relative to A340. The five conflicting cases (orange triangles, positive for PiB-PET and T217 hyperphosphorylation but negative for CSF Aβ), were all slightly above the 0.12 threshold chosen to define the amyloid status, suggesting that they may result from insufficient sensitivity of the CSF amyloid assay. PiB-PET loading (FBP Total Cortical Mean) is correlated with T217 phosphorylation state in amyloid-positive participants. Cut-off value differentiating amyloid positive from amyloid negative by PiB is 0.18.

FIG. 26A depicts the results from the entire cohort. FIG. 26B depicts an average tau profile from the cohort. The decreases identified as a, b, c, and d are described as follows. a: Decrease of 2N and 1N+2N peptide abundance consistent with 5/5/1 0N/1N/2N contribution in plasma tau. b: Decrease consistent with the presence of around 10% of phosphorylation on position 181. Phosphorylation on T181 induces a trypsin missed cleavage between residues 180 and 181. This contributes to a decrease of 175-180 and 181-190 peptide abundance proportional to the extent of phosphorylation on T181. c: Decrease consistent with tau truncation between residues 221 and 226. Cigognola et al. have reported CSF tau main cleavage occurring at residue 224. d: Decrease consistent with progressive C-terminus degradation of plasma tau from residue 224 to Microtubule Binding Region upstream region.

FIG. 27A shows measures of pT217/T217 ratios in plasma and CSF are highly correlated in both entire cohort and CSF pT217 positive subgroup. Spearman correlations and associated p-value are shown. Consistent with CSF measurement, plasma pT217/T217 ratio (FIG. 27B) and pT217 level (FIG. 27C) distinguish amyloid negative from amyloid positive groups regardless of the cognitive status. Amyloid negative with high CSF pT217 were also separated from other amyloid negative groups.

FIG. 27D shows that plasma tau level is not a biomarker for amyloid status and AD dementia. Plasma pT181/T181 ratio (FIG. 27E) and pT181 level (FIG. 27F) increase in amyloid positive groups but are less accurate than pT217 measures to detect abnormal tau phosphorylation. Separation between groups is calculated using area under receiver operating curve (AUROC).

DETAILED DESCRIPTION

Figure 22:
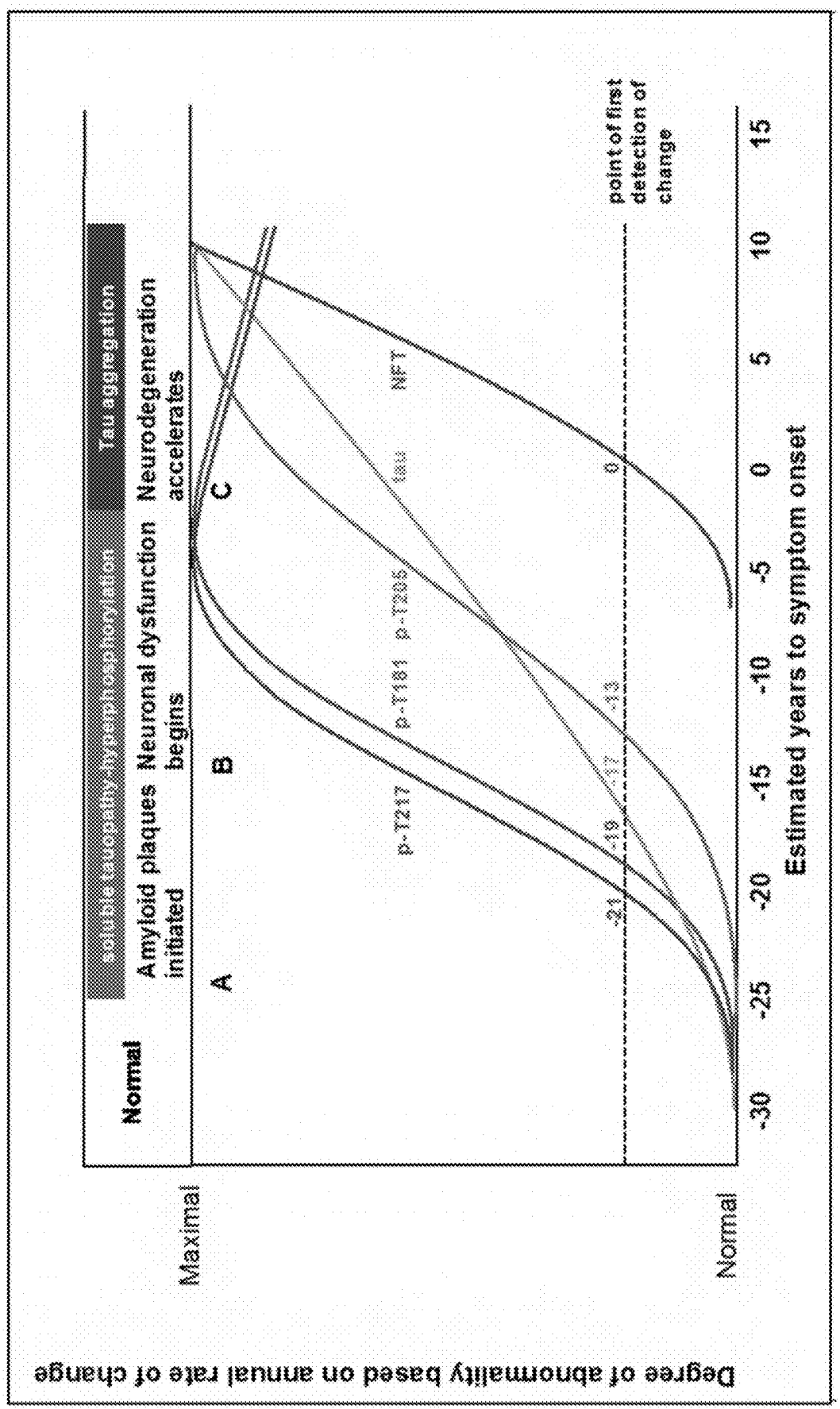
FIG. 22 is an illustration showing tau pathology evolves through distinct phases in Alzheimer Disease. Measuring four different soluble tau species and insoluble tau in a group of participants with deterministic Alzheimer disease mutations we show over the course of 35 years (x-axis) tau related changes unfold (y-axis) and differ based on the stage of disease and other measurable biomarkers. A. Starting with the development of fibrillar amyloid pathology phosphorylation at position 217 (purple) and 181 (blue) begins to increase. B. With the increase in neuronal dysfunction (based metabolic changes) phosphorylation at position 205 (green) begins to increase along with soluble tau (orange). C. Lastly, with the onset of neurodegeneration (based on brain atrophy and cognitive decline) tau PET tangles (red) begin to develop while phosphorylation of 217 and 181 begins to decrease. Together, this highlights the dynamic and diverging patterns of soluble and aggregated tau over the course of the disease and close relationship with amyloid pathology.
Figure 23A:
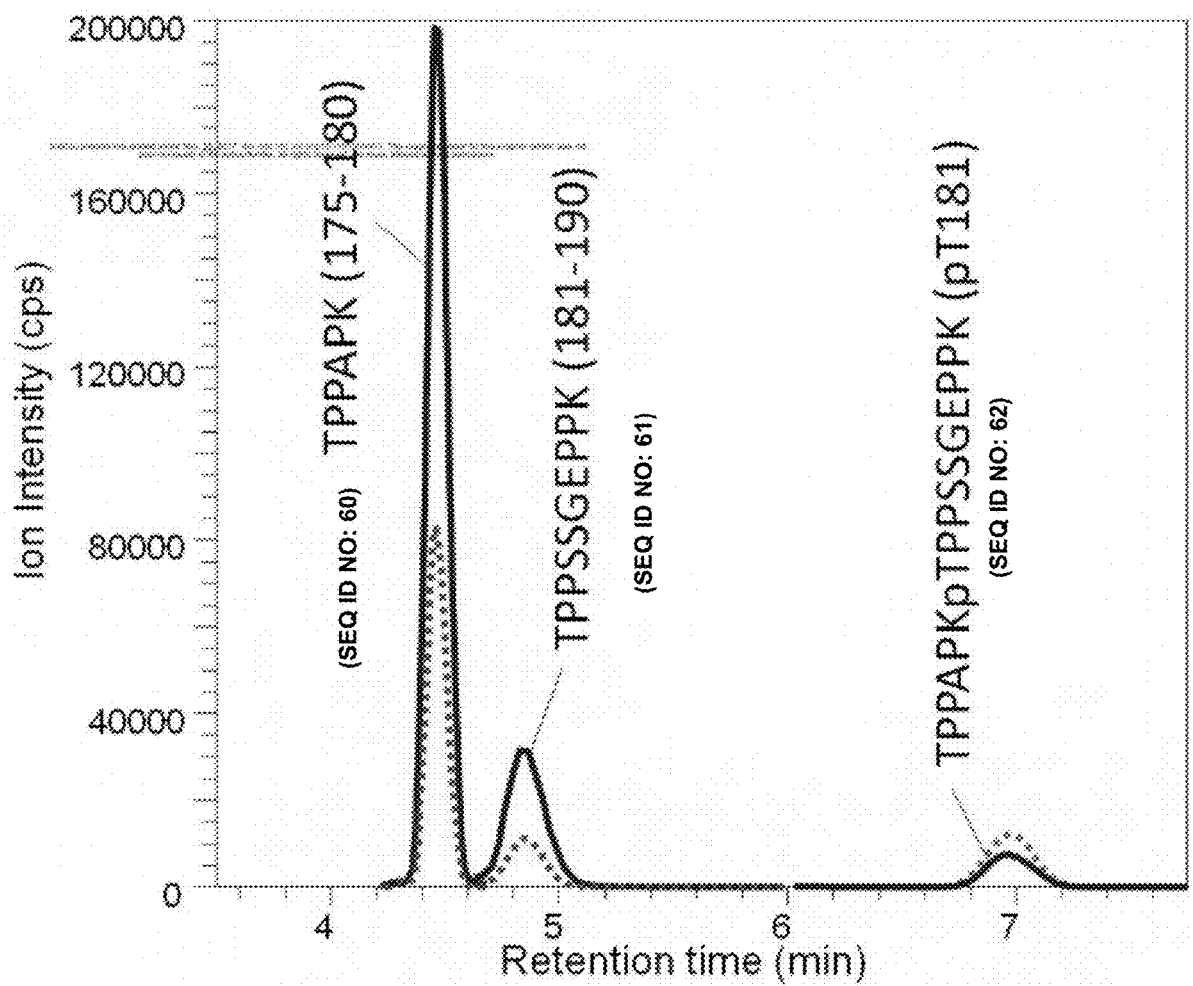
FIG. 23A, FIG. 23B, and FIG. 23C show quantitation of phosphorylated tau isoforms in CSF. Sum of Extracted Ion Chromatograms from Parallel Reaction Monitoring (PRM) analysis of tau phosphorylated peptides and the corresponding unmodified peptides in CSF.
Figure 23B:
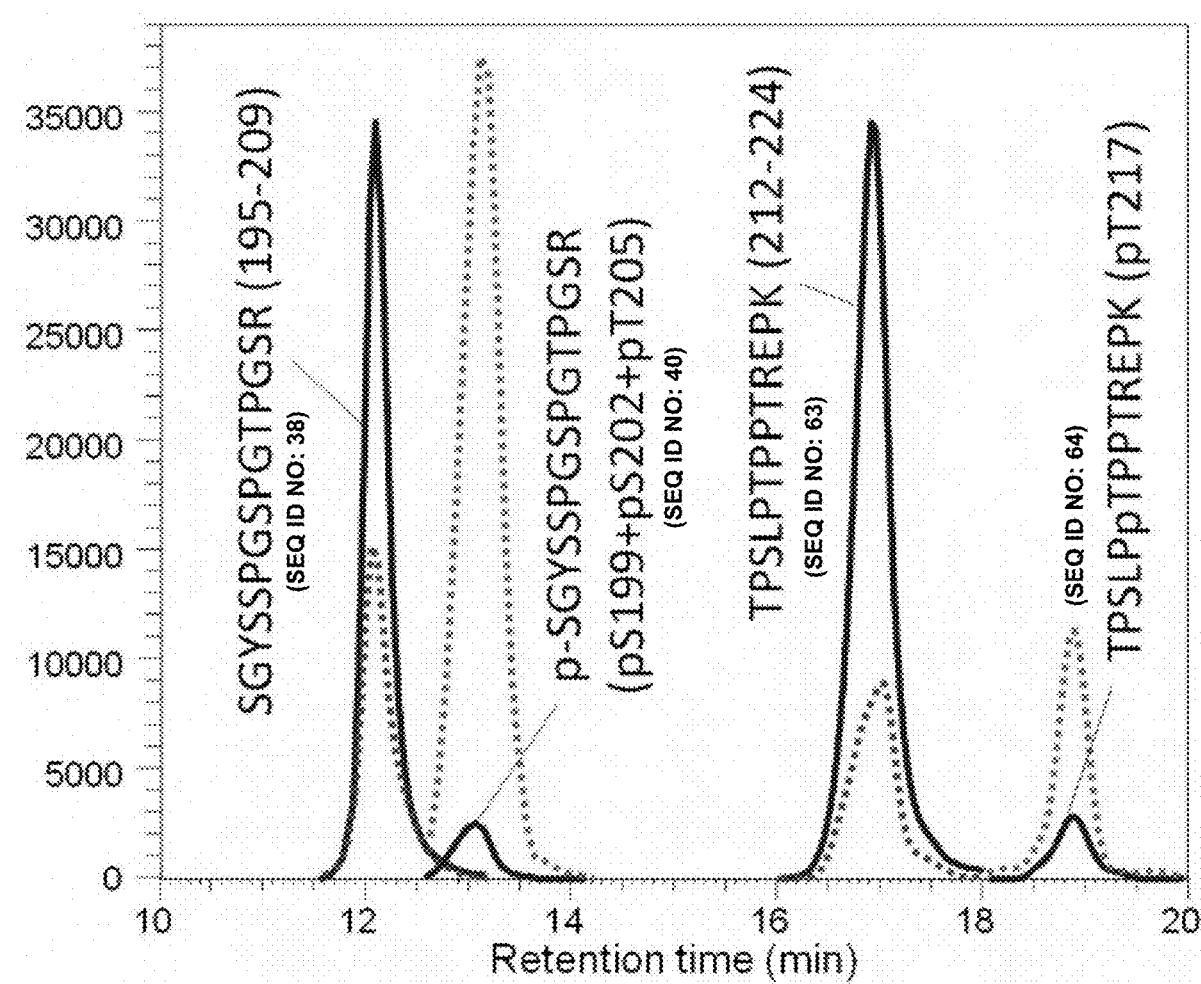
Figure 23C:
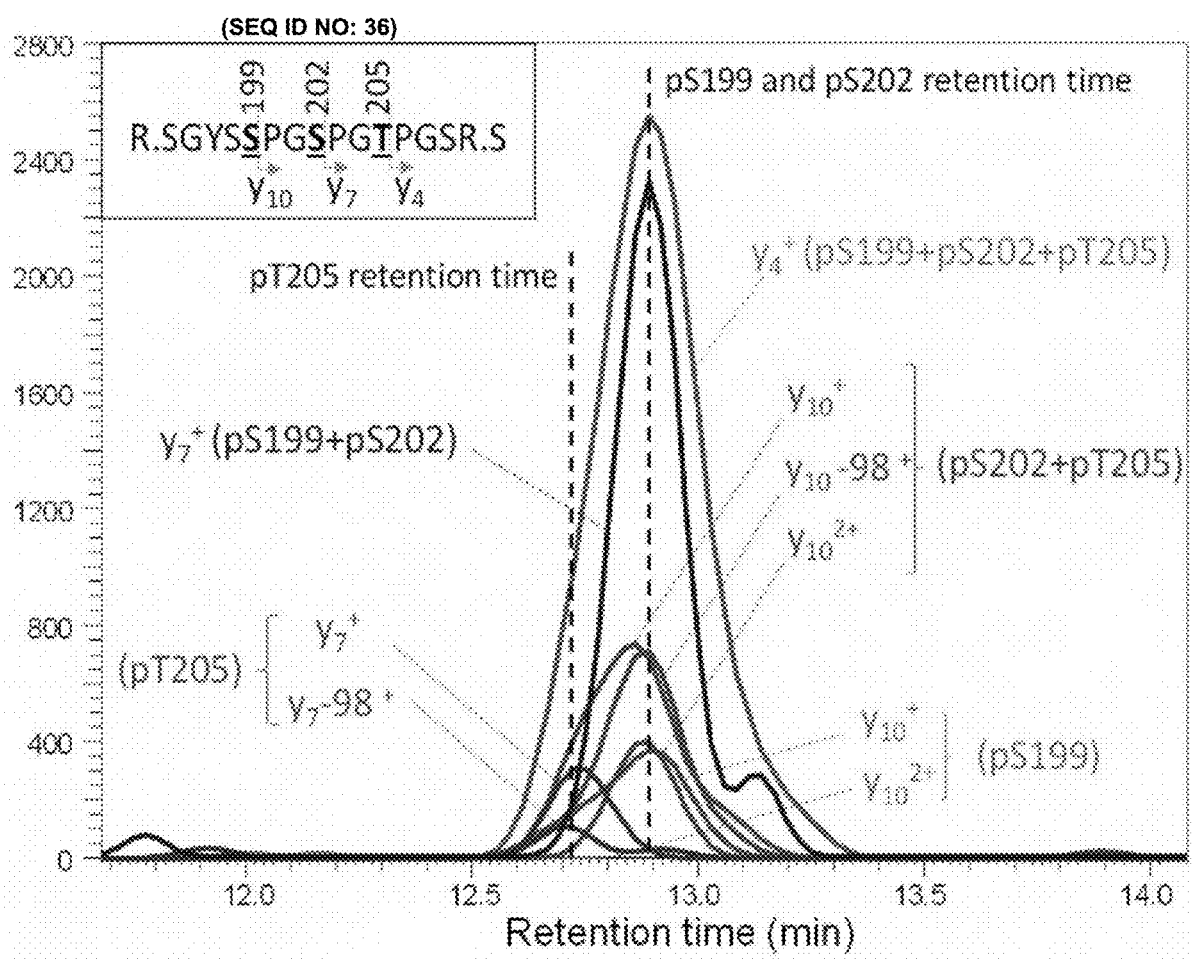

Tau protein aggregation into neurofibrillary tangles in the central nervous system contributes to the etiology of certain neurodegenerative disorders, including Alzheimer's disease (AD). Though the mechanism of tau destabilization is not fully understood yet, tau protein has been found to be hyperphosphorylated in tau aggregates. Applicants have discovered that certain methods to quantify tau phosphorylation at specific amino acid residues can be used to can track the AD process across its preclinical asymptomatic stages to symptomatic stages. FIG. 22 illustrates the dynamic pattern of tau phosphorylation measurable at T181, T205 and T217 created by the applicant's method in relation to years from onset of MCI due to AD and to the development of certain pathophysiological changes. The present disclosure encompasses use of the methods to quantify tau phosphorylation at specific amino acid residues to predict time to onset of mild cognitive impairment due to Alzheimer's disease, guide treatment decisions, select subjects for clinical trials, and evaluate the clinical efficacy of certain therapeutic interventions. Other aspects and iterations of the invention are described more thoroughly below.

I. Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation of in the numerical quantity that can occur, for example, through typical measuring techniques and equipment, with respect to any quantifiable variable, including, but not limited to, mass, volume, time, distance, and amount. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations, which can be up to ±5%, but can also be ±4%, 3%, 2%, 1%, etc. Whether or not modified by the term "about," the claims include equivalents to the quantities.

An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody and a humanized antibody. The techniques for preparing and using various antibody-based constructs and fragments are well known in the art. Means for preparing and characterizing antibodies are also well known in the art (See, e.g. Antibodies: A Laboratory Manual, Cold Spring Harbor Laboratory, 1988; herein incorporated by reference in its entirety).

As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art. See, for instance U.S. Pat. No. 7,939,313, herein incorporated by reference in its entirety.

The term "Aβ" refers to peptides derived from a region in the carboxy terminus of a larger protein called amyloid precursor protein (APP). The gene encoding APP is located on chromosome 21. There are many forms of Aβ that may have toxic effects: Aβ peptides are typically 37-43 amino acid sequences long, though they can have truncations and modifications changing their overall size. They can be found in soluble and insoluble compartments, in monomeric, oligomeric and aggregated forms, intracellularly or extracellularly, and may be complexed with other proteins or molecules. The adverse or toxic effects of Aβ may be attributable to any or all of the above noted forms, as well as to others not described specifically. For example, two such Aβ isoforms include Aβ40 and Aβ42; with the Aβ42 isoform being particularly fibrillogenic or insoluble and associated with disease states. The term "Aβ" typically refers to a plurality of Aβ species without discrimination among individual Aβ species. Specific Aβ species are identified by the size of the peptide, e.g., Aβ42, Aβ40, Aβ38 etc.

As used herein, the term "Aβ42/Aβ40 value" means the ratio of the concentration of Aβ42 in a sample obtained from a subject compared to the concentration of Aβ40 in the same sample.

"Aβ amyloidosis" is clinically defined as evidence of Aβ deposition in the brain. A subject that is clinically determined to have Aβ amyloidosis is referred to herein as "amyloid positive," while a subject that is clinically determined to not have Aβ amyloidosis is referred to herein as "amyloid negative." Aβ amyloidosis likely exists before it is detectable by current techniques. Nonetheless, there are accepted indicators of Aβ amyloidosis in the art. At the time of this disclosure, Aβ amyloidosis is typically identified by amyloid imaging (e.g., PiB PET, fluorbetapir, or other imaging methods known in the art) or by decreased cerebrospinal fluid (CSF) Aβ42 or a decreased CSF Aβ42/40 ratio. [$^{11}$C] PIB-PET imaging with mean cortical binding potential (MCBP) score >0.18 is an indicator of Aβ amyloidosis, as is cerebral spinal fluid (CSF) Aβ42 concentration of about 1 ng/ml by immunoprecipitation and mass spectrometry (IP/MS)). Values such as these, or others known in the art, may be used alone or in combination to clinically confirm Aβ amyloidosis. See, for example, Klunk W E et al. *Ann Neurol* 55(3) 2004, Fagan A M et al. *Ann Neurol*, 2006, 59(3), Patterson et. al, *Annals of Neurology*, 2015, 78(3): 439-453, or Johnson et al., *J. Nuc. Med.*, 2013, 54(7): 1011-1013, each hereby incorporated by reference in its entirety. Subjects with Aβ amyloidosis may or may not be symptomatic, and symptomatic subjects may or may not satisfy the clinical criteria for a disease associated with Aβ amyloidosis. Non-limiting examples of symptoms associated with Aβ amyloidosis may include impaired cognitive function, altered behavior, abnormal language function, emotional dysregulation, seizures, dementia, and impaired nervous system structure or function. Diseases associated with Aβ amyloidosis include, but are not limited to, Alzheimer's Disease (AD), cerebral amyloid angiopathy, Lewy body dementia, and inclusion body myositis. Subjects with Aβ amyloidosis are at an increased risk of developing a disease associated with Aβ amyloidosis.

A "clinical sign of Aβ amyloidosis" refers to a measure of Aβ deposition known in the art. Clinical signs of Aβ amyloidosis may include, but are not limited to, Aβ deposition identified by amyloid imaging (e.g. PiB PET, fluorbetapir, or other imaging methods known in the art) or by decreased cerebrospinal fluid (CSF) Aβ42 or Aβ42/40 ratio. See, for example, Klunk W E et al. Ann Neurol 55(3) 2004, and Fagan A M et al. Ann Neurol 59(3) 2006, each hereby incorporated by reference in its entirety. Clinical signs of Aβ amyloidosis may also include measurements of the metabolism of Aβ, in particular measurements of Aβ42 metabolism alone or in comparison to measurements of the metabolism of other Aβ variants (e.g. Aβ37, Aβ38, Aβ39, Aβ40, and/or total Aβ), as described in U.S. patent Ser. Nos. 14/366,831, 14/523,148 and 14/747,453, each hereby incorporated by reference in its entirety. Additional methods are described in Albert et al. Alzheimer's & Dementia 2007 Vol. 7, pp. 170-179; McKhann et al., Alzheimer's & Dementia 2007 Vol. 7, pp. 263-269; and Sperling et al. Alzheimer's & Dementia 2007 Vol. 7, pp. 280-292, each hereby incorporated by reference in its entirety. Importantly, a subject with clinical signs of Aβ amyloidosis may or may not have symptoms associated with Aβ deposition. Yet subjects with clinical signs of Aβ amyloidosis are at an increased risk of developing a disease associated with Aβ amyloidosis.

A "candidate for amyloid imaging" refers to a subject that has been identified by a clinician as an individual for whom amyloid imaging may be clinically warranted. As a non-limiting example, a candidate for amyloid imaging may be a subject with one or more clinical signs of Aβ amyloidosis, one or more Aβ plaque associated symptom, one or more CAA associated symptom, or combinations thereof. As a non-limiting example, a candidate for amyloid imaging may be a subject with genetic predisposition for Aβ amyloidosis. A clinician may recommend amyloid imaging for such a subject to direct his or her clinical care. As another non-limiting example, a candidate for amyloid imaging may be a potential participant in a clinical trial for a disease associated with Aβ amyloidosis (either a control subject or a test subject).

An "Aβ plaque associated symptom" or a "CAA associated symptom" refers to any symptom caused by or associated with the formation of amyloid plaques or CAA, respectively, being composed of regularly ordered fibrillar aggregates called amyloid fibrils. Exemplary Aβ plaque associated symptoms may include, but are not limited to, neuronal degeneration, impaired cognitive function, impaired memory, altered behavior, emotional dysregulation, seizures, impaired nervous system structure or function, and an increased risk of development or worsening of Alzheimer's disease or CAA. Neuronal degeneration may include a change in structure of a neuron (including molecular changes such as intracellular accumulation of toxic proteins, protein aggregates, etc. and macro level changes such as change in shape or length of axons or dendrites, change in myelin sheath composition, loss of myelin sheath, etc.), a change in function of a neuron, a loss of function of a neuron, death of a neuron, or any combination thereof. Impaired cognitive function may include but is not limited to difficulties with memory, attention, concentration, language, abstract thought, creativity, executive function, planning, and organization. Altered behavior may include, but is not limited to, physical or verbal aggression, impulsivity, decreased inhibition, apathy, decreased initiation, changes in personality, abuse of alcohol, tobacco or drugs, and other addiction-related behaviors. Emotional dysregulation may include, but is not limited to, depression, anxiety, mania, irritability, and emotional incontinence. Seizures may include but are not limited to generalized tonic-clonic seizures, complex partial seizures, and non-epileptic, psychogenic seizures. Impaired nervous system structure or function may include, but is not limited to, hydrocephalus, Parkinsonism, sleep disorders, psychosis, impairment of balance and coordination. This may include motor impairments such as monoparesis, hemiparesis, tetraparesis, ataxia, ballismus and tremor. This also may include sensory loss or dysfunction including olfactory, tactile, gustatory, visual and auditory sensation. Furthermore, this may include autonomic nervous system impairments such as bowel and bladder dysfunction, sexual dysfunction, blood pressure and temperature dysregulation. Finally, this may include hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators.

As used herein, the term "subject" refers to a mammal, preferably a human. The mammals include, but are not limited to, humans, primates, livestock, rodents, and pets. A subject may be waiting for medical care or treatment, may be under medical care or treatment, or may have received medical care or treatment.

As used herein, the term "healthy control group," "normal group" or a sample from a "healthy" subject means a subject, or group subjects, who is/are diagnosed by a physician as not suffering from Aβ amyloidosis, or a clinical disease associated with Aβ amyloidosis (including but not limited to Alzheimer's disease) based on qualitative or quantitative test results. A "normal" subject is usually about the same age as the individual to be evaluated, including, but not limited, subjects of the same age and subjects within a range of 5 to 10 years.

As used herein, the term "blood sample" refers to a biological sample derived from blood, preferably peripheral (or circulating) blood. The blood sample can be whole blood, plasma or serum, although plasma is typically preferred.

The term "isoform", as used herein, refers to any of several different forms of the same protein variants, arising due alternative splicing of mRNA encoding the protein, post-translational modification of the protein, proteolytic processing of the protein, genetic variations and somatic recombination. The terms "isoform" and "variant" are used interchangeably.

Unless otherwise stated herein, the term "tau protein" or "tau" encompasses all tau isoforms, whether full-length, truncated, or post-translationally modified. In many animals, including but not limited to humans, non-human primates, rodents, fish, cattle, frogs, goats, and chicken, tau is encoded by the gene MAPT. In humans, there are six isoforms of tau that are generated by alternative splicing of exons 2, 3, and 10 of MAPT. These isoforms range in length from 352 to 441 amino acids. Exons 2 and 3 encode 29-amino acid inserts each in the N-terminus (called N), and full-length human tau isoforms may have both inserts (2N), one insert (1N), or no inserts (0N). All full-length human tau isoforms also have three repeats of the microtubule binding domain (called R). Inclusion of exon 10 at the C-terminus leads to inclusion of a fourth microtubule binding domain encoded by exon 10. Hence, full-length human tau isoforms may be comprised of four repeats (4R) of the microtubule binding domain (exon 10 included) or three repeats (3R) of the microtubule binding domain (exon 10 excluded). Human tau may or may not be post-translationally modified. For example, it is known in the art that tau may be phosphorylated, ubiquinated, glycosylated, and glycated. Accordingly, the term "human tau" encompasses the (2N, 3R), (2N, 4R), (1 N, 3R), (1 N, 4R), (0N, 3R), and (0N, 4R) isoforms, isoforms that are N- and/or C-terminally truncated species thereof, and all post-translationally modified isoforms. Alternative splicing of the gene encoding tau similarly occurs in other animals. In animals where the gene is not identified as MAPT, a homolog may be identified by methods well known in the art.

A disease associated with tau deposition in the brain may be referred to as a "tauopathy". Tauopathies known in the art include, but are not limited to, progressive supranuclear palsy, dementia pugilistica, chronic traumatic encephalopathy, frontotemporal dementia and parkinsonism linked to chromosome 17, Lytico-Bodig disease, Parkinson-dementia complex of Guam, tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, argyrophilic grain disease (AGD), Frontotemporal lobar degeneration, Alzheimer's Disease, and frontotemporal dementia.

A clinical sign of a tauopathy may be aggregates of tau in the brain, including but not limited to neurofibrillary tangles. Methods for detecting and quantifying tau aggregates in the brain are known in the art (e.g., tau PET using tau-specific ligands such as [$^{18}$F]THK5317, [$^{18}$F]THK5351, [$^{18}$F] AV1451, [$^{11}$C]PBB3, [$^{18}$F]MK-6240, [$^{18}$F]RO-948, [$^{18}$F]PI-2620, [$^{18}$F]GTP1, [$^{18}$F]PM-PBB3, and [$^{18}$F]JNJ64349311, [$^{18}$F]JNJ-067), etc.).

A "candidate for tau imaging" refers to a subject that has been identified by a clinician as an individual for whom tau imaging may be clinically warranted. As a non-limiting example, a candidate for tau imaging may be a subject with one or more clinical signs of Aβ amyloidosis, one or more Aβ plaque associated symptom, one or more symptom of a tauopathy, or combinations thereof. As a non-limiting example, a candidate for tau imaging may be a subject with genetic predisposition for Aβ amyloidosis or a tauopathy. A clinician may recommend tau imaging for such a subject to direct his or her clinical care. As another non-limiting example, a candidate for tau imaging may be a potential participant in a clinical trial for a tauopathy (either a control subject or a test subject).

"Significantly deviate from the mean" refers to values that are at least 1 standard deviation, preferably at least 1.3 standard deviations, more preferably at least 1.5 standard deviations or even more preferably at least 2 standard deviations, above or below the mean.

The term "specifically binds," as used herein with regards to epitope binding agents, means that an epitope binding agent does not cross react to a significant extent with other epitopes on the protein of interest (e.g., tau), or on other proteins in general.

The phrase "Aβ and tau therapies" collectively refers to any imaging agent or therapeutic agent contemplated for, or used with, subjects at risk of developing Aβ amyloidosis or AD, subjects diagnosed as having Aβ amyloidosis, subjects diagnosed as having a tauopathy, or subjects diagnosed as having AD.

II. Measuring Total Tau and Tau Phosphorylation in an Isolated Tau Sample

Methods of the present disclose comprise providing an isolated tau sample obtained from a subject and measuring tau phosphorylation at one or more amino acid residue and optionally total tau.

(a) Isolated Tau Sample

An isolated tau sample, as used herein, refers to a composition comprising tau, wherein tau has been purified from blood or cerebrospinal fluid (CSF) obtained from a subject. A subject is a mammal, preferably a human.

CSF may be obtained by lumbar puncture with or without an indwelling CSF catheter. Multiple blood or CSF samples contemporaneously collected from the subject may be pooled. Blood may be collected by veni-puncture with or without an intravenous catheter, or by a finger stick (or the equivalent thereof). Multiple blood or CSF samples contemporaneously collected from the subject may be pooled. Once collected, and optionally pooled, blood or CSF samples may be processed according to methods known in the art (e.g., centrifugation to remove whole cells and cellular debris, use of additives designed to stabilize and preserve the specimen prior to analytical testing (e.g., protease inhibitors), etc.). Blood or CSF samples may be used immediately or may be frozen and stored indefinitely.

Alternatively, the method may use a blood or CSF sample previously obtained from a subject. Multiple blood or CSF samples previously collected from the subject may be pooled. If the previously obtained blood sample is whole blood, the method typically comprises a step where one or more blood sample is processed to obtain a plasma sample or a serum sample. Preferably, the blood sample previously obtained from a subject is a plasma sample or a serum sample.

In isolated tau samples of the present disclosure, tau has been either partially or completely purified from blood or CSF. Methods for purifying tau from blood or CSF are known in the art and include, but are not limited to, selective precipitation, size-exclusion chromatography, ion-exchange chromatography, and affinity purification. Suitable methods concentrate both phosphorylated tau and unphosphorylated tau from blood or CSF. In an exemplary embodiment, isolated tau samples of the present disclosure comprise tau that has been purified from blood or CSF by affinity purification.

(i) Method for Processing a Blood Sample to Enrich for Soluble Tau

In some embodiments where the sample is a blood sample (e.g., a plasma sample or a serum sample), this process comprises precipitating proteins from the blood sample, or pooled blood samples, thereby producing an acid soluble extract of blood, concentrating soluble tau in the acid soluble extract by solid phase extraction (SPE) and affinity purification using one or more epitope binding agent that specifically binds tau. In certain embodiments, affinity purification may be performed before solid phase extraction.

The amount of starting material (i.e., blood sample) may vary depending upon downstream uses. In some embodiments, about 0.5 ml to about 50 ml of plasma may be used (or corresponding amounts of whole blood or serum). In some embodiments, about 1 ml to about 20 ml of plasma may be used (or corresponding amounts of whole blood or serum). In some embodiments, about 10 ml to about 20 ml of plasma may be used (or corresponding amounts of whole blood or serum). In some embodiments, about 1 ml to about 10 ml of plasma may be used (or corresponding amounts of whole blood or serum). In some embodiments, about 1 ml to about 5 ml of plasma may be used (or corresponding amounts of whole blood or serum).

Plasma protein can be precipitated from one or more previously obtained blood sample using perchloric acid. As used herein, "perchloric acid" refers to 70% perchloric acid. In some embodiments, perchloric acid is added to a final concentration of about 1% v/v to about 15% v/v. In other embodiments, perchloric acid is added to a final concentration of about 1% v/v to about 10% v/v. In other embodiments, perchloric acid is added to a final concentration of about 1% v/v to about 5% v/v. In other embodiments, perchloric acid is added to a final concentration of about 3% v/v to about 15% v/v. In other embodiments, perchloric acid is added to a final concentration of about 3% v/v to about 10% v/v. In other embodiments, perchloric acid is added to a final concentration of about 3% v/v to about 5% v/v. In other embodiments, perchloric acid is added to a final concentration of 3.5% v/v to about 15% v/v, 3.5% v/v to about 10% v/v, or 3.5% v/v to about 5% v/v. In other embodiments, perchloric acid is added to a final concentration of about 3.5% v/v. Following addition of the perchloric acid, the sample is mixed well (e.g., by a vortex mixer) and held at a cold temperature, typically for about 10 minutes or longer, to facilitate precipitation. For example, samples may be held for about 10 minutes to about 60 minutes, about 20 minutes to about 60 minutes, or about 30 minutes to about 60 minutes. In other example, samples may be held for about 15 minutes to about 45 minutes, or about 30 minutes to about 45 minutes. In other examples, samples may be held for about 15 minutes to about 30 minutes, or about 20 minutes to about 40 minutes. In other examples, samples are held for about 30 minutes. The sample is then centrifuged at a cold temperature to pellet the precipitated protein, and the supernatant (i.e., the acid soluble fraction), comprising soluble tau, is transferred to a fresh vessel. As used in the above context, a "cold temperature" refers to a temperature of 10° C. or less. For instance, a cold temperature may be about 1° C., about 2° C., about 3° C., about 4° C., about 5° C., about 6° C., about 7° C., about 8° C., about 9° C., or about 10° C. In some embodiments, a narrower temperature range may be preferred, for example, about 3° C. to about 5° C., or even about 4° C. In certain embodiments, a cold temperature may be achieved by placing a sample on ice.

Soluble tau is concentrated by solid phase extraction using a reversed-phase sorbent. Briefly, the supernatant comprising soluble tau is applied to a reversed-phase sorbent, washed with a suitable mobile phase, and then eluted. Suitable reversed phase materials are known in the art and include, but are not limited to alkyl-bonded silicas, aryl-bonded silicas, styrene/divinylbenzene materials, or N-vinylpyrrolidone/divinylbenzene materials. In exemplary embodiments, the reversed phase material is a polymer comprising N-vinylpyrrolidone and divinylbenzene or a polymer comprising styrene and divinylbenzene. Prior to contact with the supernatant comprising soluble tau, the reversed-phase sorbent is preconditioned per manufacturer's instructions or as is known in the art (e.g., with a water miscible organic solvent and then the buffer comprising the mobile phase). In addition, the supernatant may be optionally acidified, as some reversed-phase materials retain ionized analytes more strongly than others. The use of volatile components in the mobile phases and for elution is preferred, as they facilitate sample drying. In exemplary embodiments, the tau may be washed with a liquid phase comprising about 0.05% v/v trifluoroacetic acid (TFA) to about 1% v/v TFA, or an equivalent thereof. In some examples, the wash may be with a liquid phase comprising about 0.05% v/v to about 0.5% v/v TFA or about 0.05% v/v to about 0.1% v/v TFA. In some examples, the wash may be with a liquid phase comprising about 0.1% v/v to about 1.0% v/v TFA or about 0.1% v/v to about 0.5% v/v TFA. Bound tau is then eluted with a liquid phase comprising about 20% v/v to about 50% v/v acetonitrile (ACN), or an equivalent thereof. In some examples, tau is may be eluted with a liquid phase comprising about 20% v/v to about 40% v/v ACN, or about 20% v/v to about 30% v/v ACN. In some examples, tau is may be eluted with a liquid phase comprising about 30% v/v to about 50% v/v ACN, or about 30% v/v to about 40% v/v ACN. The eluate may be dried by methods known in the art (e.g., vacuum drying (e.g., speed-vac), lyophilization, evaporation under a nitrogen stream, etc.).

The concentrated soluble tau may then be further processed by affinity purification using one or more ligand that specifically binds tau.

(ii) Affinity Purification

Figure 1:
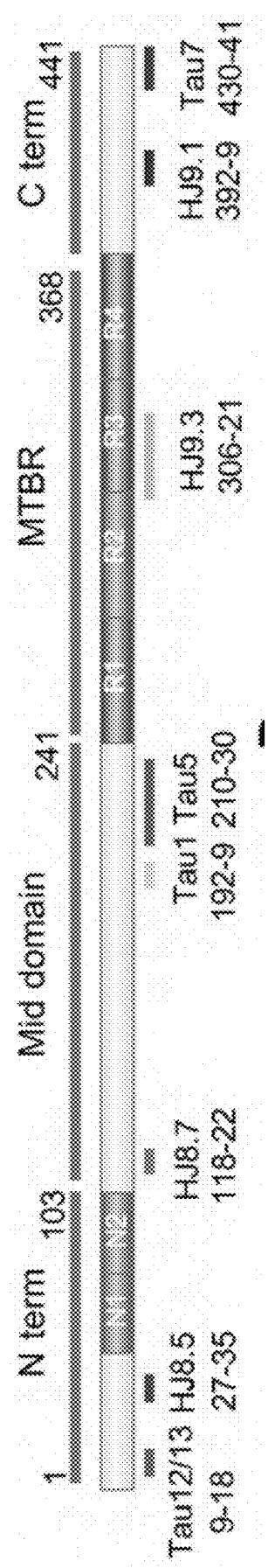
FIG. 1 is a schematic of the longest human tau isoform (2N4R) and epitopes of tau antibodies. The N-terminus, mid domain, MTBR, and C-terminus are identified for this isoform and will vary in a predictable way for other tau isoforms (e.g., 2N3R, 1 NR4, 1N3R, 0N4R, and 0N3R).

Affinity purification refers to methods that purify a protein of interest by virtue of its specific binding properties to an immobilized ligand. Typically, an immobilized ligand is a ligand attached to a solid support, such as a bead, a resin, a tissue culture plate, etc. Suitable ligands specifically bind both phosphorylated and unphosphoryated tau. In one example, a suitable ligand may bind an epitope within the mid domain of tau. In another example, a suitable ligand may bind an epitope within the N-terminus of tau, preferably within amino acids 1 to 35 of tau. In another example, a suitable ligand may bind an epitope within the MTBR of tau. In another example, a suitable ligand may bind an epitope within the C-terminus of tau. In still further embodiments, tau may be affinity purified from blood or CSF using two or more immobilized ligands. In one example, an immobilized ligand binds an epitope within the N-terminus of tau and another immobilized ligand binds an epitope within the mid domain of tau. In another example, an immobilized ligand binds an epitope within the MTBR of tau and another immobilized ligand binds an epitope within the mid domain of tau. In another example, an immobilized ligand binds an epitope within the C-terminus of tau and another immobilized ligand binds an epitope within the mid domain of tau. In another example, an immobilized ligand binds an epitope within the C-terminus of tau and another immobilized ligand binds an epitope within the N-terminus of tau. In another example, an immobilized ligand binds an epitope within the MTBR of tau and another immobilized ligand binds an epitope within the N-terminus of tau. In another example, an immobilized ligand binds an epitope within the MTBR of tau and another immobilized ligand binds an epitope within the C-terminus of tau. In each of the above embodiments, the ligand may be an antibody or an aptamer. Non-liming examples of suitable antibodies are shown in FIG. 1.

In further embodiments, one or more additional protein may be concomitantly or sequentially affinity purified by using one or more additional ligand that specifically binds the additional protein(s). Non-limiting examples of additional proteins that may be affinity purified concomitantly with tau, or sequentially to tau, are Aβ, ApoE, alpha synuclein, soluble amyloid precursor protein, alpha-2 macroglobulin, S100B, myelin basic protein, an interleukin, and TNF. In an exemplary embodiment, Aβ, ApoE, alpha synuclein, or any combination thereof is also affinity purified and therefore present in an isolated tau sample.

An isolated tau sample may be used immediately or may be stored indefinitely by methods known in the art. Isolated tau samples prepared as described herein may be used in any number of downstream applications, including but not limited to immunoassays, xMAP assays, and mass spectrometry. The assays may analyze the total amount of tau, the total amount of phospho-tau, phosphorylation at specific amino acid residues, and/or other post-translation modifications.

(b) Tau Phosphorylation at One or More Amino Acid Residue

Phosphorylation of specific amino acids (i.e. "sites" or "residues") in tau results in phosphorylated tau (p-tau) isoforms. Methods of the present disclosure provide means to measure the stoichiometry of phosphorylation at one or more specific amino acids of tau, the method comprising (a) providing an isolated tau sample, and (b) quantifying phosphorylation at one or more residue of tau. When phosphorylation at two or more residues of tau is measured, the method may further comprise calculating a ratio or another mathematical relationship between the values.

In some embodiments, methods herein comprise measuring tau phosphorylation at one or more residue chosen from T111, S113, T181, S199, S202, S208, T153, T175, T205, S214, T217, and T231. In some embodiments, methods herein comprise measuring tau phosphorylation at one or more residue chosen from T111, T181, T205, S208, S214, T217, and T231. In other embodiments, methods herein comprise measuring tau phosphorylation at one or more residue chosen from T181, S214, and T217. In other embodiments, methods herein comprise measuring tau phosphorylation at one or more residue chosen from T181, T205, and T217. In other embodiments, methods herein comprise measuring tau phosphorylation at one or more residue that includes S199. In other embodiments, methods herein comprise measuring tau phosphorylation at one or more residue that includes S202. In other embodiments, methods herein comprise measuring tau phosphorylation at one or more residue that includes S199. In other embodiments, methods herein comprise measuring tau phosphorylation at one or more residue that includes T181. In other embodiments, methods herein comprise measuring tau phosphorylation at one or more residue that includes T205. In other embodiments, methods herein comprise measuring tau phosphorylation at one or more residue that includes T217. In other embodiments, methods herein comprise measuring tau phosphorylation at two or more residues that include T153 and T175. In other embodiments, methods herein comprise measuring tau phosphorylation at two or more residue chosen from T181, T205, and T217. In other embodiments, methods herein comprise measuring tau phosphorylation at three or more residues that include T181, T205, and T217. In other embodiments, phosphorylation of tau is measured at two or more residues that include T181 and T217.

Methods for preparing an isolated tau sample are described in detail in Section II(a). In some embodiments the subject has a diagnosis of a neurodegenerative disease. In some embodiments the subject has a diagnosis of a tauopathy. In some embodiments the subject has a diagnosis of a tauopathy but does not have Aβ amyloidosis. In some embodiments the subject has a diagnosis of AD. In some embodiments the subject has a diagnosis of CAA. In some embodiments the subject has a diagnosis of MCI or dementia. In some embodiments the subject has no clinical signs of a neurodegenerative disease.

The Examples disclose a highly sensitive and specific mass spectrometry (MS) method using parallel reaction monitoring (PRM) to discover tau phosphorylation sites and initially quantify the abundance of phosphorylation sites in isolated tau proteins. However, the present disclosure is not limited to any one particular method to quantitatively assess site-specific phosphorylation of tau. Suitable methods should discriminate tau isoforms that differ only in the phosphorylation status of a single amino acid, discriminate p-tau isoforms that are phosphorylated at different amino acids, and quantify changes in phosphorylation occurring at specific sites independently from the global change in total tau. Three approaches to quantify changes in phosphorylation stoichiometry occurring at specific sites independently from the global change in total tau are detailed in the examples: 1) relative comparison between phosphorylated peptide isomers, which can be used to estimate the relative abundance of each phosphorylated peptide sharing the same sequence; 2) normalizing phosphorylated peptides with any peptide from the tau protein as reference; and 3) absolute quantitation using internal synthetic labeled standards for each phosphorylated and non-phosphorylated peptide, where absolute quantitation values for each phosphorylated peptide is normalized with any absolute quantitation value obtained for any peptide from the tau protein. All three approaches use internal normalization for comparing relative phosphorylation changes for each site. Other methods known in the art may also be used. When using an internal synthetic labeled standard for absolute quantification, the labeled standard is preferably spiked into the blood sample prior to processing the sample to enrich for soluble tau. Accordingly, the method of Section II may further comprise an additional step prior to precipitation, typically immediately prior to, wherein a labeled internal standard is added to the blood sample.

In an exemplary embodiment, site-specific phosphorylation of tau is measured by high-resolution mass spectrometry. Suitable types of mass spectrometers are known in the art. These include, but are not limited to, quadrupole, time-of-flight, ion trap and Orbitrap, as well as hybrid mass spectrometers that combine different types of mass analyzers into one architecture (e.g., Orbitrap Fusion™ Tribrid™ Mass Spectrometer from ThermoFisher Scientific). Additional processing of an isolated tau sample may occur prior to MS analysis. For example, an isolated tau sample may be divided into multiple samples so that one or more additional protein can be quantified in parallel. As another example, tau is typically proteolytically digested prior to MS analysis. Suitable proteases include, but are not limited to, trypsin, Lys-N, Lys-C, and Arg-N. When affinity purification is used to produce an isolated tau sample, digestion may occur after eluting tau from the immobilized ligand or while tau is bound to the immobilized ligand. Affinity purification is described in detail in Section II(b). Following one or more clean-up steps, digested tau peptides may be separated by a liquid chromatography system interfaced with a high-resolution mass spectrometer. The chromatography system may be optimized by routine experimentation to produce a desired LC-MS pattern. A wide array of LC-MS techniques may be used to quantitatively analysis site-specific tau phosphorylation. Non-limiting examples include selected-reaction monitoring, parallel-reaction monitoring, selected-ion monitoring, and data-independent acquisition. As stated above, all quantitative assessments of site-specific tau phosphorylation should account for global changes in total tau. In an exemplary embodiment, a mass spectrometry protocol outlined in the Examples is used.

In additional embodiments, the method may further comprise measuring total tau in a blood sample obtained from the subject, measuring one more additional plasma protein in a blood sample obtained from the subject, and/or determining ApoE status, optionally wherein a single isolated tau sample is used for all measurements. Methods for measuring total tau are described in Section II(c). Determining ApoE status means determining the ApoE variant of a subject (i.e., ApoE2, ApoE3, or ApoE4), either at the nucleic acid level (e.g., by sequencing, nucleic acid based arrays, etc.) or at the protein level (e.g., by mass spectrometry, immunoassay, etc.). Methods for measuring one or more additional plasma protein are also known in the art. For example, mass spectrometry, immunoassays, xMAP® assays, etc. are used in the art to measure a variety of plasma proteins. Non-limiting examples of additional plasma proteins that may be measured in combination with tau include amyloid beta (Aβ), apolipoprotein E, apolipoprotein J, alpha synuclein, soluble amyloid precursor protein, alpha-2 macroglobulin, S100B, myelin basic protein, an interleukin, and TNF. In some examples, one or more Aβ peptide is measured. For instance, A338, A340, and/or Aβ42 may be measured. In the above embodiments, the method may further comprise calculating a ratio or another mathematical relationship between tau phosphorylation at one or more residue and the additional measurement (e.g., total total, the amount of an additional plasma protein, ApoE status, etc.).

In each of the above embodiments, the method may further comprise performing an additional diagnostic test on the subject or administering a therapeutic agent to the subject when the measured phosphorylation level(s) significantly deviate from the mean in a control population. "Significantly deviate from the mean" refers to values that are at least 1 standard deviation, preferably at least 1.3 standard deviations, more preferably at least 1.5 standard deviations or even more preferably at least 2 standard deviations, above or below the mean (i.e., $1\sigma$, $1.3\sigma$, $1.5\sigma$, or $1.5\sigma$, respectively, where a is the standard deviation defined by the normal distribution measured in a control population. The further diagnostic test may be PET imaging (e.g., amyloid imaging, tau imaging, etc.), quantitative measurement of one more protein in a CSF sample obtained from a subject, etc. The therapeutic agent may be an anti-inflammatory agent, an angiogenesis inhibitor, a beta-secretase inhibitor, a gamma-secretase inhibitor, a cholinesterase inhibitor, a NMDA receptor antagonist, a kinase inhibitor, a phosphatase inhibitor, an anti-A$\beta$ antibody, an anti-tau antibody, an anti-ApoE antibody, an agent designed to prevent amyloid deposition from increasing, an agent designed to reduce a subject's existing plaque load, an agent to prevent tau aggregation, an agent that targets NFTs, etc.

(c) Total Tau

"Total tau," as used herein refers to all tau isoforms in a given sample. Tau can be found in soluble and insoluble compartments, in monomeric and aggregated forms, in ordered or disordered structures, intracellularly and extracellularly, and may be complexed with other proteins or molecules. Accordingly, the source of the biological sample (e.g., brain tissue, CSF, blood, etc.) and any downstream processing of the biological sample will affect the totality of tau isoforms in a given sample.

Total tau may be measured by monitoring abundance of unmodified tau peptides. For each phosphorylated tau site, a tau peptide sharing the common amino acid sequence with the phosphorylated peptide of interest may preferentially be used to measure total tau level, but any peptide from the tau sequence can be used. Tau peptides measurement can be performed by mass spectrometry and accuracy of the measurement can be improved by using labeled internal standards as reference. Alternatively, total tau can be measured by immunoassays or other method quantifying tau concentration. In a specific embodiment, total tau may be measured by mass spectrometry by quantifying the TPSL tryptic peptide (i.e., TPSLPTPPTR).

III. Methods to Diagnose Subjects Prior to the Onset of MCI Due to AD to Diagnose a Subject's Stage of AD Another aspect of the present disclosure encompasses methods to diagnose subjects as having a high risk of conversion to mild cognitive impairment due to Alzheimer's disease, and to optionally stage or classify the subject in terms of the number of years of onset to MCI due to AD. Mild cognitive impairment (MCI) due to Alzheimer's disease (AD) refers to the symptomatic predementia phase of AD. This degree of cognitive impairment is not normal for age and, thus, constructs such as age-associated memory impairment and age-associated cognitive decline do not apply. MCI due to AD is a clinical diagnosis, and clinical criteria for the diagnosis of MCI due to AD are known in the art. See, for instance, Albert et al. *Alzheimer's & Dementia*, 2011, 7(3): 270-279. Cognitive testing is optimal for objectively assessing the degree of cognitive impairment for a subject. Scores on cognitive tests for subjects with MCI are typically 1 to 1.5 standard deviations below the mean for their age and education matched peers on culturally appropriate normative data (i.e., for the impaired domain(s), when available). The designation of MCI is often supported by a global rating of 0.5 on the Clinical Dementia Rating (CDR) scale. The CDR is a numeric scale used to quantify the severity of symptoms of dementia. Other suitable cognitive tests are known in the art. While suitable tests exist to assess the severity of cognitive impairment, there is a need in the art for a test that identifies subjects with a high degree of confidence years before the onset of MCI due to AD.

In one embodiment, a method to diagnose a subject as having a high risk of conversion to MCI due to AD may comprise (a) providing an isolated tau sample obtained from a subject and measuring, in the isolated tau sample, tau phosphorylation at one or more amino acid residue chosen from chosen from T111, S113, T181, S199, S202, S208, T153, T175, T205, S214, T217, and T231, and optionally measuring total tau; and (b) diagnosing the subject as having a high risk of conversion to MCI due to AD when the measured phosphorylation level(s) significantly deviate from the mean in a control population without brain amyloid plaques as measured by PET imaging and/or A$\beta$42/40 measurement in CSF. In another embodiment, a method to diagnose a subject as having a high risk of conversion to MCI due to AD may comprise (a) providing a first and a second isolated tau sample obtained from a subject and measuring, in each isolated tau sample, tau phosphorylation at one or more amino acid residue chosen from chosen from T111, S113, T181, S199, S202, S208, T153, T175, T205, S214, T217, and T231, and optionally measuring total tau; (b) calculating the change in the site-specific phosphorylation at each residue measured and optionally the change in total tau; and (c) diagnosing the subject as having a high risk of conversion to MCI due to AD when the calculated change(s) significantly deviate from the mean in a control population without brain amyloid plaques as measured by PET imaging and/or A$\beta$42/40 measurement in CSF. "Significantly deviate from the mean" refers to values that are at least 1 standard deviation, preferably at least 1.3 standard deviations, more preferably at least 1.5 standard deviations or even more preferably at least 2 standard deviations, above or below the mean (i.e., $1\sigma$, $1.3\sigma$, $1.5\sigma$, or $1.5\sigma$, respectively, where a is the standard deviation defined by the normal distribution measured in a control population without brain amyloid plaques as measured by PET imaging and/or A$\beta$42/40 measurement in CSF). In addition to using a threshold (e.g. at least 1 standard deviation above or below the mean), in some embodiment the extent of change above or below the mean may be used to diagnose a subject. An isolated tau sample can be obtained from a subject that may or may not be asymptomatic. An "asymptomatic subject" refers to a subject that does not show any signs or symptoms of AD. A subject may however exhibit signs or symptoms of AD (e.g., memory loss, misplacing things, changes in mood or behavior, etc.) but not show sufficient cognitive or functional impairment for a clinical diagnosis of mild cognitive impairment. In further embodiments, a subject may carry one of the gene mutations known to cause dominantly inherited Alzheimer's disease. In alternative embodiments, a subject may not carry a gene mutation known to cause dominantly inherited Alzheimer's disease. Alzheimer's disease that has no specific family link is referred to as sporadic Alzheimer's disease.

Another aspect of the present disclosure encompasses methods to diagnose a subject's stage of Alzheimer's disease. In various embodiments, a "stage of AD" may be defined as an amount of time (e.g. 1, 2, 3, 4, 5, 6, 7, 8, 9, 10, 11, 12 months, etc.) that has elapsed since the onset of MCI due to AD. Although there are criteria for a clinical diagnosis of AD, it is common in the clinical setting for the timing of symptom onset to be unknown for a given subject or for there to be a questionable diagnosis of either MCI or AD. As such, there is a need in the art for a test that objectively diagnoses a subject's stage of AD.

In one embodiment, a method to diagnose a subject's stage of AD may comprise (a) providing an isolated tau sample obtained from a subject and measuring, in the isolated tau sample, tau phosphorylation at one or more amino acid residue chosen from chosen from T111, S113, T181, S199, S202, S208, T153, T175, T205, S214, T217, and T231, and optionally measuring total tau; and (b) diagnosing the stage of the subject's AD when the measured phosphorylation level(s) significantly deviate from the mean in a control population without brain amyloid plaques as measured by PET imaging and/or Aβ42/40 measurement in CSF. In another embodiment, a method to diagnose a subject prior to the onset of MCI due to AD may comprise (a) providing a first and a second isolated tau sample obtained from a subject and measuring, in each isolated tau sample, tau phosphorylation at one or more amino acid residue chosen from chosen from T111, S113, T181, S199, S202, S208, T153, T175, T205, S214, T217, and T231, and optionally measuring total tau; (b) calculating the change in the site-specific phosphorylation at each residue measured and optionally the change in total tau; and (c) diagnosing the subject as being a certain number of years from onset of MCI due to AD when the calculated change(s) significantly deviate from the mean in a control population without brain amyloid plaques as measured by PET imaging and/or Aβ42/40 measurement in CSF. "Significantly deviate from the mean" includes values that are at least 1 standard deviation, preferably at least 1.3 standard deviations or more preferably at least 1.5 standard deviations or even more preferably at least 2 standard deviations, above or below the mean (i.e., 1σ, 1.3σ, 1.5σ, or 1.5σ, respectively, where a is the standard deviation defined by the normal distribution measured in a control population without brain amyloid plaques as measured by PET imaging and/or Aβ42/40 measurement in CSF). In addition to using a threshold (e.g. at least 1 standard deviation above or below the mean), in some embodiment the extent of change above or below the mean may be used to diagnose a subject. An isolated tau sample can be obtained from a subject that may or may not have a clinical diagnosis of MCI due to AD, dementia, or AD. In further embodiments, a subject may carry one of the gene mutations known to cause dominantly inherited Alzheimer's disease. In alternative embodiments, a subject may not carry a gene mutation known to cause dominantly inherited Alzheimer's disease.

Alternatively or in addition to using a measurement of site-specific tau phosphorylation, optionally with a measurement of total tau, in any of the above embodiments, a ratio calculated from the measured phosphorylation level(s), or a ratio calculated from the measured phosphorylation level(s) and total tau, may be used. Both approaches are detailed in the examples. Mathematical operations other than a ratio may also be used. For instance, the examples use site-specific tau phosphorylation values in various statistical models (e.g., linear regressions, LME curves, LOESS curves, etc.) in conjunction with other known biomarkers (e.g. APOE ε4 status, age, sex, cognitive test scores, functional test scores, etc.). Selection of measurements and choice of mathematical operations may be optimized to maximize specificity of the method. For instance, diagnostic accuracy may be evaluated by area under the ROC curve and in some embodiments, an ROC AUC value of 0.7 or greater is set as a threshold (e.g., 0.7, 0.75, 0.8, 0.85, 0.9, 0.95, etc.).

Brain amyloid plaques in humans are routinely measured by amyloid-positron emission tomography (PET). For instance, $^{11}$C-Pittsburgh compound B (PiB) PET imaging of cortical Aβ-plaques is commonly used to detect Aβ-plaque pathology. The standard uptake value ratio (SUVR) of cortical PiB-PET reliably identifies significant cortical Aβ-plaques and is used to classify subjects as PIB positive (SUVR≥1.25) or negative (SUVR<1.25). Accordingly, in the above embodiments, a control population without brain amyloid plaques as measured by PET imaging may refer to a population of subjects that have a cortical PiB-PET SUVR<1.25. Other values of PiB binding (e.g., mean cortical binding potential) or analyses of regions of interest other than the cortical region may also be used to classify subjects as PIB positive or negative. Other PET imaging agents may also be used.

A control population without brain amyloid plaques as measured by Aβ42/40 measurement in CSF may refer to a population of subjects that has an Aβ42/40 measurement of <0.12 when measured by mass spectrometry, as described in Patterson et al, *Annals of Neurology*, 2015.

In an exemplary embodiment, a method to diagnose a subject as having a high risk of conversion to MCI due to AD or a subject's stage of AD may comprise (a) providing an isolated tau sample obtained from a subject and measuring, in the isolated tau sample, tau phosphorylation at one or more amino acid residue chosen from T181, T205 and T217 and optionally measuring total tau; and (b) diagnosing the subject as having a high risk of conversion to MCI due to AD, or as being a certain number of years from onset of MCI due to AD, or staging the subject's AD when the measured phosphorylation level(s) significantly deviate from the mean in a control population without brain amyloid plaques as measured by PET imaging and/or Aβ42/40 measurement in CSF. FIG. 22 illustrates the dynamic pattern of tau phosphorylation measurable at T181, T205 and T217 in an isolated tau sample in relation to years from onset of MCI due to AD. Phosphorylation levels at T217 that significantly deviate from the mean first occur about 21 years from onset of MCI due to AD; phosphorylation levels at T181 that significantly deviate from the mean first occur about 19 years from onset of MCI due to AD; an increase in total tau that significantly deviates from the mean first occurs about 17 years from onset of MCI due to AD; and phosphorylation levels at T205 that significantly deviate from the mean first occur about 13 years from onset of MCI due to AD. Upon symptom onset (e.g., MCI due to AD), phosphorylation levels at T217 and T181 plateau and then decrease.

As noted above, additional mathematical operations may be performed with the measurements of phosphorylation at T181, T205 and/or T217, including but not limited to ratio between the measured phosphorylation level(s) and ratio between the measured phosphorylation level(s) and total tau. A ratio calculated from the measured phosphorylation level (s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau.

In one example, a method of the present disclosure comprises (a) providing an isolated tau sample obtained from a subject and measuring tau phosphorylation at (i) T217 and T205, (ii) T181 and T205, or (iii) T181, T205 and T217; and (b) diagnosing the subject as being about 10 to about 25 years, or about 10 to about 20 years from the onset of MCI due to AD when tau phosphorylation at T217 and/or T181 is about 1.5σ or above and tau phosphorylation at T205 is about 1.5σ or below, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In various embodiments, tau phosphorylation at T217 and/or tau phosphorylation at T181 may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, tau phosphorylation at T217 and/or tau phosphorylation at T181 may be about 1.85σ, about 1.9σ, about 1.95σ, about 2σ, about 2.1σ, about 2.2σ, about 2.3σ, about 2.4σ, about 2.5σ or above 2.5σ. In each of the above embodiments, tau phosphorylation at T205 may be about 1.3σ, about 1.35σ, about 1.4σ, about 1.45σ, about 1.5σ, about 1.51σ, about 1.55σ, about 1.6σ, about 1.7σ, about 1.8σ, about 1.9σ, about 2.0σ, or below 2.0σ. Alternatively, tau phosphorylation at T205 may be about 2.0σ, about 2.05σ, about 2.1σ, about 2.2σ, about 2.3σ, about 2.4σ, about 2.5σ, or below 2.5σ. In a further example, tau phosphorylation at T217 and/or tau phosphorylation at T181 about 2σ or above and tau phosphorylation at T205 may be about 2σ or less. In addition to using a threshold (e.g. at least 1 standard deviation above or below the mean), in some embodiment the extent of change above or below the mean may be used to diagnose a subject. In still further embodiments, measured levels of tau phosphorylation at T205 and at T181 and/or T217 may be used in various mathematical operations to improve the predictive power compared to each by itself. For instance, ratio(s) may be calculated from the measured phosphorylation levels. Mathematical operations other than a ratio may also be used.

In another example, a method of the present disclosure comprises (a) providing an isolated tau sample obtained from a subject and measuring total tau and tau phosphorylation at (i) T217 and T205, (ii) T181 and T205, or (iii) T181, T205 and T217; and (b) diagnosing the subject as being about 10 to about 25 years, or about 10 to about 20 years from the onset of MCI due to AD when the ratio of tau phosphorylation at T217 to total tau and/or the ratio of tau phosphorylation at T181 to total tau is about 1.5σ or above and the ratio of tau phosphorylation at T205 to total tau is about 1.5σ or below, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF. In various embodiments, the ratio of tau phosphorylation at T217 to total tau and/or the ratio of tau phosphorylation at T181 to total tau may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, the ratio of tau phosphorylation at T217 to total tau and/or the ratio of tau phosphorylation at T181 to total tau may be about 1.85σ, about 1.9σ, about 1.95σ, about 2σ, about 2.1σ, about 2.2σ, about 2.3σ, about 2.4σ, about 2.5σ or above 2.5σ. In each of the above embodiments, the ratio of tau phosphorylation at T205 to total tau may be about 1.3σ, about 1.35σ, about 1.4σ, about 1.45σ, about 1.5σ, about 1.55σ, about 1.6σ, about 1.7σ, about 1.8σ, about 1.9σ, about 2.0σ, or below 2σ. Alternatively, the ratio of tau phosphorylation at T205 to total tau may be about 2.0σ, about 2.05σ, about 2.1σ, about 2.2σ, about 2.3σ, about 2.4σ, about 2.5σ, or below 2.5σ. In a further example, the ratio of tau phosphorylation at T217 to total tau and/or the ratio of tau phosphorylation at T181 to total tau may be about 2σ or above and the ratio of tau phosphorylation at T205 to total tau may about 2σ or less. In addition to using a threshold (e.g. at least 1 standard deviation above or below the mean), in some embodiment the extent of change above or below the mean may be used to diagnose a subject.

In another example, a method of the present disclosure comprises (a) providing an isolated tau sample obtained from a subject and measuring tau phosphorylation at (i) T181 and T205, (ii) T217 and T205, or (iii) T181, T217 and T205, and (b) diagnosing the subject as being about 15 years or less, or about 10 years or less, from the onset of MCI due to AD when tau phosphorylation at the specific sites recited in (a)(i), (a)(ii) or (a)(iii) is about 1.5σ or above, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In various embodiments, tau phosphorylation at the specific sites recited in (a)(i), (a)(ii) or (a)(iii) may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, tau phosphorylation at the specific sites recited in (a)(i), (a)(ii) or (a)(iii) may be about 1.85σ, about 1.9σ, about 1.95σ, about 2σ, about 2.1σ, about 2.2σ, about 2.36, about 2.4σ, about 2.5σ or above 2.5σ. In a further example, tau phosphorylation at the specific sites recited in (a)(i), (a)(ii) or (a)(iii) may be about 2σ or above. In addition to using a threshold (e.g. at least 1 standard deviation above or below the mean), in some embodiment the extent of change above or below the mean may be used to diagnose a subject. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In another example, a method of the present disclosure comprises (a) providing an isolated tau sample obtained from a subject and measuring total tau and tau phosphorylation at (i) T181 and T205, (ii) T217 and T205, or (iii) T181, T217 and T205; and (b) diagnosing the subject as being about 15 years or less, or about 10 years or less, from the onset of MCI due to AD when the ratio of tau phosphorylation at the specific sites recited in (a)(i), (a)(ii) or (a)(iii) to total tau is about 1.5σ or above, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF. In various embodiments, the ratio of tau phosphorylation at the specific sites recited in (a)(i), (a)(ii) or (a)(iii) to total tau may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, the ratio of tau phosphorylation at the specific sites recited in (a)(i), (a)(ii) or (a)(iii) to total tau may be about 1.85σ, about 1.9σ, about 1.95σ, about 2σ, about 2.1 σ, about 2.2σ, about 2.3σ, about 2.4σ, about 2.5σ or above 2.5σ. In a further example, the ratio of tau phosphorylation at the specific sites recited in (a)(i), (a)(ii) or (a)(iii) to total tau may be about 2σ or above. In addition to using a threshold (e.g. at least 1 standard deviation above or below the mean), in some embodiment the extent of change above or below the mean may be used to diagnose a subject.

In another example, a method of the present disclosure comprises (a) providing a first and a second isolated tau sample obtained from a subject, wherein "first" and "second" refer to the order in which the samples were collected, and measuring tau phosphorylation at (i) T181 and T205, (ii) T217 and T205, or (iii) T181, T217 and T205; (b) calculating the change in the site-specific phosphorylation at each residue measured and optionally the change in total tau; and (c) diagnosing the stage of a subject's AD when the phosphorylation level at T181 and/or T217 decreases or stays the same and the phosphorylation level at T205 and optionally total tau increases. The first and the second isolated tau samples may be collected days, weeks, or months apart. Typically, tau phosphorylation at the specific sites recited in (a)(i), (a)(ii) or (a)(iii) will also be about 1.5σ or above for both samples, where a is the standard deviation defined by the normal distribution tau phosphorylation at T217 and T205, T181 and T205, or T181, T205 and T217 measured in a control population without brain amyloid plaques as measured by PET imaging and/or Aβ42/40 measurement in CSF. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In another example, a method of the present disclosure comprises (a) providing a first and a second isolated tau sample obtained from a subject, wherein "first" and "second" refer to the order in which the samples were collected, and measuring total tau and tau phosphorylation at (i) T181 and T205, (ii) T217 and T205, or (iii) T181, T217 and T205; (b) calculating the change in the site-specific phosphorylation at each residue measured and the change in total tau; and (c) diagnosing the stage of a subject's AD when the phosphorylation level at T181 and/or T217 decreases or stays the same, the phosphorylation level at T205 decreases or stays the same, and total tau increases. The first and the second isolated tau samples may be collected days, weeks, or months apart. Typically, tau phosphorylation at the specific sites recited in (a)(i), (a)(ii) or (a)(iii) will also be about 1.5σ or above for both samples, where σ is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

Methods for measuring tau phosphorylation and total tau are described in Section II, and incorporated into this section by reference. For instance, using the protocol detailed for Examples 5-9, tau phosphorylation at T181, T205 and T217 indicated as percentage of ptau/tau ratio is 21.7±2.3, 0.34±0.13, and 1.2±0.66, respectively, in a control population without brain amyloid plaques as measured by PET imaging, as measured in an isolated tau sample that was purified from CSF (see Table 3, mutation non-carriers column). Accordingly, twice the standard deviation above the mean found for the mutation non-carrier population (i.e. 2a) for p-T181/T181, p-T205/T205 and p-T217/T217 is 43.4, 0.68, and 2.4, respectively. A skilled artisan will appreciate, however, that the absolute value may vary depending upon the protocol and the source/specifications of internal standards used for absolute quantitation.

In a preferred embodiment, an isolated tau sample comprises tau that has been purified from blood or CSF by affinity purification and tau phosphorylation is measured by mass spectrometry. In another preferred embodiment, an isolated tau sample comprises tau that has been purified from blood or CSF by affinity purification using a ligand that specifically binds an epitope within the mid domain of tau, and optionally with a second ligand that specifically binds an epitope within the N-terminus of tau, and tau phosphorylation is measured by high resolution mass spectrometry. In another preferred embodiment, an isolated tau sample comprises tau that has been purified from blood or CSF by affinity purification using a ligand that specifically binds an epitope within the mid domain of tau, and optionally with a second ligand that specifically binds an epitope within the MTBR or the C-terminus of tau, and tau phosphorylation is measured by high resolution mass spectrometry. In an exemplary embodiment, a mass spectrometry protocol outlined in the Examples is used.

IV. Methods of Treatment

Another aspect of the present disclosure is a method for treating a subject in need thereof. The terms "treat," "treating," or "treatment" as used herein, refers to the provision of medical care by a trained and licensed professional to a subject in need thereof. The medical care may be a diagnostic test, a therapeutic treatment, and/or a prophylactic or preventative measure. The object of therapeutic and prophylactic treatments is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented. In some embodiments, a subject receiving treatment is asymptomatic. An "asymptomatic subject," as used herein, refers to a subject that does not show any signs or symptoms of AD. In other embodiments, a subject may exhibit signs or symptoms of AD (e.g., memory loss, misplacing things, changes in mood or behavior, etc.) but not show sufficient cognitive or functional impairment for a clinical diagnosis of mild cognitive impairment due to Alzheimer's disease. The phrase "mild cognitive impairment due to Alzheimer's disease" is defined in Section III.

A symptomatic or an asymptomatic subject may have Aβ amyloidosis; however, prior knowledge of Aβ amyloidosis is not a requisite for treatment. In still further embodiments, a subject may be diagnosed as having AD. In any of the aforementioned embodiments, a subject may carry one of the gene mutations known to cause dominantly inherited Alzheimer's disease. In alternative embodiments, a subject may not carry a gene mutation known to cause dominantly inherited Alzheimer's disease.

In one embodiment, a method for treating a subject as described above may comprise (a) providing an isolated tau sample obtained from a subject and measuring, in the isolated tau sample, tau phosphorylation at one or more amino acid residue chosen from chosen from T111, S113, T181, S199, S202, S208, T153, T175, T205, S214, T217, and T231, and optionally measuring total tau; and (b) administering a pharmaceutical composition to the subject when the measured phosphorylation level(s) significantly deviate from the mean in a control population without brain amyloid plaques as measured by PET imaging and/or Aβ42/40 measurement in CSF. In another embodiment, a method for treating a subject as described above may comprise (a) providing a first and a second isolated tau sample obtained from a subject and measuring, in each isolated tau sample, tau phosphorylation at one or more amino acid residue chosen from chosen from T111, S113, T181, S199, S202, S208, T153, T175, T205, S214, T217, and T231, and optionally measuring total tau; (b) calculating the change in the site-specific phosphorylation at each residue measured and optionally the change in total tau; and (c) administering a pharmaceutical composition to the subject when the calculated change(s) significantly deviate from the mean in a control population without brain amyloid plaques as measured by PET imaging and/or Aβ42/40 measurement in CSF. "Significantly deviate from the mean" refers to values that are at least 1 standard deviation, preferably at least 1.3 standard deviations, more preferably at least 1.5 standard deviations or even more preferably at least 2 standard deviations, above or below the mean (i.e., 1σ, 1.3σ, 1.5σ, or 1.5σ, respectively, where a is the standard deviation defined by the normal distribution measured in a control population without brain amyloid plaques as measured by PET imaging and/or Aβ42/40 measurement in CSF). In addition to using a threshold (e.g. at least 1 standard deviation above or below the mean), in some embodiment the extent of change above or below the mean may be used as criteria for treating a subject.

Alternatively or in addition to using a measurement of site-specific tau phosphorylation, optionally with a measurement of total tau, in any of the above embodiments, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau. Mathematical operations other than a ratio may also be used. For instance, the examples use site-specific tau phosphorylation values in various statistical models (e.g., linear regressions, LME curves, LOESS curves, etc.) in conjunction with other known biomarkers (e.g. APOE ε4 status, age, sex, cognitive test scores, functional test scores, etc.). Site-specific tau phosphorylation values in combination with plasma Aβ40, Aβ42, or Aβ42/Aβ40 ratios may be used.

Many imaging agents and therapeutic agents contemplated for, or used with, subjects at risk of developing Aβ amyloidosis or AD, subjects diagnosed as having Aβ amyloidosis, subjects diagnosed as having a tauopathy, or subjects diagnosed as having AD, target a specific pathophysiological change. For instance, Aβ targeting therapies are generally designed to decrease Aβ production, antagonize Aβ aggregation or increase brain Aβ clearance; tau targeting therapies are generally designed to alter tau phosphorylation patterns, antagonize tau aggregation, or increase NFT clearance; a variety of therapies are designed to reduce CNS inflammation or brain insulin resistance; etc. The efficacy of these various agents can be improved by administering the agents to subjects that have certain tau phosphorylation levels at T111, S113, T181, S199, S202, S208, T153, T175, T205, S214, T217, and T231, as measured by methods disclosed herein.

In an exemplary embodiment, the efficacy of imaging agents and therapeutic agents contemplated for, or used with, subjects at risk of developing Aβ amyloidosis or AD, subjects diagnosed as having Aβ amyloidosis, subjects diagnosed as having a tauopathy, or subjects diagnosed as having AD (collectively referred to herein as "Aβ and tau therapies") can be improved by administering the Aβ or tau therapy to subjects that have certain tau phosphorylation levels at T181, T205 and/or T217, as measured by methods disclosed herein and illustrated, for example, in FIG. 22. For instance, when tau phosphorylation at T217 is about 1.5σ or above and tau phosphorylation at T181 and T205 is about 1.5σ or below, preferred therapeutic agents may include those designed to prevent a subject from becoming amyloid positive (e.g., amyloid targeting therapies designed to decrease Aβ production, antagonize Aβ aggregation, etc.). As another example, when tau phosphorylation at T217 and/or T181 is about 1.5σ or above and tau phosphorylation at T205 is about 1.5σ or below, preferred therapeutic agents may include those designed to prevent amyloid deposition from increasing or reduce a subject's existing plaque load. As another example, when tau phosphorylation at T217, T181 and T205 is about 1.5σ or above, preferred therapeutic agents may include those designed to prevent amyloid deposition from increasing, reduce a subject's existing plaque load, prevent tau aggregation, or target NFTs. As another example, when tau phosphorylation at T217, T181 and T205 is about 1.5σ or above, and tau phosphorylation at T217 or T181 is plateauing or decreasing, and total tau and/or tau phosphorylation at T205 is increasing, preferred therapeutic agents may include those designed to prevent amyloid deposition from increasing, reduce a subject's existing plaque load, prevent tau aggregation, or target NFTs, as well as those specific for subjects with AD. The details disclosed herein can similarly be used to administer therapeutic agents designed for other targets (e.g., CNS inflammation, ApoE, etc.), including but not limited to those identified in the following paragraphs.

In one example, the present disclosure provides a method for treating a subject having an increased risk of conversion to MCI due to AD, the method comprising (a) providing an isolated tau sample obtained from a subject and measuring tau phosphorylation at (i) T217 and T205, (ii) T181 and T205, or (iii) T181, T205 and T217; and (b) administering a pharmaceutical composition to the subject when tau phosphorylation at T217 and/or T181 is about 1.5σ or above and tau phosphorylation at T205 is about 1.5σ or below, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In various embodiments, tau phosphorylation at T217 and/or tau phosphorylation at T181 may be about 1.3σ, about 1.35σ, about 1.4σ, about 1.45σ, about 1.5σ, about 1.6σ, about 1.7σ, about 1.8σ, about 1.9σ, about 2α, or above 2α. In other embodiments, tau phosphorylation at T217 and/or tau phosphorylation at T181 may be about 1.85σ, about 1.9σ, about 1.95σ, about 2σ, about 2.1σ, about 2.2σ, about 2.3σ, about 2.4σ, about 2.5σ or above 2.5σ. In each of the above embodiments, tau phosphorylation at T205 may be about 1.3σ, about 1.35σ, about 1.4σ, about 1.45σ, about 1.5σ, about 1.51σ, about 1.55σ, about 1.6σ, about 1.7σ, about 1.8σ, about 1.9σ, about 2.0σ, or below 2.0σ. Alternatively, tau phosphorylation at T205 may be about 2.0σ, about 2.05σ, about 2.1σ, about 2.2σ, about 2.3σ, about 2.4σ, about 2.5σ, or below 2.5σ. In a further example, tau phosphorylation at T217 and/or tau phosphorylation at T181 about 2σ or above and tau phosphorylation at T205 may be about 2σ or less. In addition to using a threshold (e.g. at least 1 standard deviation above or below the mean), in some embodiment the extent of change above or below the mean may be used as criteria to treat a subject. In still further embodiments, measured levels of tau phosphorylation at T205 and at T181 and/or T217 may be used in various mathematical operations to improve the predictive power compared to each by itself. For instance, ratio(s) may be calculated from the measured phosphorylation levels. Mathematical operations other than a ratio may also be used.

In another example, the present disclosure provides a method for treating a subject having an increased risk of conversion to MCI due to AD, the method comprising (a) providing an isolated tau sample obtained from a subject and measuring total tau and tau phosphorylation at (i) T217 and T205, (ii) T181 and T205, or (iii) T181, T205 and T217; and (b) administering a pharmaceutical composition to the subject when the ratio of tau phosphorylation at T217 to total tau and/or the ratio of tau phosphorylation at T181 to total tau is about 1.5σ or above and the ratio of tau phosphorylation at T205 to total tau is about 1.5σ or below, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF. In various embodiments, the ratio of tau phosphorylation at T217 to total tau and/or the ratio of tau phosphorylation at T181 to total tau may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, the ratio of tau phosphorylation at T217 to total tau and/or the ratio of tau phosphorylation at T181 to total tau may be about 1.85σ, about 1.9σ, about 1.95σ, about 2σ, about 2.1σ, about 2.2σ, about 2.3σ, about 2.4σ, about 2.5σ or above 2.5σ. In each of the above embodiments, the ratio of tau phosphorylation at T205 to total tau may be about 1.3σ, about 1.35σ, about 1.4σ, about 1.45σ, about 1.50σ, about 1.55σ, about 1.6σ, about 1.7σ, about 1.8σ, about 1.9σ, about 2.0σ, or below 2σ. Alternatively, the ratio of tau phosphorylation at T205 to total tau may be about 2.0σ, about 2.05σ, about 2.1σ, about 2.2σ, about 2.3σ, about 2.4σ, about 2.5σ, or below 2.5σ. In a further example, the ratio of tau phosphorylation at T217 to total tau and/or the ratio of tau phosphorylation at T181 to total tau may be about 2σ or above and the ratio of tau phosphorylation at T205 to total tau may about 2σ or less. In addition to using a threshold (e.g. at least 1 standard deviation above or below the mean), in some embodiment the extent of change above or below the mean may be used as criteria to treat a subject.

In another example, the present disclosure provides a method for treating a subject having an increased risk of conversion to MCI due to AD, the method comprising (a) providing an isolated tau sample obtained from a subject and measuring tau phosphorylation at (i) T181 and T205, (ii) T217 and T205, or (iii) T181, T217 and T205; and (b) administering a pharmaceutical composition to the subject when tau phosphorylation at the specific sites recited in (a)(i), (a)(ii) or (a)(iii) is about 1.5σ or above, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In various embodiments, tau phosphorylation at the specific sites recited in (a)(i), (a)(ii) or (a)(iii) may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, tau phosphorylation at the specific sites recited in (a)(i), (a)(ii) or (a)(iii) may be about 1.85σ, about 1.9σ, about 1.95σ, about 2σ, about 2.1σ, about 2.2σ, about 2.3σ, about 2.4σ, about 2.5σ or above 2.5σ. In a further example, tau phosphorylation at the specific sites recited in (a)(i), (a)(ii) or (a)(iii) may be about 2σ or above. In addition to using a threshold (e.g. at least 1 standard deviation above or below the mean), in some embodiment the extent of change above or below the mean may be used as criteria to treat a subject. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In another example, the present disclosure provides a method for treating a subject having an increased risk of conversion to MCI due to AD, the method comprising (a) providing an isolated tau sample obtained from a subject and measuring total tau and tau phosphorylation at (i) T181 and T205, (ii) T217 and T205, or (iii) T181, T217 and T205; and (b) administering a pharmaceutical composition to the subject when the ratio of tau phosphorylation at the specific sites recited in (a)(i), (a)(ii) or (a)(iii) to total tau is about 1.5σ or above, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF. In various embodiments, the ratio of tau phosphorylation at the specific sites recited in (a)(i), (a)(ii) or (a)(iii) to total tau may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, the ratio of tau phosphorylation at the specific sites recited in (a)(i), (a)(ii) or (a)(iii) to total tau may be about 1.85σ, about 1.9σ, about 1.95σ, about 2σ, about 2.1σ, about 2.2σ, about 2.3σ, about 2.4σ, about 2.5σ or above 2.5σ. In a further example, the ratio of tau phosphorylation at the specific sites recited in (a)(i), (a)(ii) or (a)(iii) to total tau may be about 2σ or above. In addition to using a threshold (e.g. at least 1 standard deviation above or below the mean), in some embodiment the extent of change above or below the mean may be used as criteria to treat a subject.

In another example, the present disclosure provides a method for treating a subject with symptoms of AD, the method comprising (a) providing a first and a second isolated tau sample obtained from a subject, wherein "first" and "second" refer to the order in which the samples were collected, and measuring tau phosphorylation at (i) T181 and T205, (ii) T217 and T205, or (iii) T181, T217 and T205; (b) calculating the change in the site-specific phosphorylation at each residue measured and optionally the change in total tau; and (c) administering a pharmaceutical composition to the subject when the phosphorylation level at T181 and/or T217 decreases or stays the same and the phosphorylation level at T205 and optionally total tau increases. The first and the second isolated tau samples may be collected days, weeks, or months apart. Typically, tau phosphorylation at the specific sites recited in (a)(i), (a)(ii) or (a)(iii) will also be about 1.5σ or above for both samples, where σ is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In another example, the present disclosure provides a method for treating a subject with symptoms of AD, the method comprising (a) providing a first and a second isolated tau sample obtained from a subject, wherein "first" and "second" refer to the order in which the samples were collected, and measuring total tau and tau phosphorylation at (i) T181 and T205, (ii) T217 and T205, or (iii) T181, T217 and T205; (b) calculating the change in the site-specific phosphorylation at each residue measured and the change in total tau; and (c) administering a pharmaceutical composition to the subject when the phosphorylation level at T181 and/or T217 decreases or stays the same, the phosphorylation level at T205 decreases or stays the same, and total tau increases. The first and the second isolated tau samples may be collected days, weeks, or months apart. Typically, tau phosphorylation at the specific sites recited in (a)(i), (a)(ii) or (a)(iii) will also be about 1.5σ or above for both samples, where σ is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In each of the above embodiments, a pharmaceutical composition may comprise an imaging agent. Non-limiting examples of imaging agents include functional imaging agents (e.g. fluorodeoxyglucose, etc.) and molecular imaging agents (e.g., Pittsburgh compound B, florbetaben, florbetapir, flutemetamol, radionuclide-labeled antibodies, etc.).

Alternatively, a pharmaceutical composition may comprise an active pharmaceutical ingredient. Non-limiting examples of active pharmaceutical ingredients include cholinesterase inhibitors, N-methyl D-aspartate (NMDA) antagonists, antidepressants (e.g., selective serotonin reuptake inhibitors, atypical antidepressants, aminoketones, selective serotonin and norepinephrine reuptake inhibitors, tricyclic antidepressants, etc.), gamma-secretase inhibitors, beta-secretase inhibitors, anti-Aβ antibodies (including antigen-binding fragments, variants, or derivatives thereof), anti-tau antibodies (including antigen-binding fragments, variants, or derivatives thereof), stem cells, dietary supplements (e.g. lithium water, omega-3 fatty acids with lipoic acid, long chain triglycerides, genistein, resveratrol, curcumin, and grape seed extract, etc.), antagonists of the serotonin receptor 6, p38alpha MAPK inhibitors, recombinant granulocyte macrophage colony-stimulating factor, passive immunotherapies, active vaccines (e.g. CAD106, AF20513, etc.), tau protein aggregation inhibitors (e.g. TRx0237, methylthioninium chloride, etc.), therapies to improve blood sugar control (e.g., insulin, exenatide, liraglutide pioglitazone, etc.), anti-inflammatory agents, phosphodiesterase 9A inhibitors, sigma-1 receptor agonists, kinase inhibitors, phosphatase activators, phosphatase inhibitors, angiotensin receptor blockers, CB1 and/or CB2 endocannabinoid receptor partial agonists, β-2 adrenergic receptor agonists, nicotinic acetylcholine receptor agonists, 5-HT2A inverse agonists, alpha-2c adrenergic receptor antagonists, 5-HT 1A and 1D receptor agonists, Glutaminyl-peptide cyclotransferase inhibitors, selective inhibitors of APP production, monoamine oxidase B inhibitors, glutamate receptor antagonists, AMPA receptor agonists, nerve growth factor stimulants, HMG-CoA reductase inhibitors, neurotrophic agents, muscarinic M1 receptor agonists, GABA receptor modulators, PPAR-gamma agonists, microtubule protein modulators, calcium channel blockers, antihypertensive agents, statins, and any combination thereof.

In another alternative, a pharmaceutical composition may comprise a kinase inhibitor. Suitable kinase inhibitors may inhibit a thousand-and-one amino acid kinase (TAOK), CDK, GSK-3β, MARK, CDK5, Fyn, 5' adenosine monophosphate-activated protein kinase (AMPK), Calcium-calmodulin kinase II, Cyclin-dependent kinase-5 (cdk5), Casein kinase 1 (CK1), Casein kinase 2 (CK2), Cyclic AMP-dependent protein kinase (PKA), Dual-specificity tyrosine-phosphorylation regulated kinase 1A (DYRK1A), Glycogen synthase kinase-3 (GSK-3), JNK, LRRK2, Microtubule affinity-regulating kinase (MARK), MSK1, p35/41, p42/p44 mitogen-activated protein kinases (ERKs½), p38 mitogen-activated kinase (p38MAPK), p70S6 kinase, Phosphorylase kinase, PKB/AKT, Protein kinase C (PKC), Protein kinase N (PKN), Prostate-derived sterile 20-like kinase 1 alpha/beta, 90 kDa Ribosomal S6 kinase (RSK½) (PSK1/TAOK2), Prostate-derived sterile 20-like kinase 2 (PSK2/TAOK1), Stress-activated protein kinase (SAPK) 1gamma, SAPK2a, SAPK2b, SAPK3, SAPK4, SGK1, SRPK2, or Tau-tubulin kinase ½ (TTBK1/2).

In still another alternative, a pharmaceutical composition may comprise a phosphatase activator. As a non-limiting example, a phosphatase activator may increase the activity of protein phosphatase 1, 2A, 2B, or 5.

Methods for measuring tau phosphorylation and total tau are described in Section II, and incorporated into this section by reference. In a preferred embodiment, an isolated tau sample comprises tau that has been purified from blood or CSF by affinity purification and tau phosphorylation is measured by mass spectrometry. In another preferred embodiment, an isolated tau sample comprises tau that has been purified from blood or CSF by affinity purification using a ligand that specifically binds an epitope within the mid domain of tau, and optionally with a second ligand that specifically binds an epitope within the N-terminus of tau, and tau phosphorylation is measured by high resolution mass spectrometry. In another preferred embodiment, an isolated tau sample comprises tau that has been purified from blood or CSF by affinity purification using a ligand that specifically binds an epitope within the mid domain of tau, and optionally with a second ligand that specifically binds an epitope within the MTBR or the C-terminus of tau, and tau phosphorylation is measured by high resolution mass spectrometry. In an exemplary embodiment, a mass spectrometry protocol outlined in the Examples is used.

V. Clinical Trials

Another aspect of the present disclosure is a method for enrolling a subject into a clinical trial, in particular a clinical trial for an Aβ or tau therapy, provided all other criteria for the clinical trial have been met. In one embodiment, a method for a method for enrolling a subject into a clinical trial may comprise (a) providing an isolated tau sample obtained from a subject and measuring, in the isolated tau sample, tau phosphorylation at one or more amino acid residue chosen from chosen from T111, S113, T181, S199, S202, S208, T153, T175, T205, S214, T217, and T231, and optionally measuring total tau; and (b) enrolling the subject into a clinical trial when the measured phosphorylation level(s) significantly deviate from the mean in a control population without brain amyloid plaques as measured by PET imaging and/or Aβ42/40 measurement in CSF. In another embodiment, a method for a method for enrolling a subject into a clinical trial may comprise (a) providing a first and a second isolated tau sample obtained from a subject and measuring, in each isolated tau sample, tau phosphorylation at one or more amino acid residue chosen from chosen from T111, S113, T181, S199, S202, S208, T153, T175, T205, S214, T217, and T231, and optionally measuring total tau; (b) calculating the change in the site-specific phosphorylation at each residue measured and optionally the change in total tau; and (c) enrolling the subject into a clinical trial when the calculated change(s) significantly deviate from the mean in a control population without brain amyloid plaques as measured by PET imaging and/or Aβ42/40 measurement in CSF. The phrase "a control population without brain amyloid plaques as measured by PET imaging and/or Aβ42/40 measurement in CSF" is defined in Section III. "Significantly deviate from the mean" refers to values that are at least 1 standard deviation, preferably at least 1.3 standard deviations, more preferably at least 1.5 standard deviations or even more preferably at least 2 standard deviations, above or below the mean (i.e., 1σ, 1.3σ, 1.5σ, or 1.5σ, respectively, where a is the standard deviation defined by the normal distribution measured in a control population without brain amyloid plaques as measured by PET imaging and/or Aβ42/40 measurement in CSF). In addition to using a threshold (e.g. at least 1 standard deviation above or below the mean), in some embodiment the extent of change above or below the mean may be used as criteria for enrolling a subject.

Alternatively or in addition to using a measurement of site-specific tau phosphorylation, optionally with a measurement of total tau, in any of the above embodiments, a ratio calculated from the measured phosphorylation level(s), or a ratio calculated from the measured phosphorylation level(s) and total tau, may be used. A ratio calculated from the measured phosphorylation level(s) may be a ratio between p-T181 and p-T205, p-T217 and p-T205, or p-T181 and p-T217. A ratio calculated from the measured phosphorylation level(s) and total tau may be a ratio between p-T181 and total tau, p-T205 and total tau, or p-T217 and total tau.

Mathematical operations other than a ratio may also be used. For instance, the examples use site-specific tau phosphorylation values in various statistical models (e.g., linear regressions, LME curves, LOESS curves, etc.) in conjunction with other known biomarkers (e.g. APOE ε4 status, age, sex, cognitive test scores, functional test scores, etc.).

The design of clinical trials for Aβ and tau therapies can be greatly aided by the methods disclosed herein. Many clinical trials are designed to test the efficacy of imaging agents or therapeutic agents that target a specific pathophysiological change which occurs prior to the onset of AD symptoms. As discussed above in Section IV, the efficacy of these various agents can be improved by administering the agents to subjects that have certain site-specific tau phosphorylation levels, as measured by methods disclosed herein and illustrated. Similarly, clinical trials enrolling subjects with symptoms of AD (e.g., after the onset of MCI due to AD) would also benefit from being able to accurately stage an enrollee's AD status in order to determine if efficacy is associated with a particular stage of AD. Accordingly, measuring tau phosphorylation levels as described herein prior to enrolling a subject in a clinical trial, in particular into a treatment arm of a clinical trial, may result in smaller trials and/or improved outcomes. In some instances, methods described herein may be developed and used as a companion diagnostic for a therapeutic agent.

In an exemplary embodiment, a method for a method for enrolling a subject into a clinical trial may comprise (a) providing an isolated tau sample obtained from a subject and measuring, in the isolated tau sample, tau phosphorylation at one or more amino acid residue chosen from chosen from T181, T205, and T217, and optionally measuring total tau; and (b) enrolling the subject into a clinical trial when the measured phosphorylation level(s) significantly deviate from the mean in a control population without brain amyloid plaques as measured by PET imaging and/or Aβ42/40 measurement in CSF. In another exemplary embodiment, a method for a method for enrolling a subject into a clinical trial may comprise (a) providing a first and a second isolated tau sample obtained from a subject and measuring, in each isolated tau sample, tau phosphorylation at one or more amino acid residue chosen from T181, T205, and T217, and optionally measuring total tau; (b) calculating the change in the site-specific phosphorylation at each residue measured and optionally the change in total tau; and (c) enrolling the subject into a clinical trial when the calculated change(s) significantly deviate from the mean in a control population without brain amyloid plaques as measured by PET imaging and/or Aβ42/40 measurement in CSF. The phrase "a control population without brain amyloid plaques as measured by PET imaging and/or Aβ42/40 measurement in CSF" is defined in Section III. "Significantly deviate from the mean" refers to values that are at least 1 standard deviation, preferably at least 1.3 standard deviations, more preferably at least 1.5 standard deviations or even more preferably at least 2 standard deviations, above or below the mean (i.e., 1σ, 1.3σ, 1.5σ, or 1.5σ, respectively, where a is the standard deviation defined by the normal distribution measured in a control population without brain amyloid plaques as measured by PET imaging and/or Aβ42/40 measurement in CSF). In addition to using a threshold (e.g. at least 1 standard deviation above or below the mean), in some embodiment the extent of change above or below the mean may be used as criteria for enrolling a subject.

In one example, the present disclosure provides a method for enrolling a subject into a clinical trial, the method comprising (a) providing an isolated tau sample obtained from a subject and measuring tau phosphorylation at (i) T217 and T205, (ii) T181 and T205, or (iii) T181, T205 and T217; and (b) administering a pharmaceutical composition to the subject when tau phosphorylation at T217 and/or T181 is about 1.5σ or above and tau phosphorylation at T205 is about 1.5σ or below, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In various embodiments, tau phosphorylation at T217 and/or tau phosphorylation at T181 may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, tau phosphorylation at T217 and/or tau phosphorylation at T181 may be about 1.85σ, about 1.9σ, about 1.95σ, about 2σ, about 2.1σ, about 2.2σ, about 2.3σ, about 2.4σ, about 2.5σ or above 2.5σ. In each of the above embodiments, tau phosphorylation at T205 may be about 1.3σ, about 1.35σ, about 1.4σ, about 1.45σ, about 1.5σ, about 1.51σ, about 1.55σ, about 1.6σ, about 1.7σ, about 1.8σ, about 1.9σ, about 2.0σ, or below 2.0σ. Alternatively, tau phosphorylation at T205 may be about 2.0σ, about 2.05σ, about 2.1σ, about 2.2σ, about 2.3σ, about 2.4σ, about 2.5σ, or below 2.5σ. In a further example, tau phosphorylation at T217 and/or tau phosphorylation at T181 about 2σ or above and tau phosphorylation at T205 may be about 2σ or less. In addition to using a threshold (e.g. at least 1 standard deviation above or below the mean), in some embodiment the extent of change above or below the mean may be used as criteria for enrolling a subject. In still further embodiments, measured levels of tau phosphorylation at T205 and at T181 and/or T217 may be used in various mathematical operations to improve the predictive power compared to each by itself. For instance, ratio(s) may be calculated from the measured phosphorylation levels. Mathematical operations other than a ratio may also be used.

In another example, the present disclosure provides a method for enrolling a subject into a clinical trial, the method comprising (a) providing an isolated tau sample obtained from a subject and measuring total tau and tau phosphorylation at (i) T217 and T205, (ii) T181 and T205, or (iii) T181, T205 and T217; and (b) administering a pharmaceutical composition to the subject when the ratio of tau phosphorylation at T217 to total tau and/or the ratio of tau phosphorylation at T181 to total tau is about 1.5σ or above and the ratio of tau phosphorylation at T205 to total tau is about 1.5σ or below, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF. In various embodiments, the ratio of tau phosphorylation at T217 to total tau and/or the ratio of tau phosphorylation at T181 to total tau may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, the ratio of tau phosphorylation at T217 to total tau and/or the ratio of tau phosphorylation at T181 to total tau may be about 1.85σ, about 1.9σ, about 1.95σ, about 2σ, about 2.1σ, about 2.2σ, about 2.3σ, about 2.4σ, about 2.5σ or above 2.5σ. In each of the above embodiments, the ratio of tau phosphorylation at T205 to total tau may be about 1.3σ, about 1.35σ, about 1.4σ, about 1.45σ, about 1.50σ, about 1.55σ, about 1.6σ, about 1.7σ, about 1.8σ, about 1.9σ, about 2.0σ, or below 2σ. Alternatively, the ratio of tau phosphorylation at T205 to total tau may be about 2.0σ, about 2.05σ, about 2.1σ, about 2.2σ, about 2.3σ, about 2.4σ, about 2.5σ, or below 2.5σ. In a further example, the ratio of tau phosphorylation at T217 to total tau and/or the ratio of tau phosphorylation at T181 to total tau may be about 2σ or above and the ratio of tau phosphorylation at T205 to total tau may about 2σ or less. In addition to using a threshold (e.g. at least 1 standard deviation above or below the mean), in some embodiment the extent of change above or below the mean may be used as criteria for enrolling a subject.

In another example, the present disclosure provides a method for enrolling a subject into a clinical trial, the method comprising (a) providing an isolated tau sample obtained from a subject and measuring tau phosphorylation at (i) T181 and T205, (ii) T217 and T205, or (iii) T181, T217 and T205; and (b) administering a pharmaceutical composition to the subject when tau phosphorylation at the specific sites recited in (a)(i), (a)(ii) or (a)(iii) is about 1.5σ or above, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In various embodiments, tau phosphorylation at the specific sites recited in (a)(i), (a)(ii) or (a)(iii) may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, tau phosphorylation at the specific sites recited in (a)(i), (a)(ii) or (a)(iii) may be about 1.85σ, about 1.9σ, about 1.95σ, about 2σ, about 2.1 σ, about 2.2σ, about 2.3σ, about 2.4σ, about 2.5σ or above 2.5σ. In a further example, tau phosphorylation at the specific sites recited in (a)(i), (a)(ii) or (a)(iii) may be about 2σ or above. In addition to using a threshold (e.g. at least 1 standard deviation above or below the mean), in some embodiment the extent of change above or below the mean may be used as criteria for enrolling a subject. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In another example, the present disclosure provides a method for enrolling a subject into a clinical trial, the method comprising (a) providing an isolated tau sample obtained from a subject and measuring total tau and tau phosphorylation at (i) T181 and T205, (ii) T217 and T205, or (iii) T181, T217 and T205; and (b) administering a pharmaceutical composition to the subject when the ratio of tau phosphorylation at the specific sites recited in (a)(i), (a)(ii) or (a)(iii) to total tau is about 1.5σ or above, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF. In various embodiments, the ratio of tau phosphorylation at the specific sites recited in (a)(i), (a)(ii) or (a)(iii) to total tau may be about 1.3σ, about 1.35σ, about 1.4σ, about 1.45σ, about 1.5σ, about 1.6σ, about 1.7σ, about 1.8σ, about 1.9σ, about 2σ, or above 2σ. In other embodiments, the ratio of tau phosphorylation at the specific sites recited in (a)(i), (a)(ii) or (a)(iii) to total tau may be about 1.85σ, about 1.9σ, about 1.95σ, about 2σ, about 2.1 σ, about 2.2σ, about 2.3σ, about 2.4σ, about 2.5σ or above 2.5σ. In a further example, the ratio of tau phosphorylation at the specific sites recited in (a)(i), (a)(ii) or (a)(iii) to total tau may be about 2σ or above. In addition to using a threshold (e.g. at least 1 standard deviation above or below the mean), in some embodiment the extent of change above or below the mean may be used as criteria for enrolling a subject.

In another example, the present disclosure provides a method for enrolling a subject into a clinical trial, the method comprising, (a) providing a first and a second isolated tau sample obtained from a subject, wherein "first" and "second" refer to the order in which the samples were collected, and measuring tau phosphorylation at (i) T181 and T205, (ii) T217 and T205, or (iii) T181, T217 and T205; (b) calculating the change in the site-specific phosphorylation at each residue measured and optionally the change in total tau; and (c) enrolling the subject into the clinical trial when the phosphorylation level at T181 and/or T217 decreases or stays the same and the phosphorylation level at T205 and optionally total tau increases. The first and the second isolated tau samples may be collected days, weeks, or months apart. Typically, tau phosphorylation at the specific sites recited in (a)(i), (a)(ii) or (a)(iii) will also be about 1.5σ or above for both samples, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

In another example, the present disclosure provides a method for enrolling a subject into a clinical trial, the method comprising (a) providing a first and a second isolated tau sample obtained from a subject, wherein "first" and "second" refer to the order in which the samples were collected, and measuring total tau and tau phosphorylation at (i) T181 and T205, (ii) T217 and T205, or (iii) T181, T217 and T205; (b) calculating the change in the site-specific phosphorylation at each residue measured and the change in total tau; and (c) enrolling the subject into the clinical trial when the phosphorylation level at T181 and/or T217 decreases or stays the same, the phosphorylation level at T205 decreases or stays the same, and total tau increases. The first and the second isolated tau samples may be collected days, weeks, or months apart. Typically, tau phosphorylation at the specific sites recited in (a)(i), (a)(ii) or (a)(iii) will also be about 1.5σ or above for both samples, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF. In still further embodiments, measured levels of tau phosphorylation at the specific sites recited in (a)(i), (a)(ii) or (a)(iii) may be used in various mathematical operations to improve the predictive power compared to each by itself. For instance, ratio(s) may be calculated from the measured phosphorylation levels. Mathematical operations other than a ratio may also be used.

Methods for measuring tau phosphorylation and total tau are described in Section II, and incorporated into this section by reference. For instance, using the protocol detailed for Examples 5-9, tau phosphorylation at T181, T205 and T217 is 21.7±2.3, 0.34±0.13, and 1.2±0.66, respectively, in a control population without brain amyloid plaques as measured by PET imaging, as measured in an isolated tau sample that was purified from CSF (see Table 3, mutation non-carriers column). Accordingly, twice the standard deviation above the mean found for the mutation non-carrier population (i.e. 2σ) for p-T181, p-T205 and p-T217 is 43.4, 0.68, and 2.4, respectively. A skilled artisan will appreciate, however, that the absolute value may vary depending upon the protocol.

In a preferred embodiment, an isolated tau sample comprises tau that has been purified from blood or CSF by affinity purification and tau phosphorylation is measured by mass spectrometry. In another preferred embodiment, an isolated tau sample comprises tau that has been purified from blood or CSF by affinity purification using a ligand that specifically binds an epitope within the mid domain of tau, and optionally with a second ligand that specifically binds an epitope within the N-terminus of tau, and tau phosphorylation is measured by high resolution mass spectrometry. In another preferred embodiment, an isolated tau sample comprises tau that has been purified from blood or CSF by affinity purification using a ligand that specifically binds an epitope within the mid domain of tau, and optionally with a second ligand that specifically binds an epitope within the MTBR or the C-terminus of tau, and tau phosphorylation is measured by high resolution mass spectrometry. In an exemplary embodiment, a mass spectrometry protocol outlined in the Examples is used.

In each of the above embodiments, a subject may be enrolled into a treatment arm of the clinical trial. The "treatment" is defined in Section IV. Subjects enrolled in the treatment arm of a clinical trial may be administered a pharmaceutical composition. In some embodiments, a pharmaceutical composition may comprise an imaging agent. Non-limiting examples of imaging agents include functional imaging agents (e.g. fluorodeoxyglucose, etc.) and molecular imaging agents (e.g., Pittsburgh compound B, florbetaben, florbetapir, flutemetamol, radionuclide-labeled antibodies, etc.). Alternatively, a pharmaceutical composition may comprise an active pharmaceutical ingredient. Non-limiting examples of active pharmaceutical ingredients include cholinesterase inhibitors, N-methyl D-aspartate (NMDA) antagonists, antidepressants (e.g., selective serotonin reuptake inhibitors, atypical antidepressants, aminoketones, selective serotonin and norepinephrine reuptake inhibitors, tricyclic antidepressants, etc.), gamma-secretase inhibitors, beta-secretase inhibitors, anti-Aβ antibodies (including antigen-binding fragments, variants, or derivatives thereof), anti-tau antibodies (including antigen-binding fragments, variants, or derivatives thereof), stem cells, dietary supplements (e.g. lithium water, omega-3 fatty acids with lipoic acid, long chain triglycerides, genistein, resveratrol, curcumin, and grape seed extract, etc.), antagonists of the serotonin receptor 6, p38alpha MAPK inhibitors, recombinant granulocyte macrophage colony-stimulating factor, passive immunotherapies, active vaccines (e.g. CAD106, AF20513, etc.), tau protein aggregation inhibitors (e.g. TRx0237, methylthioninium chloride, etc.), therapies to improve blood sugar control (e.g., insulin, exenatide, liraglutide pioglitazone, etc.), anti-inflammatory agents, phosphodiesterase 9A inhibitors, sigma-1 receptor agonists, kinase inhibitors, phosphatase activators, phosphatase inhibitors, angiotensin receptor blockers, CB1 and/or CB2 endocannabinoid receptor partial agonists, β-2 adrenergic receptor agonists, nicotinic acetylcholine receptor agonists, 5-HT2A inverse agonists, alpha-2c adrenergic receptor antagonists, 5-HT 1A and 1D receptor agonists, Glutaminyl-peptide cyclotransferase inhibitors, selective inhibitors of APP production, monoamine oxidase B inhibitors, glutamate receptor antagonists, AMPA receptor agonists, nerve growth factor stimulants, HMG-CoA reductase inhibitors, neurotrophic agents, muscarinic M1 receptor agonists, GABA receptor modulators, PPAR-gamma agonists, microtubule protein modulators, calcium channel blockers, antihypertensive agents, statins, and any combination thereof. In an exemplary embodiment, a pharmaceutical composition may comprise a kinase inhibitor. Suitable kinase inhibitors may inhibit a thousand-and-one amino acid kinase (TAOK), CDK, GSK-3p, MARK, CDK5, or Fyn. In another exemplary embodiment, a pharmaceutical composition may comprise a phosphatase activator. As a non-limiting example, a phosphatase activator may increase the activity of protein phosphatase 2A.

In each of the above embodiments, a subject may or may not be symptomatic. An "asymptomatic subject," as used herein, refers to a subject that does not show any signs or symptoms of AD. Alternatively, a subject may exhibit signs or symptoms of AD (e.g., memory loss, misplacing things, changes in mood or behavior, etc.) but not show sufficient cognitive or functional impairment for a clinical diagnosis of mild cognitive impairment. A symptomatic or an asymptomatic subject may have Aβ amyloidosis; however, prior knowledge of Aβ amyloidosis is not a requisite for treatment. In still further embodiments, a subject may have AD. In any of the aforementioned embodiments, a subject may carry one of the gene mutations known to cause dominantly inherited Alzheimer's disease. In alternative embodiments, a subject may not carry a gene mutation known to cause dominantly inherited Alzheimer's disease.

VI. Numbered Embodiments

Embodiment 1: A method for processing a blood sample to enrich for soluble tau, the method comprising: precipitating proteins from a blood sample using perchloric acid, thereby producing an acid soluble extract of blood; and concentrating soluble tau in the acid soluble extract by solid phase extraction using a reversed-phase sorbent and affinity-purification using one or more epitope binding agent, wherein at least one epitope binding agent specifically binds an epitope within the N-terminus of tau or within the mid-domain of tau.

Embodiment 2: The method of embodiment 1, wherein the blood sample is plasma.

Embodiment 3: The method of embodiment 1, wherein the blood sample is serum.

Embodiment 4: A method of any one of the preceding embodiments, wherein perchloric acid is added to a final concentration of about 1% v/v to about 15% v/v.

Embodiment 5: The method of embodiment 4, wherein perchloric acid is added to a final concentration of about 3% v/v to about 15% v/v or about 3% v/v to about 10% v/v.

Embodiment 6: The method of embodiment 4, wherein perchloric acid is added to a final concentration of about 3% v/v to about 5% v/v.

Embodiment 7: A method of any one of the preceding embodiments, wherein the reversed-phase sorbent is a polymer comprising N-vinylpyrrolidone and divinylbenzene or a polymer comprising styrene and divinylbenzene.

Embodiment 8: The method of embodiment 7, wherein the reversed-phase sorbent is a polymer comprising N-vinylpyrrolidone and divinylbenzene.

Embodiment 9: The method of embodiment 7, wherein the solid phase extraction uses a mobile phase comprising about 0.05% v/v to about 1% v/v TFA.

Embodiment 10: The method of embodiment 9, wherein the solid phase extraction uses a mobile phase comprising about 0.05% v/v to about 0.5% v/v TFA or about 0.1% v/v TFA to about 1% v/v TFA.

Embodiment 11: The method of embodiment 7, wherein soluble tau is eluted from the reversed-phase sorbent using a mobile phase comprising about 20% v/v to about 50% v/v acetonitrile.

Embodiment 12: The method of embodiment 11, wherein soluble tau is eluted from the reversed-phase sorbent using a mobile phase comprising about 20% v/v to about 40% v/v acetonitrile or about 30% v/v to about 50% v/v acetonitrile.

Embodiment 13: A method of any one of the preceding embodiments, wherein the epitope within the N-terminus of tau comprises amino acid residues 27-35 and wherein the epitope within the mid-domain of tau comprises amino acid residues 192-199.

Embodiment 14: A method of any one of the preceding embodiments, wherein the affinity-purification uses at least one epitope binding agent that specifically binds an epitope within the N-terminus of tau and at least one epitope binding agent that specifically binds within the mid-domain of tau.

Embodiment 15: The method of embodiment 13 or embodiment 14, wherein each epitope binding agent is an antibody.

Embodiment 16: A method for processing a blood sample to enrich for soluble tau, the method comprising: (a) precipitating proteins from a blood sample using perchloric acid, wherein perchloric acid is added to a final concentration of about 1% v/v to about 15% v/v, thereby producing an acid soluble extract of blood; and (b) concentrating soluble tau in the acid soluble extract by solid phase extraction and affinity-purification, wherein: the solid phase extraction step comprises (i) mixing the acid soluble extract with a reversed-phase sorbent for a time sufficient to allow the soluble tau to adhere to the reversed-phase sorbent, wherein the reversed-phase sorbent is a polymer comprising N-vinylpyrrolidone and divinylbenzene or a polymer comprising styrene and divinylbenzene, (ii) washing the tau adhered to the reverse-phased sorbent with a mobile phase comprising about 0.05% v/v to about 1% v/v TFA, and (iii) eluting soluble tau from the reversed-phase adsorbent using a mobile phase comprising about 0.05% v/v to about 1% v/v TFA and about 20% v/v to about 50% v/v acetonitrile; and the affinity purification step comprises at least one epitope binding agent that specifically binds an epitope within the N-terminus of tau and at least one epitope binding agent that specifically binds an epitope within the mid-domain of tau.

Embodiment 17: The method of embodiment 16, wherein the mobile phase comprises about 0.05% v/v to about 0.5% v/v TFA.

Embodiment 18: The method of embodiment 16, wherein the mobile phase comprises about 0.1% v/v TFA to about 1% v/v TFA.

Embodiment 19: The method of embodiment 17 or embodiment 18, wherein the mobile phase used to elute tau comprises about 20% v/v to about 40% v/v acetonitrile.

Embodiment 20: The method of embodiment 17 or embodiment 18, wherein the mobile phase used to elute tau comprises about 30% v/v to about 50% v/v acetonitrile.

Embodiment 21: The method of any one of embodiments 16 to 20, wherein the epitope within the N-terminus of tau comprises amino acid residues 27-35 and wherein the epitope within the mid-domain of tau comprises amino acid residues 192-199.

Embodiment 22: The method of any one of embodiments 16 to 21, where each epitope binding agent is an antibody.

Embodiment 23: A method for analyzing soluble tau in a blood sample, the method comprising (a) processing a blood sample according to any one of embodiments 1 to 22 to produce a sample enriched for soluble tau; and (b) analyzing the sample enriched for soluble tau by mass spectrometry.

Embodiment 24: A method for determining the amount of total tau in a blood sample, the method comprising: (b) processing a blood sample according to any one of embodiments 1 to 22 to produce a sample enriched for soluble tau; and (b) analyzing the sample enriched for soluble tau by mass spectrometry.

Embodiment 25: A method for measuring the amount of phosphorylation at one or more residue of tau, the method comprising: (a) processing a blood sample according to any one of embodiments 1 to 22 to produce a sample enriched for soluble tau; and (b) measuring by mass spectrometry the amount of phosphorylation at one or more residue of tau.

Embodiment 26: The method of embodiment 25, wherein phosphorylation of tau is measured at one or more residue chosen from T111, S113, T181, S199, S202, S208, T153, T175, T205, S214, T217, and T231.

Embodiment 27: The method of embodiment 25, wherein phosphorylation of tau is measured at one or more residue including at least one of T181, S202, or T217.

Embodiment 28: The method of embodiment 25, wherein phosphorylation of tau is measured at two or more residues including at least one of T181, S202, or T217.

Embodiment 29: The method of any one of embodiments 23 to 28, wherein the blood sample is at least about 1 ml of plasma or at least about 2 ml of whole blood.

Embodiment 30: The method of any one of embodiments 23 to 28, wherein the blood sample is at least about 1 ml to about 20 ml of plasma.

Embodiment 31: The method of any one of embodiments 23 to 30, the method further comprising a digestion step that is carried out in the presence of trypsin, Lys-N, Lys-C, or Arg-N, wherein the digestion step occurs after processing the blood sample.

Embodiment 32: The method of any one of embodiments 23 to 30, the method further comprising a digestion step that is carried out in the presence of trypsin, Lys-N, Lys-C, or Arg-N, wherein the digestion step occurs while tau is bound to at least one epitope binding agent.

Embodiment 33: The method of embodiment 31 or 32, wherein the digestion step occurs in the presence of trypsin.

Embodiment 34: A method of any one of the preceding embodiments, wherein the blood sample was obtained from an asymptomatic subject, a subject that exhibits signs or symptoms of Alzheimer's disease but does not show sufficient cognitive or functional impairment for a clinical diagnosis of mild cognitive impairment due to Alzheimer's disease, a subject diagnosed as having AD, a subject diagnosed with a neurodegenerative disease, a subject diagnosed with a tauopathy, a subject diagnosed with dementia, or a subject diagnosed with mild cognitive impairment.

Embodiment 35: The method of embodiment 34, wherein the blood sample was obtained from a subject diagnosed with progressive supranuclear palsy (PSP), corticobasal syndrome (CBS), Down's syndrome (DS), Parkinson's disease (PD), and dementia with Lewy bodies (DLB).

Embodiment 36: A method to diagnose a subject prior to the onset of Alzheimer's disease, the method comprising (a) providing an isolated tau sample obtained from the subject and measuring tau phosphorylation at (i) T217 and T205, (ii) T181 and T205, or (iii) T181, T205 and T217; and (b) diagnosing the subject as having an increased risk for conversion to mild cognitive impairment due to Alzheimer's disease when tau phosphorylation at T217 or T181 is about $1.5\sigma$ or above and tau phosphorylation at T205 is about $1.5\sigma$ or below, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF.

Embodiment 37: The method of embodiment 26, wherein the subject is diagnosed when tau phosphorylation at T217 is above $1.5\sigma$ and tau phosphorylation at T205 is below $1.5\sigma$.

Embodiment 38: The method of embodiment 37, wherein the subject is diagnosed when (i) tau phosphorylation at T217 is above $1.75\sigma$ and tau phosphorylation at T205 is below $1.75\sigma$, (ii) tau phosphorylation at T217 is above $1.8\sigma$ and tau phosphorylation at T205 is below $1.8\sigma$, or (iii) tau phosphorylation at T217 is above $1.9\sigma$ and tau phosphorylation at T205 is below $1.9\sigma$.

Embodiment 39: The method of embodiment 37, wherein the subject is diagnosed when tau phosphorylation at T217 is above $2\sigma$ and tau phosphorylation at T205 is below $2\sigma$.

Embodiment 40: The method of embodiment 26, wherein the subject is diagnosed when tau phosphorylation at T181 is above $1.5\sigma$ and tau phosphorylation at T205 is below $1.5\sigma$.

Embodiment 41: The method of embodiment 40, wherein the subject is diagnosed when (i) tau phosphorylation at T181 is above $1.75\sigma$ and tau phosphorylation at T205 is below $1.75\sigma$, (ii) tau phosphorylation at T181 is above $1.8\sigma$ and tau phosphorylation at T205 is below $1.8\sigma$, or (iii) tau phosphorylation at T181 is above $1.9\sigma$ and tau phosphorylation at T205 is below $1.9\sigma$.

Embodiment 42: The method of embodiment 40, wherein the subject is diagnosed when tau phosphorylation at T181 is above $2\sigma$ and tau phosphorylation at T205 is below $2\sigma$.

Embodiment 43: The method of embodiment 36, wherein the subject is diagnosed when tau phosphorylation at T181 and T217 is above $1.5\sigma$ and tau phosphorylation at T205 is below $1.5\sigma$.

Embodiment 44: The method of embodiment 43, wherein the subject is diagnosed when (i) tau phosphorylation at T181 and T217 is above $1.75\sigma$ and tau phosphorylation at T205 is below $1.75\sigma$, (ii) tau phosphorylation at T181 and T217 is above $1.8\sigma$ and tau phosphorylation at T205 is below $1.8\sigma$, or (iii) tau phosphorylation at T181 and T217 is above $1.9\sigma$ and tau phosphorylation at T205 is below $1.9\sigma$.

Embodiment 45: The method of embodiment 43, wherein the subject is diagnosed when tau phosphorylation at T181 and T217 is above $2\sigma$ and tau phosphorylation at T205 is below $2\sigma$.

Embodiment 46: A method of any one of embodiments 36 to 45, wherein the diagnosis further includes an identification of the subject as about 10 to about 25 years from the onset of mild cognitive impairment due to Alzheimer's disease.

Embodiment 47: The method of embodiment 46, wherein the diagnosis further includes an identification of the subject as about 10 to about 20 years from the onset of mild cognitive impairment due to Alzheimer's disease.

Embodiment 48: A method to diagnose a subject prior to the onset of Alzheimer's disease, the method comprising (a)

providing an isolated tau sample obtained from the subject and measuring total tau and measuring tau phosphorylation at (i) T217 and T205, (ii) T181 and T205, or (iii) T181, T205 and T217; and (b) diagnosing the subject as having an increased risk for conversion to mild cognitive impairment due to Alzheimer's disease when the ratio of tau phosphorylation at T217 or T181 to total tau is above 2σ and the ratio of tau phosphorylation at T205 to total tau is below 2σ, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF.

Embodiment 49: The method of embodiment 48, wherein the subject is diagnosed when the ratio of tau phosphorylation at T217 to total tau is above 1.5σ and the ratio of tau phosphorylation at T205 to total tau is below 1.5σ.

Embodiment 50: The method of embodiment 39, wherein the subject is diagnosed when (i) the ratio of tau phosphorylation at T217 to total tau is above 1.75σ and the ratio of tau phosphorylation at T205 to total tau is below 1.75σ, (ii) the ratio of tau phosphorylation at T217 to total tau T217 is above 1.8σ and the ratio of tau phosphorylation at T205 to total tau T205 is below 1.8σ, or (iii) the ratio of tau phosphorylation at T217 to total tau is above 1.9σ and the ratio of tau phosphorylation at T205 to total tau is below 1.9σ.

Embodiment 51: The method of embodiment 39, wherein the subject is diagnosed when the ratio of tau phosphorylation at T217 to total tau is above 2σ and the ratio of tau phosphorylation at T205 to total tau is below 2σ.

Embodiment 52: The method of embodiment 48, wherein the subject is diagnosed when the ratio of tau phosphorylation at T181 to total tau is above 1.5σ and the ratio of tau phosphorylation at T205 to total tau is below 1.5σ.

Embodiment 53: The method of embodiment 52, wherein the subject is diagnosed when (i) the ratio of tau phosphorylation at T181 to total tau is above 1.75σ and the ratio of tau phosphorylation at T205 to total tau is below 1.75σ, (ii) the ratio of tau phosphorylation at T181 to total tau is above 1.8σ and the ratio of tau phosphorylation at T205 to total tau is below 1.8σ, or (iii) the ratio of tau phosphorylation at T181 to total tau is above 1.9σ and the ratio of tau phosphorylation at T205 to total tau is below 1.9σ.

Embodiment 54: The method of embodiment 52, wherein the subject is diagnosed when the ratio of tau phosphorylation at T181 to total tau is above 2α and the ratio of tau phosphorylation at T205 to total tau is below 2σ.

Embodiment 55: The method of embodiment 48, wherein the subject is diagnosed when the ratio of tau phosphorylation at T181 to total tau and the ratio of tau phosphorylation at T217 to total tau is above 1.5σ and the ratio of tau phosphorylation at T205 to total tau is below 1.5σ.

Embodiment 56: The method of embodiment 55, wherein the subject is diagnosed when (i) the ratio of tau phosphorylation at T181 to total tau and the ratio of tau phosphorylation at T217 to total tau is above 1.75σ and the ratio of tau phosphorylation at T205 to total tau is below 1.75σ, (ii) the ratio of tau phosphorylation at T181 to total tau and the ratio of tau phosphorylation at T217 to total tau is above 1.8σ and the ratio of tau phosphorylation at T205 to total tau is below 1.8σ, or (iii) the ratio of tau phosphorylation at T181 to total tau and the ratio of tau phosphorylation at T217 to total tau is above 1.9σ and the ratio of tau phosphorylation at T205 to total tau is below 1.9σ.

Embodiment 57: The method of embodiment 55, wherein the subject is diagnosed when the ratio of tau phosphorylation at T181 to total tau and the ratio of tau phosphorylation at T217 to total tau is above 2σ and tau phosphorylation at T205 is below 2σ.

Embodiment 58: A method of any one of embodiments 48 to 57, wherein the diagnosis further includes an identification of the subject as about 10 to about 25 years from the onset of mild cognitive impairment due to Alzheimer's disease.

Embodiment 59: The method of embodiment 58, wherein the diagnosis further includes an identification of the subject as about 10 to about 20 years from the onset of mild cognitive impairment due to Alzheimer's disease.

Embodiment 60: A method to diagnose a subject prior to the onset of Alzheimer's disease, the method comprising (a) providing an isolated tau sample obtained from the subject and measuring tau phosphorylation at (i) T217 and T205, (ii) T181 and T205, or (iii) T181, T205 and T217; and (b) diagnosing the subject as having an increased risk for conversion to mild cognitive impairment due to Alzheimer's disease when tau phosphorylation at (i) T217 and T205, (ii) T181 and T205, or (iii) T181, T205 and T217 is about 1.5 or above, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF.

Embodiment 61: The method of embodiment 60, wherein the subject is diagnosed when tau phosphorylation at T217 and T205 is above 1.5σ.

Embodiment 62: The method of embodiment 61, wherein the subject is diagnosed when tau phosphorylation at T217 and T205 is above 1.75σ, is above 1.8σ, or is above 1.9σ.

Embodiment 63: The method of embodiment 61, wherein the subject is diagnosed when tau phosphorylation at T217 and T205 is above 2σ.

Embodiment 64: The method of embodiment 60, wherein the subject is diagnosed when tau phosphorylation at T181 and T205 is above 1.5σ.

Embodiment 65: The method of embodiment 64, wherein the subject is diagnosed when tau phosphorylation at T181 and T205 is above 1.75σ, is above 1.8σ, or is above 1.9σ.

Embodiment 66: The method of embodiment 64, wherein the subject is diagnosed when tau phosphorylation at T181 and T205 is above 2σ.

Embodiment 67: The method of embodiment 60, wherein the subject is diagnosed when tau phosphorylation at T181, T205, and T217 is above 1.5σ.

Embodiment 68: The method of embodiment 67, wherein the subject is diagnosed when tau phosphorylation at T181, T205, and T217 is above 1.75σ, is above 1.8σ, or is above 1.9σ.

Embodiment 69: The method of embodiment 67, wherein the subject is diagnosed when tau phosphorylation at T181, T205, and T217 is above 2σ.

Embodiment 70: A method of any one of embodiments 60 to 69, wherein the diagnosis further includes an identification of the subject as about 15 years or less from the onset of mild cognitive impairment due to Alzheimer's disease.

Embodiment 71: The method of embodiment 60, wherein the diagnosis further includes an identification of the subject as about 10 years or less from the onset of mild cognitive impairment due to Alzheimer's disease.

Embodiment 72: A method to diagnose a subject prior to the onset of Alzheimer's disease, the method comprising (a)

providing an isolated tau sample obtained from the subject and measuring total tau and measuring tau phosphorylation at (i) T217 and T205, (ii) T181 and T205, or (iii) T181, T205 and T217; and (b) diagnosing the subject as having an increased risk for conversion to mild cognitive impairment due to Alzheimer's disease when the ratio of tau phosphorylation at (i) T217 and T205, (ii) T181 and T205, or (iii) T181, T205 and T217 to total tau is about 1.5σ or above, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF.

Embodiment 73: The method of embodiment 72, wherein the subject is diagnosed when the ratio of tau phosphorylation at T217 to total tau is above 1.5σ and the ratio of tau phosphorylation at T205 to total tau is above 1.5σ.

Embodiment 74: The method of embodiment 73, wherein the subject is diagnosed when (i) the ratio of tau phosphorylation at T217 to total tau is above 1.75σ and the ratio of tau phosphorylation at T205 to total tau is above 1.75σ, (ii) the ratio of tau phosphorylation at T217 to total tau is above 1.8σ and the ratio of tau phosphorylation at T205 to total tau is above 1.8σ, (iii) the ratio of tau phosphorylation at T217 to total tau is above 1.9σ and the ratio of tau phosphorylation at T205 to total tau is above 1.9σ.

Embodiment 75: The method of embodiment 73, wherein the subject is diagnosed when the ratio of tau phosphorylation at T217 to total tau is above 2σ and the ratio of tau phosphorylation at T205 to total tau is above 2σ.

Embodiment 76: The method of embodiment 72, wherein the subject is diagnosed when the ratio of tau phosphorylation at T181 to total tau is above 1.5σ and the ratio of tau phosphorylation at T205 to total tau is above 1.5σ.

Embodiment 77: The method of embodiment 76, wherein the subject is diagnosed when the ratio of tau phosphorylation at T181 to total tau is above 1.75σ and the ratio of tau phosphorylation at T205 to total tau is above 1.75σ, (ii) the ratio of tau phosphorylation at T181 to total tau is above 1.8σ and the ratio of tau phosphorylation at T205 to total tau is above 1.8σ, (iii) the ratio of tau phosphorylation at T181 to total tau is above 1.9σ and the ratio of tau phosphorylation at T205 to total tau is above 1.9σ.

Embodiment 78: The method of embodiment 76, wherein the subject is diagnosed when the ratio of tau phosphorylation at T181 to total tau is above 2σ and the ratio of tau phosphorylation at T205 to total tau is above 2σ.

Embodiment 79: The method of embodiment 72, wherein the subject is diagnosed when the ratio of tau phosphorylation at T181 to total tau is above 1.5σ, the ratio of tau phosphorylation at T205 to total tau is above 1.5σ, and the ratio of tau phosphorylation at T217 to total tau is above 1.5σ.

Embodiment 80: The method of embodiment 79, wherein the subject is diagnosed when (i) the ratio of tau phosphorylation at T181 to total tau is above 1.75σ, the ratio of tau phosphorylation at T205 to total tau is above 1.75σ, and the ratio of tau phosphorylation at T217 to total tau is above 1.75σ, (ii) the ratio of tau phosphorylation at T181 to total tau is above 1.8σ, the ratio of tau phosphorylation at T205 to total tau is above 1.8σ, and the ratio of tau phosphorylation at T217 to total tau is above 1.8σ, (iii) the ratio of tau phosphorylation at T181 to total tau is above 1.9σ, the ratio of tau phosphorylation at T205 to total tau is above 1.9σ, and the ratio of tau phosphorylation at T217 to total tau is above 1.9σ.

Embodiment 81: The method of embodiment 79, wherein the subject is diagnosed when the ratio of tau phosphorylation at T181 to total tau is above 2σ, the ratio of tau phosphorylation at T205 to total tau is above 2σ, and the ratio of tau phosphorylation at T217 to total tau is above 2σ.

Embodiment 82: A method of any one of embodiments 72 to 81, wherein the diagnosis further includes an identification of the subject as about 15 years or less from the onset of mild cognitive impairment due to Alzheimer's disease.

Embodiment 83: The method of embodiment 82, wherein the diagnosis further includes an identification of the subject as about 10 years or less from the onset of mild cognitive impairment due to Alzheimer's disease.

Embodiment 84: A method for treating a subject in need thereof, the method comprising (a) providing an isolated tau sample obtained from the subject and measuring tau phosphorylation at (i) T217 and T205, (ii) T181 and T205, or (iii) T181, T205 and T217; and (b) administering a pharmaceutical composition to the subject when tau phosphorylation at T217 or T181 is about 1.5σ or above and tau phosphorylation at T205 is about 1.5σ or below, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF.

Embodiment 85: The method of embodiment 84, wherein the subject is administered a pharmaceutical composition when tau phosphorylation at T217 is above 1.5σ and tau phosphorylation at T205 is below 1.5σ.

Embodiment 86: The method of embodiment 85, wherein the subject is administered a pharmaceutical composition when (i) tau phosphorylation at T217 is above 1.75σ and tau phosphorylation at T205 is below 1.75σ, (ii) tau phosphorylation at T217 is above 1.8σ and tau phosphorylation at T205 is below 1.8σ, or (iii) tau phosphorylation at T217 is above 1.9σ and tau phosphorylation at T205 is below 1.9σ.

Embodiment 87: The method of embodiment 85, wherein the subject is administered a pharmaceutical composition when tau phosphorylation at T217 is above 2σ and tau phosphorylation at T205 is below 2σ.

Embodiment 88: The method of embodiment 84, wherein the subject is administered a pharmaceutical composition when tau phosphorylation at T181 is above 1.5σ and tau phosphorylation at T205 is below 1.5σ.

Embodiment 89: The method of embodiment 88, wherein the subject is administered a pharmaceutical composition when (i) tau phosphorylation at T181 is above 1.75σ and tau phosphorylation at T205 is below 1.75σ, (ii) tau phosphorylation at T181 is above 1.8σ and tau phosphorylation at T205 is below 1.8σ, or (iii) tau phosphorylation at T181 is above 1.9σ and tau phosphorylation at T205 is below 1.9σ.

Embodiment 90: The method of embodiment 88, wherein the subject is administered a pharmaceutical composition when tau phosphorylation at T181 is above 2σ and tau phosphorylation at T205 is below 2σ.

Embodiment 91: The method of embodiment 84, wherein the subject is administered a pharmaceutical composition when tau phosphorylation at T181 and T217 is above 1.5σ and tau phosphorylation at T205 is below 1.5σ.

Embodiment 92: The method of embodiment 91, wherein the subject is administered a pharmaceutical composition when (i) tau phosphorylation at T181 and T217 is above 1.75σ and tau phosphorylation at T205 is below 1.75σ, (ii) tau phosphorylation at T181 and T217 is above 1.8σ and tau phosphorylation at T205 is below 1.8σ, or (iii) tau phosphorylation at T181 and T217 is above 1.9σ and tau phosphorylation at T205 is below 1.9σ.

Embodiment 93: The method of embodiment 91, wherein the subject is administered a pharmaceutical composition when tau phosphorylation at T181 and T217 is above 2σ and tau phosphorylation at T205 is below 2σ.

Embodiment 94: A method for treating a subject in need thereof, the method comprising (a) providing an isolated tau sample obtained from the subject and measuring total tau and measuring tau phosphorylation at (i) T217 and T205, (ii) T181 and T205, or (iii) T181, T205 and T217; and (b) administering a pharmaceutical composition to the subject when the ratio of tau phosphorylation at T217 or T181 to total tau is above 2σ and the ratio of tau phosphorylation at T205 to total tau is below 2σ, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF.

Embodiment 95: The method of embodiment 94, wherein the subject is administered a pharmaceutical composition when the ratio of tau phosphorylation at T217 to total tau is above 1.5σ and the ratio of tau phosphorylation at T205 to total tau is below 1.5σ.

Embodiment 96: The method of embodiment 95, wherein the subject is administered a pharmaceutical composition when (i) the ratio of tau phosphorylation at T217 to total tau is above 1.75σ and the ratio of tau phosphorylation at T205 to total tau is below 1.75σ, (ii) the ratio of tau phosphorylation at T217 to total tau T217 is above 1.8σ and the ratio of tau phosphorylation at T205 to total tau T205 is below 1.8σ, or (iii) the ratio of tau phosphorylation at T217 to total tau is above 1.9σ and the ratio of tau phosphorylation at T205 to total tau is below 1.9σ.

Embodiment 97: The method of embodiment 95, wherein the subject is administered a pharmaceutical composition when the ratio of tau phosphorylation at T217 to total tau is above 2σ and the ratio of tau phosphorylation at T205 to total tau is below 2σ.

Embodiment 98: The method of embodiment 94, wherein the subject is administered a pharmaceutical composition when the ratio of tau phosphorylation at T181 to total tau is above 1.5σ and the ratio of tau phosphorylation at T205 to total tau is below 1.5σ.

Embodiment 99: The method of embodiment 98, wherein the subject is administered a pharmaceutical composition when (i) the ratio of tau phosphorylation at T181 to total tau is above 1.75σ and the ratio of tau phosphorylation at T205 to total tau is below 1.75σ, (ii) the ratio of tau phosphorylation at T181 to total tau is above 1.8σ and the ratio of tau phosphorylation at T205 to total tau is below 1.8σ, or (iii) the ratio of tau phosphorylation at T181 to total tau is above 1.9σ and the ratio of tau phosphorylation at T205 to total tau is below 1.9σ.

Embodiment 100: The method of embodiment 98, wherein the subject is administered a pharmaceutical composition when the ratio of tau phosphorylation at T181 to total tau is above 2σ and the ratio of tau phosphorylation at T205 to total tau is below 2σ.

Embodiment 101: The method of embodiment 97, wherein the subject is administered a pharmaceutical composition when the ratio of tau phosphorylation at T181 to total tau and the ratio of tau phosphorylation at T217 to total tau is above 1.5σ and the ratio of tau phosphorylation at T205 to total tau is below 1.5σ.

Embodiment 102: The method of embodiment 101, wherein the subject is administered a pharmaceutical composition when (i) the ratio of tau phosphorylation at T181 to total tau and the ratio of tau phosphorylation at T217 to total tau is above 1.75σ and the ratio of tau phosphorylation at T205 to total tau is below 1.75σ, (ii) the ratio of tau phosphorylation at T181 to total tau and the ratio of tau phosphorylation at T217 to total tau is above 1.8σ and the ratio of tau phosphorylation at T205 to total tau is below 1.8σ, or (iii) the ratio of tau phosphorylation at T181 to total tau and the ratio of tau phosphorylation at T217 to total tau is above 1.9σ and the ratio of tau phosphorylation at T205 to total tau is below 1.9σ.

Embodiment 103: The method of embodiment 101, wherein the subject is administered a pharmaceutical composition when the ratio of tau phosphorylation at T181 to total tau and the ratio of tau phosphorylation at T217 to total tau is above 2σ and tau phosphorylation at T205 is below 2σ.

Embodiment 104: A method for treating a subject in need thereof, the method comprising (a) providing an isolated tau sample obtained from the subject and measuring tau phosphorylation at (i) T217 and T205, (ii) T181 and T205, or (iii) T181, T205 and T217; and (b) administering a pharmaceutical composition to the subject when tau phosphorylation at (i) T217 and T205, (ii) T181 and T205, or (iii) T181, T205 and T217 is about 1.5σ or above, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF.

Embodiment 105: The method of embodiment 104, wherein the subject is administered a pharmaceutical composition when tau phosphorylation at T217 and T205 is above 1.5σ.

Embodiment 106: The method of embodiment 105, wherein the subject is administered a pharmaceutical composition when tau phosphorylation at T217 and T205 is above 1.75σ, is above 1.8σ, or is above 1.9σ.

Embodiment 107: The method of embodiment 105, wherein the subject is administered a pharmaceutical composition when tau phosphorylation at T217 and T205 is above 2σ.

Embodiment 108: The method of embodiment 104, wherein the subject is administered a pharmaceutical composition when tau phosphorylation at T181 and T205 is above 1.5σ.

Embodiment 109: The method of embodiment 108, wherein the subject is administered a pharmaceutical composition when tau phosphorylation at T181 and T205 is above 1.75σ, is above 1.8σ, or is above 1.9σ.

Embodiment 110: The method of embodiment 108, wherein the subject is administered a pharmaceutical composition when tau phosphorylation at T181 and T205 is above 2σ.

Embodiment 111: The method of embodiment 104, wherein the subject is administered a pharmaceutical composition when tau phosphorylation at T181, T205, and T217 is above 1.5σ.

Embodiment 112: The method of embodiment 112, wherein the subject is administered a pharmaceutical composition when tau phosphorylation at T181, T205, and T217 is above 1.75σ, is above 1.8σ, or is above 1.9σ.

Embodiment 113: The method of embodiment 112, wherein the subject is administered a pharmaceutical composition when tau phosphorylation at T181, T205, and T217 is above 2σ.

Embodiment 114: A method for treating a subject in need thereof, the method comprising (a) providing an isolated tau sample obtained from the subject and measuring total tau and measuring tau phosphorylation at (i) T217 and T205, (ii) T181 and T205, or (iii) T181, T205 and T217; and (b) administering a pharmaceutical composition to the subject when the ratio of tau phosphorylation at (i) T217 and T205, (ii) T181 and T205, or (iii) T181, T205 and T217 to total tau is about 1.5σ or above, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF.

Embodiment 115: The method of embodiment 114, wherein the subject is administered a pharmaceutical composition when the ratio of tau phosphorylation at T217 to total tau is above 1.5σ and the ratio of tau phosphorylation at T205 to total tau is above 1.5σ.

Embodiment 116: The method of embodiment 115, wherein the subject is administered a pharmaceutical composition when (i) the ratio of tau phosphorylation at T217 to total tau is above 1.75σ and the ratio of tau phosphorylation at T205 to total tau is above 1.75σ, (ii) the ratio of tau phosphorylation at T217 to total tau is above 1.8σ and the ratio of tau phosphorylation at T205 to total tau is above 1.8σ, (iii) the ratio of tau phosphorylation at T217 to total tau is above 1.9σ and the ratio of tau phosphorylation at T205 to total tau is above 1.9σ.

Embodiment 117: The method of embodiment 115, wherein the subject is administered a pharmaceutical composition when the ratio of tau phosphorylation at T217 to total tau is above 2σ and the ratio of tau phosphorylation at T205 to total tau is above 2σ.

Embodiment 118: The method of embodiment 114, wherein the subject is administered a pharmaceutical composition when the ratio of tau phosphorylation at T181 to total tau is above 1.5σ and the ratio of tau phosphorylation at T205 to total tau is above 1.5σ.

Embodiment 119: The method of embodiment 118, wherein the subject is administered a pharmaceutical composition when the ratio of tau phosphorylation at T181 to total tau is above 1.75σ and the ratio of tau phosphorylation at T205 to total tau is above 1.75σ, (ii) the ratio of tau phosphorylation at T181 to total tau is above 1.8σ and the ratio of tau phosphorylation at T205 to total tau is above 1.8σ, (iii) the ratio of tau phosphorylation at T181 to total tau is above 1.9σ and the ratio of tau phosphorylation at T205 to total tau is above 1.9σ.

Embodiment 120: The method of embodiment 118, wherein the subject is administered a pharmaceutical composition when the ratio of tau phosphorylation at T181 to total tau is above 2σ and the ratio of tau phosphorylation at T205 to total tau is above 2σ.

Embodiment 121: The method of embodiment 114, wherein the subject is administered a pharmaceutical composition when the ratio of tau phosphorylation at T181 to total tau is above 1.5σ, the ratio of tau phosphorylation at T205 to total tau is above 1.5σ, and the ratio of tau phosphorylation at T217 to total tau is above 1.5σ.

Embodiment 122: The method of embodiment 121, wherein the subject is administered a pharmaceutical composition when (i) the ratio of tau phosphorylation at T181 to total tau is above 1.75σ, the ratio of tau phosphorylation at T205 to total tau is above 1.75σ, and the ratio of tau phosphorylation at T217 to total tau is above 1.75σ, (ii) the ratio of tau phosphorylation at T181 to total tau is above 1.8σ, the ratio of tau phosphorylation at T205 to total tau is above 1.8σ, and the ratio of tau phosphorylation at T217 to total tau is above 1.8σ, (iii) the ratio of tau phosphorylation at T181 to total tau is above 1.9σ, the ratio of tau phosphorylation at T205 to total tau is above 1.9σ, and the ratio of tau phosphorylation at T217 to total tau is above 1.9σ.

Embodiment 123: The method of embodiment 121, wherein the subject is administered a pharmaceutical composition when the ratio of tau phosphorylation at T181 to total tau is above 2σ, the ratio of tau phosphorylation at T205 to total tau is above 2σ, and the ratio of tau phosphorylation at T217 to total tau is above 2σ.

Embodiment 124: A method for enrolling a subject in a clinical trial, the method comprising (a) providing an isolated tau sample obtained from the subject and measuring tau phosphorylation at (i) T217 and T205, (ii) T181 and T205, or (iii) T181, T205 and T217; and (b) enrolling the subject in a clinical trial when tau phosphorylation at T217 or T181 is about 1.5σ or above and tau phosphorylation at T205 is about 1.5σ or below, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF.

Embodiment 125: The method of embodiment 124, wherein the subject is enrolled in the clinical trial when tau phosphorylation at T217 is above 1.5σ and tau phosphorylation at T205 is below 1.5σ.

Embodiment 126: The method of embodiment 125, wherein the subject is enrolled in the clinical trial when (i) tau phosphorylation at T217 is above 1.75σ and tau phosphorylation at T205 is below 1.75σ, (ii) tau phosphorylation at T217 is above 1.8σ and tau phosphorylation at T205 is below 1.8σ, or (iii) tau phosphorylation at T217 is above 1.9σ and tau phosphorylation at T205 is below 1.9σ.

Embodiment 127: The method of embodiment 125, wherein the subject is enrolled in the clinical trial when tau phosphorylation at T217 is above 2σ and tau phosphorylation at T205 is below 2σ.

Embodiment 128: The method of embodiment 124, wherein the subject is enrolled in the clinical trial when tau phosphorylation at T181 is above 1.5σ and tau phosphorylation at T205 is below 1.5σ.

Embodiment 129: The method of embodiment 128, wherein the subject is enrolled in the clinical trial when (i) tau phosphorylation at T181 is above 1.75σ and tau phosphorylation at T205 is below 1.75σ, (ii) tau phosphorylation at T181 is above 1.8σ and tau phosphorylation at T205 is below 1.8σ, or (iii) tau phosphorylation at T181 is above 1.9σ and tau phosphorylation at T205 is below 1.9σ.

Embodiment 130: The method of embodiment 128, wherein the subject is enrolled in the clinical trial when tau phosphorylation at T181 is above 2σ and tau phosphorylation at T205 is below 2σ.

Embodiment 131: The method of embodiment 124, wherein the subject is enrolled in the clinical trial when tau phosphorylation at T181 and T217 is above 1.5σ and tau phosphorylation at T205 is below 1.5σ.

Embodiment 132: The method of embodiment 131, wherein the subject is enrolled in the clinical trial when (i) tau phosphorylation at T181 and T217 is above 1.75σ and tau phosphorylation at T205 is below 1.75σ, (ii) tau phosphorylation at T181 and T217 is above 1.8σ and tau phosphorylation at T205 is below 1.8σ, or (iii) tau phosphorylation at T181 and T217 is above 1.9σ and tau phosphorylation at T205 is below 1.9σ.

Embodiment 133: The method of embodiment 131, wherein the subject is enrolled in the clinical trial when tau phosphorylation at T181 and T217 is above 2σ and tau phosphorylation at T205 is below 2σ.

Embodiment 134: A method for enrolling a subject in a clinical trial, the method comprising (a) providing an isolated tau sample obtained from the subject and measuring total tau and measuring tau phosphorylation at (i) T217 and T205, (ii) T181 and T205, or (iii) T181, T205 and T217; and (b) enrolling the subject in a clinical trial when the ratio of tau phosphorylation at T217 or T181 to total tau is above 2σ and the ratio of tau phosphorylation at T205 to total tau is below 2σ, where a is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF.

Embodiment 135: The method of embodiment 134, wherein the subject is enrolled in the clinical trial when the ratio of tau phosphorylation at T217 to total tau is above 1.5σ and the ratio of tau phosphorylation at T205 to total tau is below 1.5σ.

Embodiment 136: The method of embodiment 135, wherein the subject is enrolled in the clinical trial when (i) the ratio of tau phosphorylation at T217 to total tau is above 1.75σ and the ratio of tau phosphorylation at T205 to total tau is below 1.75σ, (ii) the ratio of tau phosphorylation at T217 to total tau T217 is above 1.8σ and the ratio of tau phosphorylation at T205 to total tau T205 is below 1.8б, or (iii) the ratio of tau phosphorylation at T217 to total tau is above 1.9σ and the ratio of tau phosphorylation at T205 to total tau is below 1.9σ.

Embodiment 137: The method of embodiment 135, wherein the subject is enrolled in the clinical trial when the ratio of tau phosphorylation at T217 to total tau is above 2σ and the ratio of tau phosphorylation at T205 to total tau is below 2σ.

Embodiment 138: The method of embodiment 134, wherein the subject is enrolled in the clinical trial when the ratio of tau phosphorylation at T181 to total tau is above 1.5σ and the ratio of tau phosphorylation at T205 to total tau is below 1.5σ.

Embodiment 139: The method of embodiment 138, wherein the subject is enrolled in the clinical trial when (i) the ratio of tau phosphorylation at T181 to total tau is above 1.75σ and the ratio of tau phosphorylation at T205 to total tau is below 1.75σ, (ii) the ratio of tau phosphorylation at T181 to total tau is above 1.8σ and the ratio of tau phosphorylation at T205 to total tau is below 1.8σ, or (iii) the ratio of tau phosphorylation at T181 to total tau is above 1.9σ and the ratio of tau phosphorylation at T205 to total tau is below 1.9σ.

Embodiment 140: The method of embodiment 138, wherein the subject is enrolled in the clinical trial when the ratio of tau phosphorylation at T181 to total tau is above 2σ and the ratio of tau phosphorylation at T205 to total tau is below 2σ.

Embodiment 141: The method of embodiment 134, wherein the subject is enrolled in the clinical trial when the ratio of tau phosphorylation at T181 to total tau and the ratio of tau phosphorylation at T217 to total tau is above 1.5σ and the ratio of tau phosphorylation at T205 to total tau is below 1.5σ.

Embodiment 142: The method of embodiment 141, wherein the subject is enrolled in the clinical trial when (i) the ratio of tau phosphorylation at T181 to total tau and the ratio of tau phosphorylation at T217 to total tau is above 1.75σ and the ratio of tau phosphorylation at T205 to total tau is below 1.75σ, (ii) the ratio of tau phosphorylation at T181 to total tau and the ratio of tau phosphorylation at T217 to total tau is above 1.8σ and the ratio of tau phosphorylation at T205 to total tau is below 1.8σ, or (iii) the ratio of tau phosphorylation at T181 to total tau and the ratio of tau phosphorylation at T217 to total tau is above 1.9σ and the ratio of tau phosphorylation at T205 to total tau is below 1.9σ.

Embodiment 143: The method of embodiment 141, wherein the subject is enrolled in the clinical trial when the ratio of tau phosphorylation at T181 to total tau and the ratio of tau phosphorylation at T217 to total tau is above 2σ and tau phosphorylation at T205 is below 2σ.

Embodiment 144: A method for enrolling a subject in a clinical trial, the method comprising (a) providing an isolated tau sample obtained from the subject and measuring tau phosphorylation at (i) T217 and T205, (ii) T181 and T205, or (iii) T181, T205 and T217; and (b) enrolling the subject in a clinical trial when tau phosphorylation at (i) T217 and T205, (ii) T181 and T205, or (iii) T181, T205 and T217 is about 1.5σ or above, where a is the standard deviation defined by the normal distribution of tau phosphorylation at T217 and T205, T181 and T205, or T181, T205 and T217 measured in a control population without brain amyloid plaques as measured by PET imaging and/or Aβ42/40 measurement in CSF.

Embodiment 145: The method of embodiment 144, wherein the subject is enrolled in the clinical trial when tau phosphorylation at T217 and T205 is above 1.5σ.

Embodiment 146: The method of embodiment 145, wherein the subject is enrolled in the clinical trial when tau phosphorylation at T217 and T205 is above 1.75σ, is above 1.8σ, or is above 1.9σ.

Embodiment 147: The method of embodiment 145, wherein the subject is enrolled in the clinical trial when tau phosphorylation at T217 and T205 is above 2σ.

Embodiment 148: The method of embodiment 144, wherein the subject is enrolled in the clinical trial when tau phosphorylation at T181 and T205 is above 1.5σ.

Embodiment 149: The method of embodiment 148, wherein the subject is enrolled in the clinical trial when tau phosphorylation at T181 and T205 is above 1.75σ, is above 1.8σ, or is above 1.9σ.

Embodiment 150: The method of embodiment 148, wherein the subject is enrolled in the clinical trial when tau phosphorylation at T181 and T205 is above 2σ.

Embodiment 151: The method of embodiment 144, wherein the subject is enrolled in the clinical trial when tau phosphorylation at T181, T205, and T217 is above 1.5σ.

Embodiment 152: The method of embodiment 151, wherein the subject is enrolled in the clinical trial when tau phosphorylation at T181, T205, and T217 is above 1.75σ, is above 1.8σ, or is above 1.9σ.

Embodiment 153: The method of embodiment 151, wherein the subject is enrolled in the clinical trial when tau phosphorylation at T181, T205, and T217 is above 2σ.

Embodiment 154: A method for enrolling a subject in a clinical trial, the method comprising (a) providing an isolated tau sample obtained from the subject and measuring total tau and measuring tau phosphorylation at (i) T217 and T205, (ii) T181 and T205, or (iii) T181, T205 and T217; and (b) enrolling the subject in a clinical trial when the ratio of tau phosphorylation at (i) T217 and T205, (ii) T181 and T205, or (iii) T181, T205 and T217 to total tau is about 1.5σ or above, where σ is the standard deviation defined by the normal distribution of total tau and tau phosphorylation at T217 and T205, T181 and T205, or T181, T205 and T217 measured in a control population without brain amyloid plaques as measured by PET imaging and/or Aβ42/40 measurement in CSF.

Embodiment 155: The method of embodiment 154, wherein the subject is enrolled in the clinical trial when the ratio of tau phosphorylation at T217 to total tau is above 1.5σ and the ratio of tau phosphorylation at T205 to total tau is above 1.5σ.

Embodiment 156: The method of embodiment 155, wherein the subject is enrolled in the clinical trial when (i) the ratio of tau phosphorylation at T217 to total tau is above 1.75σ and the ratio of tau phosphorylation at T205 to total tau is above 1.75σ, (ii) the ratio of tau phosphorylation at T217 to total tau is above 1.8σ and the ratio of tau phosphorylation at T205 to total tau is above 1.8σ, (iii) the ratio of tau phosphorylation at T217 to total tau is above 1.9σ and the ratio of tau phosphorylation at T205 to total tau is above 1.9σ.

Embodiment 157: The method of embodiment 155, wherein the subject is enrolled in the clinical trial when the ratio of tau phosphorylation at T217 to total tau is above 2σ and the ratio of tau phosphorylation at T205 to total tau is above 2σ.

Embodiment 158: The method of embodiment 154, wherein the subject is enrolled in the clinical trial when the ratio of tau phosphorylation at T181 to total tau is above 1.5σ and the ratio of tau phosphorylation at T205 to total tau is above 1.5σ.

Embodiment 159: The method of embodiment 158, wherein the subject is enrolled in the clinical trial when the ratio of tau phosphorylation at T181 to total tau is above 1.75σ and the ratio of tau phosphorylation at T205 to total tau is above 1.75σ, (ii) the ratio of tau phosphorylation at T181 to total tau is above 1.8σ and the ratio of tau phosphorylation at T205 to total tau is above 1.8σ, (iii) the ratio of tau phosphorylation at T181 to total tau is above 1.9σ and the ratio of tau phosphorylation at T205 to total tau is above 1.9σ.

Embodiment 160: The method of embodiment 158, wherein the subject is enrolled in the clinical trial when the ratio of tau phosphorylation at T181 to total tau is above 2σ and the ratio of tau phosphorylation at T205 to total tau is above 2σ.

Embodiment 161: The method of embodiment 154, wherein the subject is enrolled in the clinical trial when the ratio of tau phosphorylation at T181 to total tau is above 1.5σ, the ratio of tau phosphorylation at T205 to total tau is above 1.5σ, and the ratio of tau phosphorylation at T217 to total tau is above 1.5σ.

Embodiment 162: The method of embodiment 161, wherein the subject is enrolled in the clinical trial when (i) the ratio of tau phosphorylation at T181 to total tau is above 1.75σ, the ratio of tau phosphorylation at T205 to total tau is above 1.75σ, and the ratio of tau phosphorylation at T217 to total tau is above 1.75σ, (ii) the ratio of tau phosphorylation at T181 to total tau is above 1.8σ, the ratio of tau phosphorylation at T205 to total tau is above 1.8σ, and the ratio of tau phosphorylation at T217 to total tau is above 1.8σ, (iii) the ratio of tau phosphorylation at T181 to total tau is above 1.9σ, the ratio of tau phosphorylation at T205 to total tau is above 1.9σ, and the ratio of tau phosphorylation at T217 to total tau is above 1.9σ.

Embodiment 163: The method of embodiment 161, wherein the subject is enrolled in the clinical trial when the ratio of tau phosphorylation at T181 to total tau is above 2σ, the ratio of tau phosphorylation at T205 to total tau is above 2σ, and the ratio of tau phosphorylation at T217 to total tau is above 2σ.

Embodiment 164: A method as recited in any one of embodiments 124 to 163, wherein the subject is enrolled in the treatment arm of the clinical trial.

Embodiment 165: A method of embodiment 164, wherein the treatment arm of the clinical trial comprises administering a pharmaceutical composition to the subject.

Embodiment 166: A method as recited in any one of embodiments 84 to 124 or embodiment 157, wherein the pharmaceutical composition comprises an Aβ or tau therapy.

Embodiment 167: The method of embodiment 166, wherein the Aβ or tau therapy is an amyloid beta targeting therapy, a kinase, a kinase inhibitor, or a phosphatase.

Embodiment 168: A method as recited in any one of embodiments 36 to 167, wherein the subject has a gene mutation known to cause dominantly inherited Alzheimer's disease.

Embodiment 169: A method as recited in any one of embodiments 36 to 167, wherein the subject does not have a gene mutation known to cause dominantly inherited Alzheimer's disease.

Embodiment 170: A method as recited in any one of embodiments 36 to 167, wherein the isolated tau sample comprises tau that has been purified from blood or CSF by affinity purification, or the isolated tau sample comprises tau that has been purified from blood according to any one of embodiments 1 to 35.

Embodiment 171: The method of embodiment 170, wherein the isolated tau sample comprises tau that has been purified from blood or CSF by affinity purification using a ligand that specifically binds an epitope within the mid domain of tau, and optionally with a second ligand that specifically binds an epitope within the N-terminus of tau.

Embodiment 172: A method as recited in any one of embodiments 1 to 171, wherein tau phosphorylation is measured by mass spectrometry.

EXAMPLES

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

The references listed below are cited in the Examples that follow.

Alonso, A. del C., Zaidi, T., Novak, M., Grundke-Iqbal, I., and Iqbal, K. (2001). Hyperphosphorylation induces self-assembly of tau into tangles of paired helical filaments/straight filaments. PNAS 98, 6923-6928. doi:10.1073/pnas.121119298.

Arriagada, P. V., Growdon, J. H., Hedley-Whyte, E. T. & Hyman, B. T. Neurofibrillary tangles but not senile plaques parallel duration and severity of Alzheimer's disease. Neurology 42, 631-631, doi:10.1212/wnl.42.3.631 (1992).

Augustinack, J. C., Schneider, A., Mandelkow, E.-M., and Hyman, B. T. (2002). Specific tau phosphorylation sites correlate with severity of neuronal cytopathology in Alzheimer's disease. Acta Neuropathol 103, 26-35. doi: 10.1007/s004010100423.

Barthélemy, N. R., Fenaille, F., Hirtz, C., Sergeant, N., Schraen-Maschke, S., Vialaret, J., et al. (2016). Tau Protein Quantification in Human Cerebrospinal Fluid by Targeted Mass Spectrometry at High Sequence Coverage Provides Insights into Its Primary Structure Heterogeneity. J. Proteome Res. 15, 667-676. doi:10.1021/acs.jproteome.5b01001.

Bateman, R. J. et al. Clinical and biomarker changes in dominantly inherited Alzheimer's disease. N Engl J Med 367, 795-804, doi:10.1056/NEJMoa1202753 (2012).

Bateman, R. J. et al. The DIAN-TU Next Generation Alzheimer's prevention trial: Adaptive design and disease progression model. Alzheimers Dement 13, 8-19, doi: 10.1016/j.jalz.2016.07.005 (2017).

Benjamini, Y., and Hochberg, Y. Controlling the false discovery rate: a practical and powerful approach to multiple testing. Journal of the Royal Statistical Society Series B, 289-300 (1995).

Benzinger, T. L. et al. Regional variability of imaging biomarkers in autosomal dominant Alzheimer's disease. Proceedings of the National Academy of Sciences of the United States of America 110, E4502-4509, doi:10.1073/pnas.1317918110 (2013).

Biernat, J., Gustke, N., Drewes, G., Mandelkow, E.-, and Mandelkow, E. (1993). Phosphorylation of Ser262 strongly reduces binding of tau to microtubules: Distinction between PHF-like immunoreactivity and microtubule binding. Neuron 11, 153-163. doi:10.1016/0896-6273(93)90279-Z.

Braak, H., and Braak, E. (1995). Staging of alzheimer's disease-related neurofibrillary changes. Neurobiology of Aging 16, 271-278. doi:10.1016/0197-4580(95)00021-6.

Buerger, K. et al. CSF phosphorylated tau protein correlates with neocortical neurofibrillary pathology in Alzheimer's disease. Brain: a journal of neurology 129, 3035-3041, doi:10.1093/brain/awl269 (2006).

Cohen, A. D. et al. Early striatal amyloid deposition distinguishes Down syndrome and autosomal dominant Alzheimer's disease from late-onset amyloid deposition. Alzheimer's & dementia: the journal of the Alzheimer's Association, doi:10.1016/j.jalz.2018.01.002 (2018).

Chung, P. J., Song, C., Deek, J., Miller, H. P., Li, Y., Choi, M. C., et al. (2016). Tau mediates microtubule bundle architectures mimicking fascicles of microtubules found in the axon initial segment. Nature Communications 7, 12278. doi:10.1038/ncomms12278.

Crowther, R. A. Straight and paired helical filaments in Alzheimer disease have a common structural unit. Proceedings of the National Academy of Sciences 88, 2288-2292, doi:10.1073/pnas.88.6.2288 (1991).

Despres, C., Byrne, C., Qi, H., Cantrelle, F.-X., Huvent, I., Chambraud, B., et al. (2017). Identification of the Tau phosphorylation pattern that drives its aggregation. PNAS 114, 9080-9085. doi:10.1073/pnas.1708448114.

Fagan, A. M. et al. Cerebrospinal fluid tau/beta-amyloid(42) ratio as a prediction of cognitive decline in nondemented older adults. Arch Neurol 64, 343-349, doi:10.1001/archneur.64.3.noc60123 (2007).

Fitzpatrick, A. W. P. et al. Cryo-EM structures of tau filaments from Alzheimer's disease. Nature 547, 185, doi:10.1038/nature23002 (2017).

Fleisher, A. S. et al. Associations between biomarkers and age in the presenilin 1 E280A autosomal dominant Alzheimer disease kindred: a cross-sectional study. JAMA Neurol 72, 316-324, doi:10.1001/jamaneurol.2014.3314 (2015).

Funk, K. E., Thomas, S. N., Schafer, K. N., Cooper, G. L., Liao, Z., Clark, D. J., et al. (2014). Lysine methylation is an endogenous post-translational modification of tau protein in human brain and a modulator of aggregation propensity. Biochem J 462, 77-88. doi:10.1042/BJ20140372.

Gallien, S., Bourmaud, A., Kim, S. Y., and Domon, B. (2014). Technical considerations for large-scale parallel reaction monitoring analysis. Journal of Proteomics 100, 147-159. doi:10.1016/j.jprot.2013.10.029.

Gallien, S., Duriez, E., Crone, C., Kellmann, M., Moehring, T., and Domon, B. (2012). Targeted Proteomic Quantification on Quadrupole-Orbitrap Mass Spectrometer. *Molecular & Cellular Proteomics* 11, 1709-1723. doi: 10.1074/mcp.O112.019802.

Gillette, M. A., and Carr, S. A. (2013). Quantitative analysis of peptides and proteins in biomedicine by targeted mass spectrometry. Nature Methods 10, 28-34. doi:10.1038/nmeth.2309.

Goedert, M., Spillantini, M. G., Jakes, R., Rutherford, D. & Crowther, R. A. Multiple isoforms of human microtubule-associated protein tau: sequences and localization in neurofibrillary tangles of Alzheimer's disease. Neuron 3, 519-526, doi:10.1016/0896-6273(89)90210-9 (1989).

Gordon, B. A. et al. Spatial patterns of neuroimaging biomarker change in individuals from families with autosomal dominant Alzheimer's disease: a longitudinal study. The Lancet. Neurology 17, 241-250, doi:10.1016/S1474-4422(18)30028-0 (2018).

Gordon, B. A. et al. Tau PET in autosomal dominant Alzheimer disease: relationship to cognition, dementia and biomarkers. Brain: a journal of neurology Accepted for Publication (2019).

Grundke-Iqbal, I. et al. Abnormal phosphorylation of the microtubule-associated protein tau (tau) in Alzheimer cytoskeletal pathology. Proceedings of the National Academy of Sciences of the United States of America 83, 4913-4917, doi:10.1073/pnas.83.13.4913 (1986).

Hampel, H. et al. Measurement of phosphorylated tau epitopes in the differential diagnosis of Alzheimer disease: a comparative cerebrospinal fluid study. Archives of general psychiatry 61, 95-102, doi:10.1001/archpsyc.61.1.95 (2004).

Hanger, D. P., Betts, J. C., Loviny, T. L., Blackstock, W. P., and Anderton, B. H. (1998a). New phosphorylation sites identified in hyperphosphorylated tau (paired helical filament-tau) from Alzheimer's disease brain using nanoelectrospray mass spectrometry. J. Neurochem. 71, 2465-2476.

Hanger, D. P., Betts, J. C., Loviny, T. L. F., Blackstock, W. P., and Anderton, B. H. (1998b). New Phosphorylation Sites Identified in Hyperphosphorylated Tau (Paired Helical Filament-Tau) from Alzheimer's Disease Brain Using Nanoelectrospray Mass Spectrometry. Journal of Neurochemistry 71, 2465-2476. doi:10.1046/j.1471-4159.1998.71062465.x.

Hanger, D. P., Byers, H. L., Wray, S., Leung, K.-Y., Saxton, M. J., Seereeram, A., et al. (2007). Novel Phosphorylation Sites in Tau from Alzheimer Brain Support a Role for Casein Kinase 1 in Disease Pathogenesis. Journal of Biological Chemistry 282, 23645-23654. doi:10.1074/jbc.M703269200.

Hasegawa, M., Morishima-Kawashima, M., Takio, K., Suzuki, M., Titani, K., and Ihara, Y. (1992). Protein sequence and mass spectrometric analyses of tau in the Alzheimer's disease brain. J. Biol. Chem. 267, 17047-17054.

He, Z. et al. Amyloid-beta plaques enhance Alzheimer's brain tau-seeded pathologies by facilitating neuritic plaque tau aggregation. Nat Med 24, 29-38, doi:10.1038/nm.4443 (2018).

Hu, W. T. et al. Reduced CSF p-Tau181 to Tau ratio is a biomarker for FTLD-TDP. Neurology 81, 1945-1952, doi:10.1212/01.wnl.0000436625.63650.27 (2013).

Iqbal, K., Alonso, A. del C., Chen, S., Chohan, M. O., El-Akkad, E., Gong, C.-X., et al. (2005). Tau pathology in Alzheimer disease and other tauopathies. Biochim. Biophys. Acta 1739, 198-210. doi:10.1016/j.bbadis.2004.09.008.

Ittner, L. M. et al. Dendritic Function of Tau Mediates Amyloid-β Toxicity in Alzheimer's Disease Mouse Models. Cell 142, 387-397, doi:https://doi.org/10.1016/j.cell.2010.06.036 (2010).

Ittner, A. et al. Site-specific phosphorylation of tau inhibits amyloid-β toxicity in Alzheimer's mice. Science 354, 904-908 (2016).

Jack, C. R., Jr. et al. NIA-AA Research Framework: Toward a biological definition of Alzheimer's disease. Alzheimers Dement 14, 535-562, doi:10.1016/j.jalz.2018.02.018 (2018).

Jack, C. R., Jr. et al. A/T/N: An unbiased descriptive classification scheme for Alzheimer disease biomarkers. Neurology 87, 539-547, doi:10.1212/wnl.0000000000002923 (2016).

Jin, M. et al. Soluble amyloid p3-protein dimers isolated from Alzheimer cortex directly induce Tau hyperphosphorylation and neuritic degeneration. Proceedings of the National Academy of Sciences 108, 5819-5824 (2011).

Kanmert, D., Cantlon, A., Muratore, C. R., Jin, M., O'Malley, T. T., Lee, G., et al. (2015). C-Terminally Truncated Forms of Tau, But Not Full-Length Tau or Its C-Terminal Fragments, Are Released from Neurons Independently of Cell Death. J. Neurosci. 35, 10851-10865. doi:10.1523/JNEUROSCI.0387-15.2015.

Karch, C. M., Jeng, A. T., and Goate, A. M. (2012). Extracellular Tau Levels Are Influenced by Variability in Tau That Is Associated with Tauopathies. J. Biol. Chem. 287, 42751-42762. doi:10.1074/jbc.M112.380642.

Kimura, T., Sharma, G., Ishiguro, K. & Hisanaga, S.-i. Phospho-Tau Bar Code: Analysis of Phosphoisotypes of Tau and Its Application to Tauopathy. Frontiers in Neuroscience 12, doi:10.3389/fnins.2018.00044 (2018).

Köpke, E., Tung, Y. C., Shaikh, S., Alonso, A. C., Iqbal, K., and Grundke-Iqbal, I. (1993). Microtubule-associated protein tau. Abnormal phosphorylation of a non-paired helical filament pool in Alzheimer disease. J. Biol. Chem. 268, 24374-24384.

Lim, Y. Y. et al. BDNF Val66Met moderates memory impairment, hippocampal function and tau in preclinical autosomal dominant Alzheimer's disease. Brain: a journal of neurology 139, 2766-2777, doi:10.1093/brain/aww200 (2016).

Liu, W.-K., Moore, W. T., Williams, R. T., Hall, F. L., and Yen, S.-H. (1993). Application of synthetic phospho- and unphospho-peptides to identify phosphorylation sites in a subregion of the tau molecule, which is modified in Alzheimer's disease. Journal of Neuroscience Research 34, 371-376. doi:10.1002/jnr.490340315.

Luo, J., D'Angelo, G., Gao, F., Ding, J. & Xiong, C. Bivariate correlation coefficients in family-type clustered studies. Biometrical Journal 57, 1084-1109, doi:doi:10.1002/bimj.201400131 (2015).

Mair, W., Muntel, J., Tepper, K., Tang, S., Biernat, J., Seeley, W. W., et al. (2016). FLEXITau: Quantifying Post-translational Modifications of Tau Protein in Vitro and in Human Disease. Anal. Chem. 88, 3704-3714. doi:10.1021/acs.analchem.5b04509.

Maia, L. F. et al. Changes in Amyloid-β and Tau in the Cerebrospinal Fluid of Transgenic Mice Overexpressing Amyloid Precursor Protein. Science Translational Medicine 5, 194re192-194re192 (2013).

Malia, T. J., Teplyakov, A., Ernst, R., Wu, S.-J., Lacy, E. R., Liu, X., et al. (2016). Epitope mapping and structural basis for the recognition of phosphorylated tau by the anti-tau antibody AT8. Proteins: Structure, Function, and Bioinformatics 84, 427-434. doi:10.1002/prot.24988.

Matsuo, E. S., Shin, R-W., Billingsley, M. L., Van deVoorde, A., O'Connor, M., Trojanowski, J. Q., et al. (1994) Biopsy-derived adult brain tau is phosphorylated at many of the same sites as Alzheimer's disease paired helical filament tau. Neuron 13, 989-1002.

McDade, E. et al. Longitudinal cognitive and biomarker changes in dominantly inherited Alzheimer disease. Neurology 91, e1295-e1306, doi:10.1212/wnl.0000000000006277 (2018).

Medina, M. & Avila, J. Further understanding of tau phosphorylation: implications for therapy. Expert review of neurotherapeutics 15, 115-122, doi:10.1586/14737175.2015.1000864 (2015).

Morris, J. C. The Clinical Dementia Rating (CDR): current version and scoring rules. Neurology 43, 2412-2414 (1993).

Morris, J. C. et al. Developing an international network for Alzheimer research: The Dominantly Inherited Alzheimer Network. Clinical investigation 2, 975-984, doi:10.4155/cli.12.93 (2012).

Morris, M., Knudsen, G. M., Maeda, S., Trinidad, J. C., Ioanoviciu, A., Burlingame, A. L., et al. (2015). Tau post-translational modifications in wild-type and human amyloid precursor protein transgenic mice. Nature Neuroscience 18, 1183-1189. doi:10.1038/nn.4067.

Neddens, J., Temmel, M., Flunkert, S., Kerschbaumer, B., Hoeller C., Loeffler, T. et al. (2018). Phosphorylation of different tau sites during progression of Alzheimer's disease. Acta Neuropathogica Communications 6, 52. doi:10.1186/s40478-018-0557-6

Peterson, A. C., Russell, J. D., Bailey, D. J., Westphall, M. S., and Coon, J. J. (2012). Parallel Reaction Monitoring for High Resolution and High Mass Accuracy Quantitative, Targeted Proteomics. Molecular & Cellular Proteomics 11, 1475-1488. doi:10.1074/mcp.0112.020131.

Potter, R. et al. Increased in Vivo Amyloid-β42 Production, Exchange, and Loss in Presenilin Mutation Carriers. Science Translational Medicine 5, 189ra177-189ra177 (2013).

Price, J. L., Davis, P. B., Morris, J. C. & White, D. L. The distribution of tangles, plaques and related immunohistochemical markers in healthy aging and Alzheimer's disease. Neurobiology of aging 12, 295-312 (1991).

Price, J. L. & Morris, J. C. Tangles and plaques in nondemented aging and "preclinical" Alzheimer's disease. Ann Neurol 45, 358-368 (1999).

Qian, J., Hyman, B. T. & Betensky, R. A. Neurofibrillary Tangle Stage and the Rate of Progression of Alzheimer Symptoms: Modeling Using an Autopsy Cohort and Application to Clinical Trial Design. JAMA Neurol 74, 540-548, doi:10.1001/jamaneurol.2016.5953 (2017).

Quiroz, Y. T. et al. Cortical atrophy in presymptomatic Alzheimer's disease presenilin 1 mutation carriers. J Neurol Neurosurg Psychiatry 84, 556-561, doi:10.1136/jnnp-2012-303299 (2013).

Quiroz, Y. T. et al. Association Between Amyloid and Tau Accumulation in Young Adults With Autosomal Dominant Alzheimer Disease. JAMA Neurol 75, 548-556, doi:10.1001/jamaneurol.2017.4907 (2018).

Ridha, B. H. et al. Tracking atrophy progression in familial Alzheimer's disease: a serial MRI study. Lancet Neurol 5, 828-834, doi:10.1016/s1474-4422(06)70550-6 (2006).

Russell, C. L., Mitra, V., Hansson, K., Blennow, K., Gobom, J., Zetterberg, H., et al. (2016). Comprehensive Quantitative Profiling of Tau and Phosphorylated Tau Peptides in Cerebrospinal Fluid by Mass Spectrometry Provides New Biomarker Candidates. Journal of Alzheimer's Disease 55, 303-313. doi:10.3233/JAD-160633.

Ryman, D. C. et al. Symptom onset in autosomal dominant Alzheimer disease: a systematic review and meta-analysis. Neurology 83, 253-260, doi:10.1212/WNL.0000000000000596 (2014).

Saman, S. et al. Exosome-associated Tau Is Secreted in Tauopathy Models and Is Selectively Phosphorylated in Cerebrospinal Fluid in Early Alzheimer Disease. Journal of Biological Chemistry 287, 3842-3849, doi:10.1074/jbc.M111.277061 (2012).

Sato, C., Barthélemy, N. R., Mawuenyega, K. G., Patterson, B. W., Gordon, B. A., Jockel-Balsarotti, J., et al. (2018). Tau Kinetics in Neurons and the Human Central Nervous System. Neuron 97, 1284-1298.e7. doi:10.1016/j.neuron.2018.02.015.

Schelle, J. et al. Prevention of tau increase in cerebrospinal fluid of APP transgenic mice suggests downstream effect of BACE1 inhibition. Alzheimer's & Dementia: The Journal of the Alzheimer's Association 13, 701-709, doi: 10.1016/j.jalz.2016.09.005 (2017).

Schöll, M., Lockhart, S. N., Schonhaut, D. R., O'Neil, J. P., Janabi, M., Ossenkoppele, R., et al. (2016). PET Imaging of Tau Deposition in the Aging Human Brain. Neuron 89, 971-982. doi:10.1016/j.neuron.2016.01.028.

Storandt, M., Balota, D. A., Aschenbrenner, A. J. & Morris, J. C. Clinical and psychological characteristics of the initial cohort of the Dominantly Inherited Alzheimer Network (DIAN). Neuropsychology 28, 19-29, doi: 10.1037/neu0000030 (2014).

Su, Y. et al. Partial volume correction in quantitative amyloid imaging. Neuroimage 107, 55-64, doi:10.1016/j.neuroimage.2014.11.058 (2015).

Thomas, S. N., Funk, K. E., Wan, Y., Liao, Z., Davies, P., Kuret, J., et al. (2012). Dual modification of Alzheimer's disease PHF-tau protein by lysine methylation and ubiquitylation: a mass spectrometry approach. Acta Neuropathol 123, 105-117. doi:10.1007/s00401-011-0893-0.

Toledo, J. B., Xie, S. X., Trojanowski, J. Q. & Shaw, L. M. Longitudinal change in CSF Tau and Abeta biomarkers for up to 48 months in ADNI. Acta Neuropathol 126, 659-670, doi:10.1007/s00401-013-1151-4 (2013).

Vandermeeren, M. et al. Detection of tau proteins in normal and Alzheimer's disease cerebrospinal fluid with a sensitive sandwich enzyme-linked immunosorbent assay. J Neurochem 61, 1828-1834 (1993).

Villemagne, V. L., Fodero-Tavoletti, M. T., Masters, C. L., and Rowe, C. C. (2015). Tau imaging: early progress and future directions. The Lancet Neurology 14, 114-124. doi:10.1016/S1474-4422(14)70252-2.

Wang, Y., and Mandelkow, E. (2016). Tau in physiology and pathology. Nat Rev Neurosci 17, 22-35. doi:10.1038/nrn.2015.

Wang, Y. & Mandelkow, E. Tau in physiology and pathology. Nat Rev Neurosci 17, 5-21, doi:10.1038/nrn.2015.1 (2016).

Xiong, C. et al. Longitudinal relationships among biomarkers for Alzheimer disease in the Adult Children Study. Neurology 86, 1499-1506, doi:10.1212/WNL.0000000000002593 (2016).

Yamada, K. et al. In Vivo Microdialysis Reveals Age-Dependent Decrease of Brain Interstitial Fluid Tau Levels in P301S Human Tau Transgenic Mice. The Journal of Neuroscience 31, 13110-13117, doi:10.1523/jneurosci.2569-11.2011 (2011).

Yamada, K., Holth, J. K., Liao, F., Stewart, F. R., Mahan, T. E., Jiang, H., et al. (2014). Neuronal activity regulates extracellular tau in vivo. J. Exp. Med. 211, 387-393. doi:10.1084/jem.20131685.

Zempel, H., Thies, E., Mandelkow, E. & Mandelkow, E. M. Abeta oligomers cause localized Ca(2+) elevation, missorting of endogenous Tau into dendrites, Tau phosphorylation, and destruction of microtubules and spines. J Neurosci 30, 11938-11950, doi:10.1523/jneurosci.2357-10.2010 (2010).

Example 1—Phosphorylation Sites on Tau Protein in the Normal Non-AD Human Brain

In order to determine phosphorylation sites of normal soluble brain tau, extracts from healthy controls were purified by immunocapture using Tau-1 and HJ8.5 tau antibodies concentrating both phosphorylated and unphosphorylated tau. The tryptic digestion of brain tau isoforms generated 27 unmodified peptides that were long and hydrophobic enough to be detected by LC-MS (Barthélemy et al., 2016). 25 peptides contained serine and/or threonine as potential phosphorylation sites. Several peptides contained multiple potential phosphorylation sites (4-9) leading us to consider different mono-phosphorylated peptides potentially co-eluting together during the LC separation. After this, the PRM screening method described above was applied to these peptides.

Figure 3:
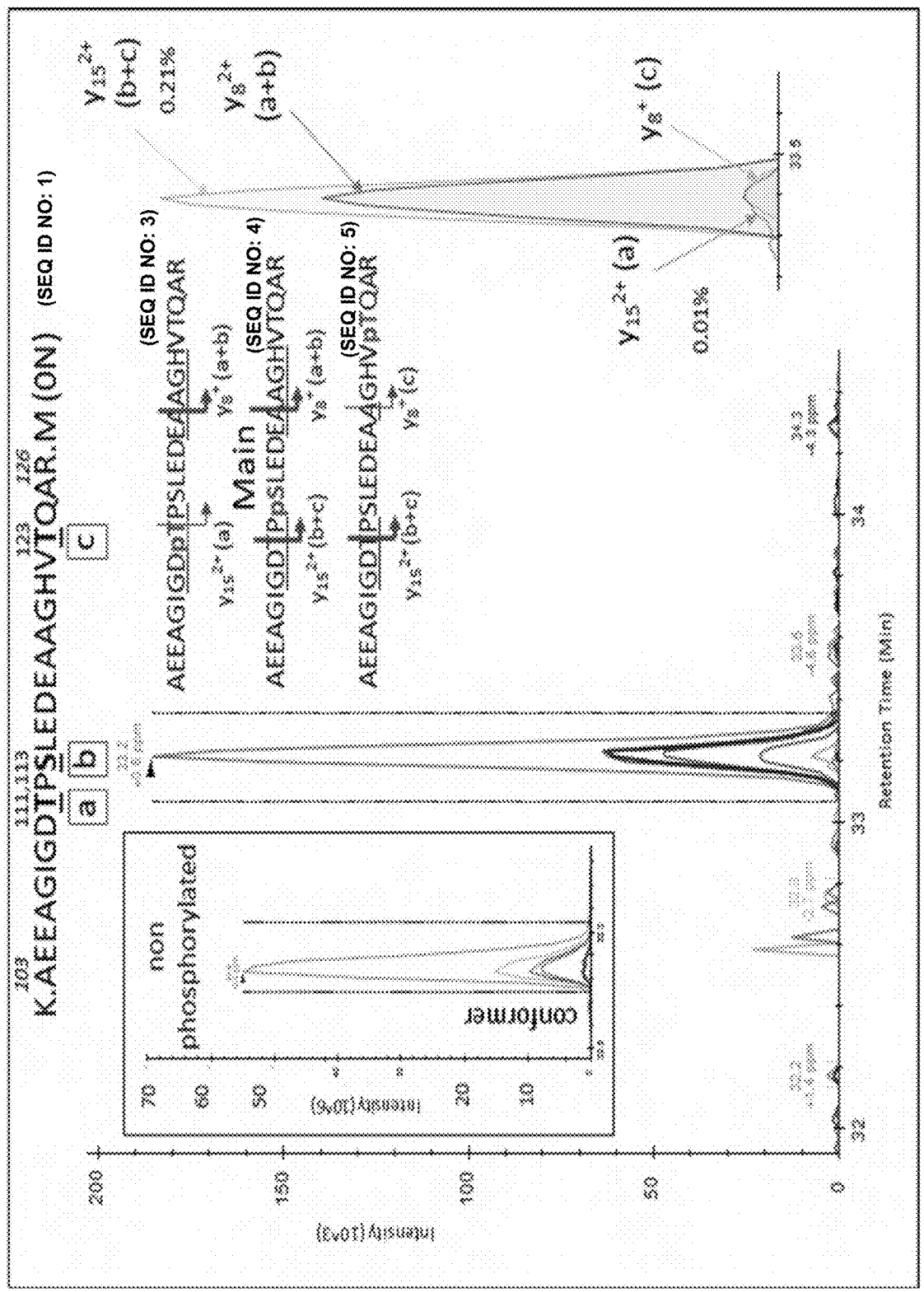
FIG. 3 shows data from a PRM screening of the mono-phosphorylated tau sequence at 103-126 (0N isoform). A unique LC-MS/MS pattern eluting closely to the unmodified peptide 103-126 and containing fragment series expected for phosphorylation at T111 (a), S113 (b) or T123 (c) was identified. Hypothetical y ion fragments from each p-tau peptide are underlined on the sequences. The potential co-elution of the three putative mono-phosphorylated peptides was deconvoluted. Ion fragment y15 without phosphate is specific to the phosphorylated peptide on residue T111 (y15 (a)) and the y8 fragment with phosphate is specific to p-tau peptide on residue T123 (y8 (c)). Corresponding extracted ion chromatograms (XIC) are detected in low abundance above the limit of detection, supporting the identification of the two corresponding mono-phosphorylated tau peptides. In contrast, the y15 fragment with phosphate, shared by pT111 and pS113 (y15 (a+b)), and the y8 fragment without phosphate, shared by pS113 and pT123 (y8 (b+c)), are much more abundant. These signal differences support the existence of the tau peptide mono-phosphorylated at residue S113 (b) as the main specie of the pattern. For each chromatogram, the x-axis is retention time (minutes) and the y-axis is intensity.
Figure 4:
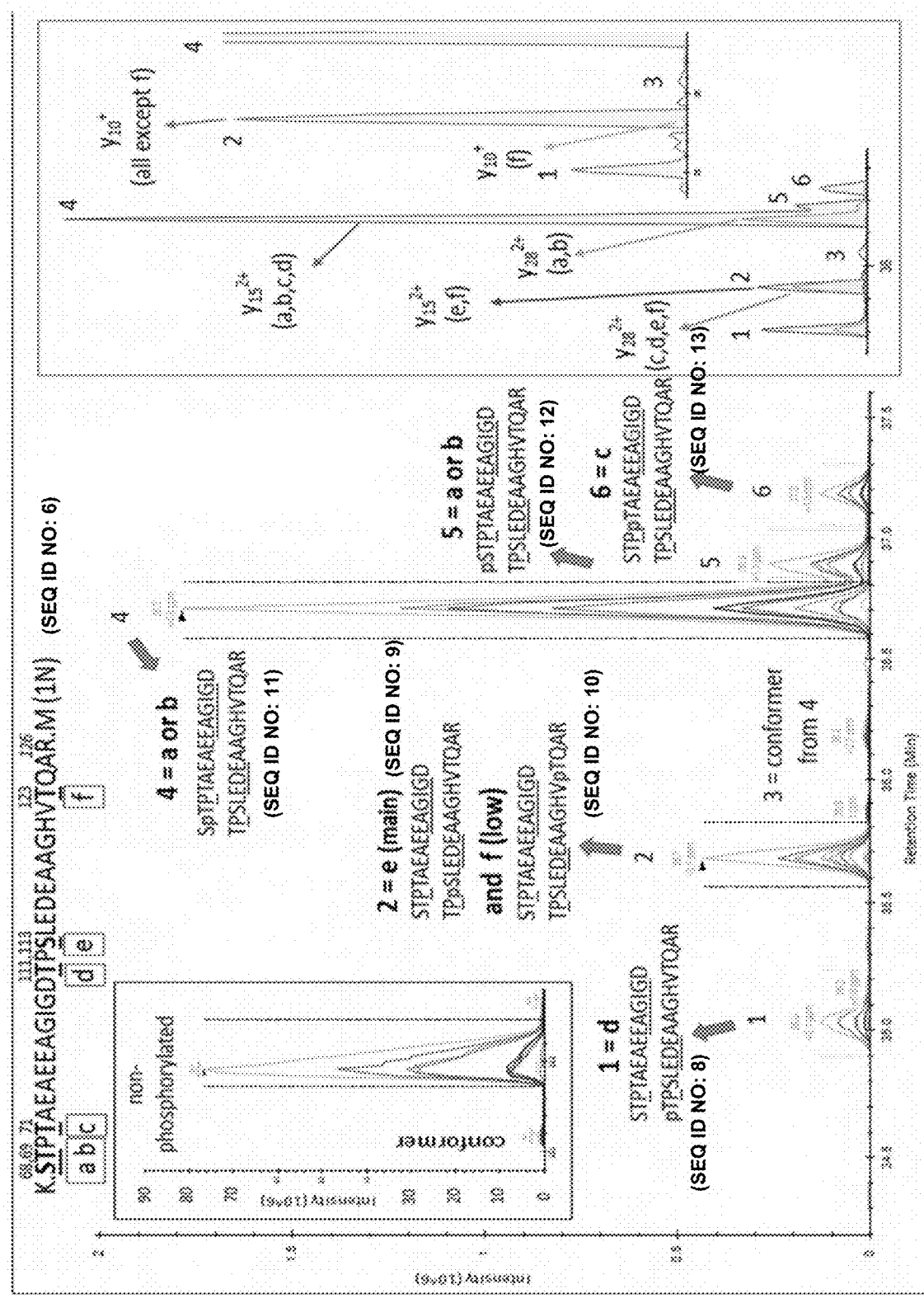
FIG. 4 shows data from a PRM screening of mono-phosphorylated tau sequence 68-126 (1N isoform) containing six potential phosphorylation sites. Three phosphorylation sites are shared by peptides containing residues 103-126 as described in FIG. 3 (d-f). Six LC-MS patterns were identified. The Y28 fragment carrying phosphate, shared by pS68 (a) or pT69 (b), is found in the two LC-MS patterns 4 and 5. This demonstrates the existence of the two phosphorylated peptides but corresponding LC-MS patterns cannot be strictly assigned without the detection of ion fragment y29 to differentiate pS68 and pT69. Specific fragments corresponding to pT71 (c) and pT111 (d) are found in LC-MS patterns 6 and 1, respectively. Specific fragments for pS113 (e) and pT123 (f) (y15 with phosphate) are found in the LC-MS pattern 2. This pattern contained both y10 fragments with and without phosphate, suggesting the co-elution of these two phosphorylated peptides. Since y10 without phosphate has the major signal in comparison to y10 with phosphate, the degree of pT123 is likely lower than pS113. LC-MS pattern 3 is attributed to a minor conformer or LC artifact from the phosphorylated peptide from pattern 4 as found for the non-phosphorylated peptide. For each chromatogram, the x-axis is retention time (minutes) and the y-axis is intensity.
Figure 5:
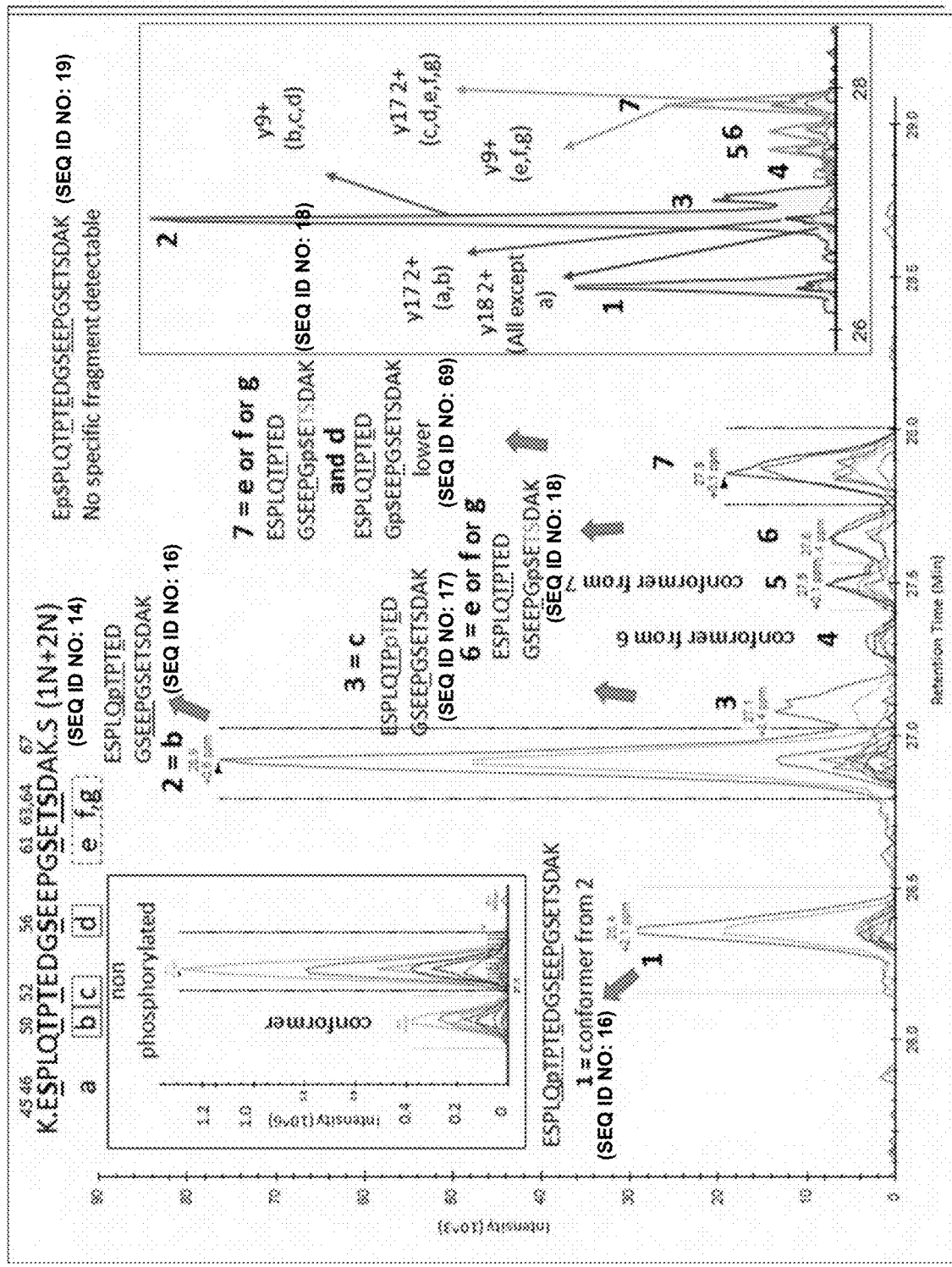
FIG. 5 shows data from a PRM screening of mono-phosphorylated tau sequence 45-67 (1N and 2N isoforms). A strong signal from a conformer was identified on the front of a non-phosphorylated peptide LC-MS pattern. Thus, it was predicted that corresponding LC-MS patterns for phosphorylated peptides would also have conformers separable by LC. Indeed, PRM scan interpretation led to the detection of pT50 (b) as the main phosphorylation site on this sequence (pattern 2). Pattern 1, with a similar fragmentation fingerprint, was attributed to a conformer of pT50. pS46 (a), able to differentiate signals from pT50 (b), was not detected, suggesting this phosphorylation would be absent or low and co-eluted with other phosphorylated peptides sharing similar non-specific fragments. Co-elution of y9, y15 without phosphate, and y17 with phosphate in LC-MS pattern 3 identified a phosphorylation on residue T52 (c). Patterns 4/6 and 5/7 were respectively paired as conformers. Thus, two phosphorylated peptides could not be separated. Fragments found in these patterns were consistent with phosphorylation on one of the S61 (e), T63 (f), and S64 (g) residues. MS/MS intensities were insufficient to identify the sites but at least 2 of these 3 sites were likely phosphorylated on this sequence. Additionally, a minor y9 fragment without phosphate was found in the shoulder of pattern 7, which could be attributed to minor phosphorylation on residue S56 (d). For each chromatogram, the x-axis is retention time (minutes) and the y-axis is intensity.
Figure 6:
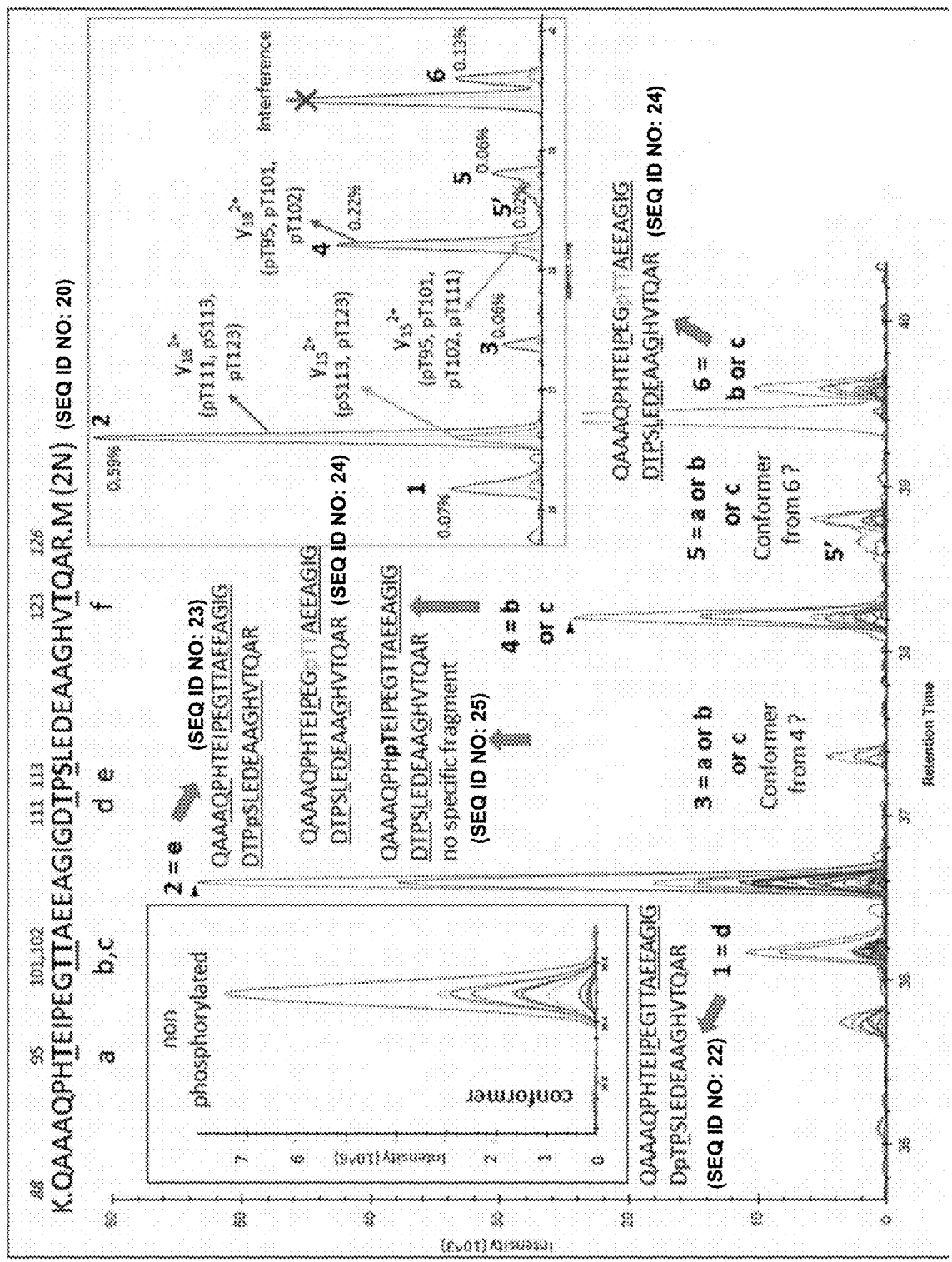
FIG. 6 shows data from a PRM screening of mono-phosphorylated tau sequence 88-126 (2N isoform). 6 potential phosphorylation sites are located in this sequence and 6 LC-MS patterns were identified. Fragments found in pattern 1 and 2 were consistent with phosphorylated peptides at residues T111 (d) and S113 (e), respectively. No specific fragment from the phosphorylated peptide at residue T123 (f) was found. Patterns 4 and 6 contained a low signal of the y29 fragment matching with phosphorylation on residue T101 (b) or T102 (c), but no specific fragment able to differentiate them was detected. Patterns 3 and 5 shared fragments found in patterns 4 and 6 but in lower abundance, locating the phosphorylated residue at the N-terminus on residue G109. This could indicate the presence of an additional phosphorylated peptide, likely at residue T95 (a) or abundant conformers from peptides found in patterns 4 and 6. For each chromatogram, the x-axis is retention time (minutes) and the y-axis is intensity.
Figure 7:
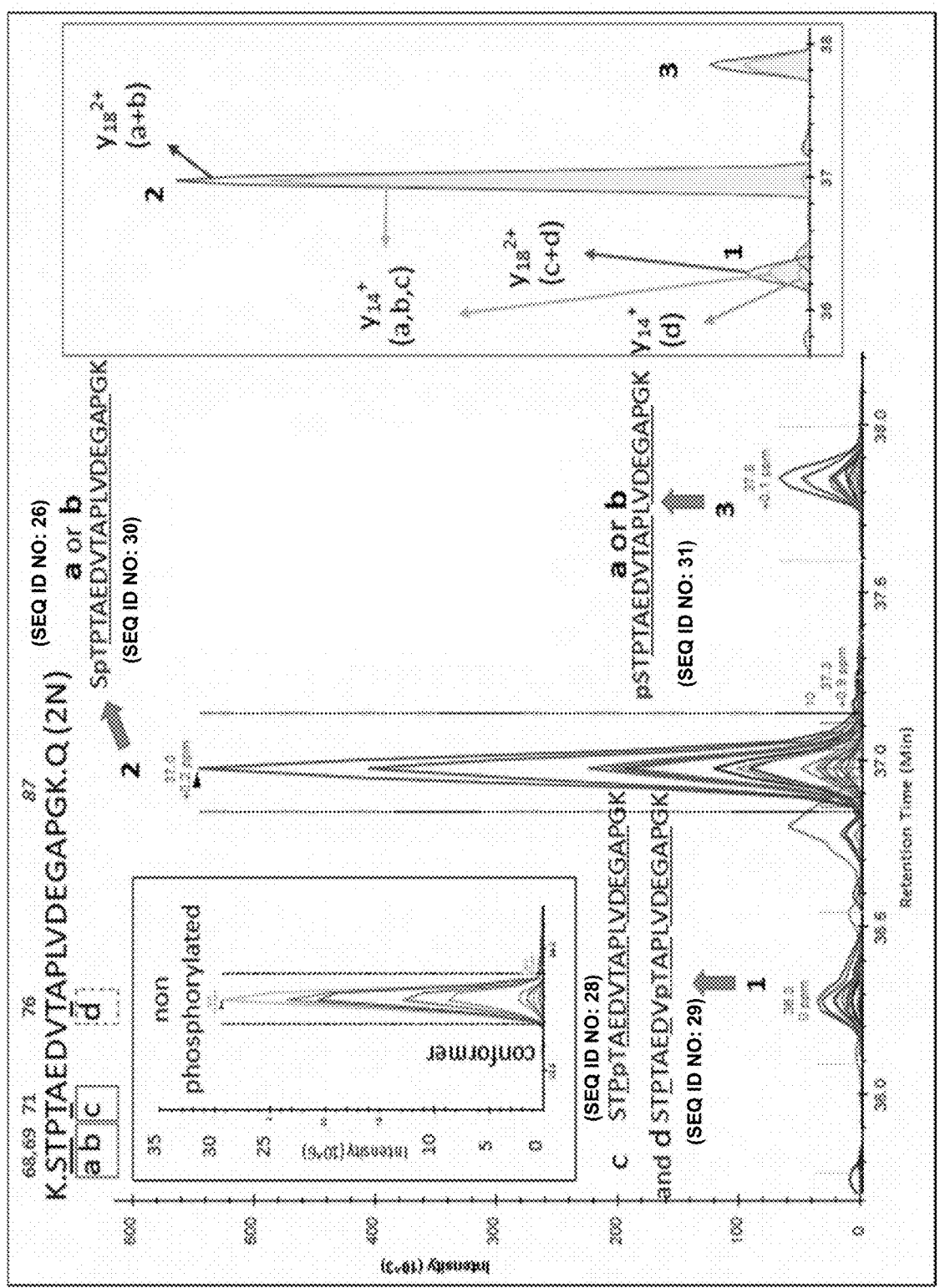
FIG. 7 shows a PRM scan of mono-phosphorylation tau sequence 68-87, containing 4 potential phosphorylation sites. 3 LC-MS patterns were detected. Patterns 2 and 3 were consistent with phosphorylation at residues S68 (a) or T69 (b). Pattern 1 contained both fragments compatible with the presence of two co-eluted phosphorylated peptides at T71 (c) and T76 (d). Comparison of y14 XIC with and without phosphate in pattern 1 indicates pT71 (c) is more abundant than pT76 (d). For each chromatogram, the x-axis is retention time (minutes) and the y-axis is intensity.
Figure 8A:
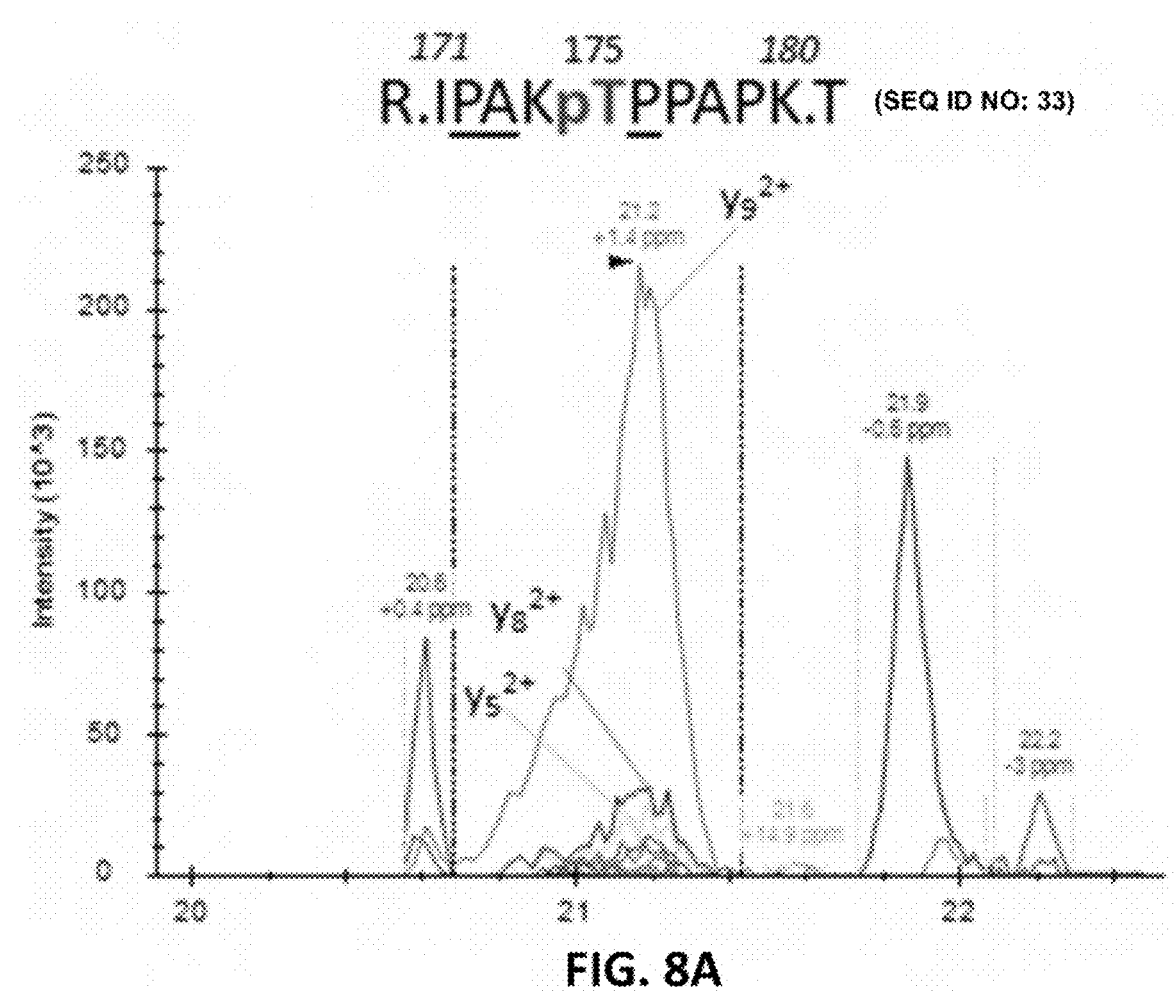
FIG. 8A, FIG. 8B, FIG. 8C, FIG. 8D, FIG. 8E, FIG. 8F, FIG. 8G, FIG. 8H, FIG. 8I, FIG. 8J, FIG. 8K, and FIG. 8L show detection of phosphorylation sites in the mid-domain and C-terminus of brain p-tau protein. For each chromatogram, the x-axis is retention time (minutes) and the y-axis is Intensity.
Figure 8B:
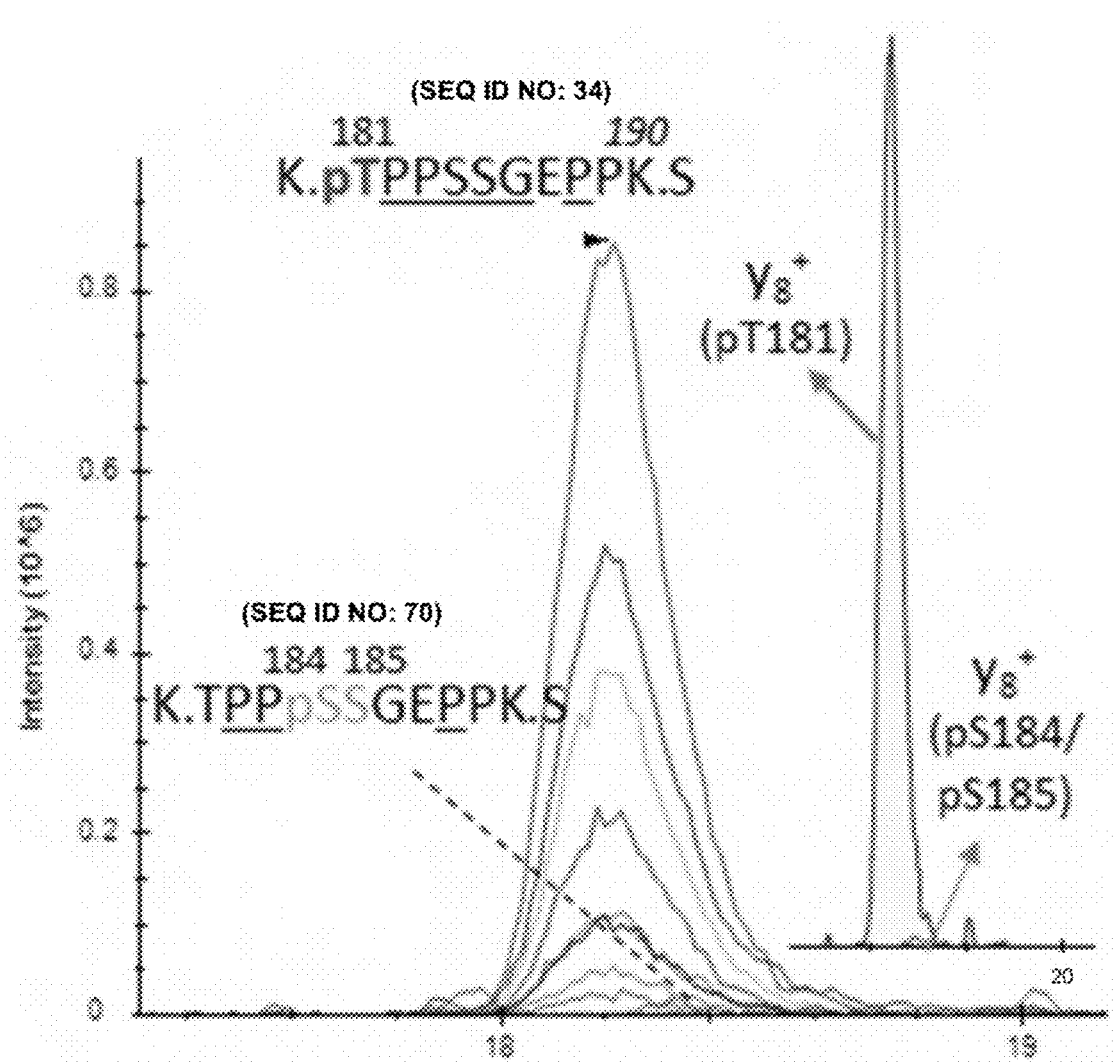
Figure 8C:
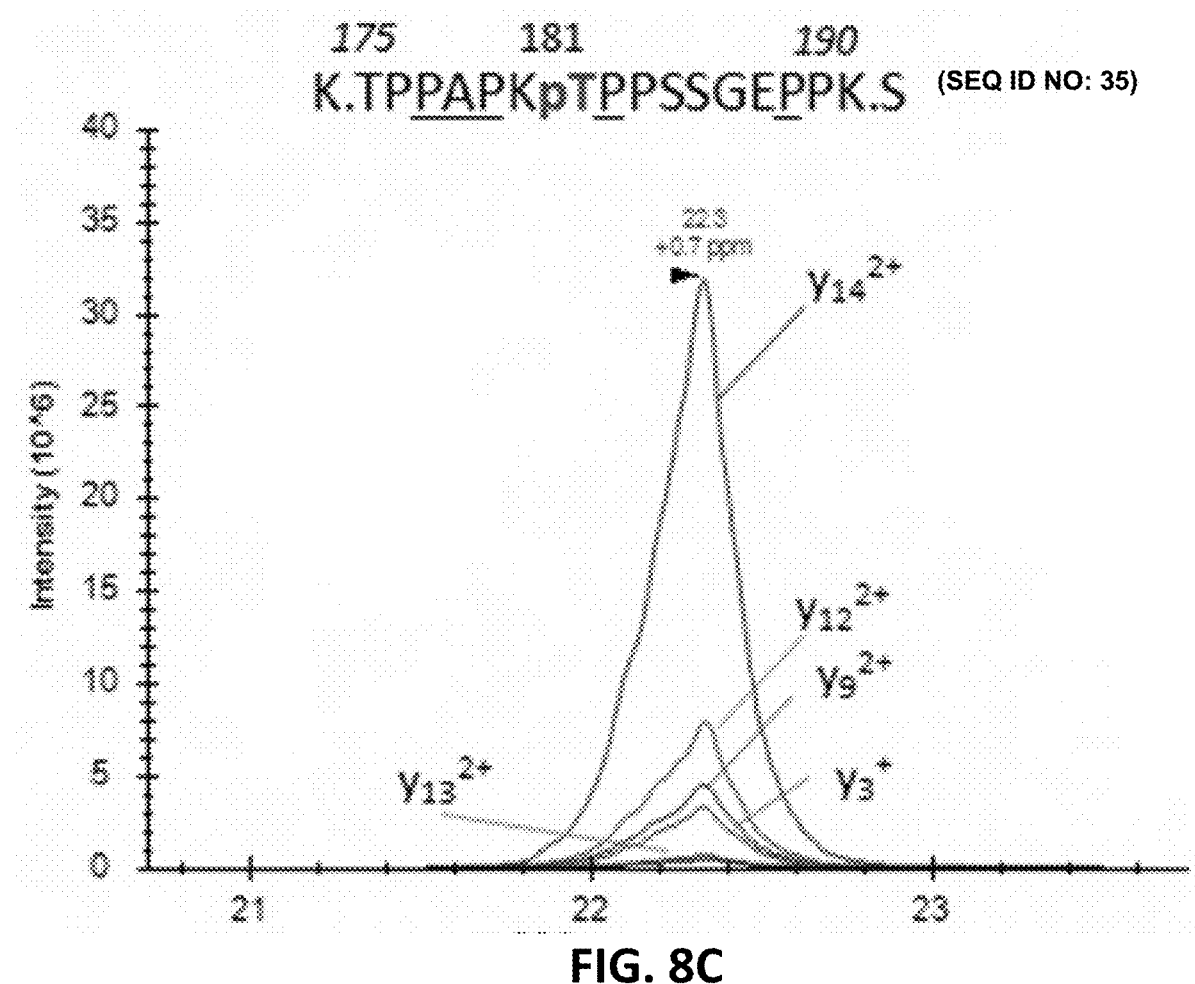
Figure 8D:
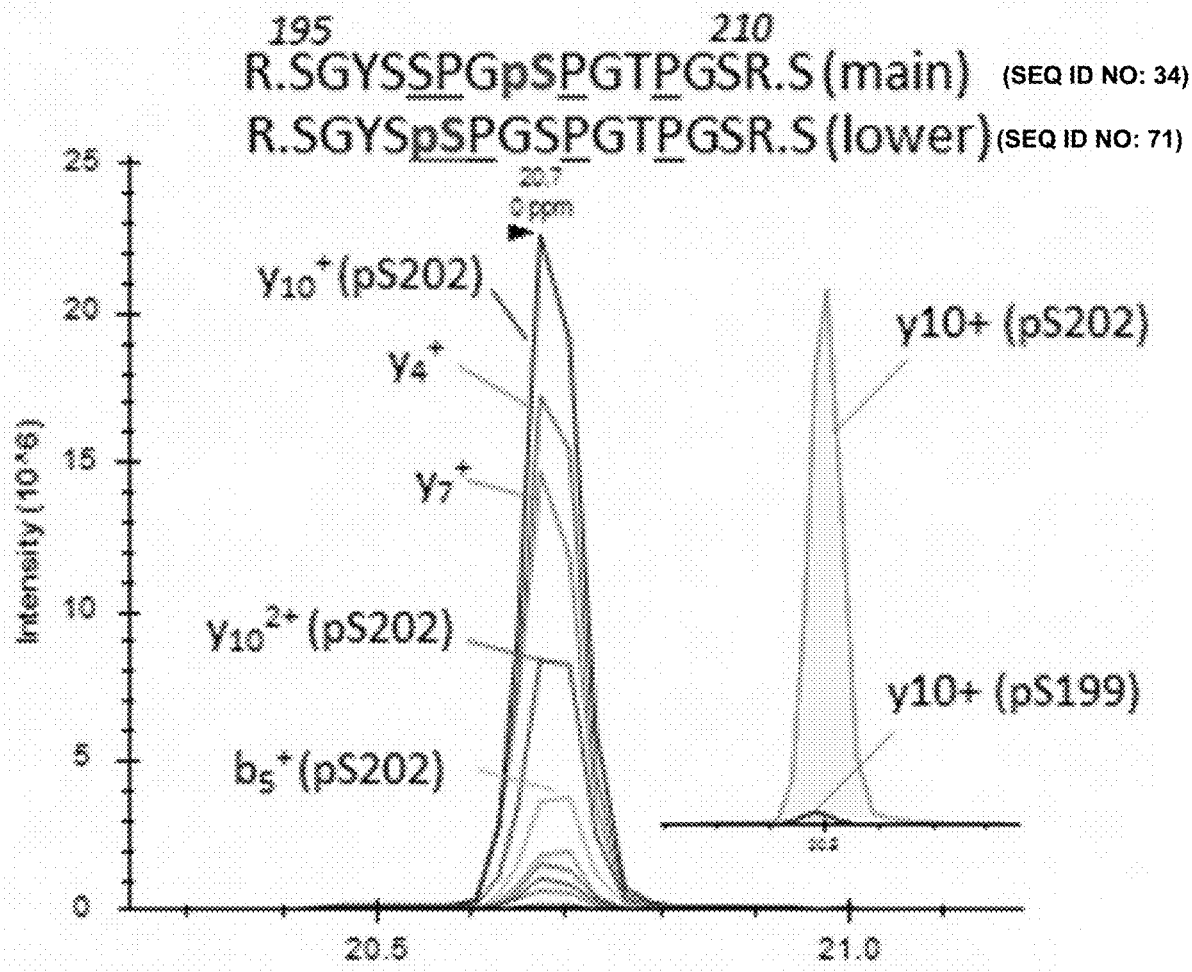
Figure 8E:
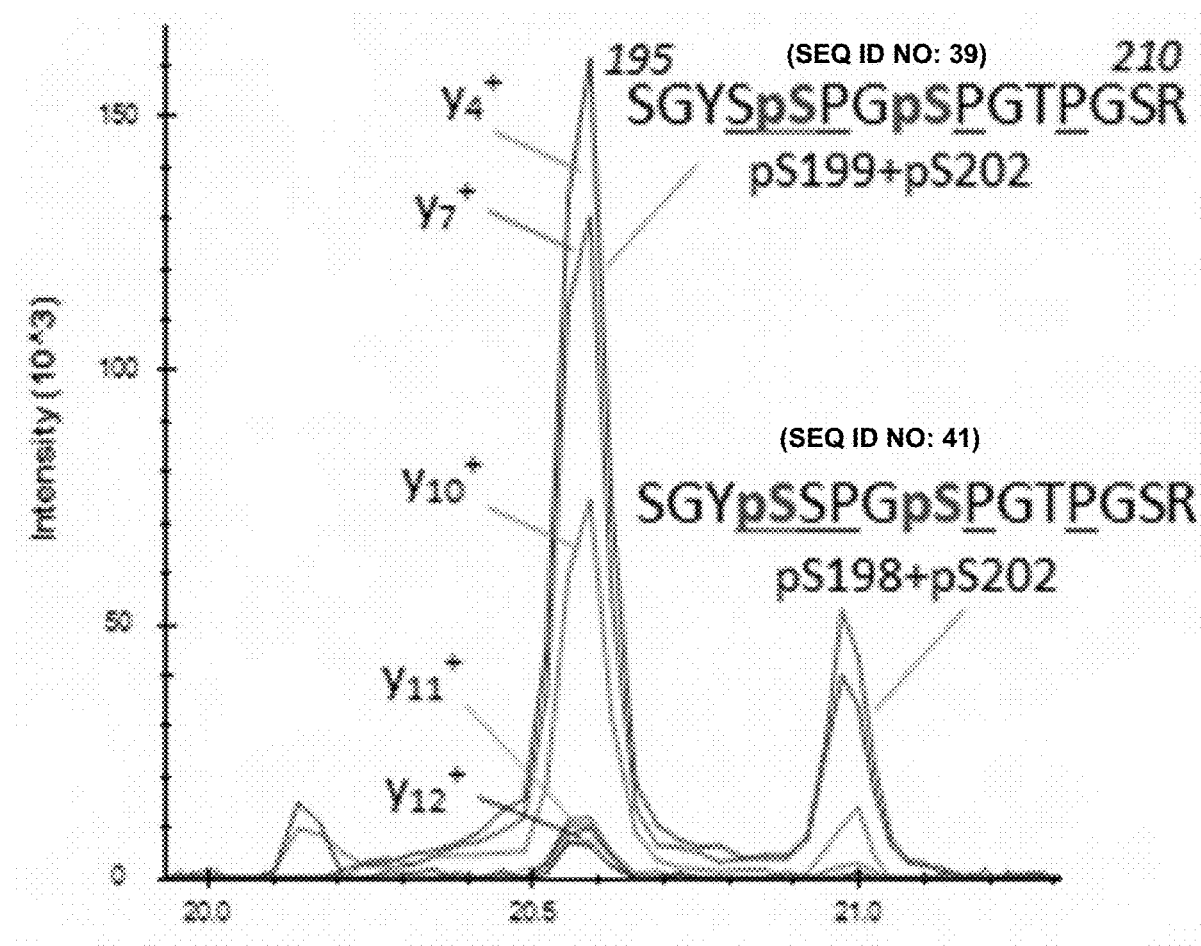
Figure 8F:
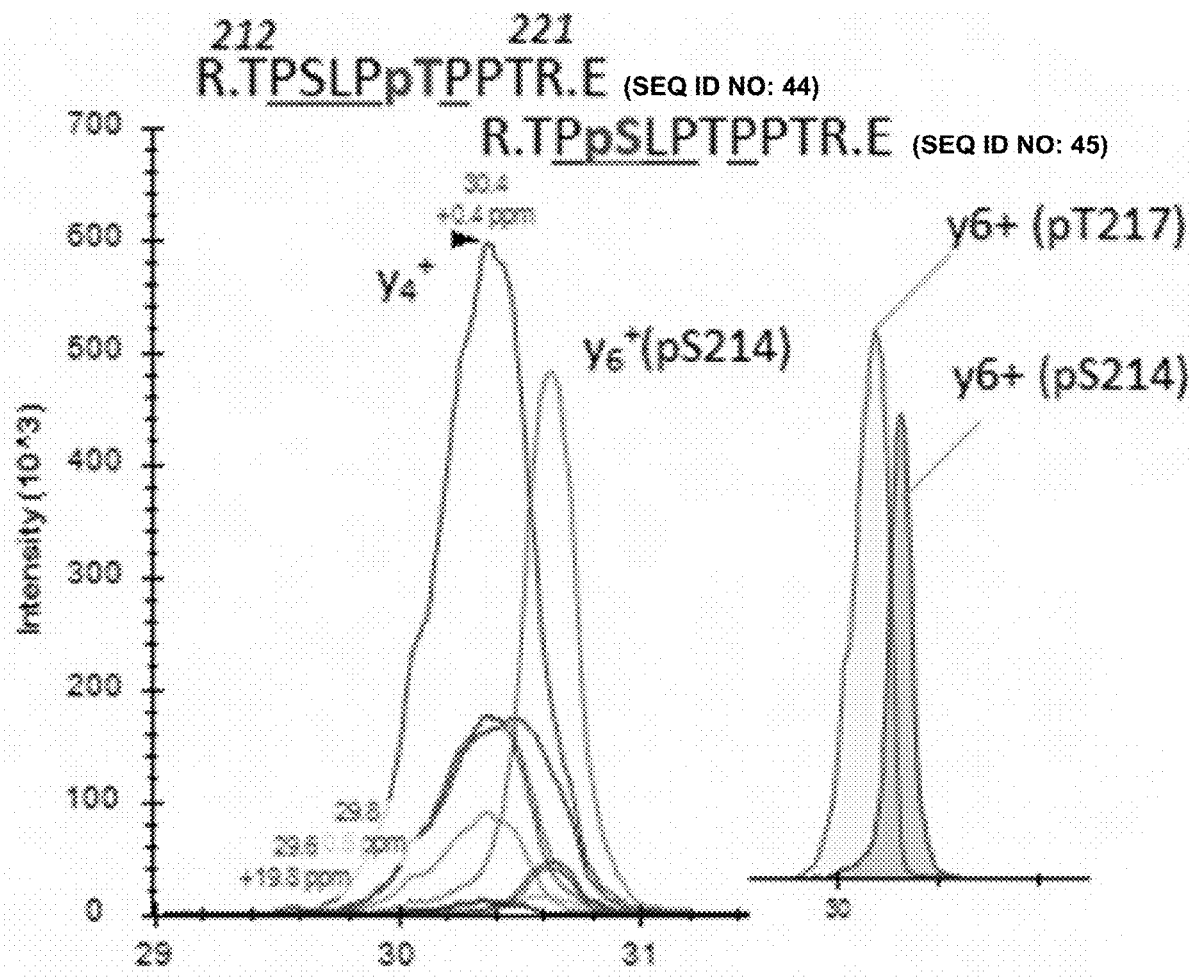
Figure 8G:
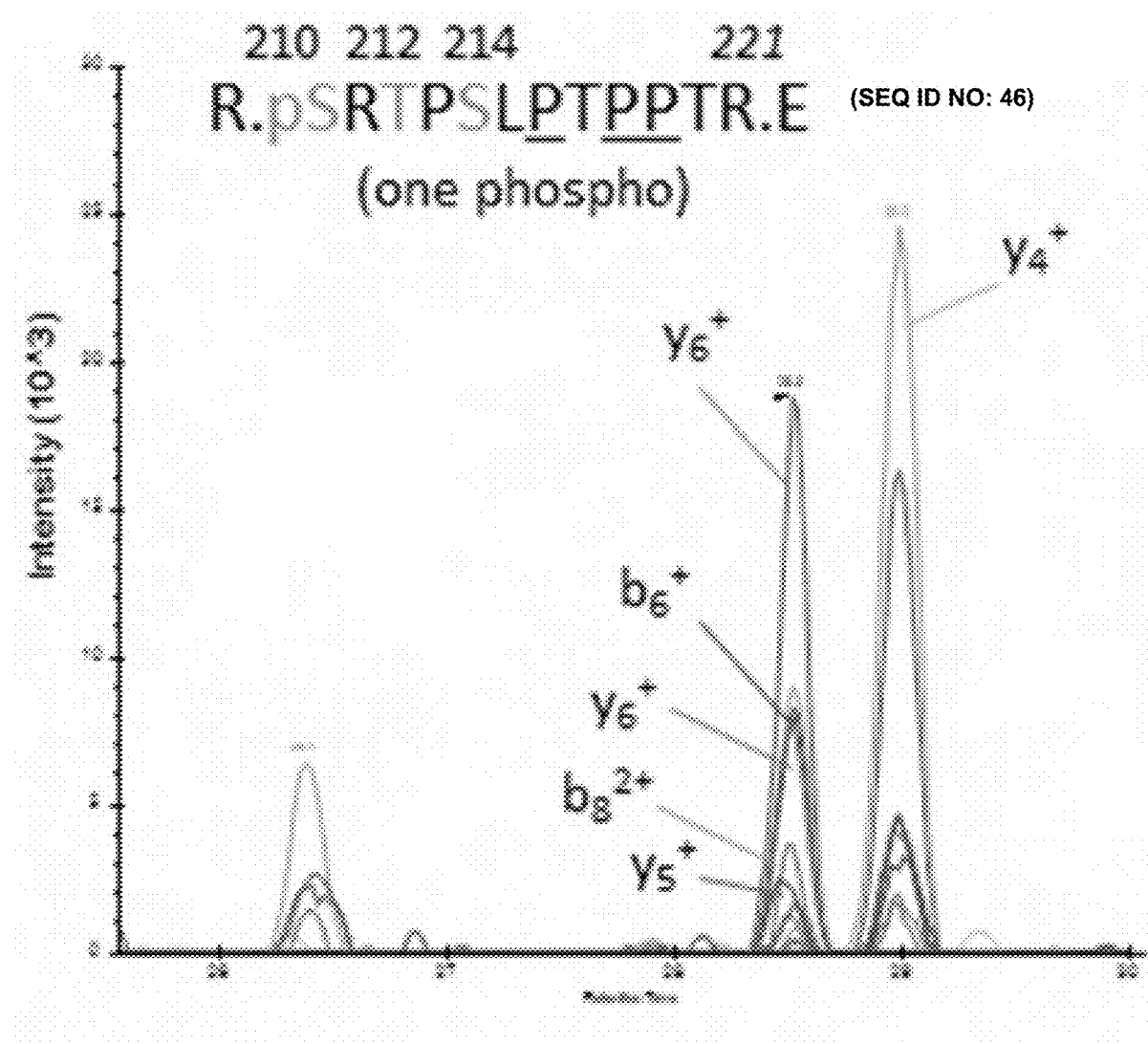
Figure 8H:
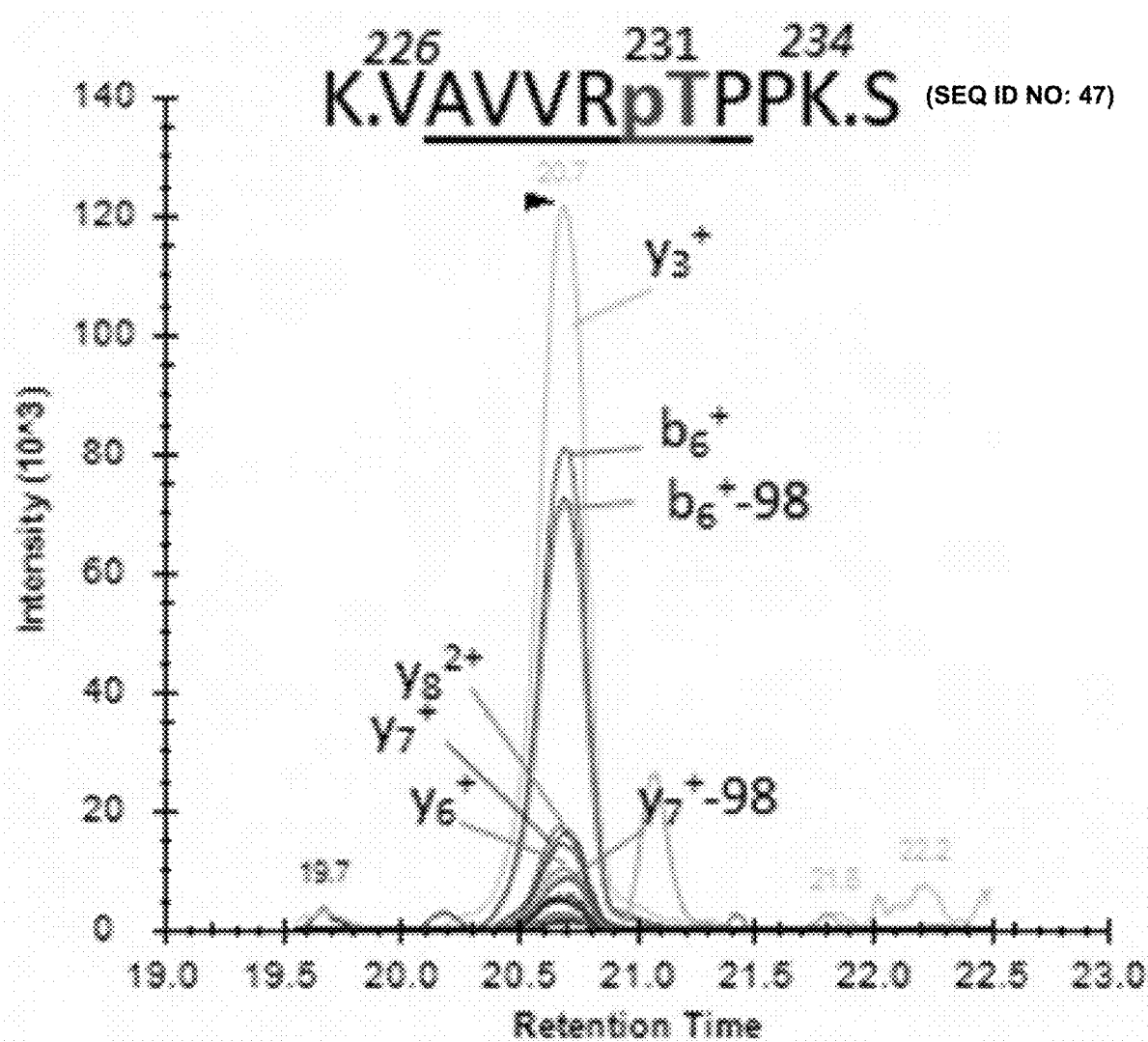
Figure 8I:
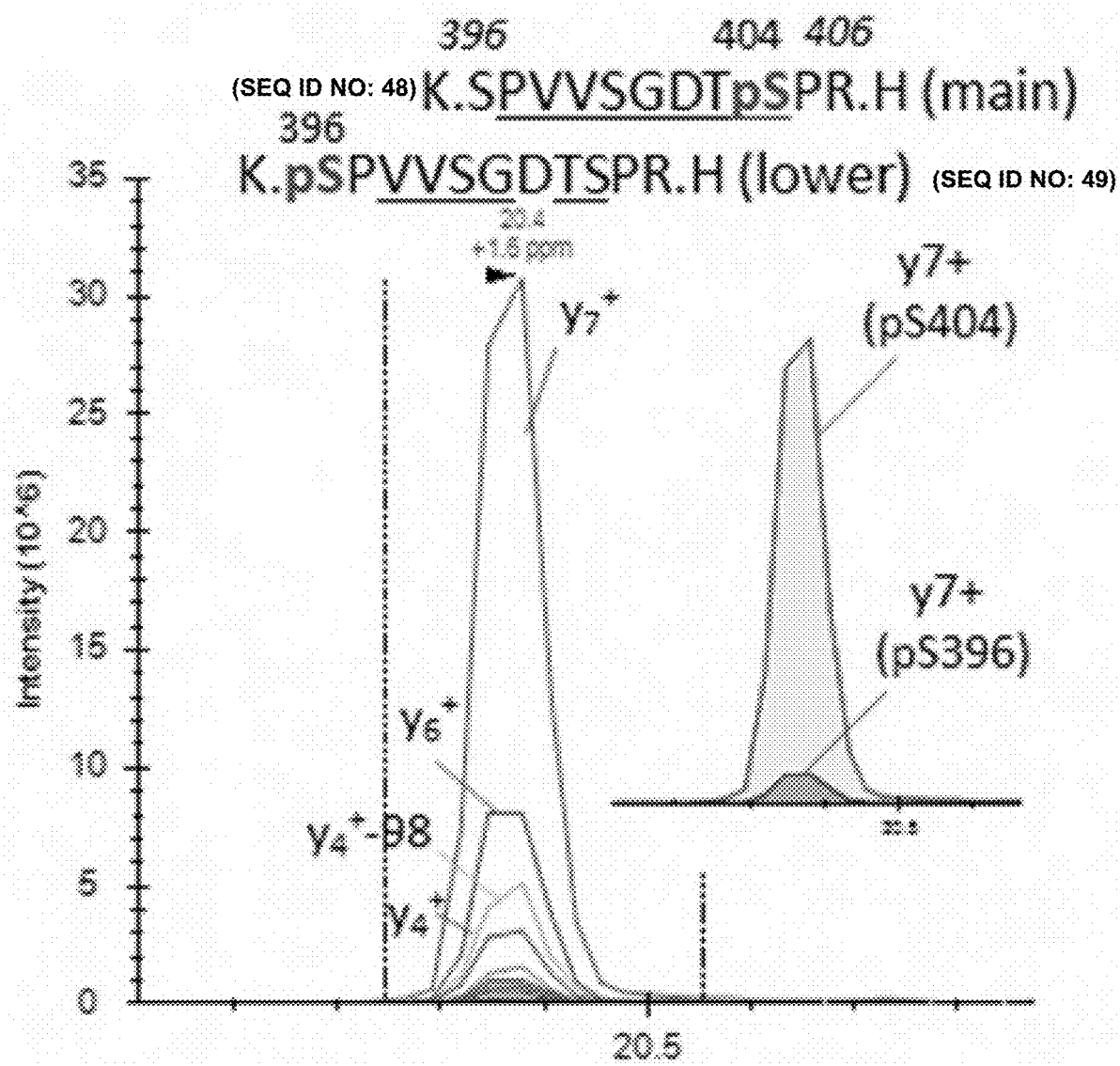
Figure 8J:
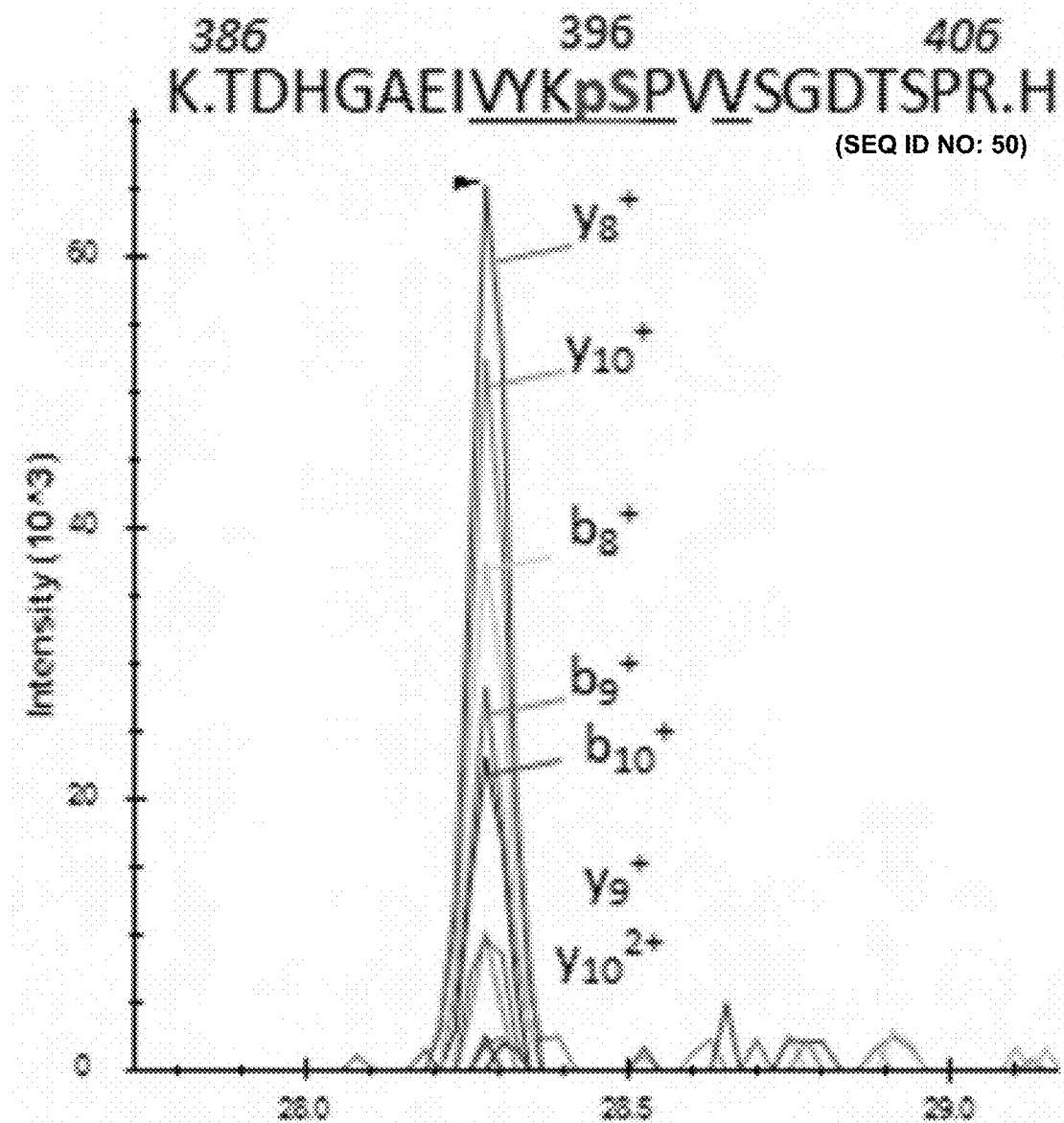
Figure 8K:
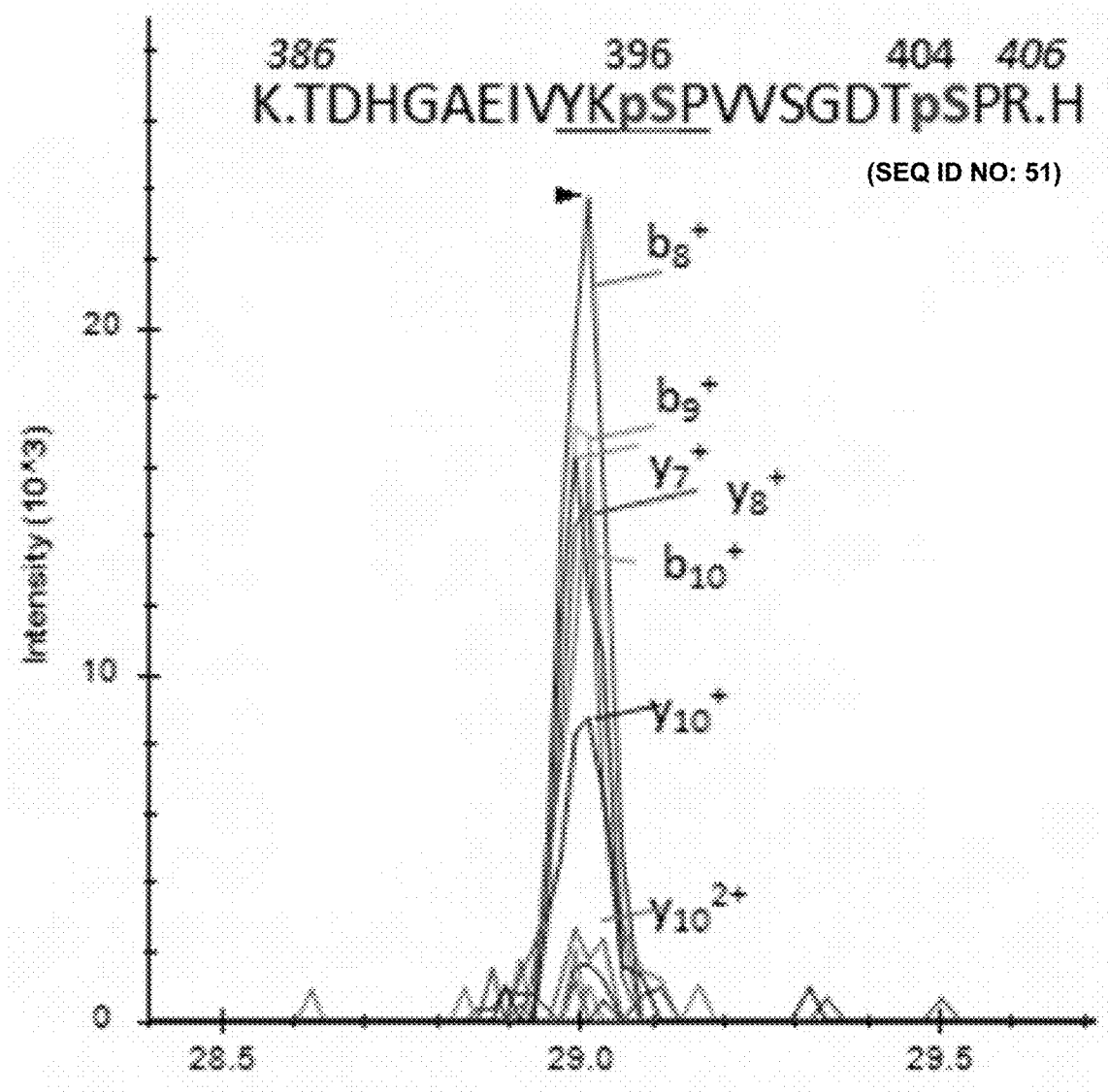
Figure 8L:
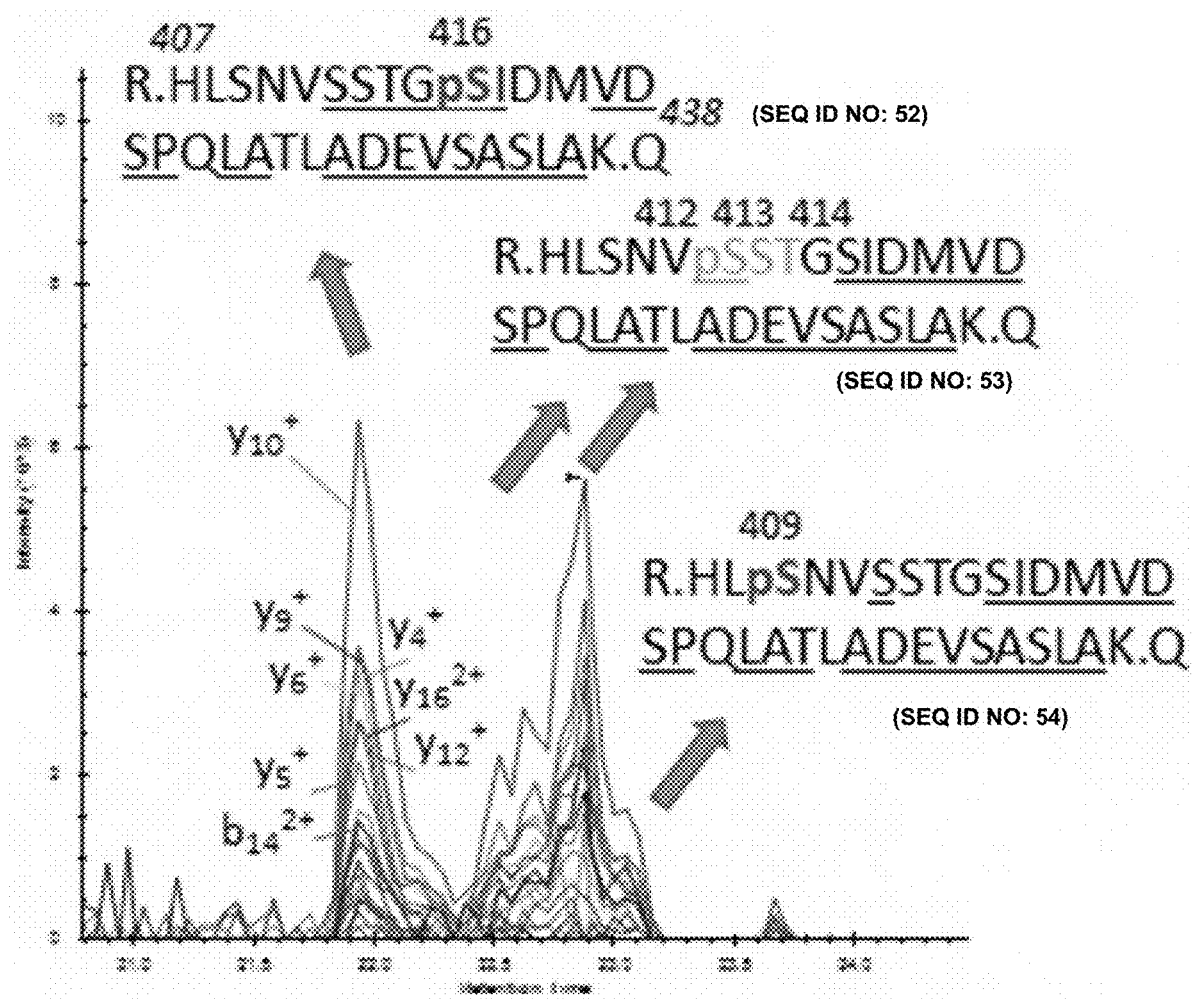
Figure 9A:
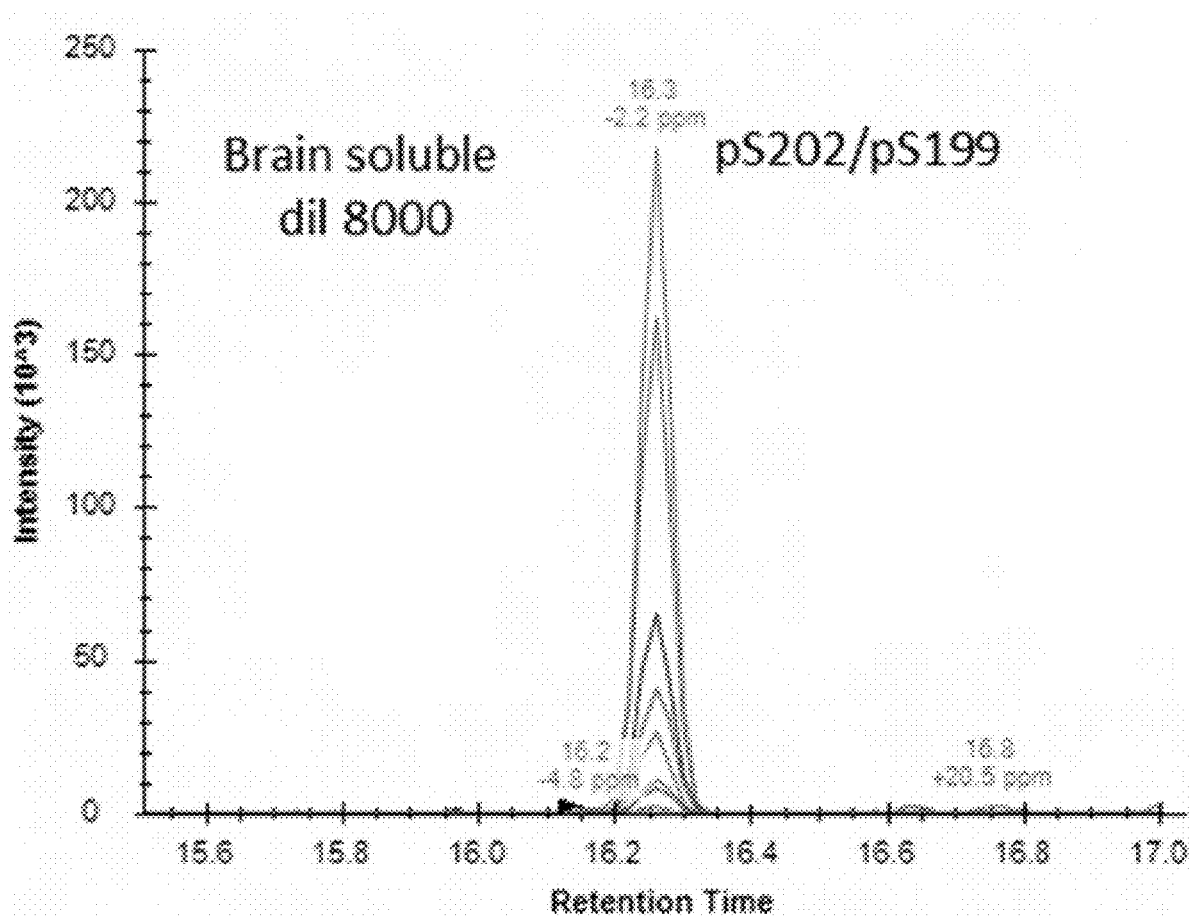
FIG. 9A, FIG. 9B, FIG. 9C, FIG. 9D, FIG. 9E, and FIG. 9F show phosphorylated peptide profiles from tau sequences 195-209 (SEQ ID NO: 38) and 212-221 (SEQ ID NO: 64) are variable between the soluble brain fraction, normal CSF, and AD CSF tau protein. Brain soluble tau extracts are diluted as indicated to approximately match corresponding CSF tau level. Phosphorylated peptides on 195-209: in brain lysate, one signal corresponding to the co-elution of two phosphorylated peptides pS199 and pS202 is observed. In CSF, two additional signals are observed. Fragment analysis allowed the assignment of the signal on left to pT205. In AD CSF, the two signals are increased allowing the identification of specific fragments assigning the signal on the right to pS208. Phosphorylated peptides on 212-221: two signals with similar MS intensities corresponding to pT217 and pS214 are identified in brain lysate. In CSF, the signal corresponding to pT217 is the most intense while pS214 is close to the limit of detection, indicating a dramatic change in their relative abundance in comparison to the brain extract. In AD CSF, pT217 is significantly increased due to specific hyperphosphorylation. For each chromatogram, the x-axis is retention time (minutes) and the y-axis is Intensity.
Figure 9B:
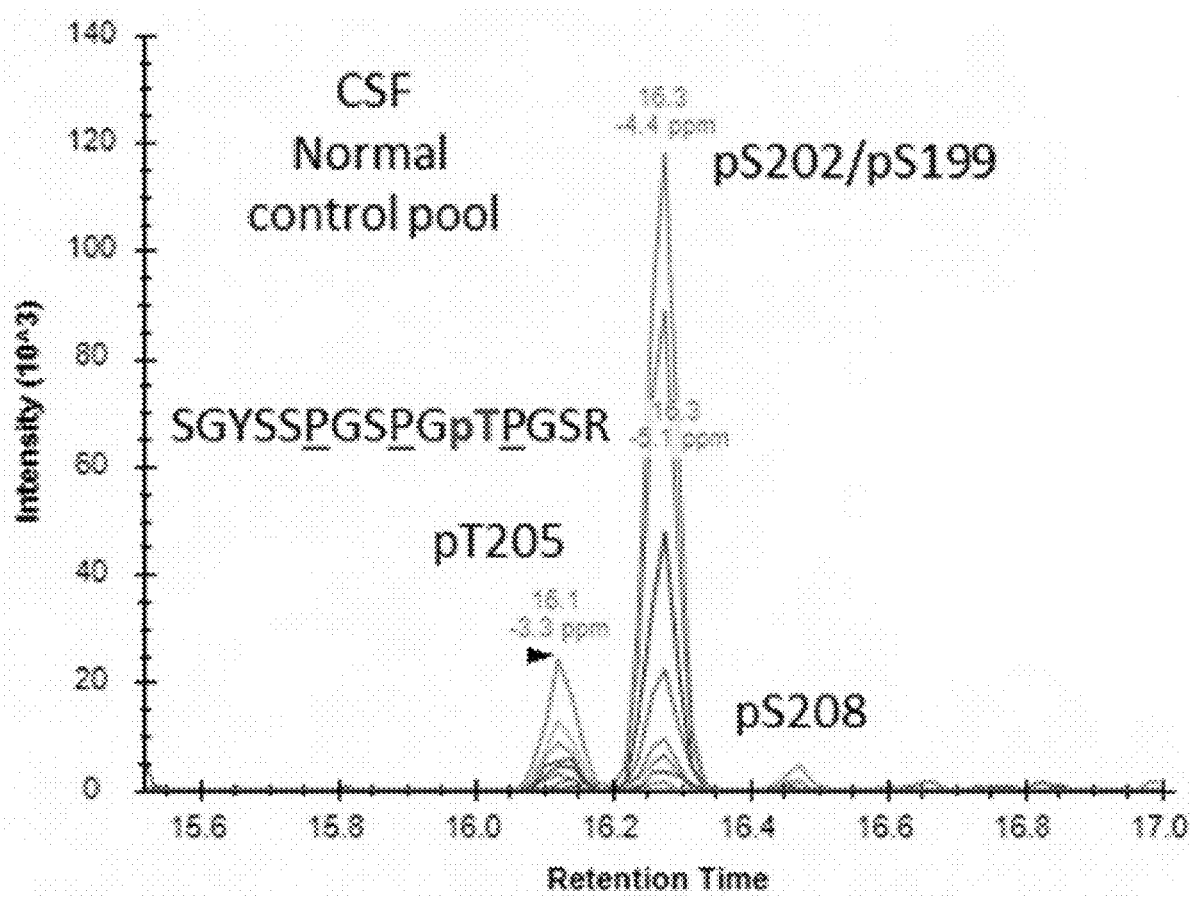
Figure 9C:
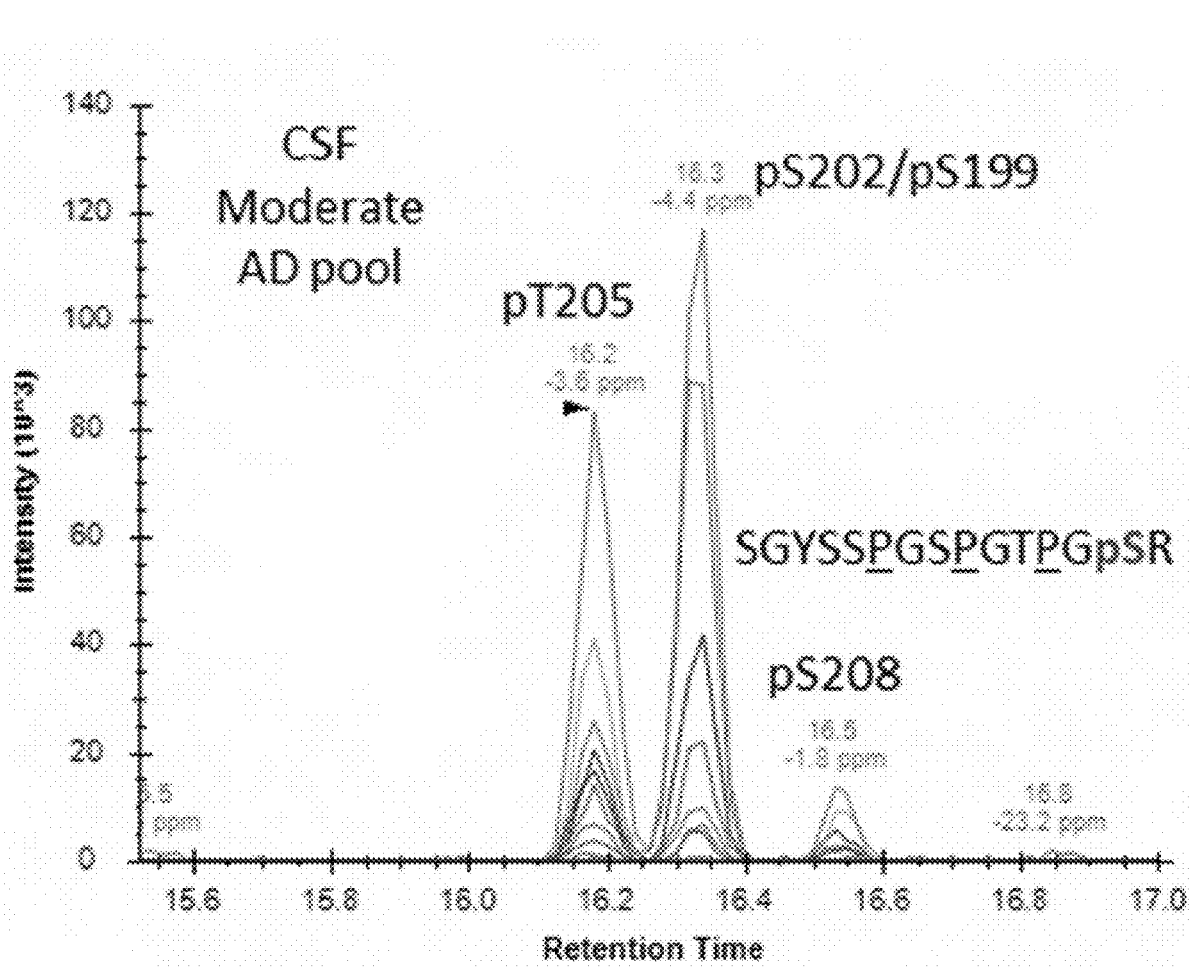
Figure 9D:
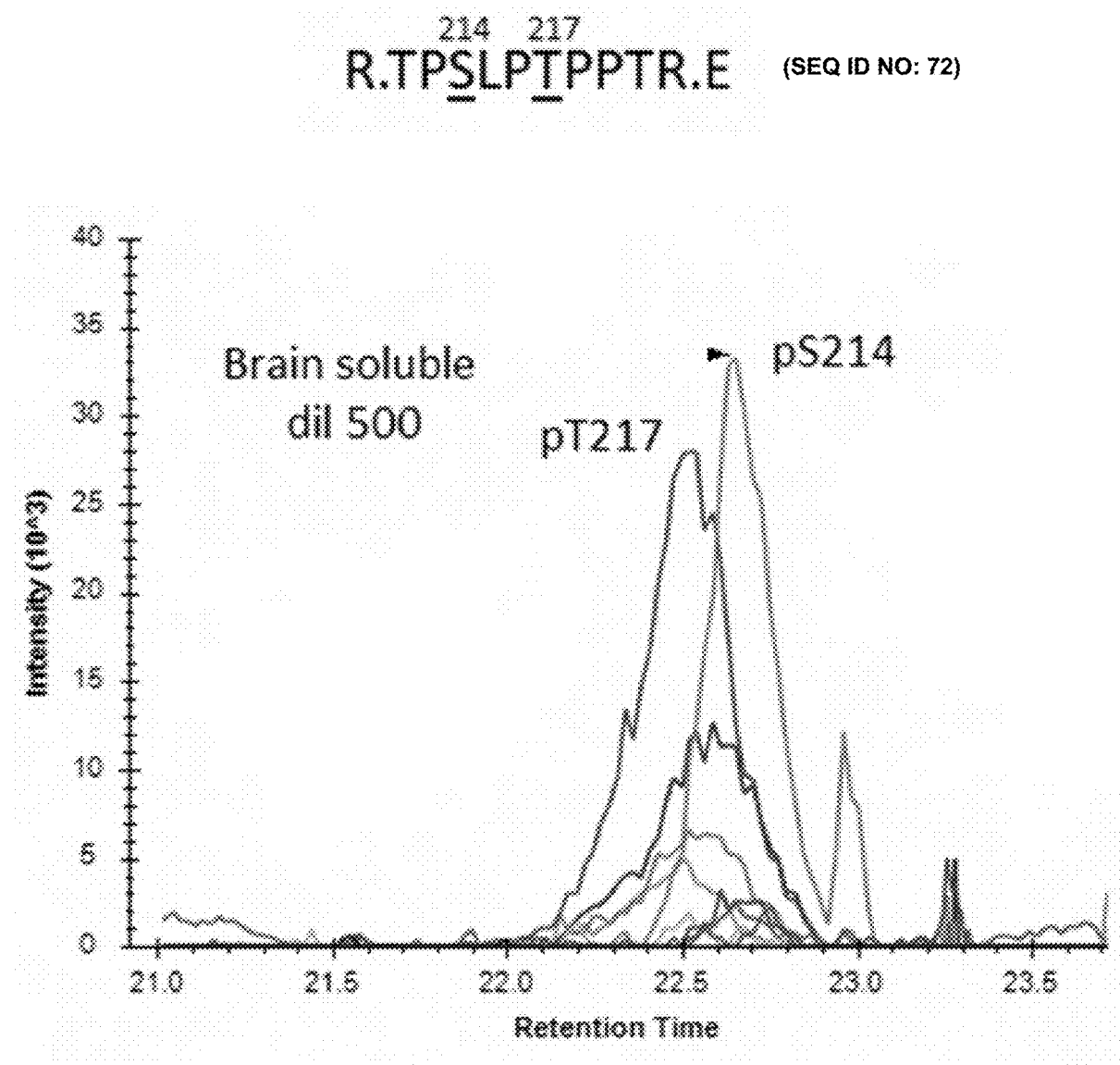
Figure 9E:
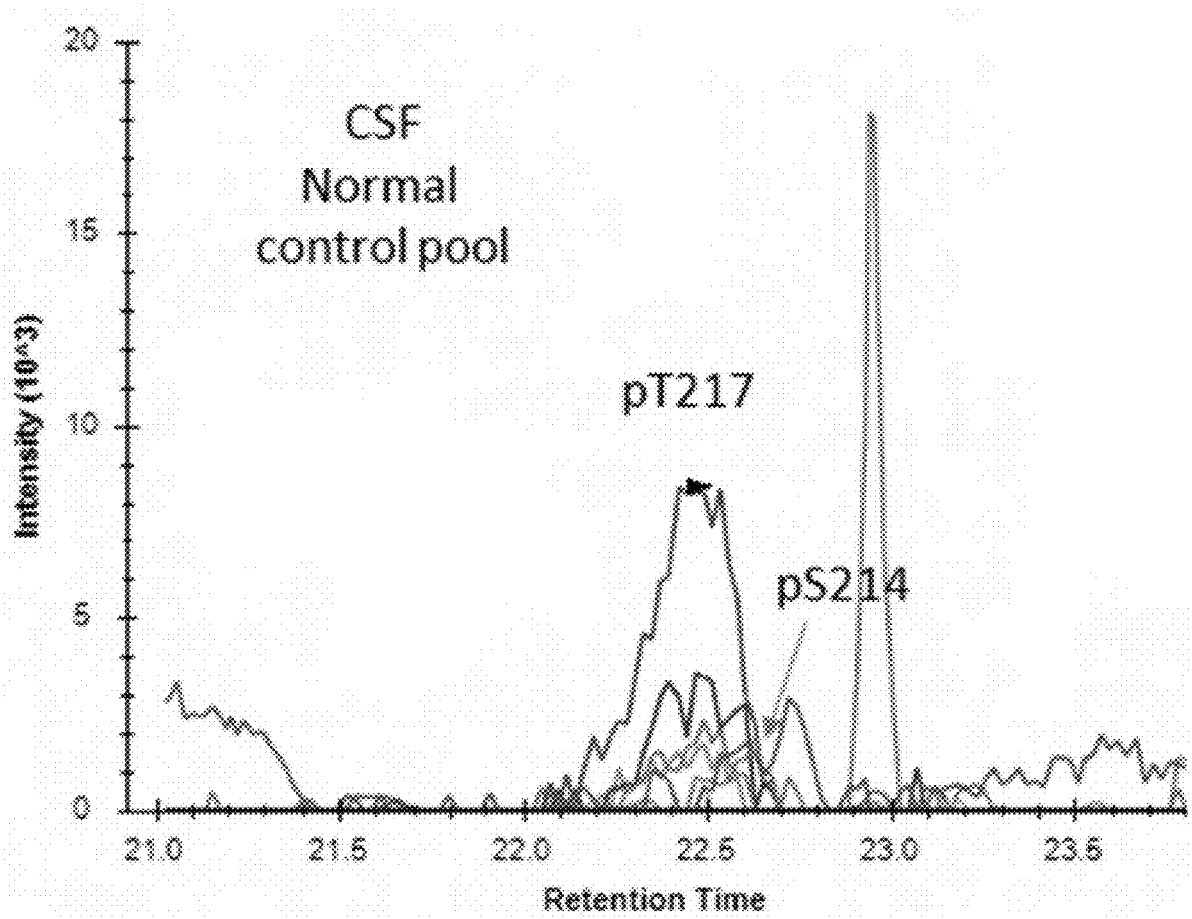
Figure 9F:
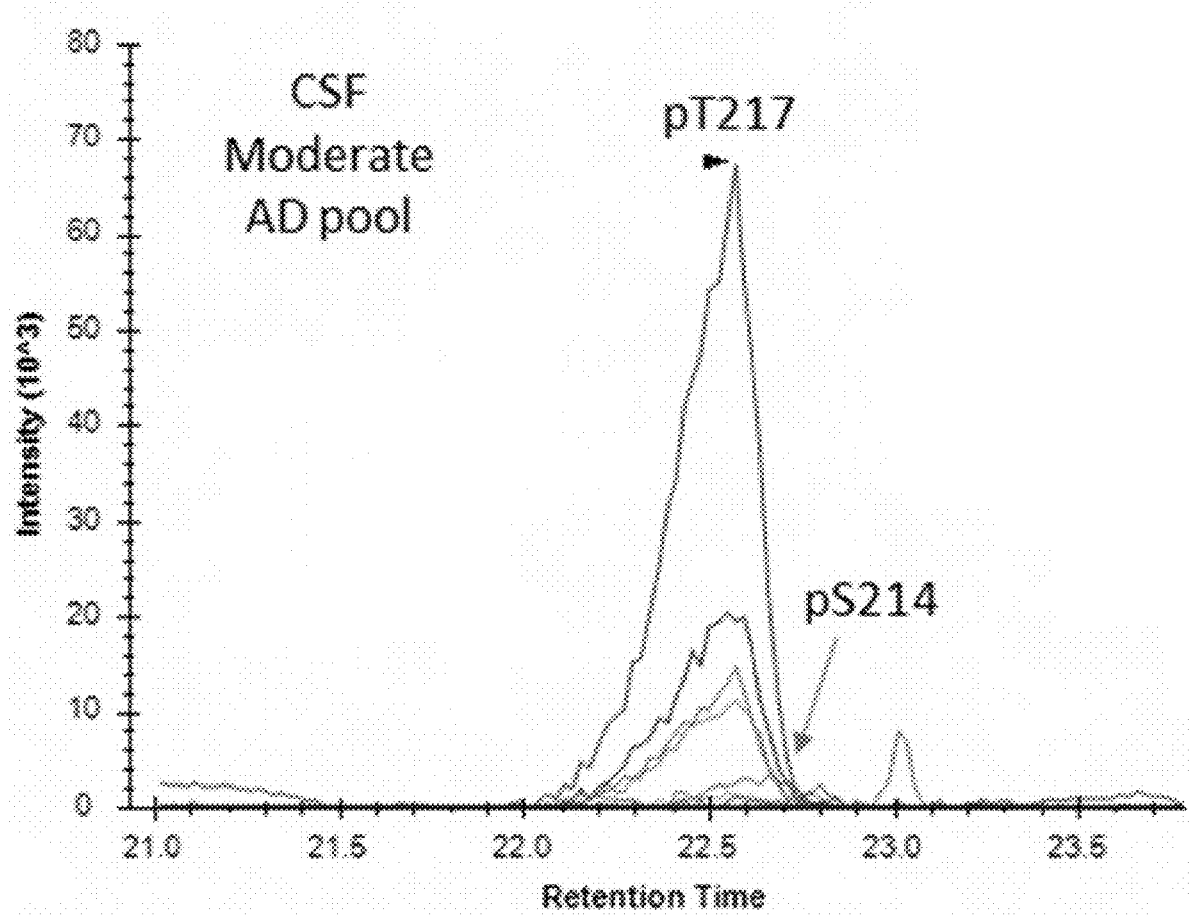
Figure 10A:
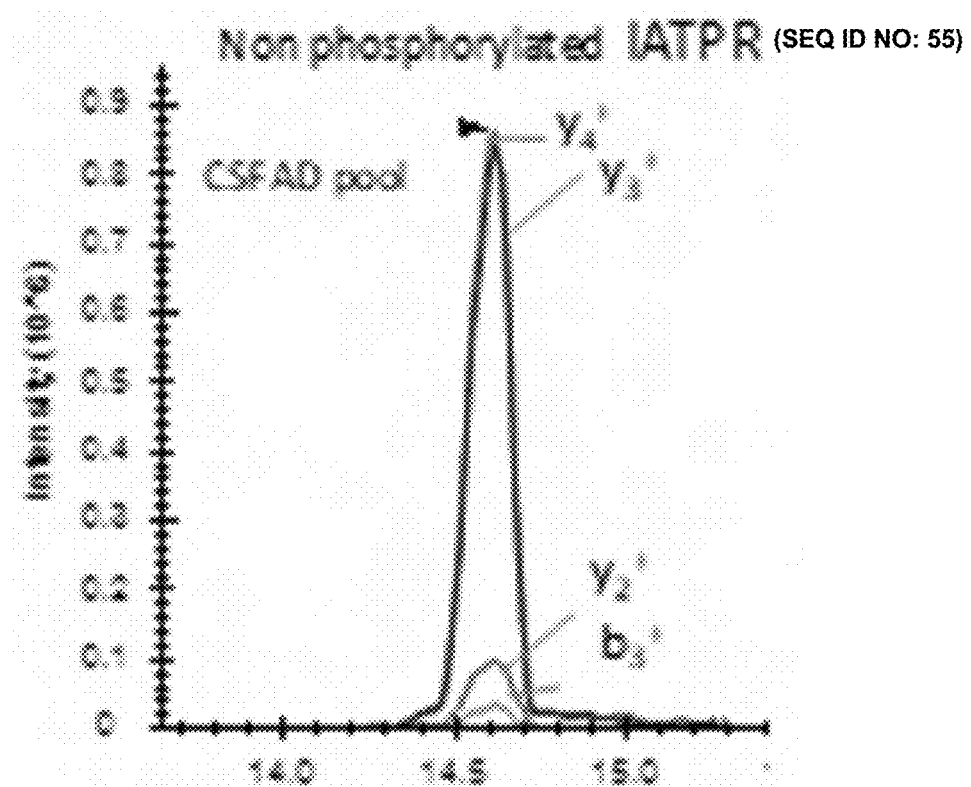
FIG. 10A, FIG. 10B, FIG. 10C, FIG. 10D, FIG. 10E, FIG. 10F, FIG. 10G, FIG. 10H, and FIG. 10I show pT153, pT175 and pT231 phosphorylated peptides identified in CSF. AQUA internal standard signals are shown for pT175 and pT231. Fragmentation pattern of pT153 is similar to unmodified. For each chromatogram, the x-axis is retention time (minutes) and the y-axis is Intensity.
Figure 10B:
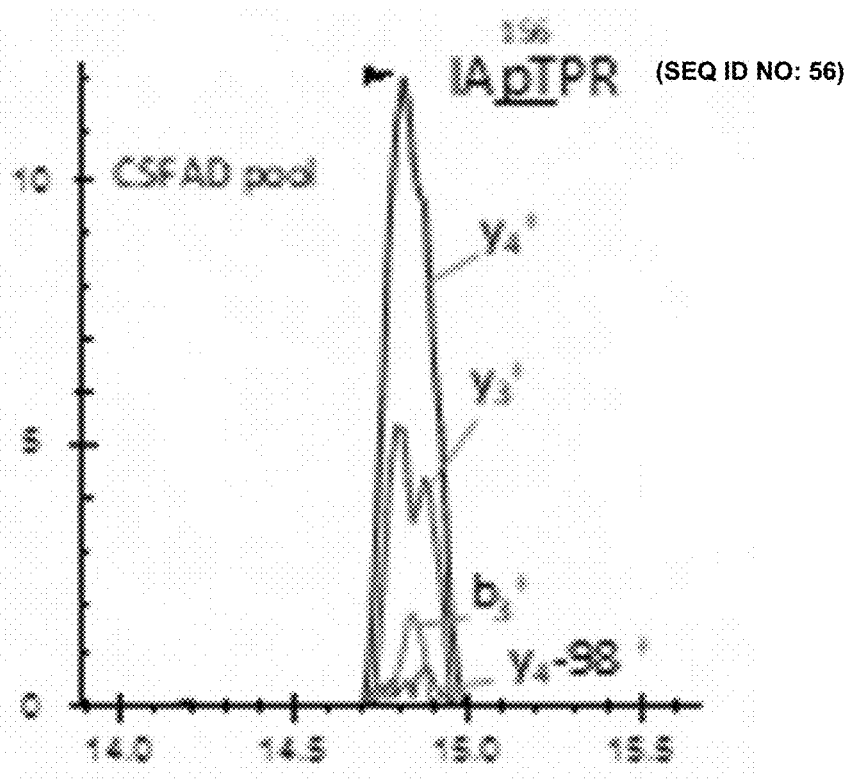
Figure 10C:
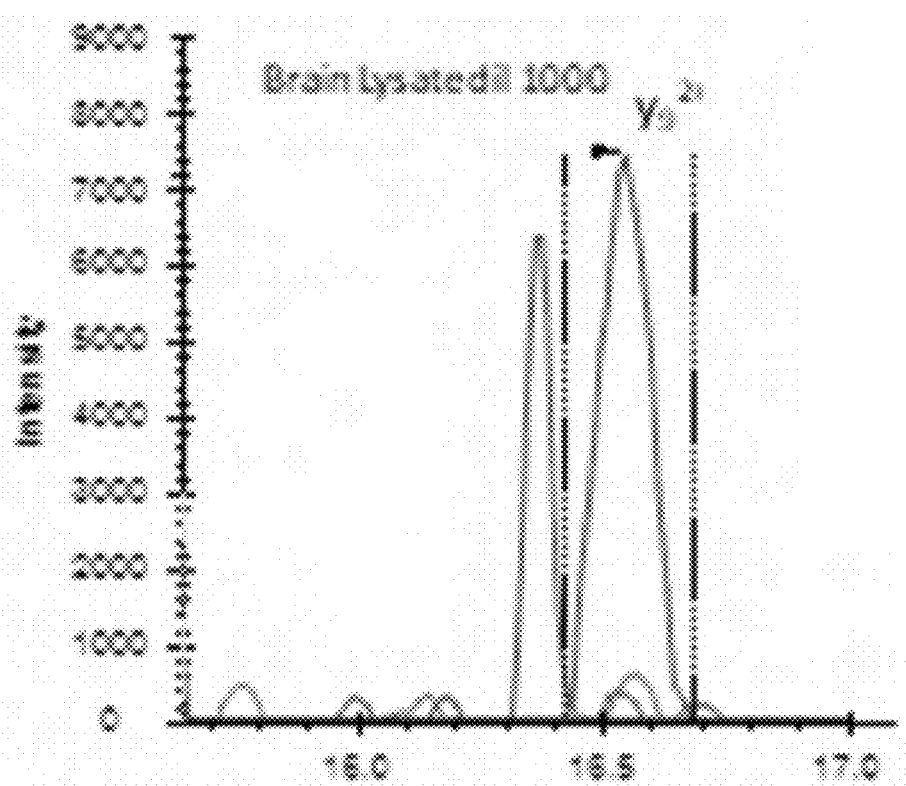
Figure 10D:
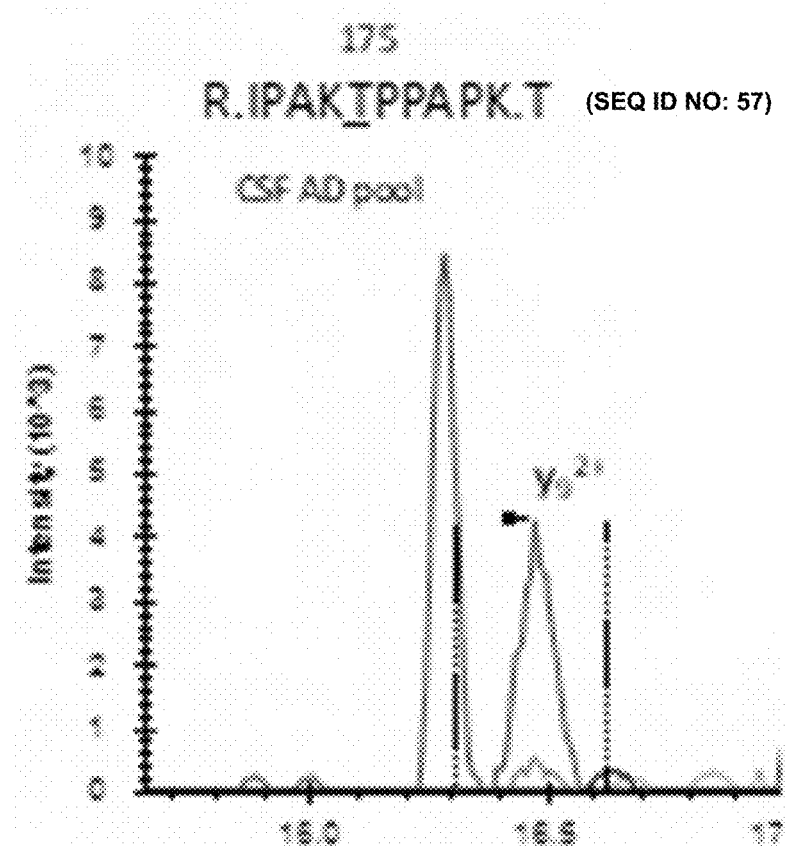
Figure 10E:
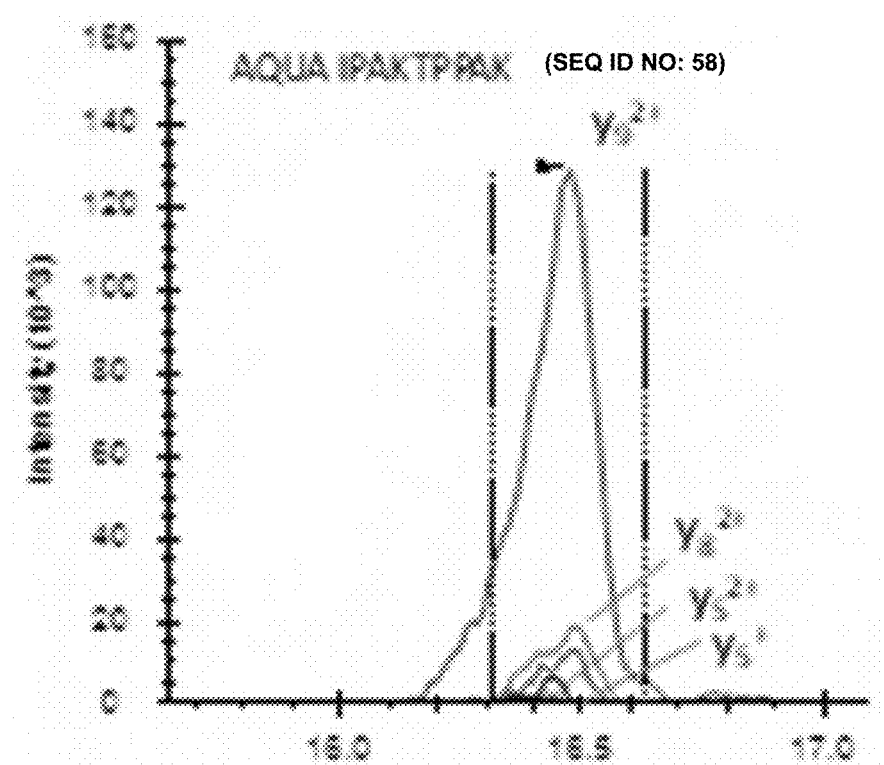
Figure 10F:
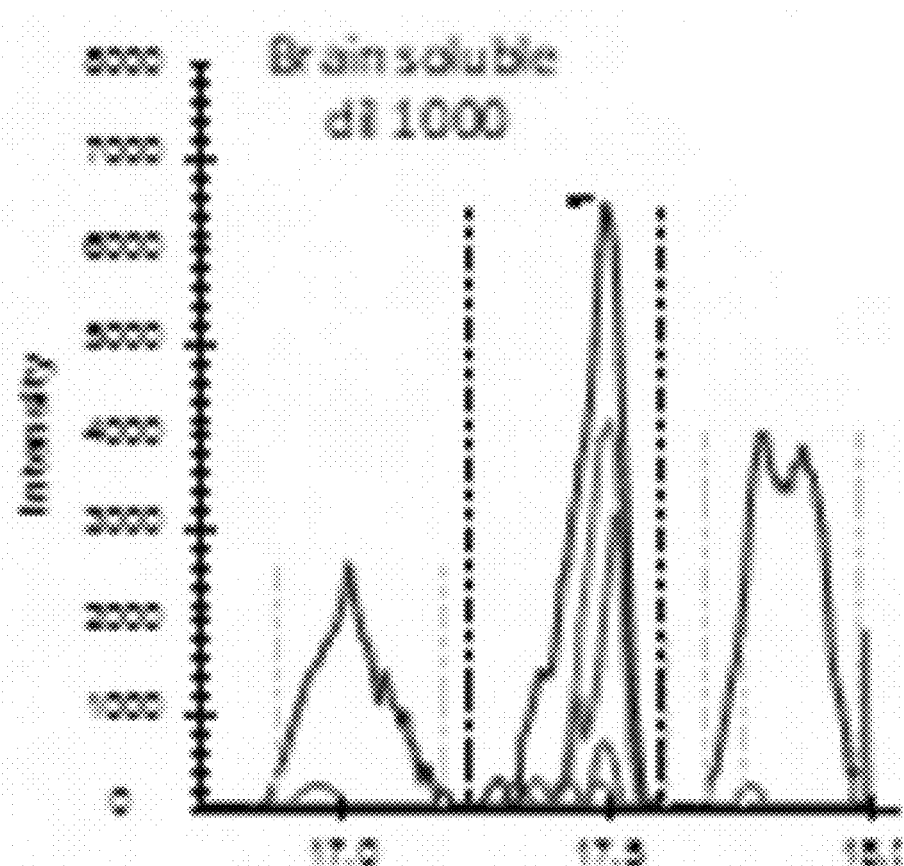
Figure 10G:
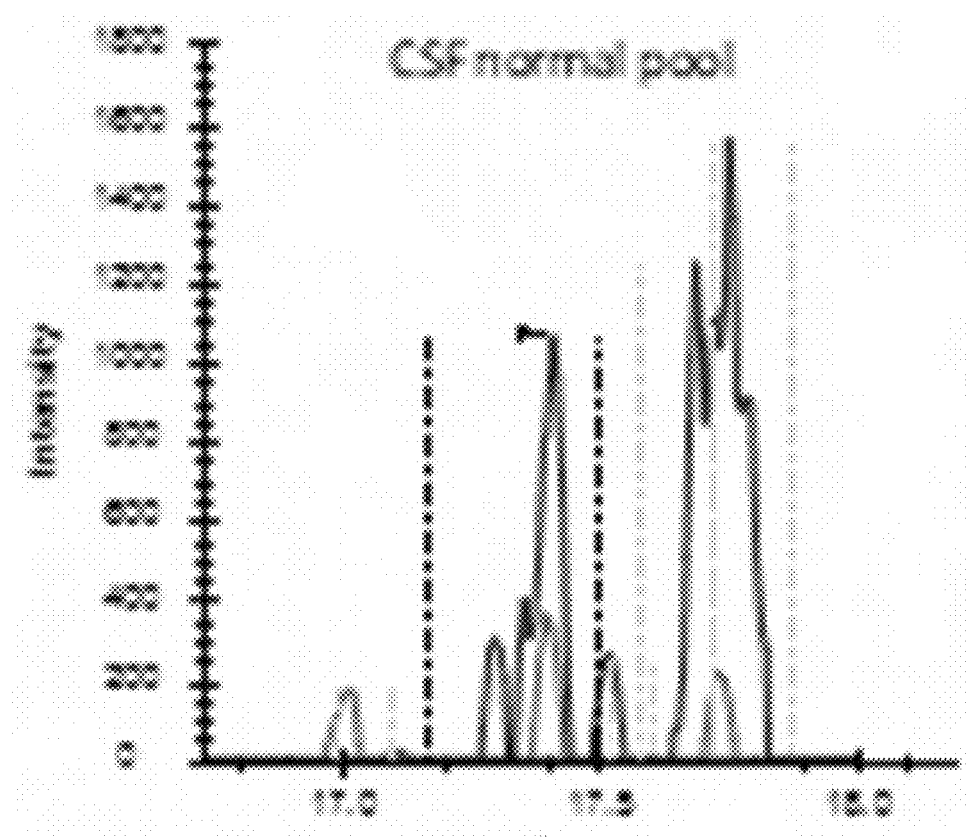
Figure 10H:
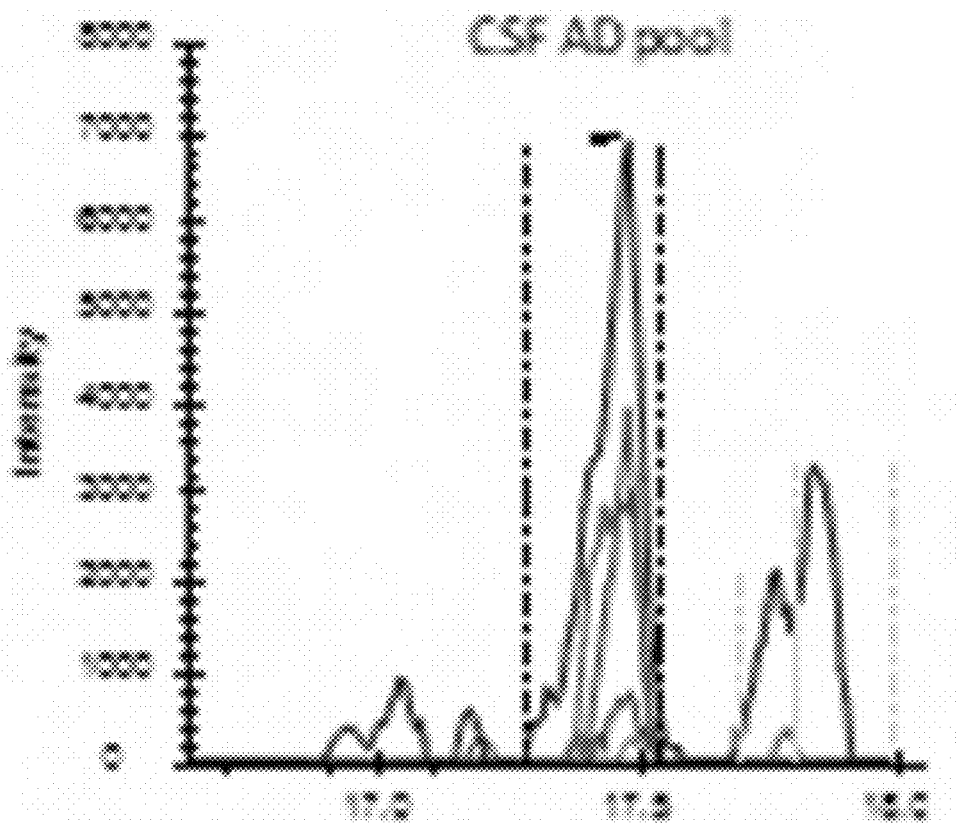
Figure 10I:
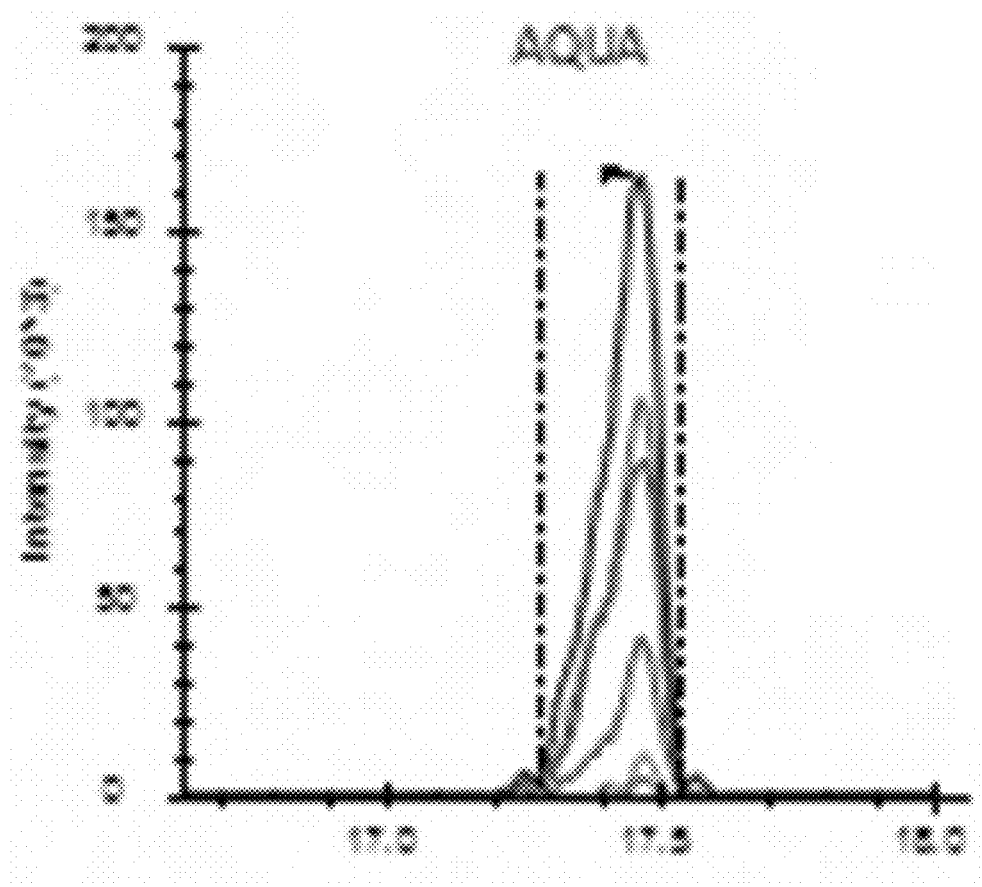

Results from analysis of the projection domains in the tau sequence (103-126) revealed multiple p-tau peptides eluting into overlapping complex LC-MS/MS patterns (FIG. 3-7). We identified 3 phosphorylation sites from the 0N isoform, the shortest isoform of the tau protein. Although the LC system did not have the resolution for differentiating the 3 phosphorylated peptides, fragment identification and corresponding intensities were used to deconvolute a signal composed of one major phosphorylation site at residue S113, and two minor phosphorylation sites at residues T111 and T123 (FIG. 3). In contrast, when PRM screening tau sequences from the longer 1N and 2N isoforms, further chromatographic separation was necessary to simplify phosphorylated peptide elution patterns, especially when multiple potential mono-phosphorylation sites were predicted within the same peptide sequence (FIG. 4-6). LC separation allowed us to identify co-eluted, semi-specific MS/MS fragments which contained differentially phosphorylated residues. However, we have also identified a few signals that could result from LC artifacts, likely due to dual conformations of the same peptide in solution (FIG. 5). This effect was important for peptide sequence containing amino acid residues 45-67 (in the 0N isoform) for both unmodified and phosphorylated peptides (FIG. 5) and less prevalent for sequences 68-126 (1N) and 88-126 (2N) (FIGS. 4 and 6).

Phosphorylation at residues S113, T111 and T123 were confirmed on peptide sequences 68-126 (1N) and 88-126 (2N). In all cases, the S113 signal was the most abundant of the three with a phosphorylation rate of 0.2-0.5% (FIG. 4 and FIG. 6, Table 1). Phosphorylation at residues T50, T52 and S56 were clearly identified on the peptide sequence 45-67 (shared by 1N and 2N isoforms). On the same peptide, LC-MS signals indicated at least two of the three residues (S61, T63, and S64) were phosphorylated (FIG. 5). No specific signals were found to identify potential phosphorylation at residue S46. Phosphorylation at residues S68 and T69 were evidenced in sequences 68-126 (1N) and 68-87 (2N) but no specific fragments were detected to differentiate their LC-MS patterns. On the same 1N and 2N peptide sequences, lower phosphorylation levels were detected on T71. 2N specific phosphorylations on the T76, T101, and T102 residues were also identified (summarized in FIG. 8).

Induction of trypsin missed cleavage was also considered for the screening of phosphorylated residues located after a tryptic site as reported previously (sites T175, T181, S212, T231 and S396) (Hanger et al. 1998). Our PRM screening successfully detected LC-MS patterns corresponding to phosphorylated tau peptides already described in normal brain tissue by Hanger et al (T181, S199, S202 and S404. FIG. 8). Corresponding LC-MS signals were high, suggesting that p-tau peptides previously reported in normal human brains are likely the most abundant. Our comparison of S199 and S202 phosphorylation indicated a much more prevalent abundance of phosphorylation at S202 (FIG. 8). The use of an anti-Tau1 antibody for tau extraction, associating with a non-phosphorylated epitope on the 192-199 amino acid sequence, could explain the low recovery of S199 phosphorylation in the extract. Given the abundance of S202 and S404 phosphorylation in the extract, we searched for the presence of di-phosphorylated peptides from sequences 195-209 and 386-406. We detected two LC-MS patterns with specific fragments corresponding to double phosphorylation at S202/S199 and S202/S198 and one LC-MS pattern corresponding to a double phosphorylation at 396/404 (FIG. 8).

Additional screenings of soluble tau in brain extract evidenced other less abundant mono-phosphorylated peptides corresponding to phosphorylated residues at T175, S214, T217, T231, and S396. Signals from fragments corresponding to a phosphorylated peptide at S184 or S185 were also detected at low levels when the mono-phosphorylated peptide sequence 181-190 was screened (FIG. 8). The search for mono-phosphorylation on the long sequence 407-438 discovered a pattern consistent with phosphorylation at residues S409 and S416 and at least one phosphorylation on the group of residues S412/S413/T414.

Overall, we identified a minimum of 29 unique phosphorylation sites detectable in the soluble tau fraction extracted from normal non-AD brains using the PRM screening method (Table 1). 25 of them can be unambiguously assigned to unique LC-MS signals and 4 additional phosphorylation sites were evidenced without assignment to the exact LC-MS patterns. These sites were located on three clusters: a minimum of 14 phosphorylated sites were located in the N-terminal projection domain, 10 on the proline-rich domain in the middle of the sequence, and 6 on the C-terminus (FIG. 14).

TABLE 1

Brain/CSF pool phosphorylation rate comparison (HJ8.5 + Tau1 IP-MS).

| Phosphorylated site | Peptide sequence | Isoform | Brain lysate soluble (1 ml 10X) | Brain lysate soluble (1 ml 500X) | Normal CSF (500 ul) | AD CSF (500 ul) |
|---|---|---|---|---|---|---|
| S46 | 45-67 | 1N/2N | ? | nd | x | x |
| T50 | 45-67 | 1N/2N | 0.5$^§$ | nd | x | x |
| T52 | 45-67 | 1N/2N | 2.2$^§$ | nd | x | x |
| S56 | 45-67 | 1N/2N | 0.01$^§$ | nd | x | x |
| S61/T63/S64 (2 sites minimum) | 45-67 | 1N/2N | 0.5/0.2$^§$ | nd | x | x |
| S68 | 68-126 | 1N | 1.4/0.3$^§$ | nd | x | x |
|  | 68-87 | 2N | 0.3/0.05$^§$ | nd | x | x |
| T69 | 68-126 | 1N | 1.4/0.3$^§$ | nd | x | x |
|  | 68-87 | 2N | 0.3/0.05$^§$ | nd | x | x |
| T71 | 68-126 | 1N | 0.2$^§$ | nd | x | x |
|  | 68-87 | 2N | 0.02$^§$ | nd | x | x |
| T76 | 68-87 | 2N | 0.01$^§$ | nd | x | x |
| T95 | 88-126 | 2N | ? | nd | x | x |
| T101 | 88-126 | 2N | 0.06-0.22$^§$ | nd | x | x |
| T102 | 88-126 | 2N | 0.06-0.22$^§$ | nd | x | x |
| T111 | 103-126 | 0N | 0.02$^§$ | nd | 0.8$^{§§}$ | 8.1$^{§§}$ |
|  | 68-126 | 1N | 0.2$^§$ | nd | x | x |
|  | 88-126 | 2N | 0.07$^§$ | nd | x | x |
| S113 | 103-126 | 0N | 0.2$^§$ | nd | x | low |
|  | 68-126 | 1N | 0.53$^§$ | nd | x | x |
|  | 88-126 | 2N | 0.59$^§$ | nd | x | x |
| T123 | 103-126 | 0N | 0.02$^§$ | nd | x | x |
|  | 68-126 | 1N | 0.02$^§$ | nd | x | x |
|  | 88-126 | 2N | X | nd | x | x |
| T153 | 151-155 | all | X | nd | x | 0.8$^{§§}$ |
| T175 mc | 171-180 | all | nd | 0.1*$^§$ | x | 0.1$^§$ |
| T181 mc | 175-190 | all | nd | 9.5*$^§$ | 10.1* | 13.3* |
| S184/S185 | 181-190 | all | 0.1$^§$ | nd | x | x |
| S199 (1) | 195-209 | all | 0.29 | 1.3*$^§$ | 0.2*$^{§§}$ | 0.2*$^§$ |
| S202 | 195-209 | all | 3.9 | 9.7*$^§$ | 2*$^{§§}$ | 1.5* |

TABLE 1-continued

Brain/CSF pool phosphorylation rate comparison (HJ8.5 + Tau1 IP-MS).

| Phosphorylated site | Peptide sequence | Isoform | Brain lysate soluble (1 ml 10X) | Brain lysate soluble (1 ml 500X) | Normal CSF (500 ul) | AD CSF (500 ul) |
|---|---|---|---|---|---|---|
| S199 + S202 | 195-209 | all | 0.02§ | nd | x | x |
| S198 + S202 | 195-209 | all | 0.01§ | nd | x | x |
| T205 | 195-209 | all | x | x | 2.3*§§ | 4*§§ |
| S208 | 195-209 | all | x | x | 0.001§§ | 0.003§§ |
| T212 | 210-221 | all | ? | nd | x | |
| S214 | 212-221 | all | 0.14 | 0.08§ | 0.04 | 0.07 |
| T217 | 212-221 | all | 0.43 | 0.5*§ | 1.9*§§ | 8.5*§§ |
| T231 mc | 226-234 | all | nd | 0.1*§ | 0.8*§§ | 1.4* |
| S396 | 396-406 | all | 1.2§ | nd | x | x |
| S404 | 396-406 | all | 95§ | 110* | x | x |
| S396 + S404 mc | 386-406 | all | nd | nd | x | x |
| S409 | 407-438 | all | 0.3§ | nd | x | x |
| S411/S412/T413 (2 sites minimum) | 407-438 | all | 1.2§ | nd | x | x |
| S416 | 407-438 | all | 1.0§ | nd | x | x |
| Number of unique sites | | | 29 | | 9 | 12 |

Values indicate phosphorylated/unphosphorylated ratio in %.
x: not detected.
*measured using AQUA internal standards
nd: not determined
?: not confidently assigned
(1) likely underestimated due to lower recovery using Tau1 immunocapture.'
§value considered as normal/reference for the considered site
§§hyperphosphorylation
§§§hyporphosphorylation

Example 2—Phosphorylation Sites on Tau Protein in the CSF

In comparison to the brain tau digest, CSF tau purification using tau-specific antibodies and digestion generated detectable peptides mainly from the mid-domain of the protein sequence (residues 150-221). Peptides were detectable to a lesser extent from the N-terminus, and almost no sequence was detectable from the microtubule binding repeat (MTBR) domain or the C-terminus of tau (Barthélemy et al., 2016; Sato et al., 2018). This difference in signal recovery may result from tau truncation during its release from neurons (Sato et al., 2018). The peptide recovery of this mid-domain was sufficient to monitor corresponding minor phosphorylated isoforms using the current PRM method. Conversely, a significant technological advance in MS method will be required to detect phosphorylated peptides in the MTBR and C-terminal domains.

PRM screening of tau phosphopeptides from normal control CSF identified several phosphorylation sites in common with brain soluble tau at T181 (not shown), S199, S202 and T217 (FIG. 9). A low signal corresponding to pS214 was also detected (FIG. 9). A specific fragmentation pattern corresponding to pT205 was identified in the CSF extract and was separated by chromatography from the pS199/pS202 signals (FIG. 9).

Figure 11:
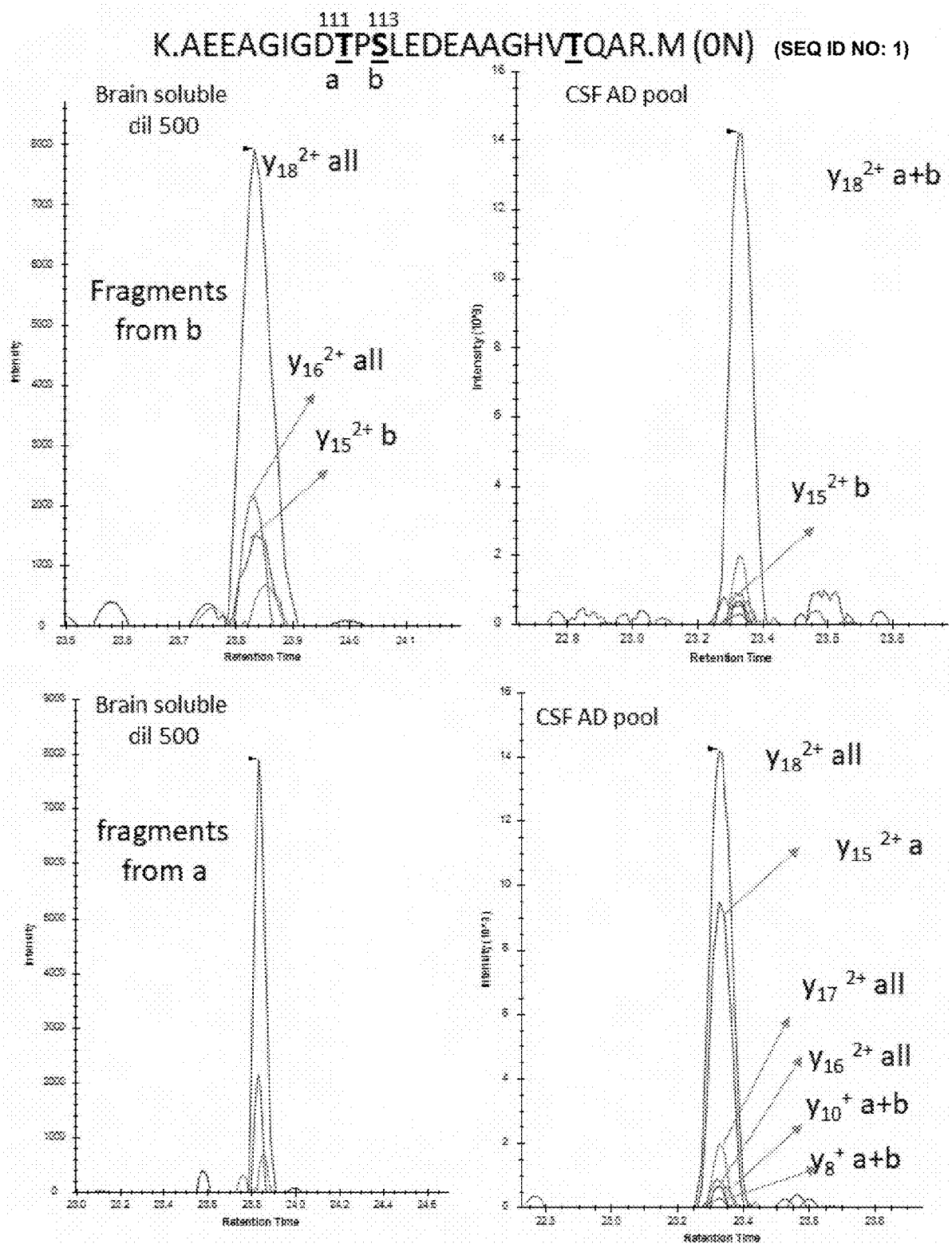
FIG. 11 shows phosphorylation abundance on T111 is higher in the CSF than the brain relative to S113 phosphorylation. In both brain and CSF, the MS/MS fragment y18 common to all mono-phosphorylated peptides on tau sequence 103-126 is detected. The relative abundance of the y15 fragment from pS113 (b) is significantly lower in CSF in comparison to brain extract. Inversely the y15 fragment from pT111 (a) is abundant in CSF and not detectable in brain soluble extract diluted to match the AD CSF tau level. For each chromatogram, the x-axis is retention time (minutes) and the y-axis is Intensity.
Figure 12:
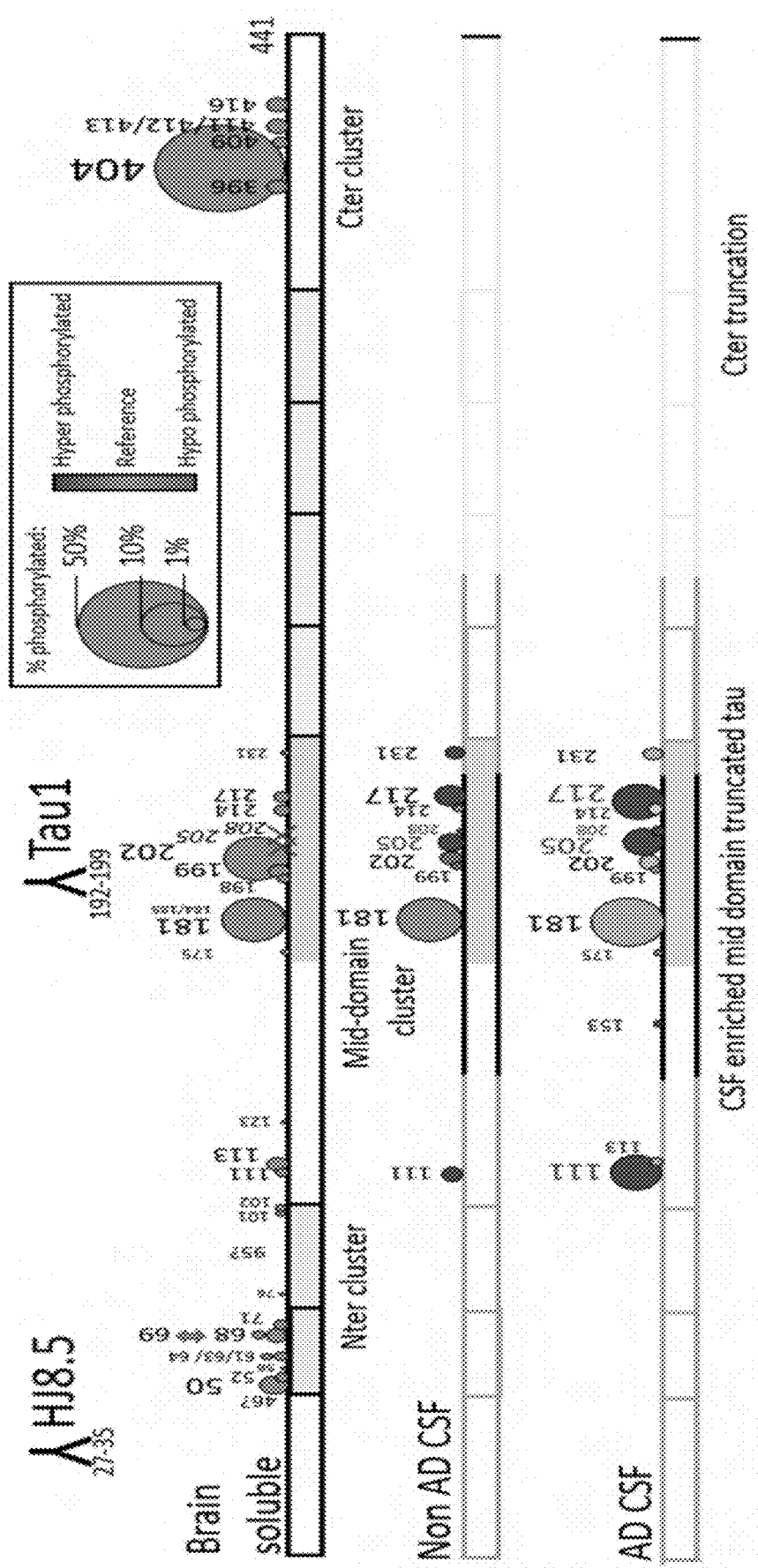
FIG. 12 shows relative abundance of tau phosphorylation depends on the biological extract and varies across the protein sequence. Comparison of tau phosphorylation abundance measured by MS in normal brain lysate, normal CSF and AD CSF extracted by immuno capture using HJ8.5 and Tau1. Circle area is proportional to site phosphorylation abundance. Red and green colors indicate an increase or decrease, respectively, in comparison to the brain soluble profile taken as reference (blue). Tau is c-terminally truncated in CSF, which explains the absence of detection of the C-terminal cluster of phosphorylation sites. Phosphorylation on T205 and S208 is specific to CSF (red X on Brain Soluble—top).

To increase the probability of detecting additional phosphorylated sites in CSF tau, we analyzed CSF pools from AD patients with mild to moderate dementia. We expected AD CSF pools would contain increased concentrations of tau as well as increased levels of phosphorylated tau. The same phosphorylated residues found in normal CSF (T181, S199, S202, T217 and T231) were detected in AD CSF. Additionally, signals corresponding to pS113 and pT175 previously found in tau from the brain but not in the normal CSF were detected in AD CSF (FIG. 9, FIG. 10). A LC-MS/MS pattern containing specific fragments and distinct retention times from S202/S199 phosphorylated peptides allowed the identification of a new phosphorylated peptide at S208. When we reexamined pS208 in normal CSF, we detected the corresponding signal in low abundance. A LC-MS/MS pattern matching with a new phosphorylated peptide at residue T153 was detected close to the level of corresponding unphosphorylated peptide (FIG. 10). Careful reexamination of brain extract data suggested the presence of a low abundant signal corresponding to this site. Finally, we found specific signals corresponding to phosphorylation on the 103-126 amino acid sequence from the 0N isoform in AD CSF, indicating T111 as the main phosphorylation site on this peptide, while S113 was barely phosphorylated (FIG. 11). Altogether, 12 phosphorylation sites were detected in CSF tau, two of which were not detectable in brain lysate (FIG. 12).

Example 3—CSF p-Tau Abundance Measurements Highlight Differences Compared to p-Tau Abundance in Brain In the brain, S404 was the most highly phosphorylated of the examined phosphorylation sites (pS404/S404=110%, i.e. 52% of S404 is phosphorylated). Thus, more than half of the brain tau was phosphorylated at S404 compared to other highly phosphorylated sites at S202 and T181 (9.7% and 9.5%, respectively). 1.3% of S199 was phosphorylated but this could be underestimated due to the inability of the Tau1 antibody used for extraction to bind its corresponding phosphorylated epitope (Liu et al., 1993). Phosphorylation on C-terminal sites other than S404 was found to be around 1%. On the N-terminus, T52, S68/T69, T50, and S113 were also phosphorylated with abundances ranging from around 0.5% to 2%. Other detected sites appeared to be phosphorylated at much lower levels (<0.5%).

Figure 13:
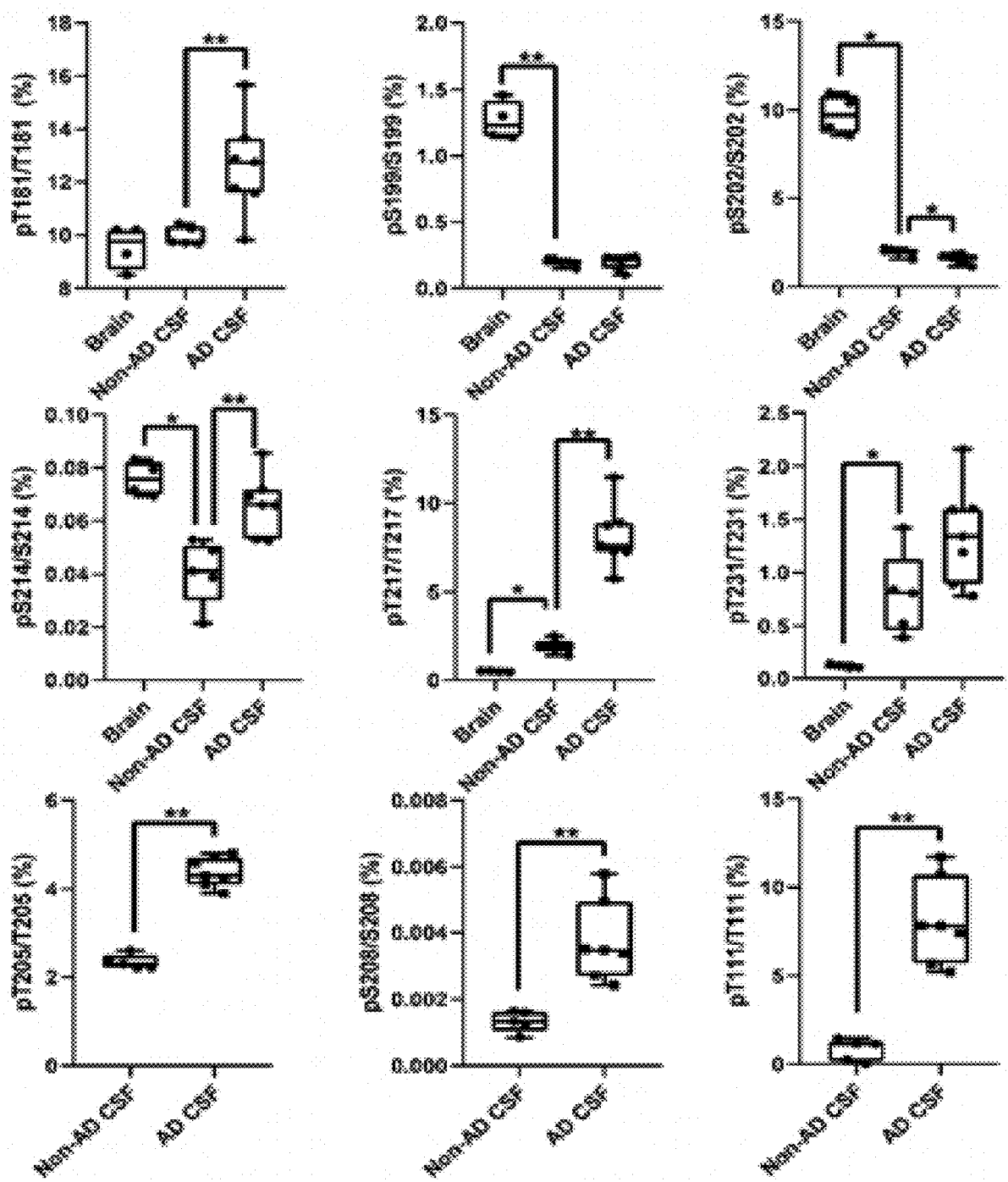
FIG. 13 shows tau phosphorylation sites are differentially modified in brain, normal CSF and AD CSF. Measurements are the relative abundances of the phosphorylated signal compared to the corresponding non phosphorylated site (HJ8.5+Tau1 IP-MS). Brain results are obtained from diluted lysates from 500× to 8000× factors to match the CSF tau level. Phosphorylations on T205 and S208 are undetectable in brain tissue. Phosphorylation on T111 is undetectable in 500× diluted lysate but was detected in 10× diluted lysate with a corresponding abundance of 0.02%. Legend: ** indicates significance at p=0.01 level and * indicates significance at p=0.05 level.
Figure 14A:
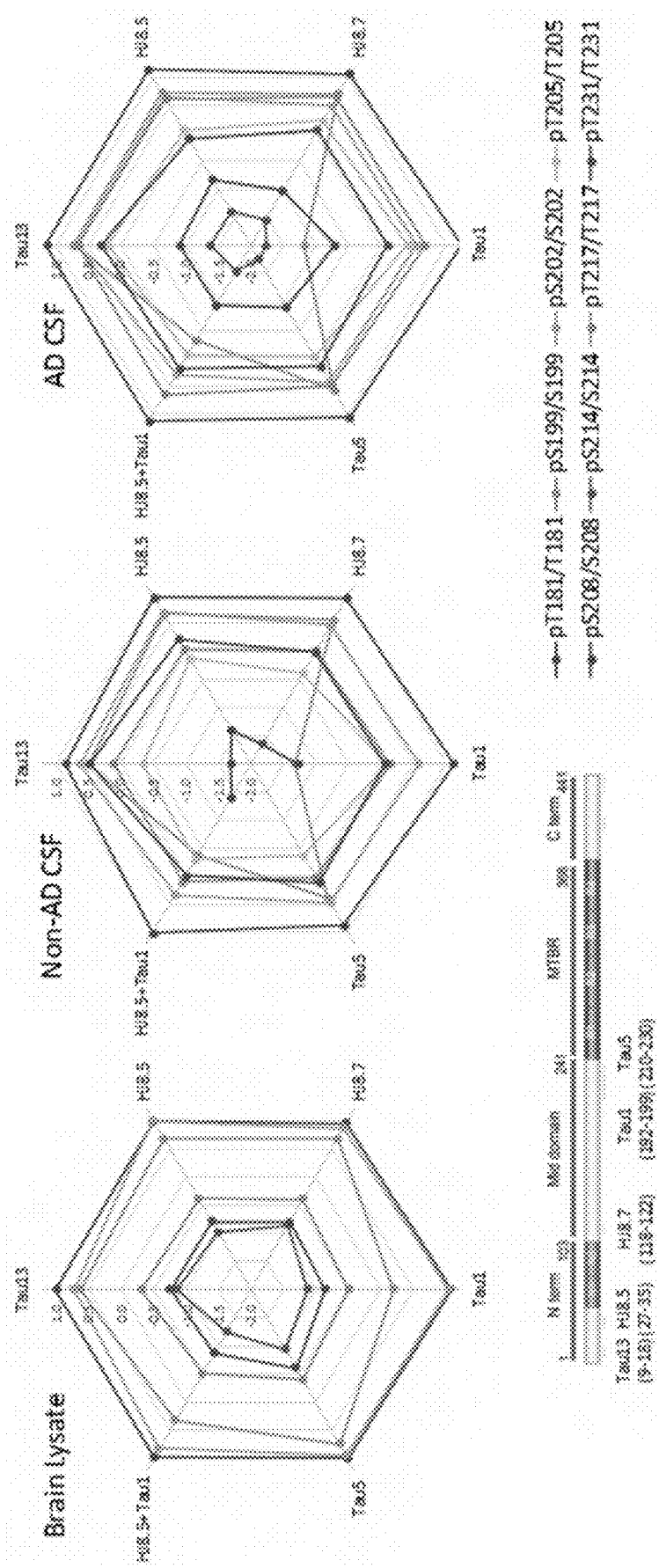
FIG. 14A, FIG. 14B, FIG. 14C, and FIG. 14D show antibody effect on phosphorylation ratio measurement by IP-MS. Brain lysate pool, non-AD (n=1) and AD CSF (n=1) pools were immunoprecipitated in parallel with antibodies against tau N-terminus projection domain (Tau13 or HJ8.5) or mid domain (HJ8.7, Tau1 or Tau5). Radar plots of phosphorylation ratios measured on main CSF sites ($\log_{10}$ scale) are shown in brain lysate (FIG. 14A, left panel), non-AD CSF (FIG. 14A, middle panel) and AD CSF (FIG. 14A, right panel).
Figure 14B:
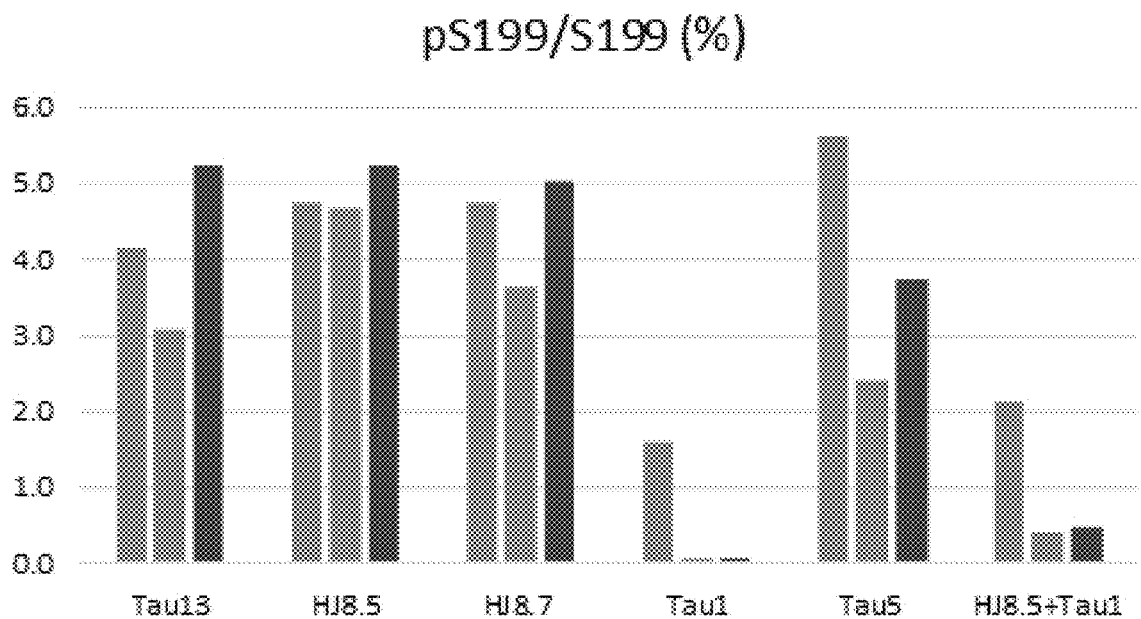
Figure 14C:
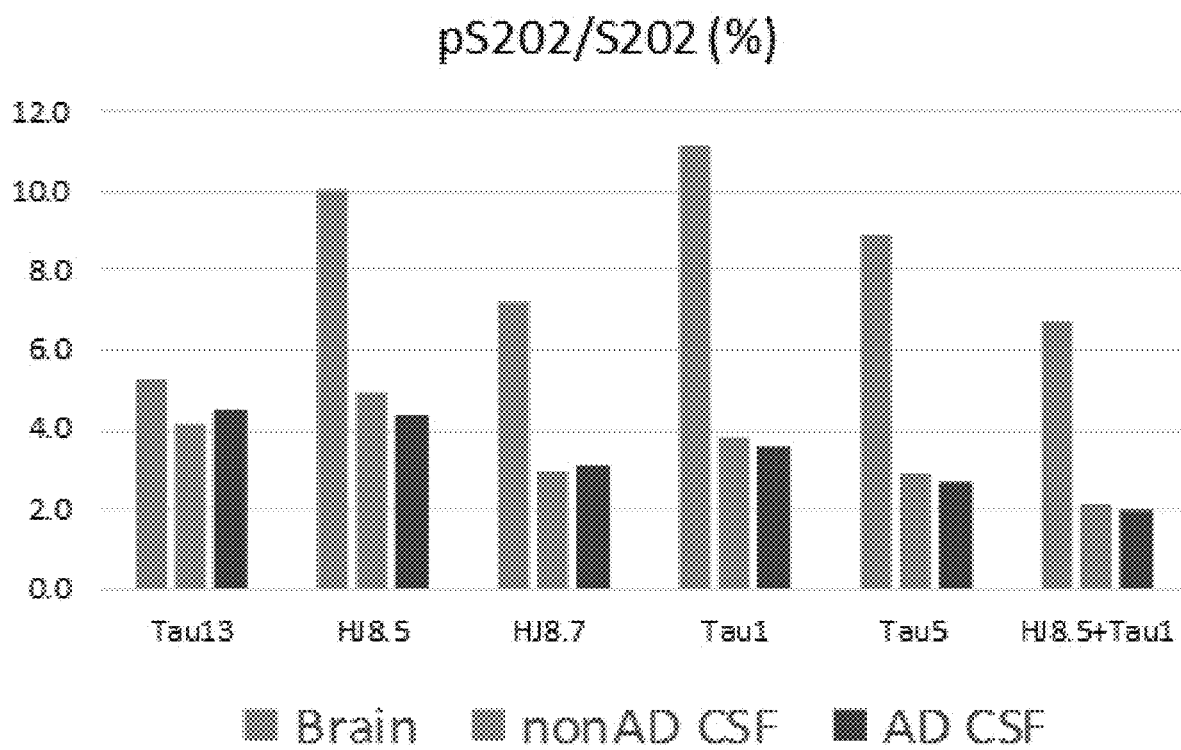
Figure 14D:
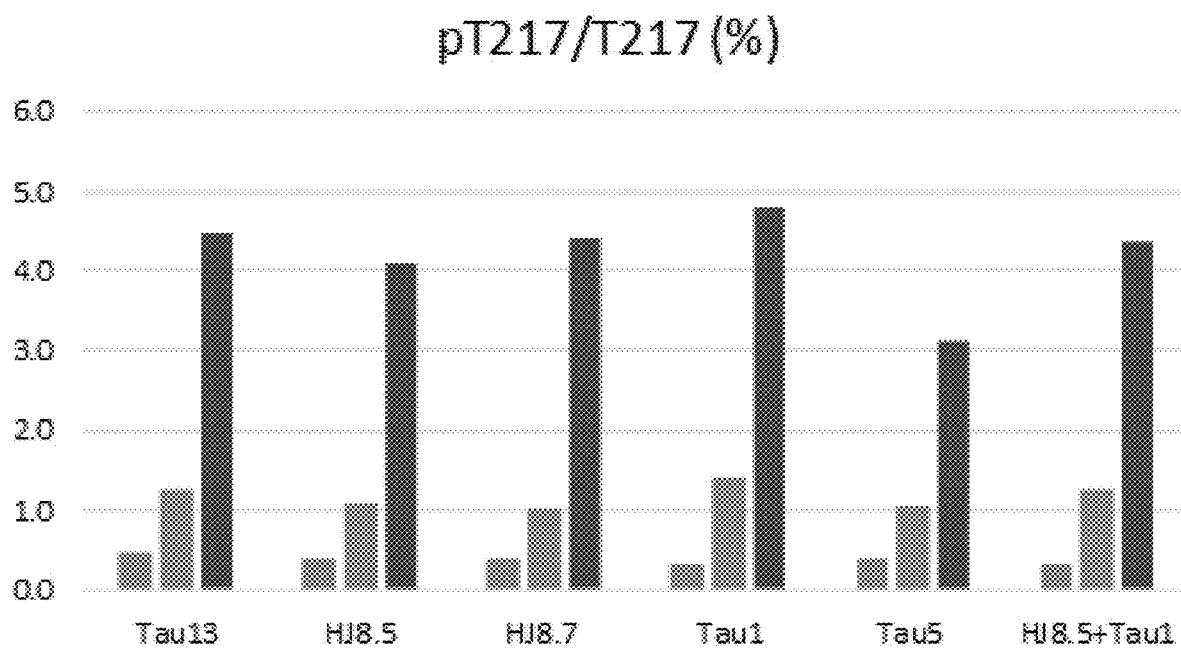

In addition to the unique detection of pT205 and pS208 in CSF tau but not brain, the relative phosphorylation abundance of certain other phosphorylation sites detected in brain tau were altered in comparison to control CSF tau (FIG. 13). Compared to brain, CSF tau phosphorylation was significantly lower at sites pS199 (6-fold decrease, p=0.008), pS202 (5 fold decrease, p=0.016), and pS214 (2 fold-decrease, p=0.016). Conversely, CSF tau phosphorylation was significantly higher at sites pT217 (4-fold increase, p=0.016), pT231 (7-fold increase, p=0.016) and pT111 from 0N (16-fold increase). PT181 abundance was similar in the CSF and the brain (~10%). When measured in AD CSF, pT175 remained low (0.1-0.2% compared to 0.1% in brain).

Brain and CSF tau have different truncation patterns: brain tau isoforms are mainly full length while CSF tau isoforms are truncated. Brain and CSF tau isoforms and corresponding peptides recovered after IP depend on the antibody used for the immunoprecipitation (Sato et al., 2018). Similarly, antibodies used to immunoprecipitate tau could impact tau phosphorylation recovery. To evaluate this impact on p-tau recovery, we compared IP-MS results on phosphorylation rates using different antibodies (Tau13, HJ8.5, HJ8.7, Tau1 and Tau5) in addition to the Tau1+HJ8.5 combination (FIG. 14). A significant decrease of pS199/S199 rate was observed when Tau1 or Tau1+HJ8.5 were used in brain and CSF. This suggests CSF truncation between the N-terminus and the mid-domain could affect pS199 phosphorylation measurement compared to brain. PS199/S199 rate measured in brain and CSF with other antibodies appeared to be relatively similar. Interestingly, some reactivity was still observed for pS199 in brain extract and to a lesser extent in CSF, suggesting nonspecific binding of Tau1, though S199 phosphorylation is present at the end of the reported Tau1 epitope (192-199).

Since phosphatase activity during the post-mortem interval (PMI) before autopsy can decrease tau phosphorylation measured in brain extracts, we investigated the impact of the PMI on phosphorylation rates commonly found in CSF and brain extracts. 10 brains samples (middle frontal gyrus) without tau pathology collected from participants with PMI ranging from 5 to 16 hours were analyzed. None of the brain extracts originally analyzed had a PMI of greater than 16 hours. We did not find significant association (Spearman test, 95% confidence interval, not shown) between PMI and phosphorylation rates measured on T181, S199, S202, S214, T217, T231 and S404 sites.

Example 4—AD Specific p-Tau Change in CSF

The increased CSF p-tau commonly reported in AD could be the consequence of two potential effects: 1) the global increase of tau regardless of its phosphorylation status, or 2) increased hyperphosphorylation at specific sites. Normalizing p-tau signal or level using non-phosphorylated tau allows for quantifying changes in phosphorylation stoichiometry (i.e. hyper- or hypo-phosphorylation compared to normal CSF or brain tau) occurring at specific sites independently from the global change in total tau. As we recently demonstrated, soluble tau production is increased in AD and correlates with amyloid plaques. Therefore, controlling for not just the amount, but the rate of phosphorylation is key to understand. pT181, pT217, pT231, pT205, pS208 and pS214 were hyperphosphorylated in AD CSF as was 0N-specific pT111 (FIG. 13). pT153 and pT175 were not detected in non-AD and likely increased slightly in AD. The sites showing significant hyperphosphorylation compared to non-AD were pT181 (p=0.010), pS214 (p=0.005), and pT217 (p=0.003). pT181, pS214, and pT217 showed approximately 1.2-fold, 1.6-fold, and 4-fold increases in phosphorylation respectively. Interestingly, not all the monitored sites were hyperphosphorylated: pS199/S199 was not significantly changed and pS202/S202 was significantly lower (p=0.030) with an approximately 1.2-fold decrease.

Figure 15:
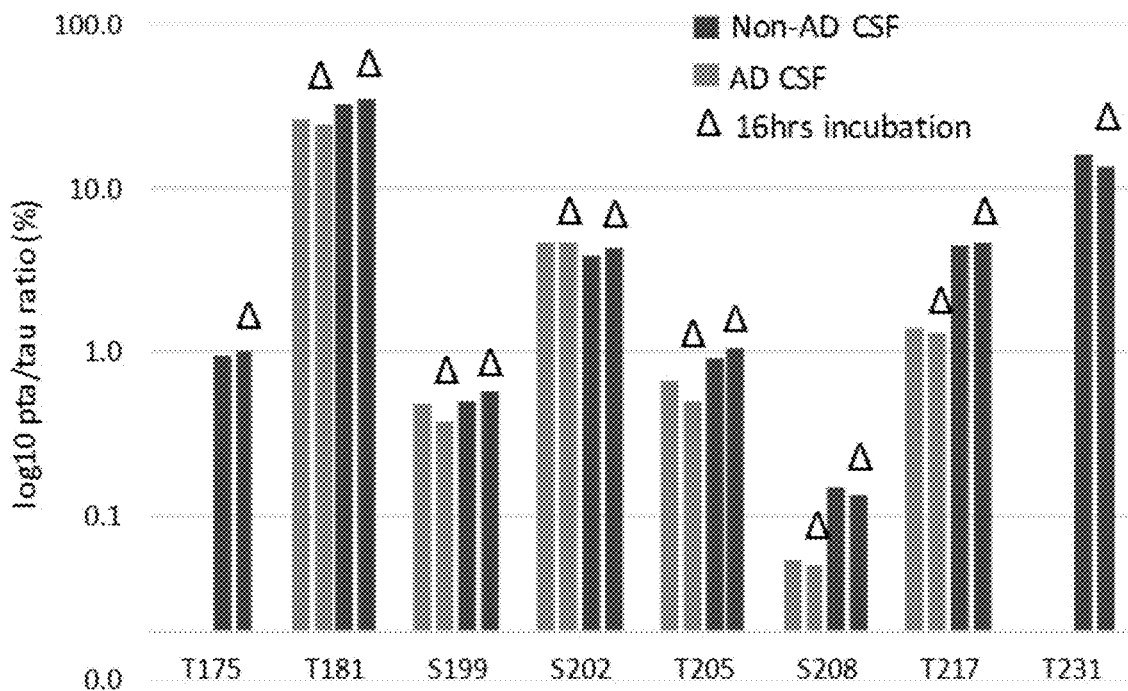
FIG. 15 shows CSF incubation does not impact phosphorylation rate measurement on tau.

Robustness of phosphorylation ratios was assessed by incubating CSF for 16 hours. Incubation did not significantly affect tau phosphorylation ratio differences observed between non-AD and AD CSF (FIG. 15). Moreover, absence of kinase activity on CSF tau was confirmed by the non-detectability of phosphorylation on recombinant 15N-tau spiked in CSF after incubation (not shown).

Discussion for Examples 1-4

Technological advancement of PRM on p-tau measurement—We report the most comprehensive qualitative and quantitative analyses of p-tau in normal brain tissue and CSF to date. Our approach contrasts with previous DDA studies on tau phosphorylation which may not have captured potential minor phosphorylation sites. However, our approach uses highly sensitive targeted-MS in PRM mode to detect and quantify minor phosphorylation. Phosphorylation site identification depends on the careful manual interpretation of LC-MS/MS patterns to identify co-elution of specific ion fragments for each examined phosphopeptide. In prior studies, brain tau phosphorylation has been mainly investigated in insoluble extracts enriched in hyperphosphorylated tau from PHF and, to date, the most detailed study has reported 9 phosphorylation sites in normal human tau protein (Hanger et al. 2007). Our in-depth PRM data analysis detected more than 29 phosphorylated residues with a majority being very low in abundance. Indeed, the previously reported 9 sites were amongst the most abundant modifications in the protein. Application of PRM analysis to normal CSF tau, present in much lower abundance compared to the brain, led to the detection of 9 phosphorylation sites initially, with 3 additional sites detected in AD CSF.

In addition to the significantly increased number of phosphorylation sites detected, we demonstrated how sensitive PRM screening enabled us to quantitatively assess the tau phosphorylation rate or stoichiometry, independent of global tau concentration. This concept is frequently overlooked but critical in assessing changes in AD when absolute CSF p-tau concentration may increase solely due to increase in global tau isoforms concentration, and not due to change of relative phosphorylated tau abundance. Phosphorylation rate measurement from this study enabled for the first time the comparison of the degree and distribution of phosphorylation rate changes (hyper- vs hypo-phosphorylation) across the protein, in different compartments (intracellular brain vs extracellular CSF), and in different pathological conditions (AD vs non-AD).

Some caveats of the PRM screening process are the low throughput for discovery and the risk of missing p-tau species or other post-translational modification (PTM) not hypothesized in the study. Identifications from MS data can be further used in a larger validation or clinical cohort to design scheduled LC-MS methods, increasing multiplexing and throughput (Gillette and Carr, 2013). Other proteases such as AspN could provide a different set of tau and p-tau peptides than from trypsin digest, allowing for a better coverage of tau, i.e. the C-terminal domain (Hanger et al. 1998; Sato et al. 2018). The search could be further refined by screening additional doubly- or triply-phosphorylated tau peptides not considered in this study, although their abundance may be minimal unless there is biological coordination of site phosphorylation.

Identification of a cluster of phosphorylation sites on the tau projection domain—We found a cluster of previously undescribed phosphorylated residues on the N-terminus projection domain of tau containing alternative splicing-dependent peptides. Interestingly, this domain was not previously found to be extensively phosphorylated in PHF in the insoluble human brain fraction (Funk et al., 2014; Hanger et al., 2007; Russell et al., 2016; Thomas et al., 2012). This cluster was also not extensively characterized in the recent comprehensive study performed in mouse tau protein in the murine brain (Morris et al., 2015). These discrepancies could be attributed to the difficulty of characterizing complex mixtures of phosphorylated peptides, distinguishable only by few specific MS/MS fragments and/or subtle retention time shifting on LC. For example, S46 is the only phosphorylated site previously reported in this domain in normal human tau (Hanger et al. 1998). However, we did not detect a specific signal for this species, which can be confounded by search algorithms with neighboring phosphorylated sites at T50 or T52, sharing a close fragmentation pattern. In this regard, manual inspection is essential to clearly interpret and decipher corresponding LC-MS/MS patterns for each phosphorylated site. Another possible explanation of this discrepancy could be the relatively low abundance of the N-terminal domain in PHF in comparison to the MTBR domain, the mid-domain, and the C-terminus (Mair et al., 2016).

This N-terminus projection domain has been recently assigned as a part of the dominant component of the repulsive barrier that prevents neighboring microtubules (associated to tau via the MTBR domain) from getting close to each other (Chung et al., 2016). This sequence contains numerous acidic residues and an increase in phosphorylation may contribute to increased global acidity, enforcing the repulsive barrier. Together with a variable amount of N-terminal extension induced by alternative splicing on exon 2-3, tau phosphorylation could regulate tau/tau N-terminal interactions and microtubule intermolecular distance.

Biological implications of different p-tau profiles in the brain vs CSF—Tau is mainly an intracellular protein that functions in microtubule stability, and was traditionally considered to only be released extracellularly upon nerve injury or cell death. However, recent studies have suggested that tau is secreted under physiological and pathological conditions in a regulated manner (Karch et al. 2012; Yamada et al. 2014). By comparing soluble brain tau and CSF tau profiles in parallel to intracellular and extracellular tau profiles and metabolism in neuronal models, we have recently shown that tau secretion is an active process that involves different turnover rates of tau isoforms including truncated tau and p-tau (Sato et al., 2018). Understanding the association between this active secretion and phosphorylation of tau through comparison between brain and CSF p-tau profiles provides potential insight into AD pathogenesis.

We speculate that p-tau isoforms enriched in the CSF have less affinity for microtubules and a higher likelihood to be secreted. Inversely, p-tau isoforms impoverished in the CSF could have more propensity to stay inside the neurons and/or avoid cleavage. Our results demonstrate that several phosphorylated residues are significantly enriched in the CSF compared to brain extracts, such as T217, T231, T153 and T111. All are proline-directed sites, are potential substrates of GSK-3β protein kinase, and may be subject to kinase-dependent regulation. Unlike pT217, pS214 was not elevated in the CSF compared to the brain. This extracellular enrichment of pT217 over pS214 agreed with kinetic differences we previously identified within cells for these isoforms (Sato et al., 2018), with pT217 having a shorter turnover rate than unphosphorylated tau and tau-pS214. Alternatively, decreased phosphorylation observed on some of the tau sites in brain extract compared to CSF could also result from partial dephosphorylation occurring during the PMI (Matsuo et al., 1994). Though such a decrease was not observed within the 5-16 hour PMI range, modification of phosphorylation ratios between death and this investigated interval cannot be excluded. Assessing the kinetics of dephosphorylation of these tau sites from brain biopsies by mass spectrometry would help to address the impact of this phenomenon on CSF/brain comparison results in the future. The consideration of potential brain phosphatase bias affecting brain tau phosphorylation measurement would support that CSF tau phosphorylation status is more likely to reflect the in vivo tau phosphorylation status in neurons than brain extracts collected post mortem. However, in vivo tau phosphorylation monitoring in CSF would be limited to sites detected mainly in the tau mid-domain due to CSF tau truncation.

Conversely, pS202 was significantly lower in the CSF and pS199 and pS202 were not elevated in AD, indicating that these phosphorylations may promote tau sequestration inside neurons. T181 is equally phosphorylated in the CSF and the brain. pT205 and pS208 were exclusively detected in CSF tau and not in soluble tau protein in the brain. This is interesting considering that the triple phosphorylation at S202, T205 and S208 is recognized by the anti-AT8 antibody (Malia et al., 2016) commonly used to characterize Braak stages of tau aggregation in brain (Braak and Braak, 1995). Indeed, pS208 was detected by MS in PHF (Hanger et al. 1998). pT205 and pS208 were absent in normal soluble brain tau in our study, confirming the unlikeliness to detect immunoreactivity of AT8 in normal brain tau. Furthermore, a recent study implicates pT205 and pS208 as a combinational phosphorylation pattern that, together with pS202, leads to tau self-aggregation (Despres et al., 2017). Exclusive presence of pT205 and pS208 in the CSF and further increased rates of phosphorylation at both sites in AD could indicate a potential protective clearance mechanism for neurons to remove these pathology-prone p-tau species from the cells. Simultaneous decrease of pS202 in AD CSF could also correspond to an increased sequestration of associated isoforms when aggregated with pT205 and pS208 in enriched AT8-positive tangles in the AD brain. Alternatively, absence of phosphorylation on pT205 and pS208 in brain extracts could result from their specific degradation by phosphatases occurring during the PMI. The rapid disappearance (<3 hours) of AT8 reactivity reported on tau, collected from brain biopsy, supports this idea (Matsuo et al., 1994). Thus, such phosphatase activity efficiently targeting pT205 and pS208 could also be seen as an additional mechanism preventing long half-life of AT8-positive material in neurons. The increase of pT205 and pS208 found in AD CSF would then indicate potentially pathological decreasing of this protective mechanism. Finally, simultaneous decrease of pS202 in AD CSF could also correspond to an increased sequestration of associated isoforms when aggregated with pT205 and pS208 in enriched AT8-positive tangles in the AD brain.

We were unable to provide convincing detection of phosphorylated residues from the MTBR domain in the soluble fraction from normal brain. Phosphorylation sites on the MTBR domain have been purported to reduce the affinity of tau to microtubules (Biernat et al., 1993). The absence of such phosphorylation in normal tau could support the abnormality of these modifications found in PHF (Hanger et al. 2007). CSF tau truncation restricts the examination of phosphorylation changes in vivo since the MTBR domain likely degraded within the cell after tau truncation (Kanmert et al., 2015), and so was not recovered by the immuno-capture method used in this study.

CSF p-tau rates as AD biomarkers—In addition to the significantly increased number of phosphorylation sites detected, we demonstrated how tau phosphorylation rate or stoichiometry can be quantified independent of global tau concentration. This concept is frequently overlooked but critical in assessing CSF tau phosphorylation changes in AD when absolute CSF p-tau concentration may increase solely due to increased total tau concentration (i.e. pT181), and not due to an increase in the relative phosphorylation rate itself. Phosphorylation rate measurements from this study enabled for the first time the comparison of the degree and distribution of phosphorylation rate changes (hyper- vs hypo-phosphorylation) across the protein, in different compartments, (intracellular brain vs extracellular CSF) and in different pathological conditions (AD vs non-AD). This method could be used in the future to look at modifications of AD brain phosphorylations on numerous sites across brain regions and Braak stages as recently performed using immunochemistry (Neddens et al. 2018).

In this study, we demonstrated that tau in AD CSF is generally hyperphosphorylated in comparison to non-AD CSF. However, the degree of hyperphosphorylation is site dependent. T111, T205, S208 and T217 were more hyperphosphorylated than T181, which is the most commonly measured target used as a p-tau biomarker for AD (Fagan et al. 2009). We have also identified T153 phosphorylation that was exclusively found in AD CSF. Interestingly, the sites found hyperphosphorylated in AD CSF correspond to the sites already significantly increased in normal CSF compared to the brain (i.e., T111, T205, S208, and T217, and to a lesser extent T231). This would indicate AD pathology exacerbates cellular mechanisms contributing to specific p-tau isoforms enrichment during tau release into the CSF. Overall, the high magnitude of change found on these sites lets us envision their use as sensitive biomarkers to detect AD. Our study relied on a limited number of CSF pools and future studies on larger CSF cohorts would better establish potential relationships between p-tau changes and brain amyloidosis and tau aggregation over the course of the disease. We can also ask whether there are any specific p-tau profile changes in other non-AD tauopathies such as PSP, CBD, and FTD. Alternatively, this method could be used to track different kinase activities in vivo and in vitro and may also provide a promising tool to assess new drugs targeting abnormal tau metabolism.

Methods for Examples 1-4

Brain soluble tau extraction—Brain and CSF studies involving participants were approved by the Washington University Human Studies Committee and the General Clinical Research Center. Written informed consent was obtained from all participants prior to inclusion in the study. Brain soluble tau was extracted as described previously (Sato et al., 2018). Briefly, frozen human brain tissues from controls without amyloid and tau pathologies as described before (Sato et al., 2018) were obtained from Knight Alzheimer's Disease Research Center (ADRC) at Washington University School of Medicine (St. Louis, Mo.). Sarkosyl-soluble tau was separated from putative tau aggregates by ultracentrifugation as reported in the literature (Hanger et al. 1998) and pooled. Frozen human brain (200-400 mg, frontal regions) were homogenized in Tris-HCl buffer (25 mM Tris-HCl, 150 mM NaCl, 10 mM EDTA, 10 mM EGTA, 1 mMDTT, phosphatase inhibitor Cocktail 3, Roche Protease Inhibitor, pH 7.4. Final 3.25 mL/mg tissue) on ice. Homogenates were centrifuged at 4° C. for 60 minutes at 11,000×g. The supernatant was solubilized in 1% Sarkosyl for 60 min and centrifuged for 2 hrs at 100,000×g. Sarkosyl soluble fractions were pooled and 50 uL fraction was diluted 10 times with 0.5% human plasma before immunoprecipitation. For brain/CSF comparison, brain lysate pool was diluted from 500 to 8000 times before immunopurification to match CSF tau levels.

CSF tau extraction—Human CSF was pooled from a cohort of 80 participants, including amyloid negative and cognitively normal (CDR=0) controls (n=47, age 60+) and amyloid positive and CDR>0 AD patients (n=33, age 60+). Five and seven pools of 500 uL CSF aliquots were generated from the control and AD groups, respectively. At time of initial collection, CSF was spun down at 1,000×g for 10 min to remove cell debris and immediately frozen at −80° C. Protease inhibitor cocktail was added during experiments. Tau was immunoprecipitated and desalted as previously described with some modifications (Sato et al., 2018). Briefly, CNBr-activated Sepharose beads (GE Healthcare 17-0430-01) were crosslinked to antibodies Tau1 and HJ8.5, separately at a concentration of 3 mg antibody per g of beads. Samples are spiked with AQUA peptides (ThermoFisher Scientific) corresponding to 10 fmol phosphorylated and 100 fmol unphosphorylated tau for each sequence of interest per mL of sample. Tau and p-tau concentration is calculated using these internal standards. Soluble tau was immunoprecipitated in detergent (1% NP-40), chaotropic reagent (5 mM guanidine), and protease inhibitors (Roche Complete Protease Inhibitor Cocktail). Anti-Tau1 and HJ8.5 antibodies conjugated to sepharose beads were diluted 10 and 5-fold, respectively, in inactivated sepharose beads, and 30 uL of 50% slurry of the antibody beads were rotated with the solution for 90 min at room temperature. The beads were washed three times in 25 mM triethyl ammonium bicarbonate buffer (TEABC, Fluka 17902). The bound tau was digested on-beads with 400 ng MS grade trypsin (Promega, V5111) for 16 hours at 37° C. Digests were loaded onto TopTip C18 (Glygen, TT2C18.96), desalted, and eluted per manufacturer's instructions. The eluted peptides were dried by vacuum centrifugation (CentriVap Concentrator Labconco) and were resuspended in 25 uL of a solution of 2% acetonitrile and 0.1% formic acid in MS grade water.

Mass spectrometry—A 5 uL aliquot of the peptide resuspension was injected into nano-Acquity LC for MS analysis. The nano-Acquity LC (Waters Corporation, Milford, Mass.) was fitted with HSS T3 75 umx 100 um, 1.8 um column and a flow rate of 0.5 uL/min of a gradient of solution A and B was used to separate the peptides. Solution A was composed of 0.1% formic acid in MS grade water and solution B was composed of 0.1% formic acid in acetonitrile. Peptides were eluted from the column with a gradient of 2% to 20% of solution B in 28 minutes, then 20% to 40% solution B for another 13 minutes before ramping up to 85% solution B in another 3 minutes to clean the column. The Orbitrap Fusion Lumos was equipped with a Nanospray Flex electrospray ion source (Thermo Fisher Scientific, San Jose, Calif.). Peptide ions sprayed from a 10 um SilicaTip emitter (New Objective, Woburn, Ma) into the ion-source were targeted and isolated in the quadrupole. These were then fragmented by HCD and ion fragments were detected in the Orbitrap (resolution of 60,000, mass range 150-1200 m/z). Monitoring of hydrophilic peptides (SSRcalc<9, all without leucine) for peptide profiling was performed on a HSS T3 300 um×100 um, 1.8 mm column at a flow rate of 4 ul/min with an elution occurring with a 2% to 12% solution B gradient and a spray operating on a 30 mm SilicaTip emitter.

Figure 2:
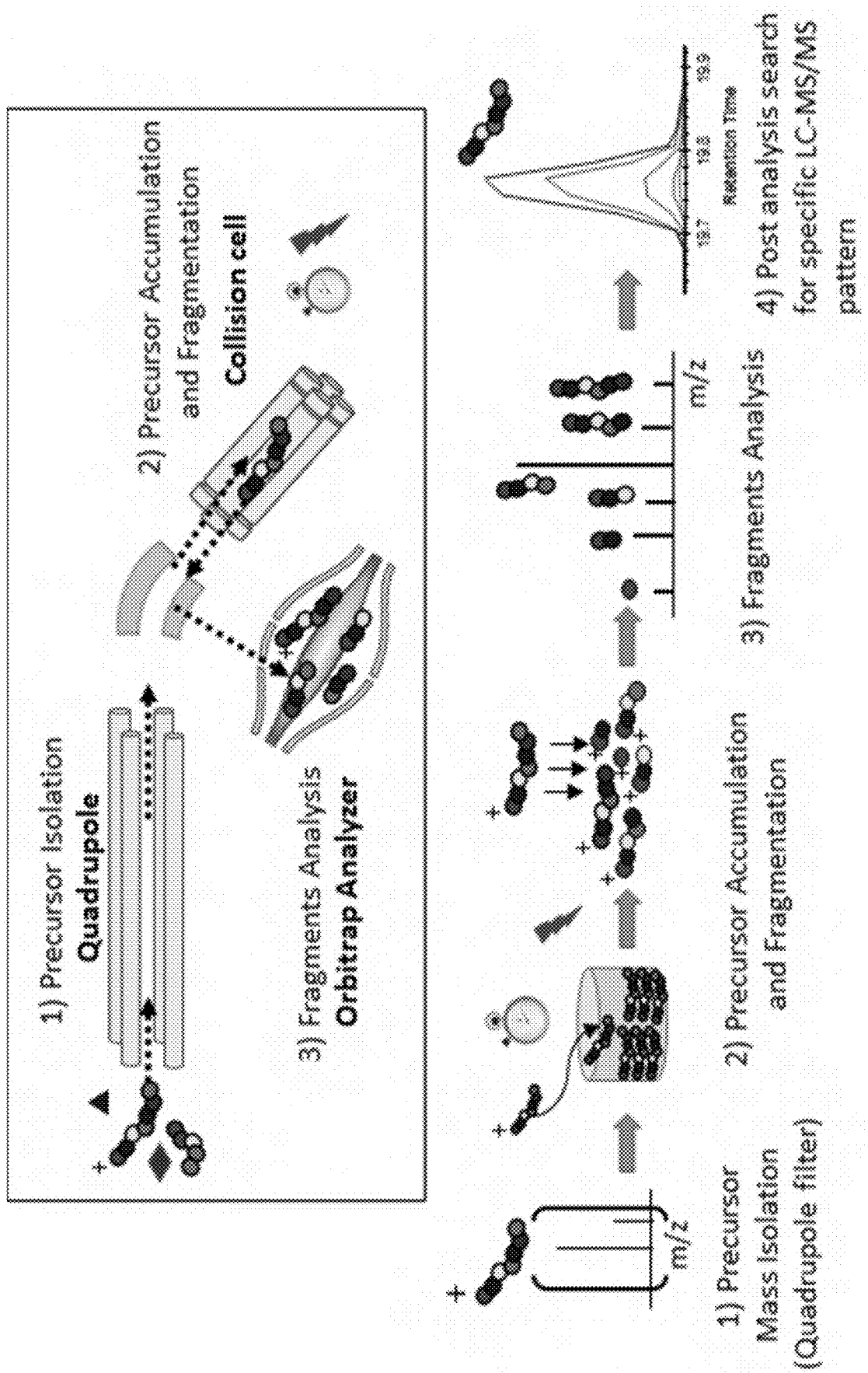
FIG. 2 is a schematic showing the principle of the Parallel Reaction Monitoring experiment.

Principles of PRM for p-tau peptides discovery—Tau peptides containing hypothesized phosphorylation sites were generated by digestion of protein from a tau-enriched biological extract such as human brain soluble fraction. These peptides are screened by targeted-MS analysis using a quadrupole-orbitrap instrument, such as the Thermo Fisher Orbitrap Lumos. For each phosphorylated peptide, the selection of targeted-MS parameters such as precursor mass, collision energy, or expected retention time is performed in silico and refined using biophysical properties measured for corresponding unmodified peptides that are much more abundant in the sample. For detecting phosphorylated peptides, the quadrupole is set to select a mass window including the hypothesized precursor mass. After precursor collision, all generated fragments are simultaneously measured in the Orbitrap over the time of chromatographic elution. Potentially phosphorylated peptides can be searched in post analysis of the generated data. Skyline software (MacCoss Lab, University of Washington, Wash.) was used to extract LC-MS/MS data. The hypothetical peptide being screened is detected as a LC-MS/MS fingerprint constituted by the strict co-elution of the extracted masses from predicted MS/MS fragments (FIG. 2). The advantage of the PRM method over classic DDA or targeted-MS methods is its ability to use the MS instrument in the highest sensitive configuration possible and conserve discovery capability.

Maximum sensitivity of the Quadrupole-Orbitrap instrument during the screening is essential to detect minor ion fragments and facilitates the identification of phosphorylated peptide together with the localization of phosphorylated sites. Sensitivity of the PRM measurement depends mainly on the number of ions from the target of interest transferred into the Orbitrap analyzer. This number was enhanced by increasing the fill time used to acquire one MS/HRMS scan. The fill time corresponds to the time spent to accumulate the targeted precursor mass from the ion beam into the ion trap device. Accumulated precursors are then fragmented and product fragments are transferred into the Orbitrap to be analyzed. Thus, fill time is set to a maximum limited by the need for a sufficient MS scan rate to acquire enough data points to describe the chromatogram signal (i.e. 8-15 scans per chromatographic peak). Fill time for PRM screening on each investigated phosphorylated peptides was typically set to 1 second.

Fill time is also limited by risk of trap saturation. This occurs when too many ions are sampled within the same scan and transferred to the Orbitrap, leading to inaccurate mass measurement due to space charge effects. To avoid such saturation, narrow precursor isolation (0.7 Da) together with appropriate sample purification (immuno purification) enriching the target over matrix were chosen to decrease the contribution of potential near-isobaric interferences.

Specificity of the PRM discovery experiment depends on the resolving power of the LC-Q Orbitrap system. Resolving power can be improved by different analytical parameters, with the ultimate goal to obtain interference-free LC-MS/MS fingerprints for the targeted peptides. This limits the risk of ambiguous fragment assignment due to false positive signals. Sample purification preferentially enriching p-tau can also improve the specificity in the discovery of minor phosphorylated tau peptides. High chromatographic peak capacity and resolution limit the likeliness of co-elution. A narrow quadrupole isolation window for the precursor decreases the probability of interference on the MS/MS spectrum together with limiting the risk of trap saturation as described above. High Orbitrap resolution and analyzer calibration allow the accurate extraction of mass fragments during data processing limiting, the risk of transitions interference (Gallien et al., 2012; Peterson et al., 2012). The choice of Orbitrap resolution (60k) is a balance between high resolution requiring more acquisition time and reasonable scan rates compatible with the chromatographic acquisition.

Quantitative assessment of site specific phosphorylation rate of tau—To quantitatively assess the relative abundance of phosphorylation of specific sites in tau from the brain and CSF, we measured the extent of phosphorylation on each site detected. We used three methods for this purpose: 1) Relative comparison between phosphorylated peptide isomers: Signal comparison from transition ions are used to identify each phosphorylated site. This can estimate the relative abundance of each phosphorylated peptides sharing the same sequence. 2) Phosphorylated peptides are normalized with the non-phosphorylated peptide as reference: LC-MS/MS transition specific to each phosphorylated peptide is compared to the corresponding transition from the non-phosphorylated peptide. Each phosphorylated site ratio obtained can be compared across the protein sequence. This strategy may be biased by difference in fragmentation efficiency between the non-phosphorylated and the phosphorylated peptides. This method cannot be applied when the phosphorylated sites are part of a tryptic missed cleavage. 3) Absolute quantitation using internal synthetic labeled standards (e.g. AQUA) for each phosphorylated and non-phosphorylated peptide: Signals from phosphorylated and non-phosphorylated standards are used to define an internal ratio. This strategy takes into account the fragmentation specificity of each compared peptide but requires peptides synthesis for each monitored species.

In this study, except for those including missed trypsin cleavage, the second method was utilized to calculate phosphorylation rates. We also applied the third method (AQUA normalization) on a limited set of phosphorylated sites found in both brain and CSF extracts when synthetic phosphorylated peptides were available (i.e. T175, T181, S199, S202, T205, T217 and T231) and one site found only in brain (S404) (Table 1). For AQUA measurement, brain extracts were diluted 500 to 8000 times to be comparable to CSF tau levels. This dilution minimized the matrix effect that may results from significantly different ratio of AQUA internal standard to tau peptide levels in the brain versus CSF. The first method was used for initial interpretation of the complex LC-MS/MS patterns from p-tau sequence containing numerous phosphorylated residues.

Statistics—Data are represented as mean±SD, unless otherwise specified. After confirming the normal distribution of the data, one-way ANOVA followed by post hoc analyses (Tukey test) were performed for comparing tau phosphorylation rates. Additional statistical analysis was completed using GraphPad version 8.0.1 (244) from GraphPad Software Inc. Statistical significance between relevant groups was determined with a 2-tailed, unpaired, Mann-Whitney t-test. Significance was evaluated at the 0.01 and 0.05 level.

Figure 16A:
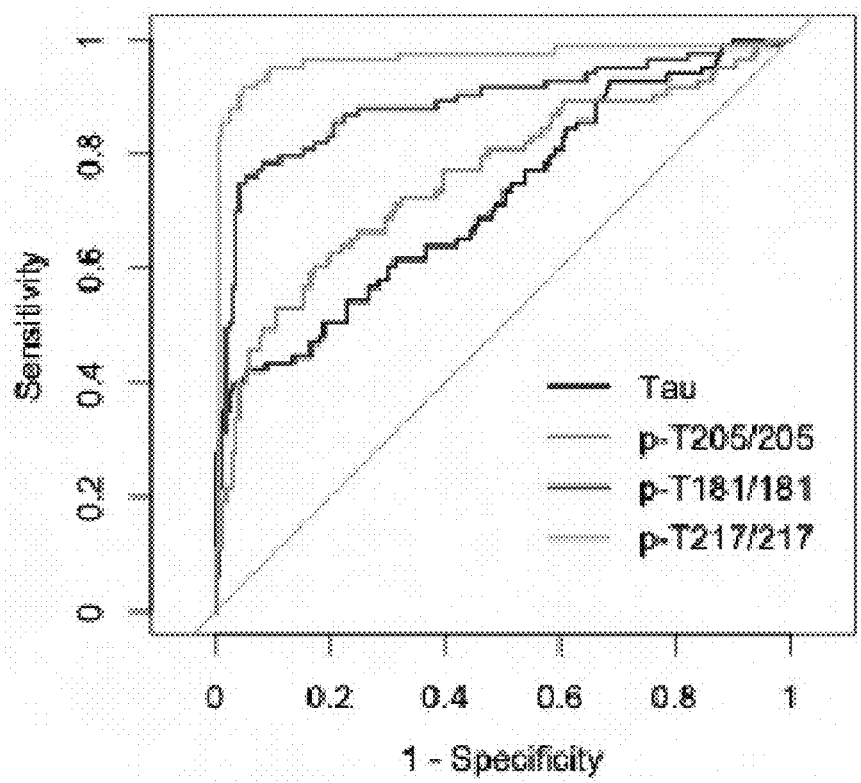
FIG. 16A, FIG. 16B, FIG. 16C, FIG. 16D, FIG. 16E, FIG. 16F, and FIG. 16G show amyloid plaques are strongly correlated with tau hyperphosphorylation but differ by site of phosphorylation.

Example 5: Cerebral Amyloid Pathology is Associated with Site-Specific Differences in Tau Hyperphosphorylation The standard uptake value ratio (SUVR) of cortical PiB-PET reliably identifies significant cortical Aβ-plaques and is used to classify subjects as PIB positive (Amyloid+, SUVR≥1.25) or negative (Amyloid−, SUVR<1.25). To explore the relationship of amyloid plaques and soluble tau species, we compared the SUVR of cortical PiB-PET with CSF total tau and with phosphorylation of CSF tau at multiple sites (i.e. ratio of phosphorylated to unphosphoryated sites of tau). (FIG. 16A) Phosphorylation of tau at Thr217 (p-T217) had a 97.2% area under the curve (AUC) (95% Confidence Interval (CI) of 0.94, 0.99)); phosphorylation of tau at Thr181 (p-T181) had an 89.1% AUC (CI 0.83, 0.94); phosphorylation of tau at Thr205 (p-T205) had a 74.5% AUC (CI 0.69, 0.82); and total tau had a 72% AUC (CI 0.65, 0.79) to classify mutation carriers (MC) as having cortical Aβ-plaques (i.e., Amyloid+). These data indicate that at the early stages of significant fibrillar Aβ positive plaques, an increase of phosphorylation has already begun at specific sites linking these two processes in time. These data also demonstrate that an increase in the phosphorylated to unphosphorylated ratio of T217 could serve as a sensitive diagnostic marker for fibrillar Aβ plaque pathology.

Figure 16B:
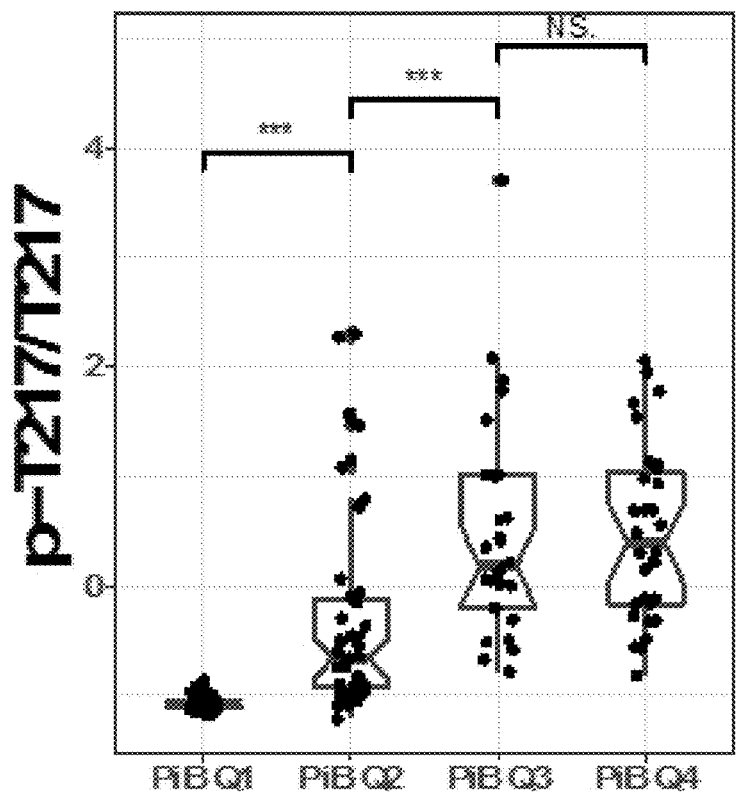

We then compared the mean, standardized phosphorylation ratios of four phosphorylation sites and total tau levels by PiB-PET SUVR quartiles to explore the relationship between total Aβ-plaque load and phosphorylation, FIG. 16B. All phosphorylation sites except Ser202 (p-S202) demonstrated increased phosphorylation with greater Aβ-plaque pathology. Differences among the other three sites were also discovered. p-T217 and p-T181 showed the largest increases once plaques had started (quartiles 2-3), but the magnitude of these increases diminished with greater plaque burden; in contrast, the increases in phosphorylation at p-T205 and total tau levels continued to grow along with the Aβ plaques. These results suggest that the events initially leading to increased tau phosphorylation in AD are likely related to Aβ-plaque pathology, potentially through regulation of distinct kinases and phosphatases that are phosphorylation site specific. Further, the data suggest that p-T217 could serve as a surrogate biomarker for fibrillar Aβ-plaque pathology, identifying a potentially unique signature of Aβ-related tau processing. Importantly, among mutation non-carriers (NCs), the only participants who showed an increase in phosphorylation at T217 were those who were PiB+(SUVR>1.25, n=4).

Figure 16C:
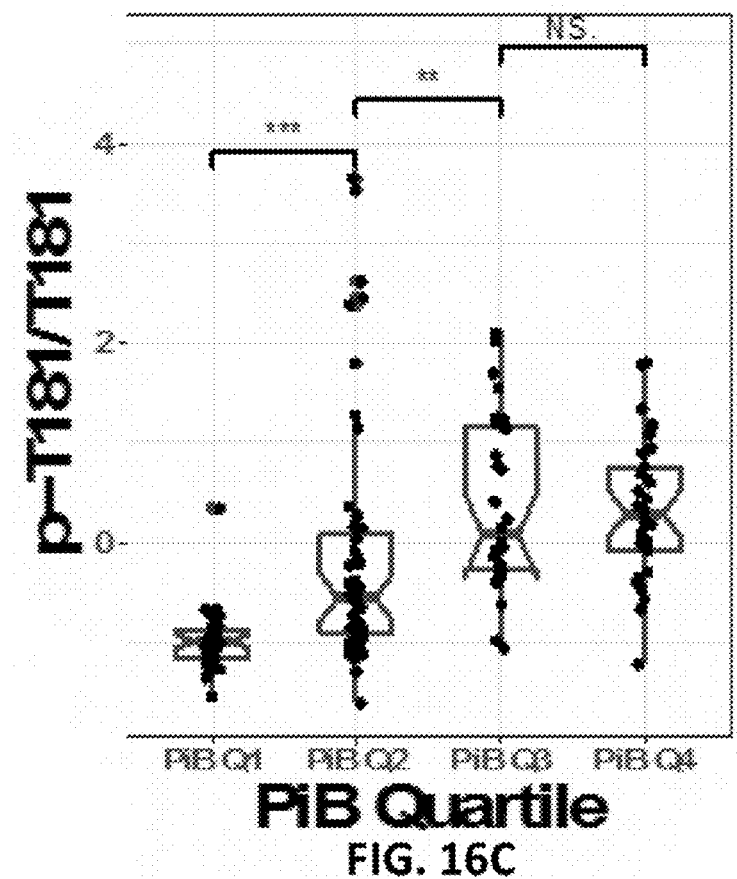
Figure 16D:
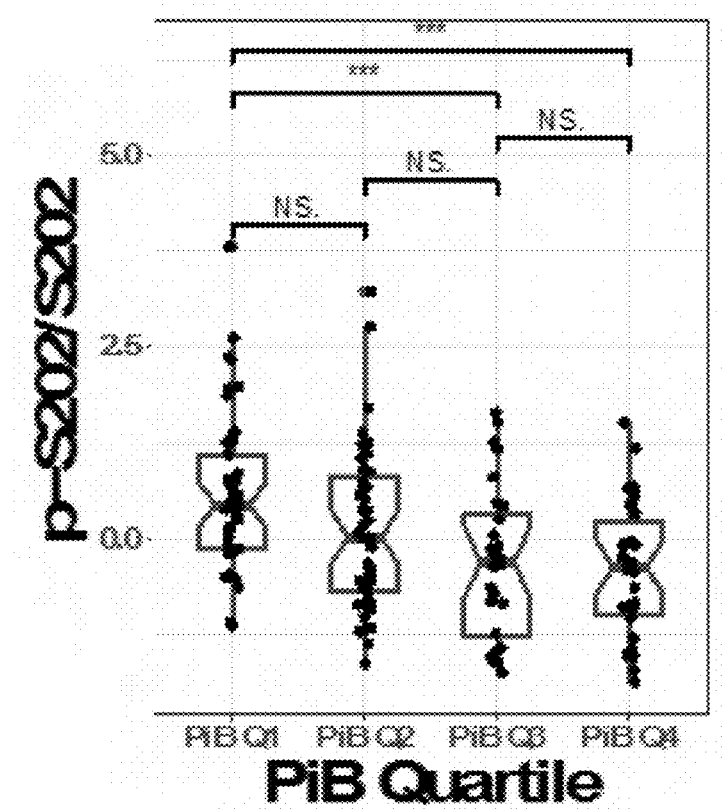
Figure 16E:
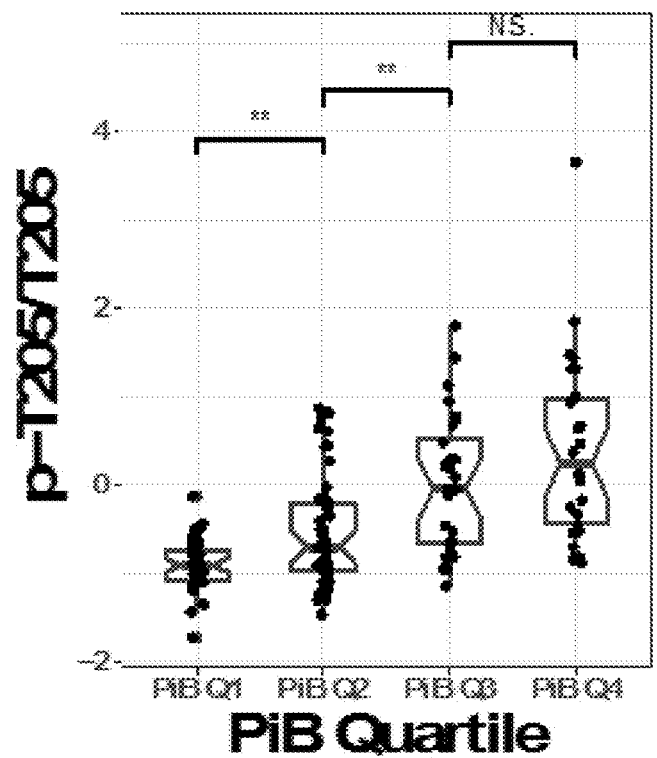
Figure 16F:
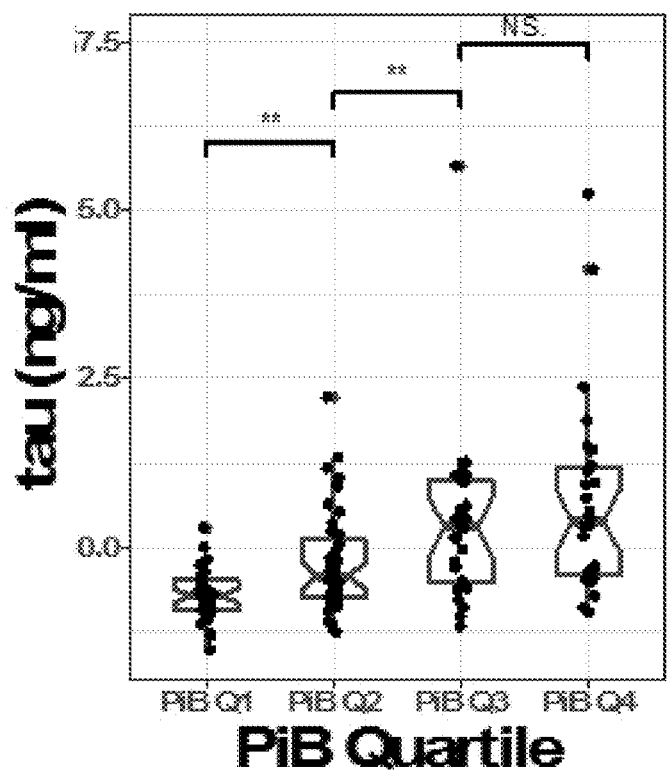
Figure 16G:
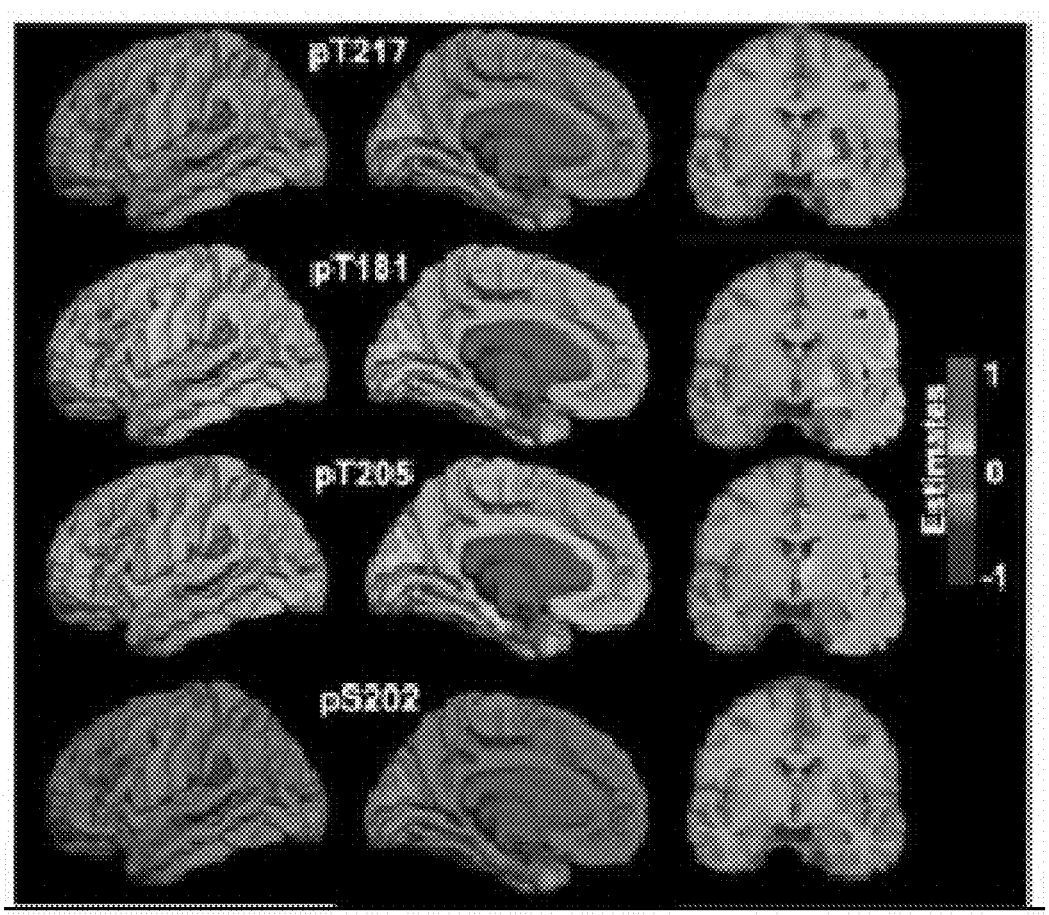
Figure 17A:
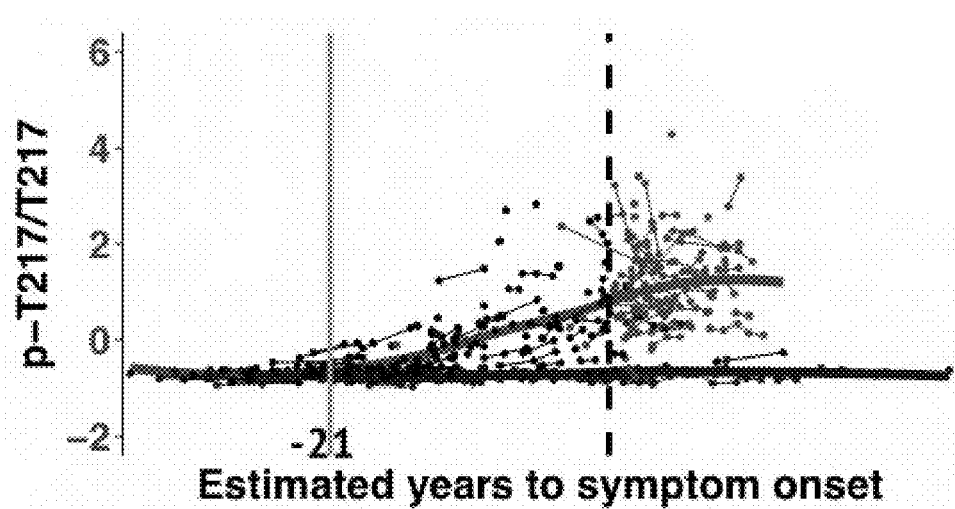
FIG. 17A, FIG. 17B, FIG. 17C, FIG. 17D, FIG. 17E, and FIG. 17F show longitudinal changes of different phosphorylated-tau sites are stage of disease specific and change in opposite directions as AD progresses. Individual, z-transformed, longitudinal changes in the ratio of phosphorylation of (FIG. 17A) p-T217, (FIG. 17B) p-T181 (FIG. 17C) total tau, (FIG. 17D) p-T205, and (FIG. 17E) p-S202 for mutation carriers (black=asymptomatic mutation carriers, (n=152), red=symptomatic mutation carriers (77)) and non-carriers (blue, (n=141)) across the estimated years to symptom onset (EYO). The vertical dashed line is the point of expected symptom onset, the green line represents the model estimated time when the rate of change for each p-tau isoform becomes greater for mutation carriers compared to non-carriers.
Figure 17B:
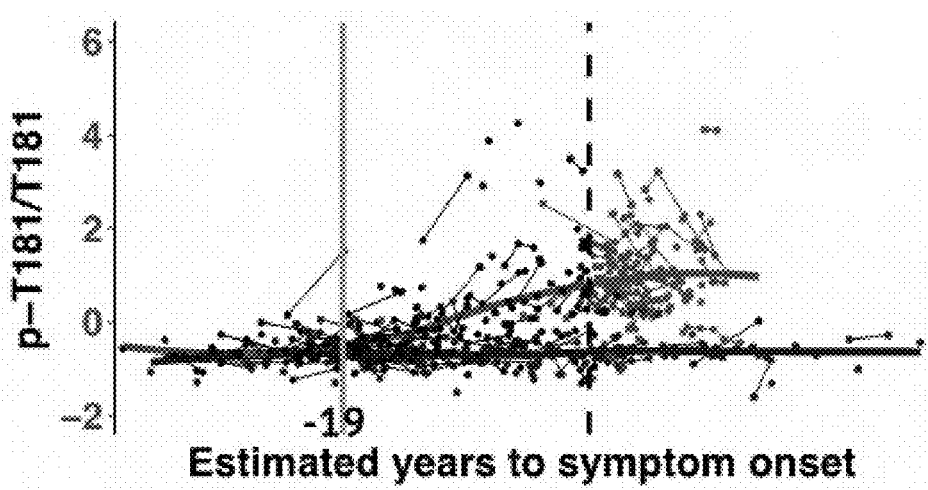
Figure 17C:
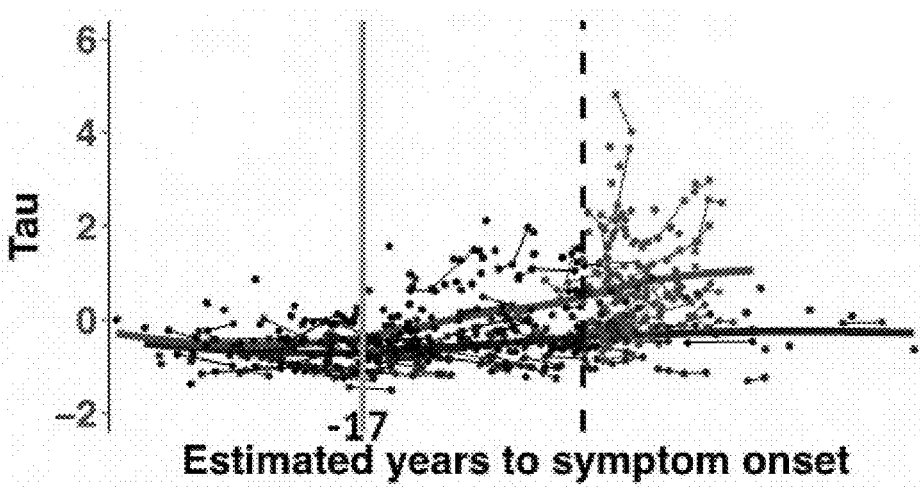
Figure 17D:
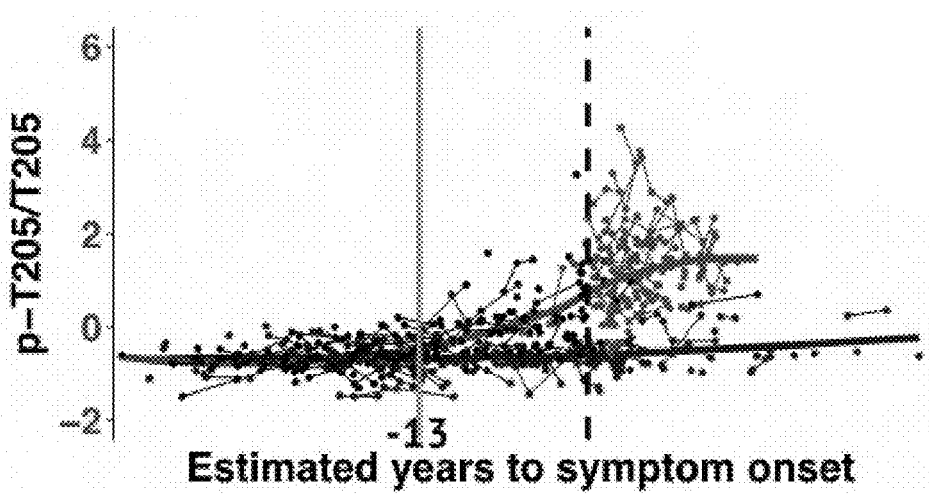
Figure 17E:
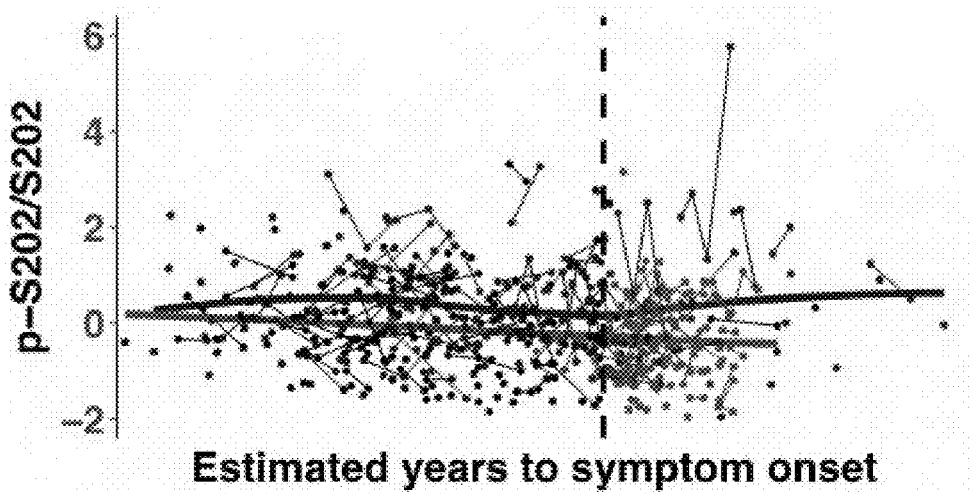
Figure 17F:
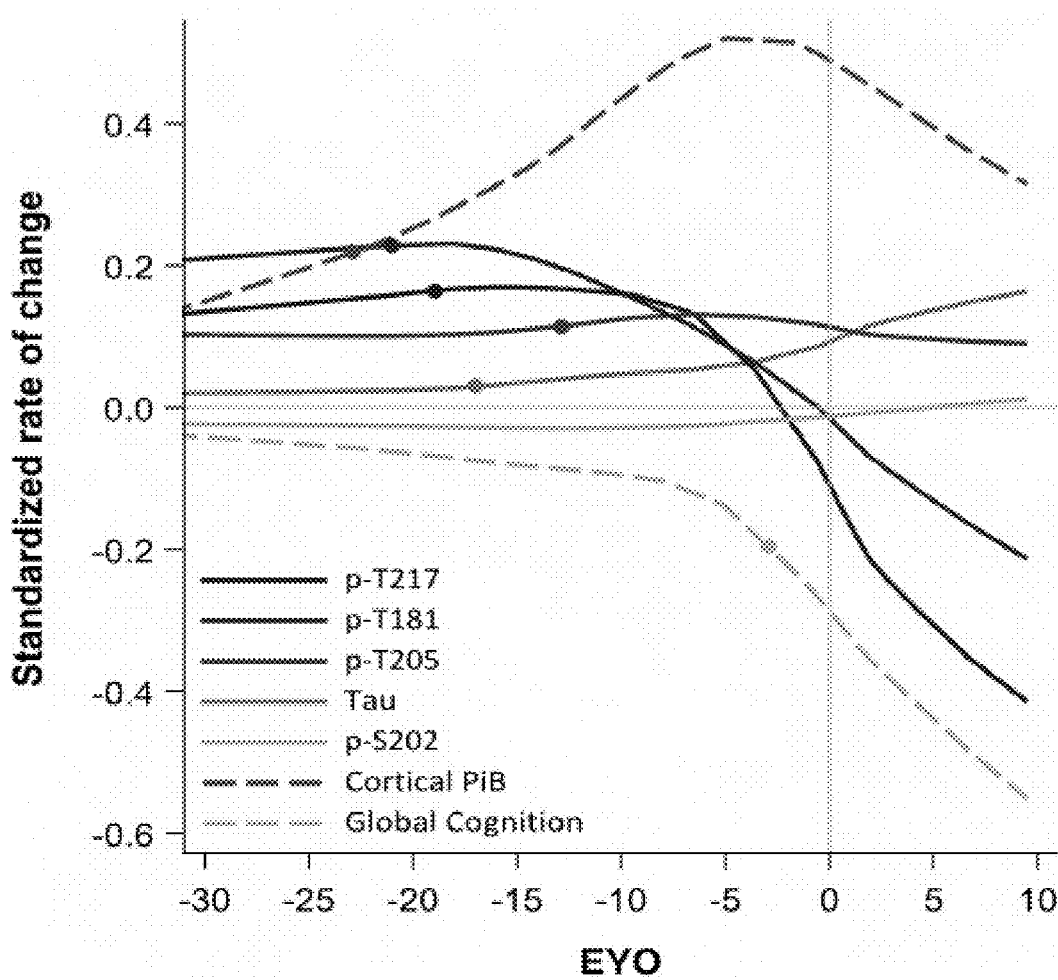

We next assessed whether site-specific tau phosphorylation was associated with the anatomical distribution of cerebral Aβ-plaque pathology by exploring the correlations between specific tau phosphorylation sites and cortical and sub-cortical regions of amyloid plaque deposition as measured by PiB-PET SUVR, FIG. 16C. Phosphorylation at T217, T181, and T205 positively correlated with Aβ-plaques throughout the brain, but phosphorylation at S202 was negatively correlated. In the precuneus, a region of early amyloid plaque deposition, correlations with tau isoforms were compared based on the strength of bivariate regression controlling for age, gender, and estimated years to symptom onset (EYO) and adjusted for multiple comparisons. We found a rank order of correlations of p-T217 (β=0.68, p<10-30), p-T181 (β=0.46, p<10-6), p-T205 (β=0.41, p<10-5), and total tau (β=0.35, p<0.001) with positive correlations with Aβ-plaques. In contrast, p-S202 had an inverse correlation (β=−0.47, p<10-7), suggesting that phosphorylation at this site is lowered with increasing Aβ pathology. These relationships were present in pre-symptomatic MCs when there is little evidence of neurodegeneration, suggesting that the increase in phosphorylated tau in the CSF is not a consequence of passive release from dying neurons, but more likely an active process related to the presence of Aβ-plaque pathology[22].

Example 6: Disease Stage and Progression are Associated with Site-Specific Differences in Tau Hyperphosphorylation and Longitudinal Rates of Change The certainty of disease onset and predictability of symptom onset of DIAD enables the staging of individuals based on EYO 9,10,30 (i.e. the age of an individual at the time of assessment relative to the age of onset of others with the mutation). We next determined whether there were temporal differences in the pattern of phosphorylation of CSF tau. This was done by estimating the differences in the amount and rate of change in phosphorylation over time between MCs and NCs based on EYO. There were two important findings. First, there was evidence that increases in total tau and phosphorylation at specific sites occurred in a discreet order: Phosphorylation of T217 occurred around −21 EYO, and was followed by phosphorylation of T181 around −19 EYO, then an increase in total tau around −17 EYO, and then phosphorylation of T205 around −13 EYO (FIG. 17A-F). The initial increase in phosphorylation at T217, and to a lesser extent at T181, occurred at a similar time to when Aβ-plaques began to increase (−19 EYO). Second, the ratio of phosphorylation of T217 and T181 began to decline significantly near the time of symptom onset, while phosphorylation at T205 remained elevated and total tau levels continued to increase. Of note, the concentration of all unphosphorylated peptides increased with disease progression (data not shown) suggesting that the decrease in the phosphorylation ratio for T217 and T181 was not a result of a disproportionate rise in unphosphorylated peptides specifically spanning these sites. For S202 there was no significant change in phosphorylation over the course of the disease, FIG. 17E. These results indicate that phosphorylation of tau occurs differentially for each site, increasing or decreasing at specific sites by disease stage. These site specific changes suggest a cascade of changes in soluble tau that is more dynamic than previously realized, and that tau does not monotonically increase in phosphorylation states or ratios. The emergence of Aβ amyloid plaques and the onset of clinical decline, separated by two decades, mark two important demarcations of stages during which soluble tau phosphorylation changes.

Example 7: Neuroimaging Markers of Disease Progression are Associated with Site-Specific Differences in Tau Hyperphosphorylation In addition to estimating the onset of symptoms using family history (EYO), disease progression in DIAD can also be estimated using neuroimaging measures that track various components of disease progression, e.g. brain atrophy and metabolic decline. These measures have been shown to change at different periods of time before symptom onset, with declining cerebral metabolism (measured by [F18] fluorodeoxyglucose [FDG]-PET) occurring up to 18 years and brain atrophy (determined by MRI) occurring up to 13 years before symptom onset[28,31-33]. This raises the question of whether these biomarkers are likewise correlated with tau phosphorylation at specific sites. To examine this, we performed bivariate cross-sectional correlations between the phosphorylation sites and total tau with imaging measurements from 34 cortical and 6 subcortical brain regions, controlling for gender, age and EYO. We focused the analyses on asymptomatic MCs in order to identify any associations at the earliest stages of disease progression. The phosphorylation state of tau at S202 was not included in these analyses given its lack of change over disease progression.

Figure 18A:
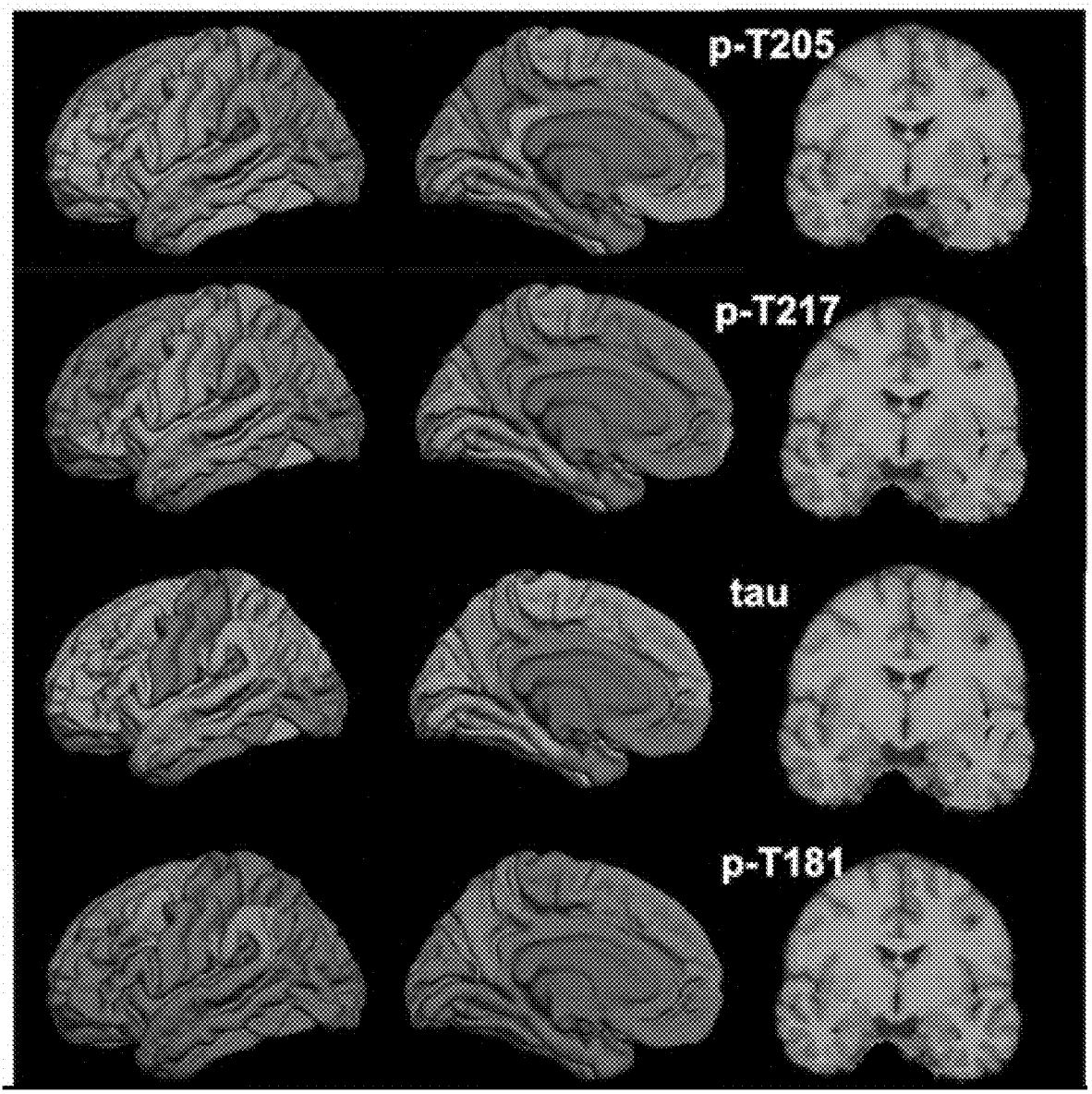
FIG. 18A and FIG. 18B show phosphorylated-tau sites are differentially related to brain hypometabolism and atrophy.

MRI—Hyperphosphorylation was inversely associated with cortical thickness in asymptomatic MCs: p-T205 was most strongly associated with a decrease in cortical and subcortical thickness throughout the brain, FIG. 18A, while p-T217 and total tau levels showed fewer regional associations and weaker correlations. Hyperphosphorylation at p-T181 had the lowest overall correlation with cortical atrophy, restricted to the medial and lateral parietal lobes and medial dorsal-medial frontal lobes. This suggests that the initial rise in p-T205 at −13 EYO may be related to the underlying etiology of cortical atrophy, which we have previously shown to begin approximately at −13 EYO in the precuneus[28].

Figure 18B:
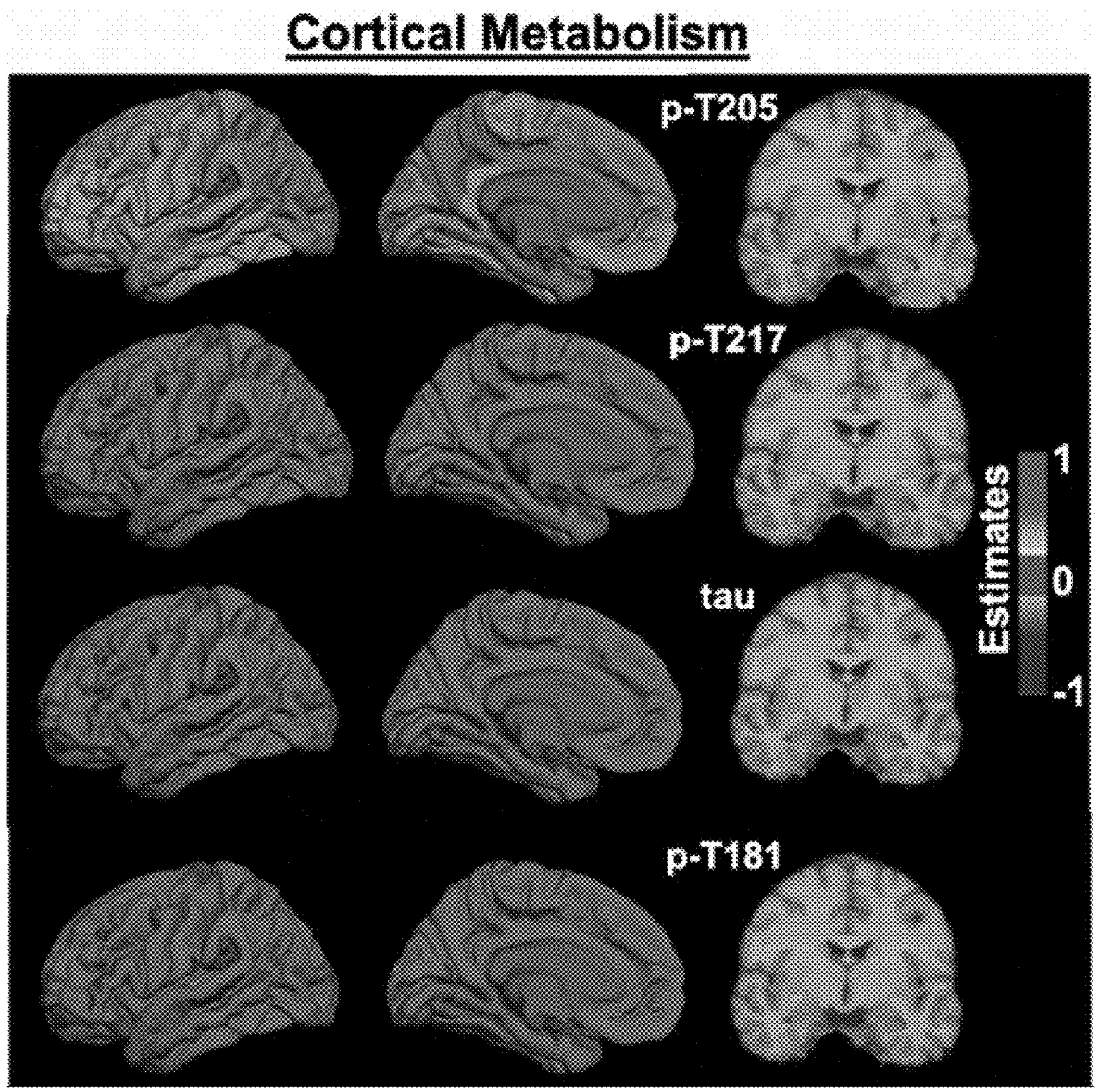
Figure 19A:
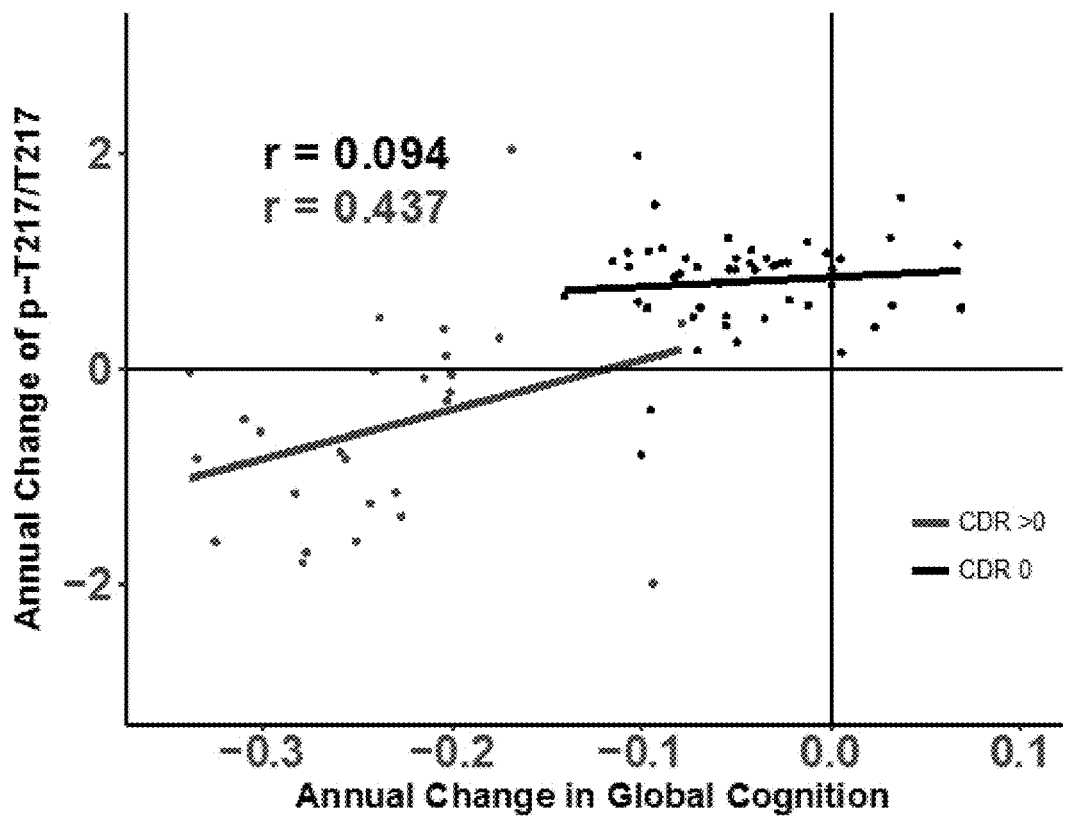
FIG. 19A, FIG. 19B, FIG. 19C, and FIG. 19D show decreasing phosphorylation at p-T217, p-T181 and p-T205 is associated with dementia and cognitive decline. Individual estimated annualized rates of change of p-tau isoforms and total tau (y-axis) for mutation carriers were correlated with the annualized change in global cognitive function; the lines represent simple linear regression with shaded area representing 95% confidence interval. Each point represents an individual level correlation between measures. The linear regression was fit to those with no dementia (black, n=47) and dementia (red, n=25). A decline in p-T217 (FIG. 19A), r=0.43(p=0.02), p-T181 (FIG. 19B), r=0.72 (p<0.001) and p-T205 (FIG. 19C), r=0.41(p=0.03) phosphorylation rate was associated with cognitive decline after symptom onset (red). For total tau there was a trend suggesting an inverse correlation with cognition (FIG. 19D) but it was not significant.
Figure 19B:
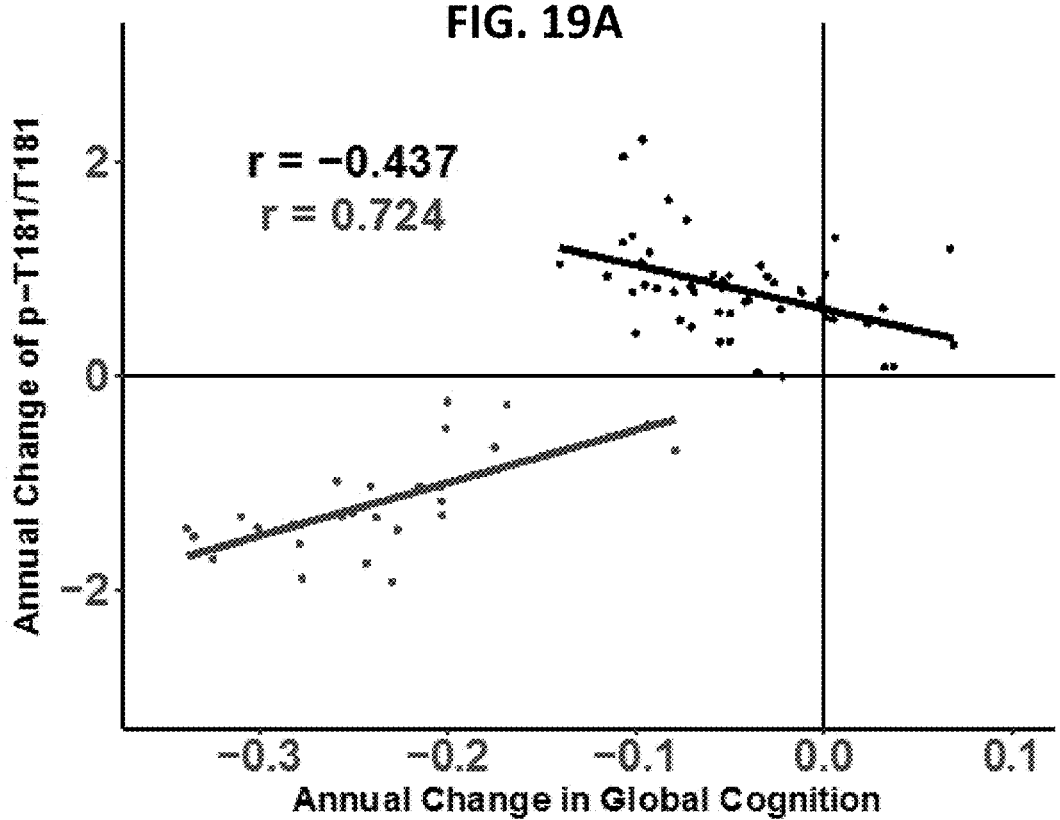
Figure 19C:
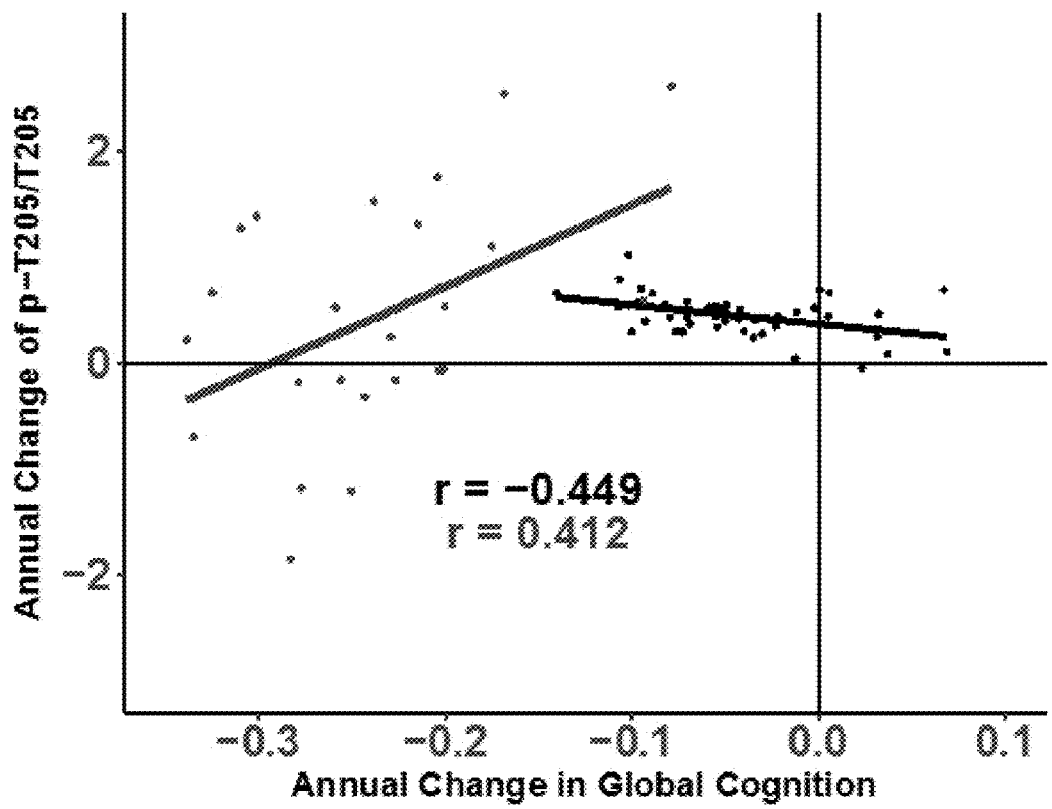
Figure 19D:
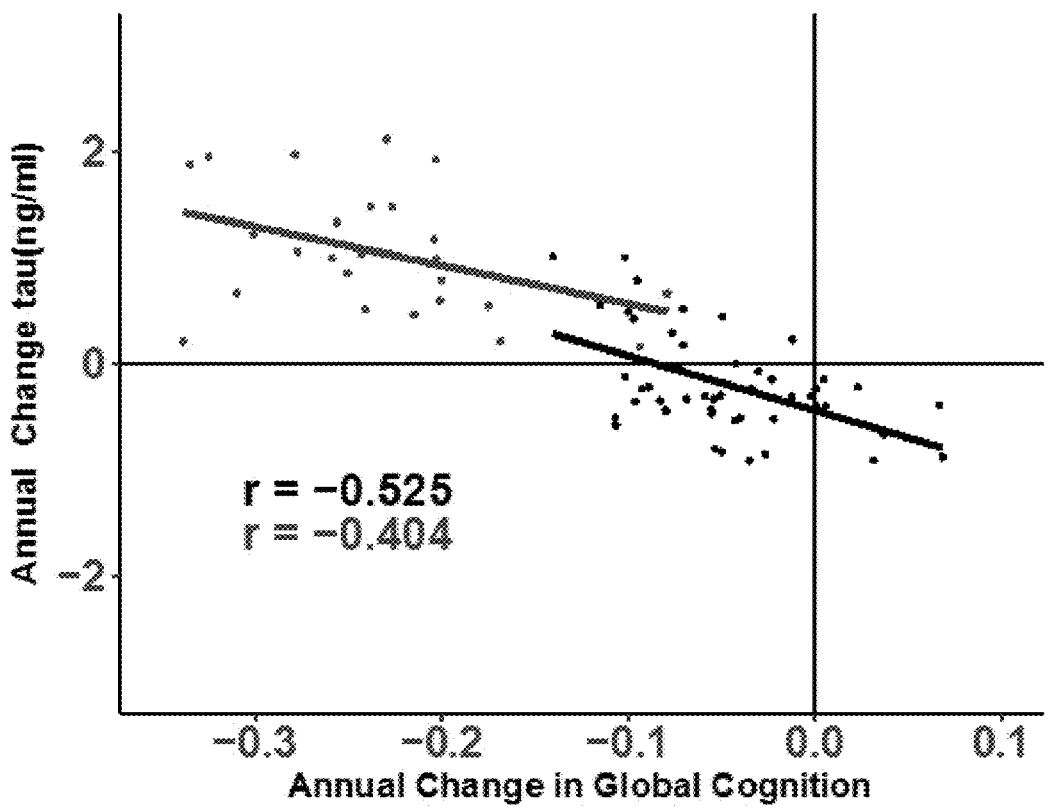

FDG PET—In addition to cortical atrophy, a decline in glucose metabolism in neurons and glia is associated with disease progression in AD. Therefore, we tested whether there were distinct associations between cortical or subcortical metabolic impairment and tau phosphorylation. In the asymptomatic MCs, phosphorylation at T205 was correlated with glucose hypo-metabolism throughout the cortex and sub-cortical regions, as measured by FDG-PET, FIG. 18B. There were minimal associations identified for the other p-tau sites or total tau level in asymptomatic MCs.

Together, these results indicate that the underlying processes leading to neuronal impairment and neurodegeneration during asymptomatic disease progression, as measured by neuroimaging, are most closely correlated with p-T205. Recent studies have identified a protective role for p-T205 in the post-synaptic terminals in response to AB-induced post-synaptic cytotoxicity[34] through the fyn-kinase pathway. It is possible that the association found here, when synaptic function is declining, could represent a protective process resulting in increased phosphorylation at T205. Over time, however, hyperphosphorylation could predispose tau to aggregation. Whereas, phosphorylation at T181 and T217 appears to be more strongly associated with the presence of cortical Aß-plaque pathology and, potentially, occurs upstream of T205 hyperphosphorylation and elevation of soluble unphosphorylated tau levels.

Example 8—Cognitive Decline is Specifically and Differentially Associated with Site-Specific Differences in Tau Hyperphosphorylation Prior studies have shown that AD dementia is more closely related to neocortical NFT pathology than neocortical Aβ pathology[35], yet the relationship between soluble tau and cognition remains uncertain. Therefore, we assessed the longitudinal change in the soluble tau phosphorylation ratio and total tau levels over time in comparison to clinical outcomes[36]. We performed a mixed effect model with longitudinal cognitive performance on the neuropsychological composite as the outcome, and change in CSF tau measures (derived from individual linear mixed effect models), time, and their interactions as the predictor, adjusting for age, gender, education, and familial relations. We tested all MCs (symptomatic and asymptomatic) for this analysis and found differential effects between phosphorylation site and clinical and cognitive decline. Non-phosphorylated tau monotonically increased with worsening cognition and phosphorylation at T217 and T181 decreased with worsening cognition, while pT205 demonstrated no change relative to cognitive decline.

As the phosphorylation ratios of T217 and T181 decreased, cognitive decline accelerated (t value 2.35, p=0.02 and 2.11, p=0.04), Table 3 and FIG. 19. This suggests that decreased phosphorylation of T217 and T181, more than increased soluble tau, presents an important marker of cognitive decline.

These findings challenge the current paradigm that a continuous rise in CSF p-tau is associated with cognitive dysfunction. In this work, we uncovered two general patterns: for some sites, phosphorylation decreased significantly as cognitive decline began, whereas other sites showed a continuous increase or no change with disease progression (see increasing vs. decreasing rates in FIG. 19). Additionally, the associations between other markers of disease progression (Aβ-plaques, brain atrophy and metabolism) and total tau levels and phosphorylation at different sites which we identified further emphasize that the processes leading to tau phosphorylation in AD are likely multifactorial and are not equivalent.

Example 9—Increases in Unphosphorylated Tau are Correlated with Cortical NFTs by Tau PET, but Canonical Phospho-Tau Species are not Recent tau-PET ([18]F AV-1451, or flortaucipir) studies with DIAD participants have suggested that NFT increase only occurs following the onset of clinical symptoms[37,38]. We tested the hypothesis that soluble p-tau is a marker of NFT pathology while soluble unphosphorylated tau is passively released from dying neurons[14] as a measure of neurodegeneration. We explored the relationship between longitudinal change of CSF tau and p-tau isoforms leading up to the time when tau-PET was performed. In a limited number of participants (10 MCs and 4 NCs), a single tau-PET scan was performed within 72 hours of the CSF sample being obtained. For these individuals, CSF samples had also been obtained on previous visits (within 1-3 years) allowing us to assess the ability of longitudinal change in soluble tau measures to predict tau-PET levels.

Figure 20:
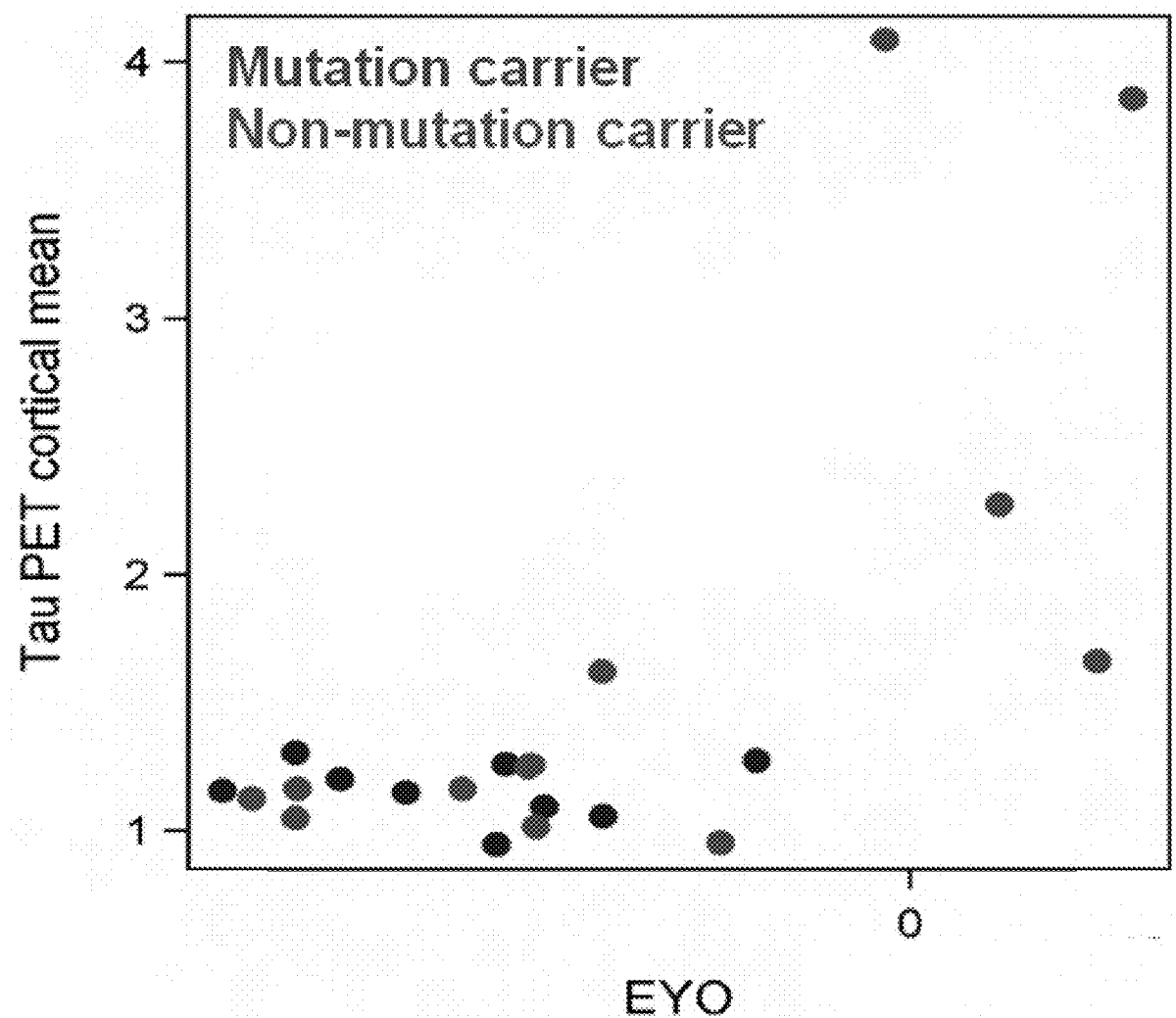
FIG. 20 shows tau PET increases near symptom onset in DIAD mutation carriers. The mean cortical standardized unit value ratio (SUVR), y-axis, for mutation carriers (red, n=12) and non-carriers (blue, n=9) over estimated years to symptom onset (EYO), x-axis, for those participants with a longitudinal CSF evaluation preceding the time of tau-PET. The plot shows that for mutation carriers there is little elevation in tau-PET until the point of estimated symptom onset (EYO=0). This figure shows that the neurofibrillary tangle (NFT) pathology detected by AV-1451 occurs much later than the increase in multiple soluble phosphotau sites suggesting that these soluble markers of tau are likely a marker of NFT pathology, but rather might predispose to the development of the hyperphosphorylated, insoluble tau deposits characteristic of AD pathology.
Figure 21A:
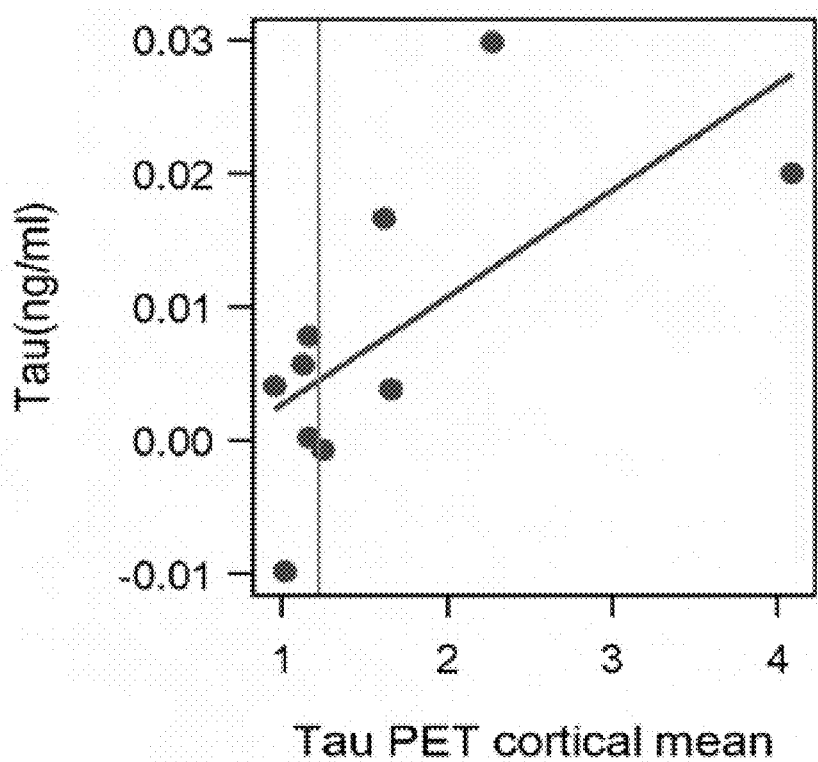
FIG. 21A, FIG. 21B, FIG. 21C, FIG. 21D, and FIG. 21E show longitudinal change in tau and tau phosphorylation sites are differentially related to neurofibrillary tau (tau-PET) in dominantly inherited AD. Individual, estimated rates of change of phosphorylation and total tau (y-axis) leading up to the time of tau-PET scan (x-axis). The vertical line is an SUVR of 1.22 and represents a conservative estimate of the point when NFT tau-PET (a composite of multiple cortical and limbic regions) is considered elevated compared to non-carriers. The plots suggest that increases in soluble tau and p-T205 are associated with higher levels of aggregated tau, whereas the rate of phosphorylation at p-T217 and p-T181 decrease as levels of aggregated tau increase. These findings suggest that there are differences between increasing levels of tau and phosphorylation at different sites and may indicate that, in some instances, soluble p-tau is sequestered as the burden of hyperphosphorylated aggregates increase with the spreading of tau pathology. They also suggest that with the increase in aggregated tau there is a rise in soluble tau levels which could represent either passive or active release with greater burden of aggregated tau pathology.
Figure 21B:
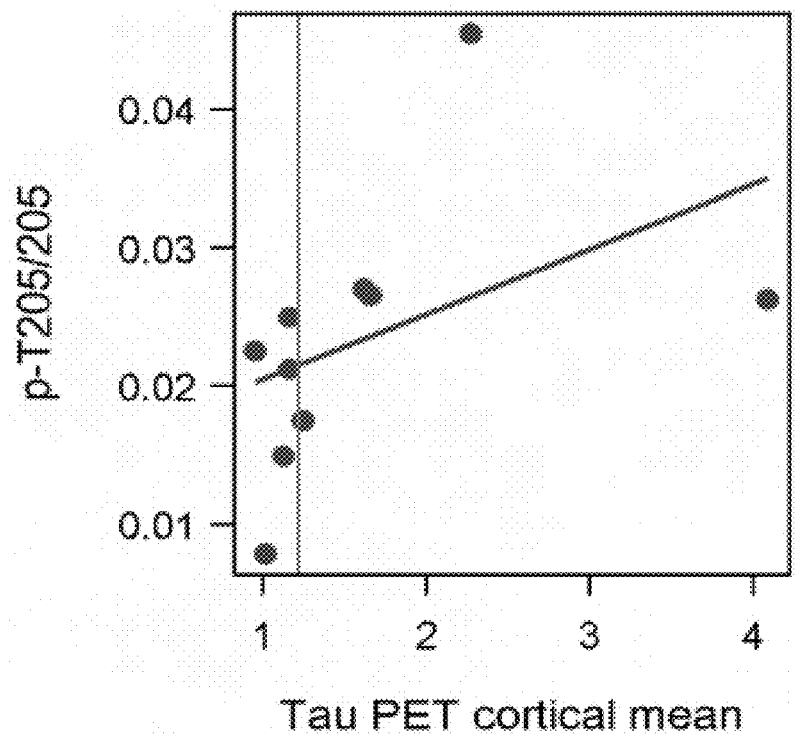
Figure 21C:
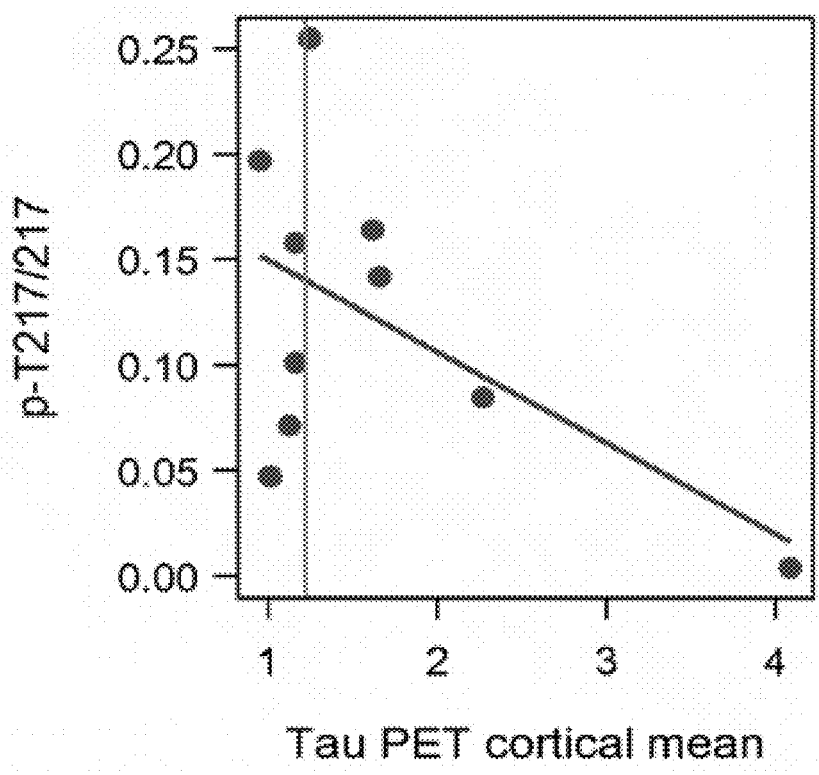
Figure 21D:
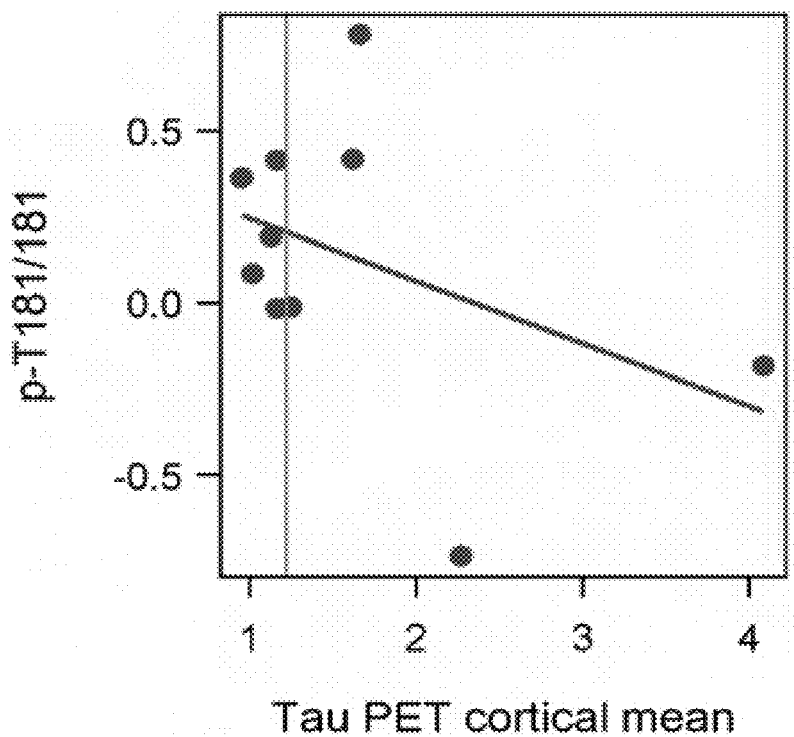
Figure 21E:
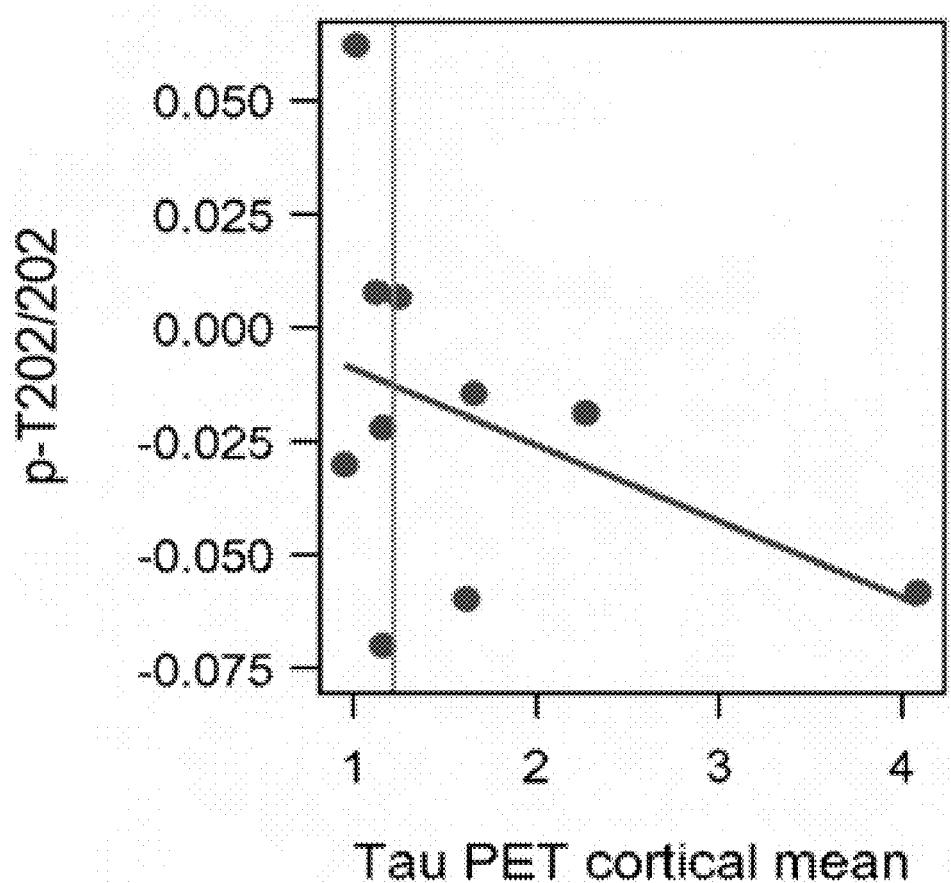

First, we confirmed that cortical NFT levels in MCs only increased near the time of symptom onset, FIG. 20, suggesting that in DIAD MCs, clinical decline begins when tau aggregates start to increase. Second, we found that the longitudinal increase in CSF unphosphorylated tau was associated with an elevated cortical tau-PET (p=0.03) value, Table 4. There were trends for an increase in phosphorylation for T205 being associated with higher levels of tau-PET and, contrarily, that decreasing phosphorylation of T217, T181 and S202 were associated with increasing levels of tau-PET, FIG. 21. Together, these findings suggest that increasing unphosphorylated tau in the CSF, rather than p-tau, is more closely linked to the spread of NFT pathology. In contrast, a soluble p-tau species decline when aggregated tau is increasing which could represent a process of sequestration by hyperphosphorylated aggregates.

TABLE 2

Demographic, cerebrospinal fluid, neuroimaging and cognition measures for mutation carriers and non-carriers.

|  |  | Mutation Carriers | | Mutation non- | |
|---|---|---|---|---|---|
|  | N | Asymptomatic (N = 152) | Symptomatic (N = 77) | carriers (N = 141) | p-value |
| Age | 370 | 34.4 ± 8.9 | 46.2 ± 9.2 | 38.5 ± 12.2 | <.0001 |
| Female, n (%) | 370 | 84 (55.3) | 39 (50.7) | 88 (62.4) | 0.15 |
| APOE ε4, n (%) | 370 | 48 (31.6) | 23 (29.9) | 51 (36.2) | 0.67 |
| EYO, MEAN ± SD | 370 | −13.4 ± 8.7 | 3.42 ± 3.47 | −9.2 ± 12.5 | <.0001 |
| Cortical PiB PET SUVR | 304 | 1.76 ± 0.89 | 2.82 ± 1.27 | 1.06 ± 0.17 | <.0001 |
| *PiB+, n (%) | 304 | 81 (60.9) | 48 (96.0) | 2 (1.65) | <.0001 |
| CSF p-T181 (phospho/unphospho) | 370 | 26.5 ± 7.2 | 34.2 ± 7.7 | 21.7 ± 2.3 | <.0001 |
| CSF T181 total (ng/ml) | 370 | 0.14 ± 0.09 | 0.30 ± 0.19 | 0.088 ± 0.034 | <.0001 |
| CSF p-T205 (phospho/unphospho) | 370 | 0.44 ± 0.24 | 0.93 ± 0.36 | 0.34 ± 0.13 | <.0001 |
| CSF T205 total (ng/ml) | 370 | 0.003 ± 0.003 | 0.011 ± 0.008 | 0.002 ± 0.001 | <.0001 |
| CSF p-T217 (phospho/unphospho) | 370 | 3.49 ± 3.08 | 8.42 ± 4.05 | 1.25 ± 0.66 | <.0001 |
| CSF T217 total (ng/ml) | 370 | 0.015 ± 0.018 | 0.054 ± 0.047 | 0.004 ± 0.004 | <.0001 |
| CSF p-T208 (phospho/unphospho) | 370 | 0.00030 ± 0.0004 | 0.0010 ± 0.0006 | 0.00008 ± 0.00014 | <.0001 |
| CSF p-S202 (phospho/unphospho) | 370 | 2.77 ± 0.80 | 2.52 ± 0.68 | 3.10 ± 0.72 | <.0001 |
| CSF S202 total (ng/ml) | 370 | 0.016 ± 0.006 | 0.025 ± 0.011 | 0.014 ± 0.005 | <.0001 |
| Tau (ng/ml) | 370 | 0.51 ± 0.21 | 0.82 ± 0.41 | 0.40 ± 0.14 | <.0001 |
| Precuneus (mm) | 344 | 2.37 ± 0.15 | 2.10 ± 0.24 | 2.38 ± 0.14 | <.0001 |
| Cortical FDG PET SURV | 318 | 1.73 ± 0.14 | 1.57 ± 0.18 | 1.71 ± 0.14 | <.0001 |
| Hippocampal volume (mm$^3$) | 344 | 8863 ± 970 | 7290 ± 1214 | 8787 ± 775 | <.0001 |
| Cognitive Composite (z-score) | 356 | −0.096 ± 0.640 | −1.67 ± 0.85 | −0.03 ± 0.59 | <.0001 |

EYO—estimated years to onset of symptoms;

PiB—Pittsburgh compound B;

p—phosphorylated;

S—serine;

SUVR—standard uptake value ratio;

T—threonine.

TABLE 3

Longitudinal change in global cognition as predicted by the longitudinal change of phosphorylated-tau sites and total tau levels in mutation carriers.

| | | CSF Tau | | | | p-T181 | | | |
|---|---|---|---|---|---|---|---|---|---|
| Outcome | Predictor | estimate | SE | t value | p value | estimate | SE | t value | p value |
| Change in Cognition | Change in CSF * time | 0.16 | 1.91 | 0.09 | 0.93 | −2.01 | 0.38 | −5.23 | <.0001 |

| | | p-T205 | | | | p-T217 | | | |
|---|---|---|---|---|---|---|---|---|---|
| | | estimate | SE | t value | p value | estimate | SE | t value | p value |
| Change in Cognition | Change in CSF * time | −0.06 | 0.5 | −0.13 | 0.9 | −2.41 | 0.45 | −5.32 | <.0001 |

TABLE 4

The longitudinal change of phosphorylation ratio and total tau were predicted for each individual that had a Tau-PET scan performed at the time of a follow-up cerebrospinal fluid examination (n = 14 (10 mutation carriers, 4 non-carriers) was used to predict the cortical tau standardized unit value ratio (SUVR). The table indicates that only predictor of an increase of tau-PET in this limited population was increasing levels of soluble tau in the CSF, with an increase of 36 ng/ml associated with an increase of 1 unit cortical SUVR.

|  | Predictor | tau (ng/ml) | | | p-T181 | | | p-T205 | | |
|---|---|---|---|---|---|---|---|---|---|---|
|  |  | estimate | SE | p value | estimate | SE | p value | estimate | SE | p value |
| Tau-PET SUVR | age | 0.02 | 0.02 | 0.26 | 0.03 | 0.02 | 0.12 | 0.03 | 0.02 | 0.22 |
|  | Slope MC | 43.8 | 20.01 | 0.05 | −0.68 | 0.63 | 0.3 | 15.3 | 22.87 | 0.52 |
|  | Slope NC | 31.15 | 47.31 | 0.53 | −0.45 | 1.88 | 0.82 | 21.38 | 54.76 | 0.7 |

|  | Predictor | p-T217 | | | p-S202 | | |
|---|---|---|---|---|---|---|---|
|  |  | estimate | SE | p value | estimate | SE | p value |
| Tau-PET SUVR | age | 0.03 | 0.02 | 0.18 | 0.03 | 0.02 | 0.06 |
|  | Slope MC | −2.69 | 3.16 | 0.41 | −10.28 | 5.74 | 0.1 |
|  | Slope NC | 11.55 | 13.91 | 0.43 | −12.17 | 17.81 | 0.51 |

Discussion for Examples 5-9

Although tau comprises a hallmark AD pathology and can be measured in aggregated or soluble forms, important gaps remain in our understanding of how the post-translational modifications of this critical neuronal protein leads to the development of NFT[2] and neurodegeneration in humans. Here we demonstrate how patterns of phosphorylation of tau in the CSF vary over the course of AD progression. We add to the existing clinical literature the demonstration that in DIAD, the process of tau phosphorylation and release into the central nervous system is a dynamic process that: 1) begins once Aβ-plaque burden (as measured by PiB-PET) is established (decades prior to symptoms), and subsequently unfolds over a period of nearly two decades, during which time the different phosphorylation sites of the tau protein are phosphorylated in distinct phases in association with different markers of disease progression; and 2) decreases significantly in a site-dependent manner near the time of cognitive decline and the rise in aggregated tau (as measured by tau-PET). Together, these results indicate that this method of quantifying soluble phosphorylated/unphosphorylated tau peptides can track the AD process across its preclinical to symptomatic stages, providing a signature of phospho-tau pathology in this disease. Moreover, they challenge the purported roles of tau/p-tau in DIAD, and possibly AD in general, and recapitulate in humans those findings from animal studies that link Aβ pathology to tau hyperphosphorylation[21,23,25,39] and active cellular release rather than a consequence of release of dying neurons.

Although causality needs to be addressed in future studies, the contemporaneous increases in p-T217, p-T181 and PiB-PET suggest that the widespread phosphorylation of tau levels in AD is closely linked to Aβ pathology. This hypothesis is consistent with recent work in AD transgenic mice20, 21,23,34,40 and in Stable Isotope Labeling Kinetics (SILK) which demonstrate that p-tau isoforms are released from cells in an active process that is increased in the presence of Aβ-plaques22. Our results link Aβ pathology to a distinct change in soluble tau peptide concentrations and phosphorylation patterns, shedding light on the phenomenon in which significant elevation of p-tau occurs in AD but not in other neurodegenerative tauopathies.16,17 These findings also yield important insights into potential therapeutic targets as well as biomarkers of early AD pathology prior to the onset of clinical symptoms.

Recent work has shown an increase and spread of neuritic tau aggregates (paired helical filaments in dystrophic neurites) induced by NFT isolates from AD brains in Aβ transgenic mice, occurring well before established somatic NFTs20. It is possible that the very early increase in p-T217 and p-T181 may reflect this "early" tau aggregation in response to Aβ-plaques and might explain the global association of PiB PET with these isoforms that we identified. Additionally, this might better explain the lack of clinical symptoms seen during this early elevation in p-tau as it occurs years before significant neurodegeneration. This work also proposes p-T217 as a very early biomarker with promising application as an indicator of therapeutic response in amyloid targeting therapies. This could be particularly important in prevention studies where surrogate markers of disease progression are vital to identifying effective therapies.

Some common assumptions about the diagnostic roles of soluble tau and p-tau are called into question here. Specifically, the current diagnostic framework in AD emphasizes the presence of biomarkers representing AD specific and non-specific pathologies (e.g. Aβ, p-tau and tau)[14]. Within this diagnostic framework, soluble p-tau and unphosphorylated tau are often presumed to be passively released from degenerating neurons, with p-tau associated with aggregated NFTs and unphosphorylated tau associated with axonal degeneration. Alternatively, our results in DIAD suggest AD tauopathy could be defined as a modification of soluble tau phosphorylation status (ratio of phosphorylation). Moreover, considering the timings of status changes at specific phosphorylation sites (21 to 13 years before estimated symptoms onset), this would also suggest that increased phosphorylation, although a marker of pathology, is not necessarily a marker of tau-related toxicity or cell body NFTs. In fact, our results indicate that for pT217 and pT181, rather than continuing to increase when NFT pathology is rapidly increasing[37], there is a dramatic decrease in phosphorylation. One possible explanation for this is similar to what has been observed with soluble/aggregated Aβ[41]: that the dramatic increase of aggregated tau sequesters phosphorylated tau[42] in the brain, decreasing CSF levels. However, a reduction of tau through proteostatic mechanisms cannot be excluded. In either case, our finding of the negative correlation between the phosphorylation ratios of T217 or T181 and longitudinal cognitive decline highlights the importance of this event in the disease progression. Elucidating the cause for this decline could lead to a better understanding of the links between soluble tau and neuronal dysfunction and the use of CSF p-tau/tau in AD prognostication.

Given the role of kinases in the phosphorylation of tau, this group of enzymes is currently viewed as a potential target for AD therapeutics43. As we have demonstrated here that not all forms of p-tau are associated with markers of disease progression, and some may in fact work against it, certain kinase/phosphatase activities that result in p-tau alterations may not be detrimental, at least early in the disease process.

In summary, we have now demonstrated that in AD associated with autosomal dominant mutations, CSF tau hyperphosphorylation occurs very early and exhibits pattern of site-specific changes at different stages of the disease. The underlying mechanisms behind these findings will have important implications understanding the disease and for tau-directed therapies for AD.

Material and Methods for Examples 5-9

Participants—Participants with at least 50% risk of inheriting an DIAD mutation from families with a confirmed genetic mutation in PSEN1, PSEN2 or APP were enrolled in the Dominantly Inherited Alzheimer Network study (DIAN, NIA U19 AG032438) (dian.wustl.edu; clinicaltrials.gov number NCT00869817)[44]. All procedures were approved by the Institutional Review Board (IRB) of Washington University and conformed to local IRB and Ethics Committees where the study was being performed. The presence or absence of a DIAD mutation was determined using PCR-based amplification of the appropriate exon followed by Sanger sequencing. At each study visit, participants underwent comprehensive clinical assessments, cognitive testing, neuroimaging, and CSF studies; however, at each visit, each participant may not have completed all study procedures. The details of study structure and assessments can be found in prior publications[10,44]. Follow-up intervals were determined by clinical status (normal or impaired) of each participant and by their estimated years to symptom onset (EYO) and ranged from yearly to every three years. Data was obtained from quality-controlled data (yearly quality assessments for irregular results and missing data from Jan. 26, 2009 to Jun. 30, 2017) and included 370 participants (n=150 with longitudinal CSF evaluations with a median time between visits of 2.8 years).

Estimated Years to Symptom Onset (EYO)—In dominantly inherited AD there is near 100% penetrance, with age at symptom onset in mutation carriers being relatively consistent for each mutation and within each family. This allows for the designation of estimated years to symptom onset (EYO). EYO was defined as follows: A parental age at earliest symptom onset was established for each participant by semi-structured interview. The parental age at onset for each mutation was then entered into a database consisting of the combined symptom onset values from DIAN and from prior publications from DIAD cohorts. These were used to compute an average age of onset specific to each mutation[29]. The mutation-specific age of onset was subtracted from each participant's age at the time of clinical assessment to define the individual's EYO. When a specific mutation average age of onset was unknown, the parental or proxy age of onset was used to define EYO[29]. For participants who were symptomatic at baseline, as assessed by a CDR>0, the reported age of actual symptom onset was subtracted from age at each clinical assessment to define EYO.

Clinical Assessments—Standardized clinical evaluations, including the use of a study partner, were performed for each participant. The Clinical Dementia Rating Scale (CDR) was used to indicate dementia stage. Participants were rated as cognitively normal (CDR=0) or having very mild dementia (CDR=0·5), mild dementia (CDR=1) or moderate dementia (CDR=2)45. Evaluating clinicians were blind to genetic status. A comprehensive neuropsychological battery assessing general cognitive function, memory, attention, executive function, visuospatial function, and language was performed at each visit46. From these tests we developed a cognitive composite that reliably detects decline across the range of EYO and CDR47. The composite represents the average of the z scores from tests including episodic memory, complex attention, and processing speed and a general cognitive screen (Mini Mental State Examination).

CSF Tau Analyses—CSF was collected via standard lumbar puncture procedures (L4/L5) using an atraumatic Sprotte spinal needle (22Ga) into two 13 ml polypropylene tubes. CSF was flash-frozen upright on dry ice. Samples collected in the United States were shipped overnight on dry ice to the DIAN biomarker core laboratory at Washington University, St. Louis, Mo., USA, whereas samples collected at international sites were stored at −80° C. and shipped quarterly on dry ice. Upon arrival, each sample was subsequently thawed, combined into a single polypropylene tube, and aliquoted (500 μl each) into polypropylene microcentrifuge tubes (#05-538-69C, Corning Life Science, Corning, N.Y., USA), after which they were re-flash frozen on dry-ice and stored at −80° C.

Each thawed CSF sample was mixed with 25 μl of a solution containing 15N-441 tau internal standard (2.5 ng per sample), 50 mM Guanidine, 10% NP-40 and 10× protease inhibitor cocktail (Roche). Tau was extracted by immune capture using incubation under rotation at room temperature during 2 hours with 20 μl of sepharose beads cross-linked to Tau1 (tau epitope 192-199) and HJ8.5 (tau epitope 27-35) antibodies. Beads were spun by centrifugation, then rinsed three times with 1 ml of 25 mM TEABC. Samples were digested overnight at 37° C. with 400 ng of trypsin Gold (Promega, Madison, Wis.). AQUA peptides (Life Technologies, Carlsbad, Calif.) were spiked to obtain an amount of 5 fmol per labeled phosphorylated peptide and 50 fmol per labeled unmodified peptide in each sample. The peptide mixture was loaded on TopTip C18 tips, washed with 0.1% Formic Acid (FA) solution and eluted with 60% ACN 0.1% FA solution. Eluates were dried using a Speedvac and dried samples were stored at −80° C. prior to analysis. Samples were resuspended in 25 μl of 2% ACN 0.1% FA. Extracts were analyzed by nanoLC-MS/HRMS using Parallel Reaction Monitoring using HCD fragmentation. NanoLC-MS/MS experiments were performed using a nanoAcquity UPLC system (Waters, Mildford, Mass.) coupled to a Fusion Tribrid mass spectrometer (Thermo Scientific, San Jose, Calif.). 5 μl was injected for each sample. Peptide separation was achieved at 60° C. in 24 minutes on a Waters HSS T3 column (75 μm×100 mm, 1.8 μm). Mobile phases were (A) 0.1% formic acid in water and (B) 0.1% formic acid in acetonitrile. Gradient used was: 0 min-0.5% B; 7.5 min-5% B; 22 min-18% B; then the column was rinsed 2 minutes with 95% B. Flow rate was set at 700 nl/min for 7.5 min then 400 nl/min for the rest of the analysis. Data were acquired in the positive ion mode at a spray voltage of 2200V (Nanospray Flex Ion Source, Thermo Scientific) and ion transfer tube set at 270° C. S-lens RF voltage was set at 60 V. MS/HRMS transitions and were extracted using Skyline software (MacCoss lab, University of Washington). CSF tau phosphorylation levels were calculated using measured ratios between MS/HRMS transitions of endogenous unphosphorylated peptides and 15N labeled peptides from protein internal standard. Ratio of phosphorylation on T181, S202, T205 and T217 were measured using the ratio of the MS/HRMS transitions from phosphorylated peptides and corresponding unphosphorylated peptides. Each phosphorylated/unphosphorylated peptide endogenous ratio was normalized using the ratio measured on the MS/HRMS transitions of the corresponding AQUA phosphorylated/unphosphorylated peptide internal standards.

Brain Imaging—Amyloid deposition, glucose metabolism, tau (NFT) PET and cortical thickness/subcortical volumes were assessed using $^{11}$C-PiB-PET, $^{18}$F-FDG-PET, $^{18}$F-AV-1451 (a.k.a flortaucipir) and volumetric T1-weighted MRI scans, respectively. Standard procedures were used to ensure consistency in the data collection of all DIAN sites28. The 11C-PiB-PET scan consisted of 70 minutes of dynamic scanning after a bolus injection of ~13 mCi of PiB with regional standard uptake ratios (SUVR) determined from the 40-70 minute timeframe. The 18F-FDG-PET scan started thirty minutes after a ~5 mCi bolus injection and lasted thirty minutes. The 18F-AV-1451 data was acquired from the 80-100 minute window after bolus injection and were converted to SUVRs. The T1 MR sequence was an accelerated magnetization-prepared rapid acquisition with gradient echo (MPRAGE) acquired on 3T scanners (parameters: TR=23000, TE=2.95, and 1.0×1.0× 1.2 mm3 resolution).

The PIB and FDG SUVRs from 34 cortical and 6 subcortical regions of interests (ROIs) were obtained using FreeSurfer software (surfer.nmr.mgh.harvard.edu/). The SUVRs were processed with grey cerebellum as reference regions and ROI data were corrected for partial volume effects using a regional point spread function (RSF)[48] in geometric transfer matrix framework.

Statistical analysis—Baseline characteristics of the participants were summarized as mean±SD for continuous variables and n (column percent) for categorical variables. P-values for comparing the differences among asymptomatic MC, symptomatic MC and NC as defined at baseline are obtained using general linear mixed effects models (LME) for continuous variables and generalized linear mixed effects models, with a logistic link for categorical variables. All of the models incorporated a random family effect to account for the correlations on the outcome measures between participants within the same family. The cut point for baseline cortical PiB PET SUVR is chosen such that the difference in the longitudinal rate of change of cortical PiB PET between MC and NC first starts to differ significantly different from 0.

The cross-sectional relationship of the different tau phosphorylation sites with PiB, FDG, and Cortical thickness/Subcortical volume were evaluated in all asymptomatic MCs (CDR=0, n=152) using bivariate LME on each ROI. The models included fixed effects of EYO, education, sex, and random intercepts at the family level. Compared with the simple correlation estimation method (Pearson or Spearman correlation), the bivariate LME can adjust for covariates such as EYO as well as accounting for the correlation within the family cluster49,50. P-values for testing the correlations were corrected using the Benjamini Hochberg method51 to control the false discovery rate due to multiple testing.

For within-individual annual rate of change over the longitudinal follow up, the best linear unbiased predictors for each biomarker were estimated using LME, which were then plotted against baseline EYO to examine biomarkers trajectories. Linear or linear spline mixed effects models, where appropriate, were then used to determine the baseline EYO point from which MC became significantly different from NC in baseline level and the rate of change for each biomarker. The details of the linear spline mixed effects models can be found in a recent publication[9]. The linear or linear spline mixed effects models included the fixed effects of mutation group (MC or NC), baseline EYO, time since baseline and all possible two-way or three-way interactions among them. Sex, years of education, and APOE ε4 status were considered as covariates, but only those effects that were significant were retained in the models. Random effects included in the models are the random intercepts for family clusters, individual random intercept and random slope with unstructured covariance matrix to account for the within-subject correlation due to repeated measures. The adjusted difference in the mean level at baseline and difference in the rates of change between MC and NC were then tested using the approximate t-test derived from the models to determine the first EYO point where the difference became significant.

To visualize the difference in the rate of change among total tau, tau phosphorylation site, cortical PiB, and global cognition across the range of EYO, measures of MC were first standardized using the mean and standard deviation of the NC. The rate of change of each measure for each MC were then calculated using LME, and LOESS curves were fitted to visually represent the trajectories of the standardized rates of change over EYO.

The utility of baseline total tau and p-tau in predicting longitudinal cognitive decline were evaluated using LME. Fixed effects in the models included mutation group, baseline age, sex, APOE ε4 status, time and all possible two-way or three-way interactions among them. Random effects in the models included the random intercepts for family clusters, individual random intercept and random slope with unstructured covariance matrix.

Linear regressions were used to examine whether the annual rate of change of tau and phospho-tau position for MC and NC, leading up to and including the point when the tau PET was performed, could predict tau PET SUVR, controlling for the effect of age. Due to the limited number of participants, a family cluster was not included.

All analyses were conducted using SAS 9.4 (SAS Institute Inc., Cary, N.C.). A p-value<0.05 was considered to be statistically significant.

Example 10

Alzheimer disease (AD) is the leading cause of dementia worldwide. Its diagnosis and treatment remain extremely challenging in absence of specific and early biomarkers. Recent developments of cerebrospinal fluid (CSF) biomarkers and brain Positron-Emission Tomography (PET) imaging provided valuable tools to detect the pathognomonic AD brain pathologies of amyloid-Aβ plaques and neurofibrillary hyperphosphorylated tau tangles. Currently, the CSF profile of AD patients is characterized by decreased amyloid-Beta 42 (Aβ342) and increased total and phosphorylated tau (p-tau 181) measured with standard immuno-assays. This profile allows the discrimination of AD versus non-AD pathologies and the detection of AD process many years prior to cognitive symptoms or complaint. However, changes in CSF tau and p-tau are not specific of AD. Although the increased p-tau181 has been interpreted as a consequence of hyperphosphorylation due to tangle formation, CSF p-tau increases concomitantly with total tau. Brain studies indicate tau phosphorylation on numerous sites, but the diagnostic relevance of these additional phosphorylation sites in CSF has not been fully addressed. Mass spectrometry (MS)-based methods are more relevant than immunoassays to assess changes in phosphorylation levels of specific sites independently of total tau levels as they allow independent quantification of phosphorylated peptides and their corresponding unmodified counterparts. Accordingly, correlations between phosphopeptide and unphosphorylated peptide slopes can be compared to evaluate the rate of phosphorylation. To quantify phosphorylated tau isoforms in CSF we used an innovative targeted high-resolution MS (HRMS) method targeting tau phosphorylated peptides in the mid-domain of the protein sequence, which is the most abundant domain in CSF and is phosphorylated on numerous sites in brain tau and AD tau aggregates.

We analyzed tau phosphorylation on T181, S199, S202, T205 and T217 in CSF using a cohort comprising cognitively normal individuals and patients with mild cognitive impairment stratified by their amyloid status based on CSF Aβ42/40 ratio and PET-PIB imaging. This validation allowed us to highlight the potential of CSF pT217 for AD diagnosis and to establish correlations between pT217 and amyloidosis underlying tau modification at an early stage of the disease Participants—Eighty-six participants cognitively normal (CDR=0) or with mild cognitive impairment were recruited from the Washington University in Saint Louis ADRC study previously reported by Patterson et al. 2015 with CSF and amyloid PiB-PET data available. This cohort included 29 amyloid positive and 47 amyloid negative participants according to the results of PiB-PET (considered positive above 0.18 used as cut-off) and CSF Aβ342/A340 ratio measured by MS (considered pathological below 0.12 used as cut-off) and 10 cases with conflicting results between PET-PIB and CSF profiles (5 with a PiB-PET(+)/CSF(−) and 5 with PiB-PET(−)/CSF(+) amyloidosis profile). Seven CSF samples were extracted in duplicate and one in triplicate to assess variability.

CSF tau purification using immunoprecipitation—800 μl of CSF supernatant obtained after Aβ immuno-precipitation and storage at −80 C was used for tau analysis. Thawed supernatants were spiked with 15N tau internal standard (5 ng per sample) and extracted using Tau1 immunoprecipitation. 5 mM Guanidine, 1% NP-40 and protease inhibitor cocktail were added to the sample, then samples were mixed 3 hours at room temperature with 20 μl of sepharose beads cross-linked to Tau1 antibody. Beads were precipitated then rinsed with 0.5 M Guanidine and TEABC 25 mM. Samples were digested with 400 ng of trypsin. AQUA peptides (Life Technologies, Carlsbad, Calif.) were spiked to achieve individual quantity of 10 fmol per labeled phosphopeptide and 100 fmol per labeled peptide per sample. AQUA TPSLPpTPPTR (pT217) substituted the missed cleavage version used in the discovery cohort. Tryptic peptides were loaded on TopTip C18 tips, washed with 0.1% FA solution and eluted with 60% ACN 0.1% FA solution. Eluates were dried on speedvac. Samples were stored at −80 C. Before LC-MS analysis, samples were resuspended in 25 μl 2% ACN 0.1% FA. Extracts were analyzed by nanoLC-MS/HRMS.

Tau peptides and phosphorylated peptide quantitation (Validation)—Stable Isotope dilution MS quantitation using 15N labeled peptides was used to calculate absolute levels of unmodified peptides. Phosphorylation rate for each site was calculated by single point calibration comparing area ratio obtained on AQUA unphosphorylated and phosphorylated peptides counterpart to the area ratio measured for corresponding endogenous peptides. Phosphorylated peptide level was calculated by combining unmodified peptide level counterpart and rate of phosphorylation of the corresponding site.

Statistics—Statistical analyses, including comparison of the slopes of regression lines, were performed using the GraphPad Prism software (7.0). Statistical significances between values obtained across investigated groups were calculated using non-parametric Mann-Whitney tests. Non-parametric Spearman's rho rank correlation coefficients were used to assess the correlations between two series of values. Statistical significance was defined by $p<0.05$.

Figure 24A:
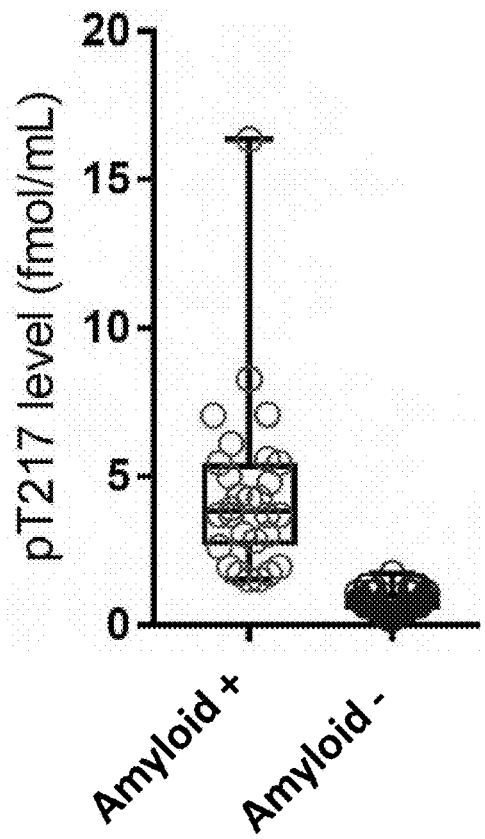
FIG. 24A, FIG. 24B, FIG. 24C, and FIG. 24D show CSF tau phosphorylation on T217 is associated to amyloidosis status.
Figure 24B:
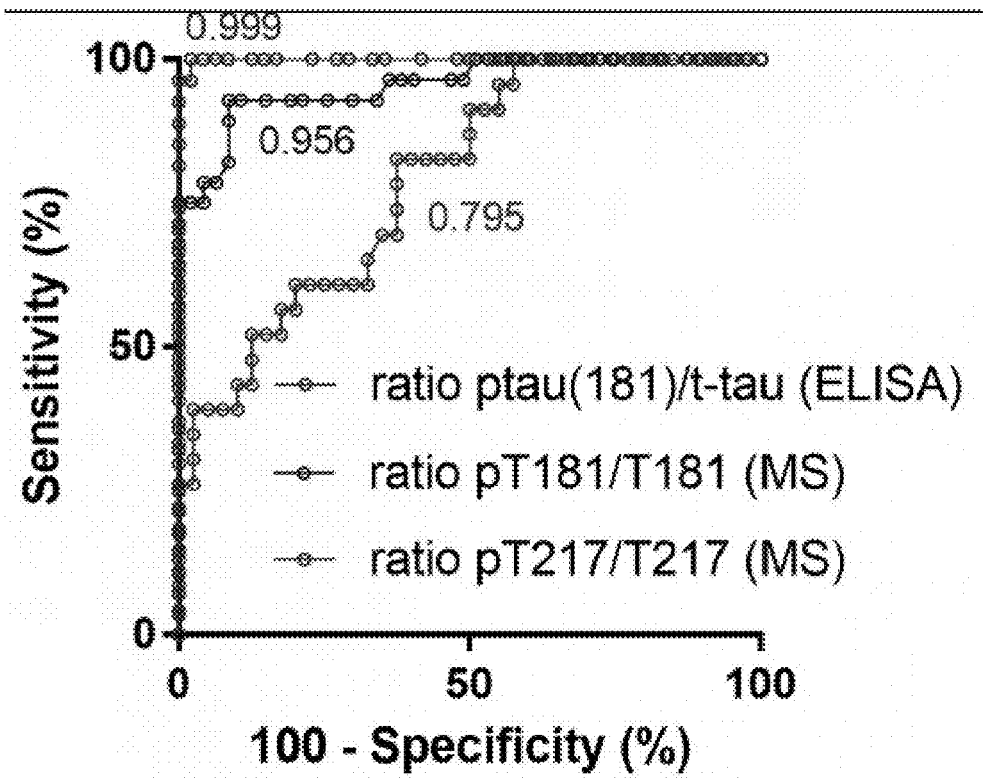
Figure 24C:
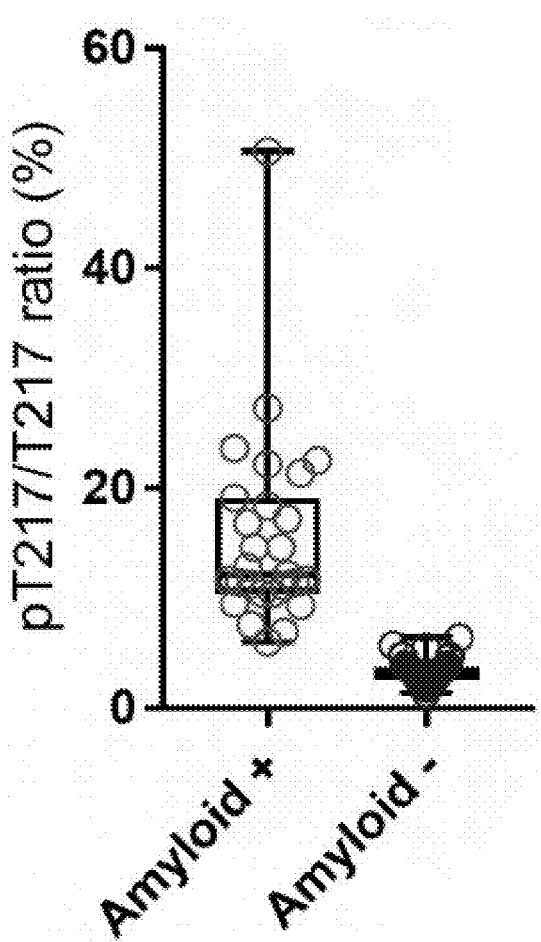

Quantification of CSF tau phosphorylated peptides (Results)—Increased phosphorylation of tau at T217 in AD was detected in a cohort from the Knight AD Research Center (ADRC) at Washington University in Saint Louis comprising 86 participants with no cognitive complaint or mild cognitive impairment. Consistent with the results of PiB-PET and CSF Aβ342/A340 ratio measured by MS, participants were stratified in 29 amyloid-positive, 47 amyloid-negative participants and 10 cases with conflicting results between PET-PIB and CSF profile. To improve the assay sensitivity, immunopurification with the Tau1 antibody was performed. Isotopically labeled versions of both phosphorylated and unphosphorylated peptides were used to measure site phosphorylation ratio. All phosphorylated peptides targeted were detected in all samples, with the exception of pS199 containing peptide not recovered by the Tau1 antibody. In this cohort, we confirmed the positive diagnosis relevance of pT217 biomarker at early stage of the disease. The pT217/T217 ratio clearly separated amyloid positive and negative groups (FIG. 24B and FIG. 24C, AUC 0.999). In addition, the measurement of pT181/T181 ratio discriminated the amyloid-positive and amyloid-negative groups (FIG. 24B, AUC 0.956). T217 and T181 phosphorylation ratios were also correlated, ($r=0.524$, $p=0.0002$), suggesting that the phosphorylation of these sites could result from a common pathway. However, the diagnosis sensitivity of pT181 was lower than that of pT217. Both phosphorylation ratios were better discriminators than p-tau(181) and t-tau levels measured by ELISA (AUC 0.874 and 0.932 respectively).

Figure 24D:
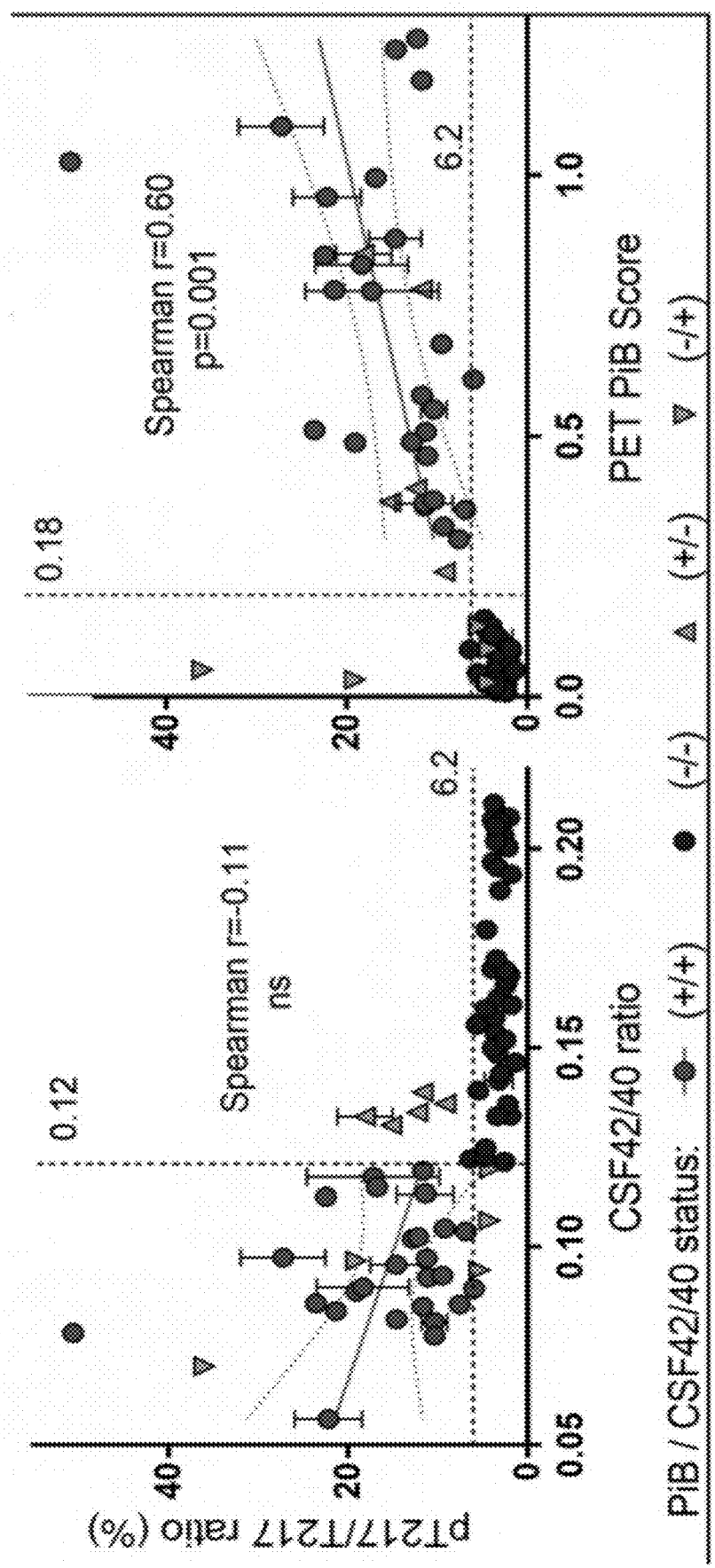
Figure 25:
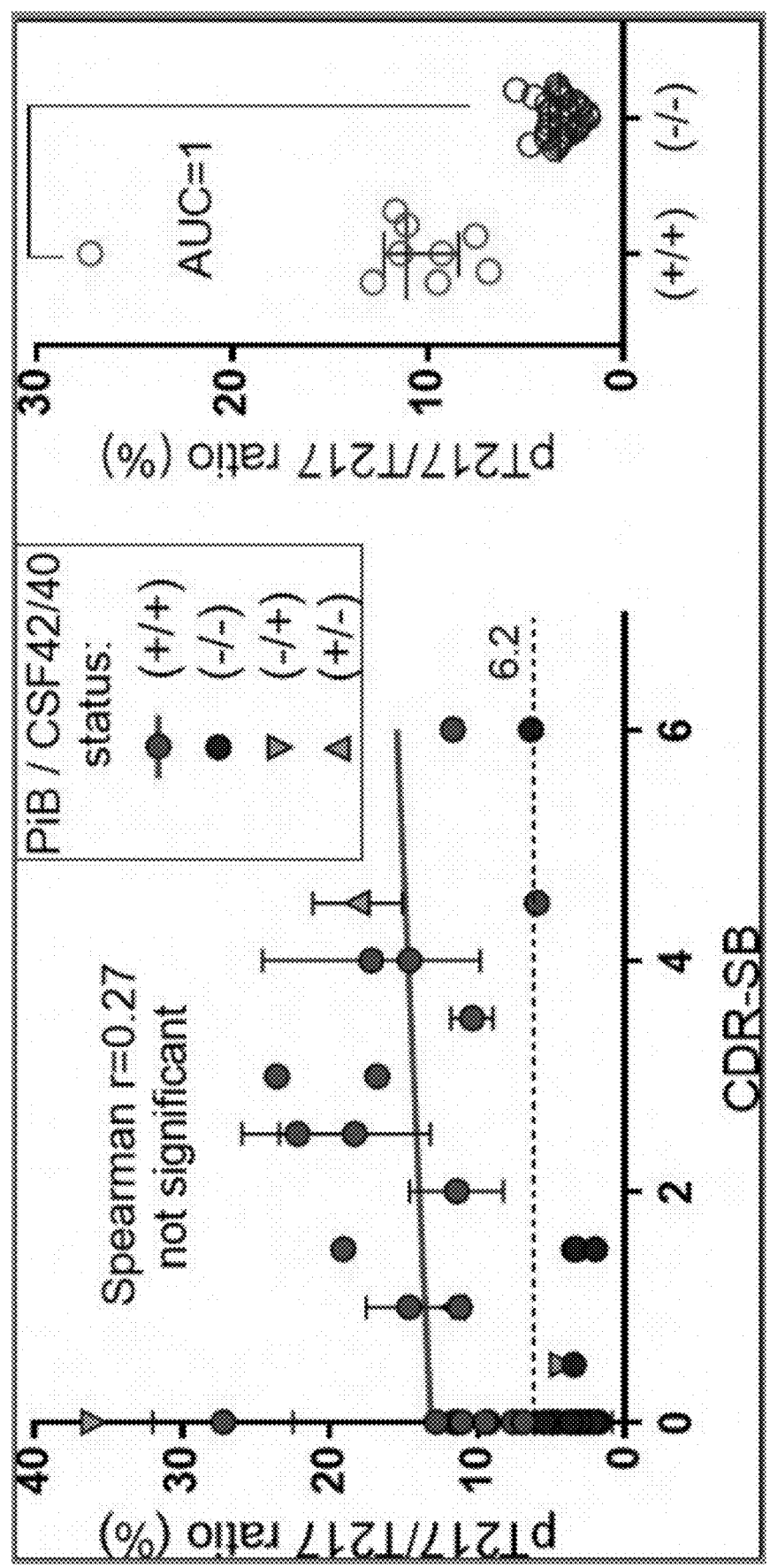
FIG. 25 shows CSF tau phosphorylation on T217 is independent from cognitive status and is significantly modified in preclinical AD. Left Panel: No correlation exists between T217 phosphorylation and the cognitive profile measured by the clinical dementia rating sum of boxes (CDR-SB). Right Panel: Amongst participants with no cognitive decline (CDR-SB=0), T217 is already significantly hyper phosphorylated in the amyloid-positive group.

Correlations between T217 hyperphosphorylation, amyloid pathology and cognitive status (Results)—We next determined the correlations between this new biomarker and the amyloid process. Results from the ADRC cohort suggested a strong relationship between T217 hyperphosphorylation and amyloid status. Importantly, T217 phosphorylation rate was significantly correlated with the extent of PiB-PET measured by FBP Total Cortical Mean (FIG. 24E, $r=0.60$, $p=0.001$). Moreover, all the five conflicting cases with PiB-PET(+)/CSF(−) amyloidosis profiles were hyperphosphorylated on T217 (FIG. 24D, E). In contrast, no significant correlation was found between T217 phosphorylation and CSF Aβ342/A340 ratio. Discrepancy between PiB-PET and CSF Aβ342/A340 could be attributed to an insufficient sensitivity of the CSF amyloid assay, as corresponding CSF Aβ342/A340 MS ratios were close to the threshold of quantification (0.12±0.02, FIG. 24E). Among the five participants with opposite PiB-PET(−)/CSF(+) amyloidosis, two exhibited hyperphosphorylated T217 (FIG. 24D, E). This suggests these cases highlighted by their high tau hyperphosphorylation could have significant CSF Aβ changes prior to amyloid plaques deposits detection. Combination of CSF Aβ342/A340 ratio with T217 phosphorylation rate confidently identifies amyloid-positive participants without PiB-PET data even with CSF Aβ342/A340 ratio values in the intermediate range slightly above the threshold (0.12±20%). Amongst participants with no cognitive complaint (CDR-SB=0), T217 phosphorylation was able to completely distinguish amyloid-positive (n=9) from amyloid-negative participants (n=26, AUC 1.00, FIG. 25), further supporting the ability of this marker to confidently identify preclinical AD participants. However, no correlation was observed between global cognitive performances measured with CDR-SB and T217 phosphorylation ratio in this population (FIG. 25).

Discussion—Using innovative targeted-HRMS methods simultaneously measuring low-abundant phosphorylated tau peptides and their unmodified counterparts in CSF, we provide for the first-time direct evidence of changes in CSF tau phosphorylation rates concomitant with amyloid-changes and distinct from increased CSF tau concentration. This approach allows for studying AD-specific tau phosphorylation rates assessing hyper- and hypo-phosphorylation to indicate underlying abnormal metabolism.

The most striking result of the current study is the highly specific hyperphosphorylation of T217 in CSF tau from preclinical, mild and moderate AD participants investigated in two independent and well-characterized cohorts. Amyloid-pathology, which likely occurs before AD tauopathy, and tau hyperphosphorylation on T217 were strongly associated throughout the disease stages. This supports the hypothesis that amyloidosis can be related to tau phosphorylation changes. The absence of participants with Aβ-amyloidosis and normal T217 phosphorylation in this study suggests that this tau phosphorylation site could follow the amyloid process. The hyperphosphorylation of T217 could be a key player in the AD pathophysiological process and its role differed from other tau biomarkers. In our cohorts, the increase in the levels of CSF tau or p-tau, as assessed by ELISA, was less effective in identifying amyloidosis status than pT217/T217 ratio. The specificity of these AD tau biomarkers may improve the prediction of the risk of cognitive decline in individuals who ultimately progress to clinical AD. Thus, combining amyloidosis biomarkers with pT217/T217 ratio measurement to detect AD, should dramatically improve diagnosis of preclinical AD. Although T217 hyperphosphorylation is highly correlated to amyloid plaques measured with PiB-PET load than amyloid markers in the CSF, tau modification may not be exclusively caused by the presence of fibrillary plaques. For the two participants with T217 hyperphosphorylation and low CSF Aβ 42/40 without brain amyloid load (FIG. 24E), they could be cases with diffuse plaques or Aβ oligomeric formation only, not detected by PiB-PET but contributing to reduce CSF Aβ42 levels.

The wide-spread use of pT181 as an AD marker in clinics is likely due to its high level of detectability, but not necessarily high specificity. Measurement of pT181 highlights a slight change in its phosphorylation stoichiometry in AD, compared with non-AD dementia. The increased phosphorylation rate of T181 was even more apparent in a well-characterized amyloid-positive group investigated in the validation cohort. In both studies, the ratio combining ELISA t-tau and p-tau181 failed to demonstrate the change of phosphorylation ratio occurring on T181, stressing the limitations of ELISA to monitor accurately these changes. Thus, the increasing of pT181 broadly reported in AD CSF mainly results from the concomitant increasing of tau isoforms level rather than significant change on the T181 phosphorylation stoichiometry. Amyloid-Aβ pathology induces hyperphosphorylation on T181 but the resulting modification appears less specific or significant in comparison to the relative increasing observed on T217.

Modifications of the phosphorylation stoichiometry observed on S199, S202 and T205 in AD CSF likely reflect specific changes in tau phosphorylation previously observed in AD brain. Indeed, pS202 and pT205 are part of the doubly phosphorylated epitope recognized by the AT8 antibody. AT8 binds to tau aggregates found in AD brain autopsies and the extent of AT8-immunoreactive aggregates correlates with the severity of tauopathy (Braak stages). AT8 has no reactivity for normal tau or tau related to AD measured in CSF. Moreover, the Tau1 antibody that binds to normal tau at a non-phosphorylated epitope containing S199 has no affinity for AD tau aggregates. Together, these findings support a concomitant and abundant hyperphosphorylation of S199, S202 and T205 in tau aggregates from AD brain. However, controversy exists about the intrinsic property of such phosphorylated tau isoforms to promote tau aggregation in AD. Decreased amounts of S199 and S202 phosphorylation observed in mild and moderate AD CSF is consistent with an accumulation of the corresponding phosphorylated tau isoforms in aggregates. Furthermore, the detection of T205 phosphorylation mainly in moderate AD CSF suggests an important role of this site in pathological mechanisms underlying amyloid-related tauopathy. Modification in S202/T205 phosphorylation was not detected in the second cohort composed of preclinical and mild AD participant (data not shown), suggesting a dynamic process of tau phosphorylation on specific sites during the course of the disease.

The present findings could suggest an interplay between AD amyloidosis and hyperphosphorylation of tau on T217 and, to a lesser extent, on T181. These sites are both substrates for the serine/threonine proline-directed kinase GSK-3, and the activation of GSK-3 by Aβ oligomers has been proposed as a link between amyloid peptide and tau phosphorylation. The common and relatively well-correlated hyperphosphorylation on these two GSK-3 sites in patients with amyloidosis could be consistent with such a mechanism. Further studies designed to compare tau phosphorylation rates in CSF and brain, including tau aggregates measured by tau PET, are likely to provide novel insights into AD pathophysiology and may identify novel therapeutic approaches. These findings point to a specific link between amyloid plaques and tauopathy in AD and provide a potential link in the cascade of molecular events that leads to AD. Thus, given the specificity of pT217 within the AD process, it may represent an important target for future therapeutic development and an interesting tool to follow potential effects of anti-amyloid drugs in limiting this abnormal tau metabolism.

Example 11

Plasma aliquots of 1 mL were thawed at 4° C. overnight. Approximately 20 mL plasma sample (corresponding to approximately 40 mL whole blood) was pooled by combining 1 mL plasma aliquots from the same participant in 50 mL Falcon tubes. After 30 minutes of centrifugation at 16,000 g, 20 mL was transferred into a new tube, the volume was measured, and samples were spiked with 1 ng of 15N- labeled recombinant 2N4R tau. Tau and p-tau concentration was calculated using these internal standards.

Plasma proteins were precipitated with perchloric acid (3.5% v/v final), the sample was mixed by vortex, and left for 30 minutes on ice. Samples were centrifuged for 30 minutes at 4° C. at 16.000 g. Supernatants containing soluble tau were transferred to new tubes.

The supernatants were then spiked with TFA to a final concentration of 1%. Samples were loaded on Oasis HLB VAC RC 30 mg extraction cartridge (Waters, Milford, Mass.), previously conditioned with 1 mL MeOH and 1 mL 0.1% TFA. After loading, samples were desalted with 1 mL 0.1% TFA and then eluted with 700 µl 27.5% ACN 0.1% TFA. Eluates were lyophilized by speed-vac and re-suspended in 2X-PBS.

Tau was immunoprecipitated as previously described with some modifications (Ref. 14 and Ref. 18). Briefly, CNBr-activated Sepharose beads (GE Healthcare 17-0430-01) were crosslinked to antibodies Tau1 and HJ8.5, separately at a concentration of 3 mg antibody per g of beads. Anti-Tau1 and HJ8.5 antibodies conjugated to sepharose beads were mixed with the reconstituted eluate for 90 min at room temperature. The beads were washed three times in 25 mM triethyl ammonium bicarbonate buffer (TEABC, Fluka 17902). The bound tau was digested on-beads with 400 ng MS grade trypsin (Promega, V5111) for 16 hours at 37° C. Digests were loaded onto TopTip C18 (Glygen, TT2C18.96), desalted, and eluted per manufacturer's instructions. The eluted peptides were dried by vacuum centrifugation (CentriVap Concentrator Labconco) and resuspended in 25 uL of a solution of 2% acetonitrile and 0.1% formic acid in MS grade water.

LC-MS was also performed as previously described (Ref. 14 and Ref. 18). A 5 µL aliquot of the peptide resuspension was injected into nano-Acquity LC for MS analysis. The nano-Acquity LC (Waters Corporation, Milford, Mass., USA) was fitted with HSS T3 75 µm×100 µm, 1.8 µm column and a flow rate of 0.5 µL/min of a gradient of solution A and B was used to separate the peptides. Solution A was composed of 0.1% formic acid in MS grade water and solution B was composed of 0.1% formic acid in acetonitrile. Peptides were eluted from the column with a gradient of 2%-20% of solution B in 28 min, then 20%-40% solution B for another 13 min before ramping up to 85% solution B in another 3 min to clean the column. The Orbitrap Fusion Lumos was equipped with a Nanospray Flex electrospray ion source (Thermo Fisher Scientific, San Jose, Calif., USA). Peptide ions sprayed from a 10 µm SilicaTip emitter (New Objective, Woburn, Mass., USA) into the ion source were targeted and isolated in the quadrupole. These were then fragmented by HCD and ion fragments were detected in the Orbitrap (resolution of 60,000, mass range 150-1,200 m/z). Monitoring of hydrophilic peptides (SSRcalc<9, all without leucine) for peptide profiling was performed on a HSS T3 300 µm×100 µm, 1.8 mm column at a flow rate of 4 µl/min with an elution occurring with a 2%-12% solution B gradient and a spray operating on a 30 mm SilicaTip emitter.

Example 12

This example demonstrates the feasibility of measuring very low concentrations of tau isoforms in plasma using an enrichment protocol and mass spectrometry. The data show peripherally produced tau has a different phosphorylation status, but a similar truncation profile, compared to CNS produced tau. Despite the differences between peripheral p-tau and CNS p-tau, this example demonstrates the described method can be used to measure changes in plasma p-tau, especially p-tau217 and p-tau181, which mirror highly specific modifications in CSF that indicate amyloidosis.

Participants, sample collection, sample selection: 58 participants enrolled in the Tau Stable Isotope Labeling Kinetics (SILK) Studies formed the initial participant pool18. During the Tau SILK study, participants received 16 hours of labeled 13C leucine infusion followed by 5 lumbar punctures (LPs) over 4 months 18. Approximately 10 mL of plasma was collected each at 12 time points over 19.5 hrs during the infusion procedure and at each LP in order to monitor leucine enrichment 30.

CSF from the 58 participants were analyzed by MS for CSF42/40 and tau isoforms as reported 14,31. Eleven of these participants were identified as amyloid positive using amyloid AV45 PET (cutoff 1.3) and included in this plasma study. Four additional amyloid positive participants with no amyloid PET data were identified by CSF42/40 ratio (cut off 0.086) and included. All amyloid positive participants were abnormal for CSF pT217/T217 ratio (cutoff 4.6%). The fifteen amyloid positive participants had various clinical dementia rating (CDR) of 0 (five participants), 0.5 (seven participants), and 1 (two participants). All preclinical AD participants (amyloid positive, CDR=0) had negative Tau PET AV-1451 scans (Table 5). Two participants with normal CSF42/40 but abnormal pT217/T217 were included. The forty one remaining participants were amyloid negative by AV45 when available or by CSF42/40 and negative for pT217/217. Seventeen of them were selected as controls (9 young controls and 8 aged controls). Finally, three participants identified as mild cognitively impaired (MCI, including 1 participant with Corticobasal Syndrome (CBS) and 2 with undetermined dementia) completed the plasma cohort of 38 participants.

Plasma and CSF tau IP-LC-MS analysis: Plasma samples were processed as described in Example 11. CSF samples were processed as described in Ref14 and Ref 18. The LC-MS protocol is the same as described in Ref 14 and Ref 18.

Statistics: One-way ANOVA and post hoc analyses (Kruskal-Wallis test) were used for comparing p-tau ratios across subgroups of AD and control. Pearson correlations were used to analyze correlations between plasma and CSF tau. Data are represented as mean±SD, unless otherwise specified.

Figure 26A:
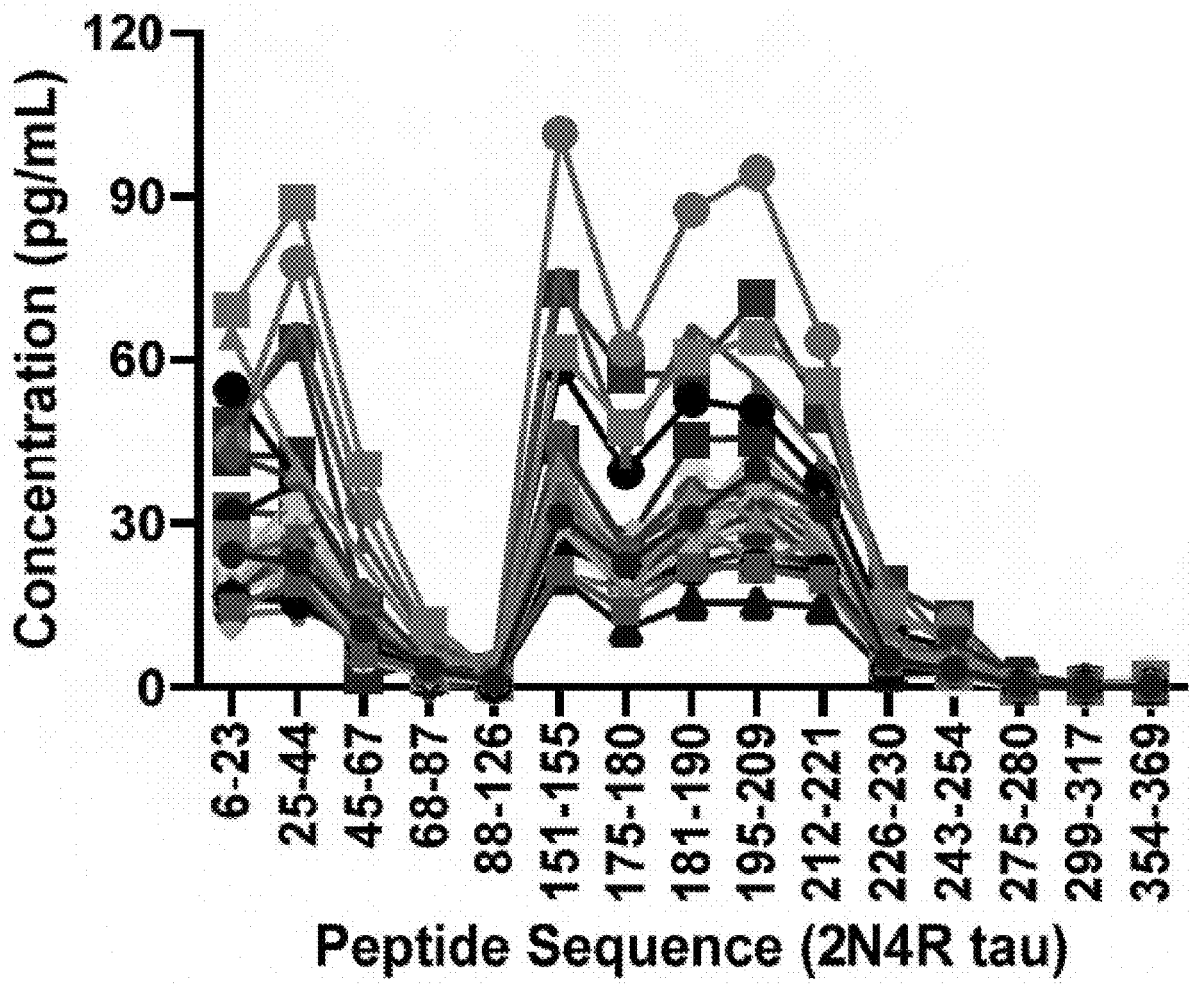
FIG. 26A and FIG. 26B illustrate plasma tau truncation profiles after chemical extraction and immunopurification.
Figure 26B:
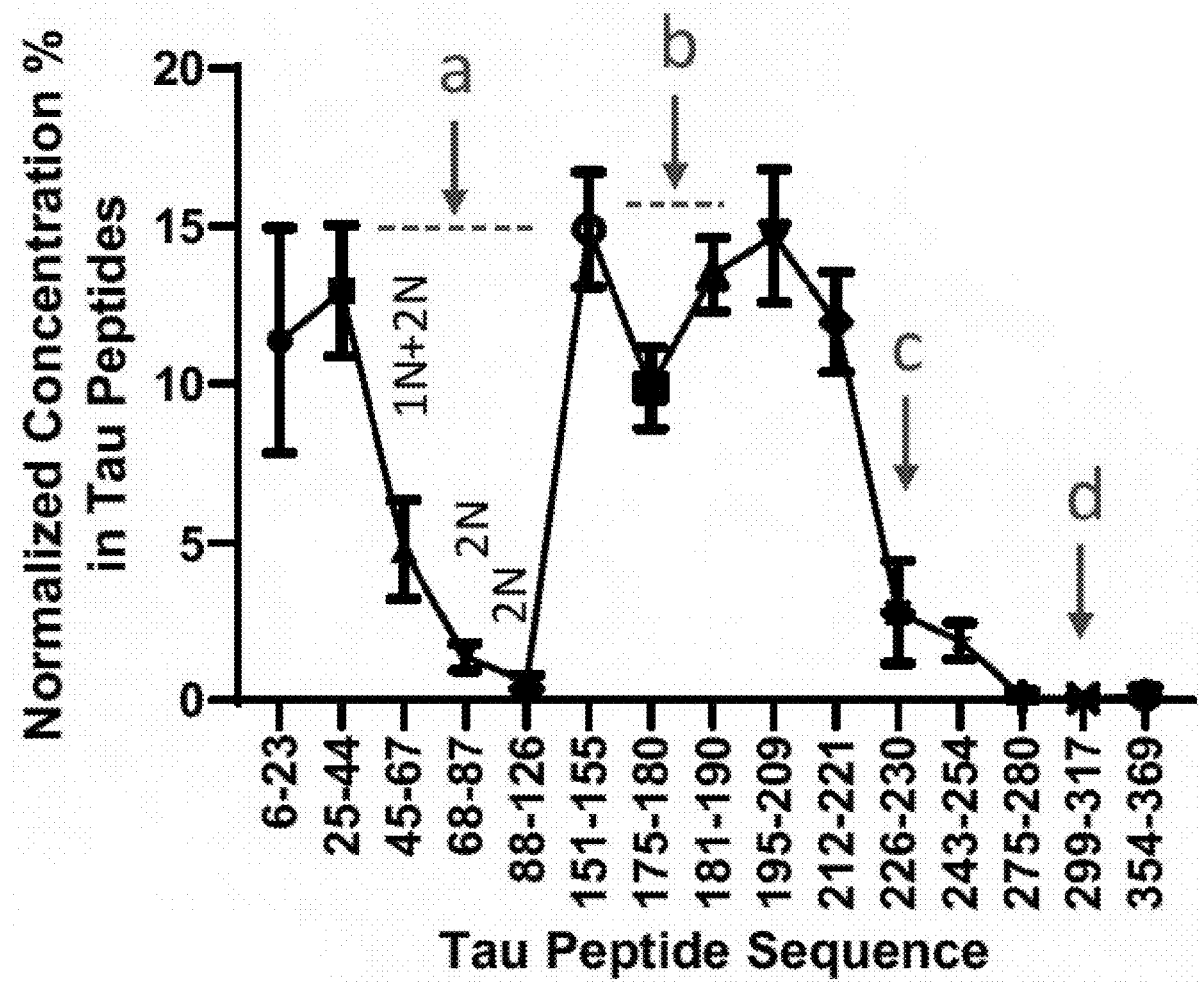

Plasma tau is truncated as in CSF: Amongst all investigated samples, 15 tau peptides from residues 6 to 254 were detected including 0N, 1N, 2N, and 3R specific peptides. Inferred abundance of 0N/1N/2N peptides indicated similar contributions to what was previously reported in brain and CSF (approximately 5/5/1, respectively). Notably, no peptides after residues 254 (excepting 3R peptide found in low abundance residues equivalent to 306-317 residues in 2N4R-tau) were detected suggesting no detectable full-length tau or microtubule-binding region containing isoforms in the plasma extract. Plasma tau peptide abundances dropped significantly after residues 221 (FIG. 26) as previously reported in CSF 18,20,21, suggesting that similar to neuronal cells 18, peripheral cells may release truncated tau. However, additional degradation of tau by plasma proteases preferentially at the tau C-terminus cannot be excluded.

Detection of tau phosphorylated peptides in plasma extracts: Phosphorylated peptides on T181, S202, and T217 from tau mid-domain were quantified in all plasma extracts, demonstrating the feasibility of MS measurements of these low abundance peptides. LC-MS signals obtained for pT181, pS202, and pT217 phosphorylated peptides in samples with lowest abundance in the cohort were approximately 7, 3 and 2 times above the lower limit of quantification (LLOQ), respectively. Notably, pT217 levels were quantified in controls at an average concentration of 0.13 pg/mL (28 amol/mL) (Table 5). To our knowledge, this is the lowest concentration ever measured by mass spectrometry for a protein marker in human plasma. Phosphorylated peptide at T205 was inconsistently detected in 19 of the 38 samples below LLOQ and was not included in further analyses. Other low abundant phosphorylated sites reported in CSF14 at T231, T175, S214, S199, T153 or S208 were not detected in the extracts.

Figure 27A:
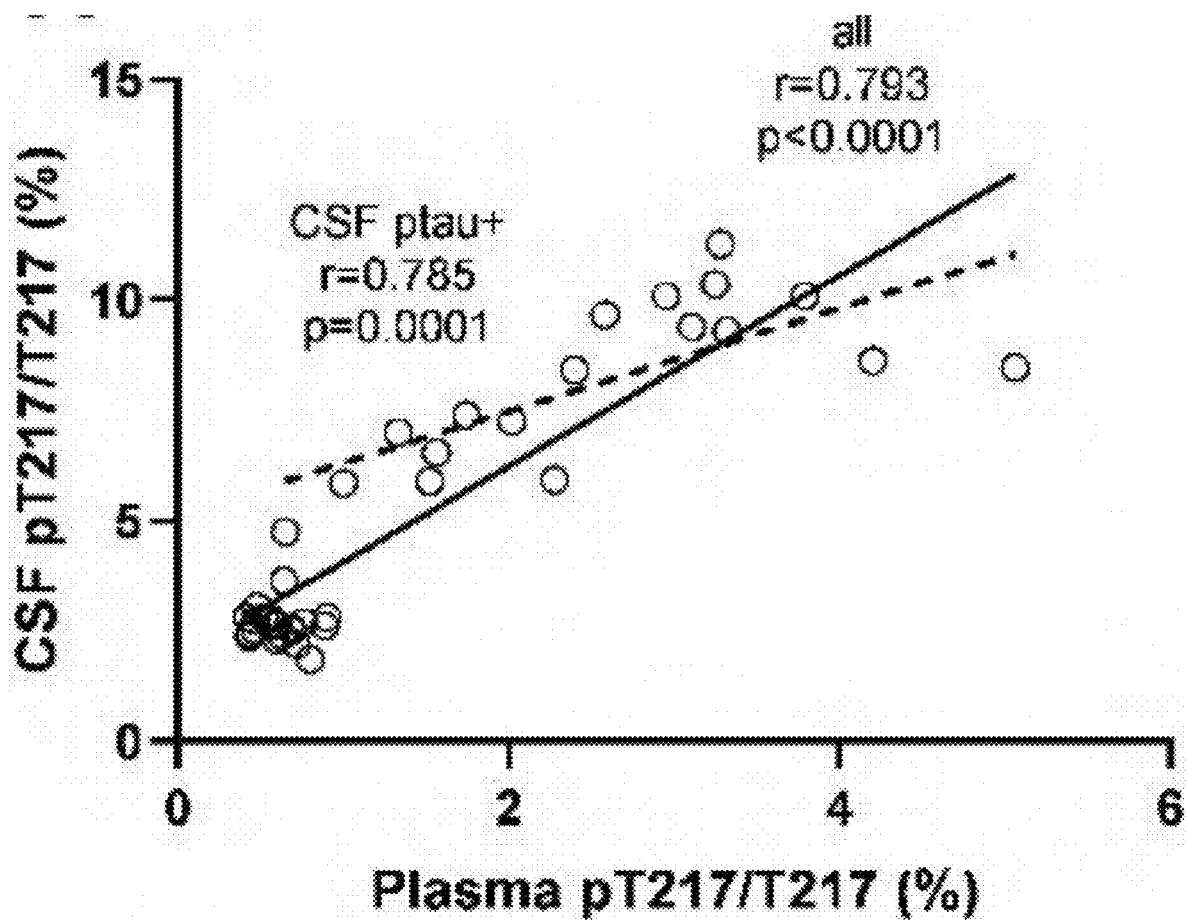
FIG. 27A, FIG. 27B, FIG. 27C, FIG. 27D, FIG. 27E, and FIG. 27F are graphs illustrating plasma tau and plasma phosphorylated tau changes across groups.

Association between CSF and plasma tau isoforms: No correlation was found between CSF and plasma t-tau levels as previously reported by immunoassays 9,10. However, a high correlation was found between CSF and plasma ptau217 measures (FIG. 27A, Table 6, pT217 level and pT217/T217 ratio, Spearman rho 0.79 and 0.79 respectively for all cohort). Also, a significant correlation was found between CSF and plasma for ptau181 measures to a lower extent (Table 6, pT181 level and pT181/T181 ratio, Spearman rho 0.69 and 0.59 respectively for all cohort). No correlation was found between CSF and plasma measures of pS202. All significant CSF/plasma correlations were mainly driven by amyloid positive/phospho-tau positive participant values since no correlations were found in amyloid negative/p-tau negative groups (not shown). Consistently, plasma ptau-217 and ptau-181 measures recapitulated separations obtained in CSF between amyloid positive and negative participants regardless of their cognitive status (FIG. 26, Table 6, AUC in CSF and plasma respectively: 1.00 and 0.98 for pT217/T217; 0.95 and 0.98 for pT181/T181). This suggests that plasma ptau-217 and ptau-181 can act as proxies for changes in CNS soluble tau and thus serve as useful biomarkers.

Figure 27B:
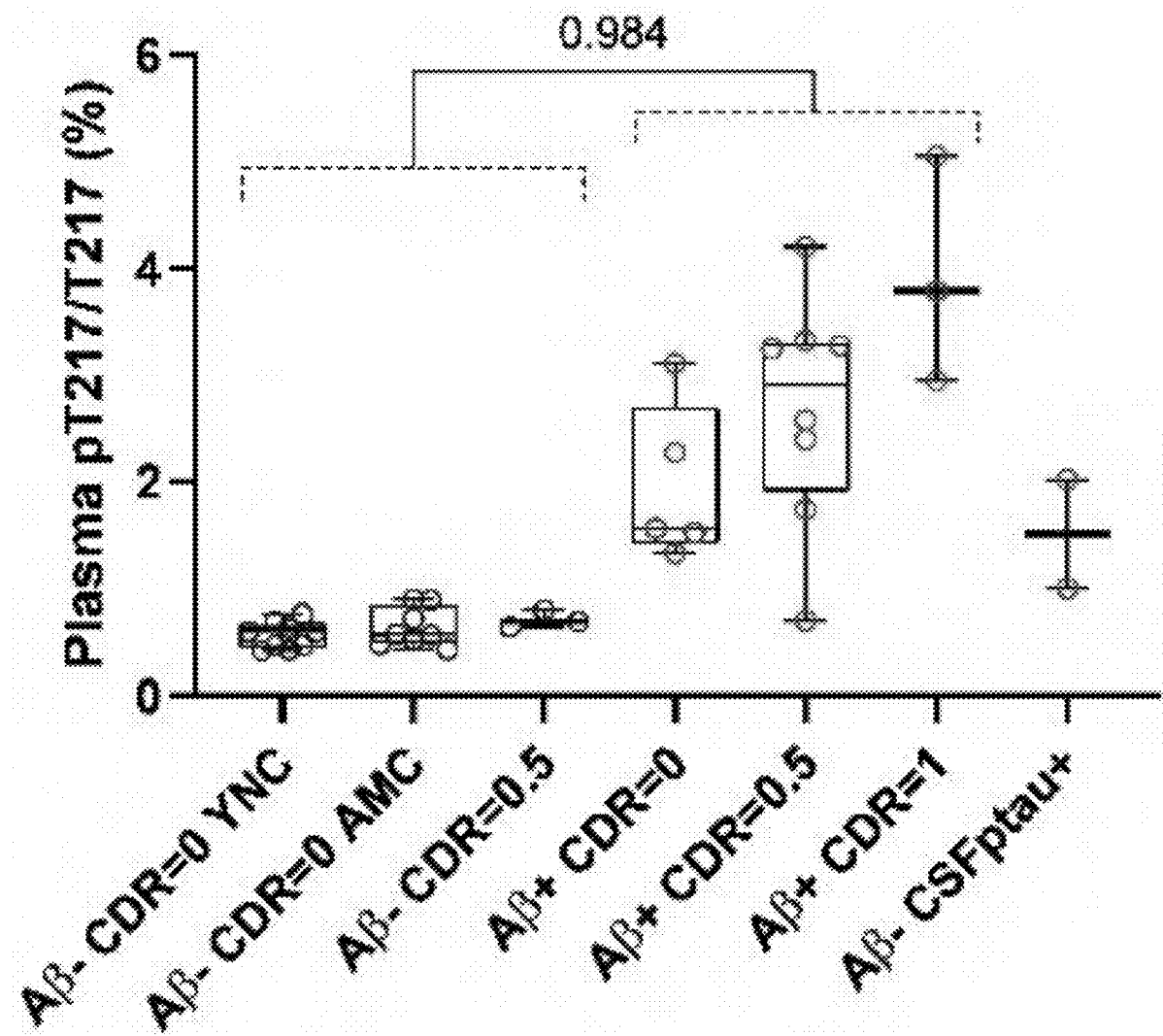
Figure 27C:
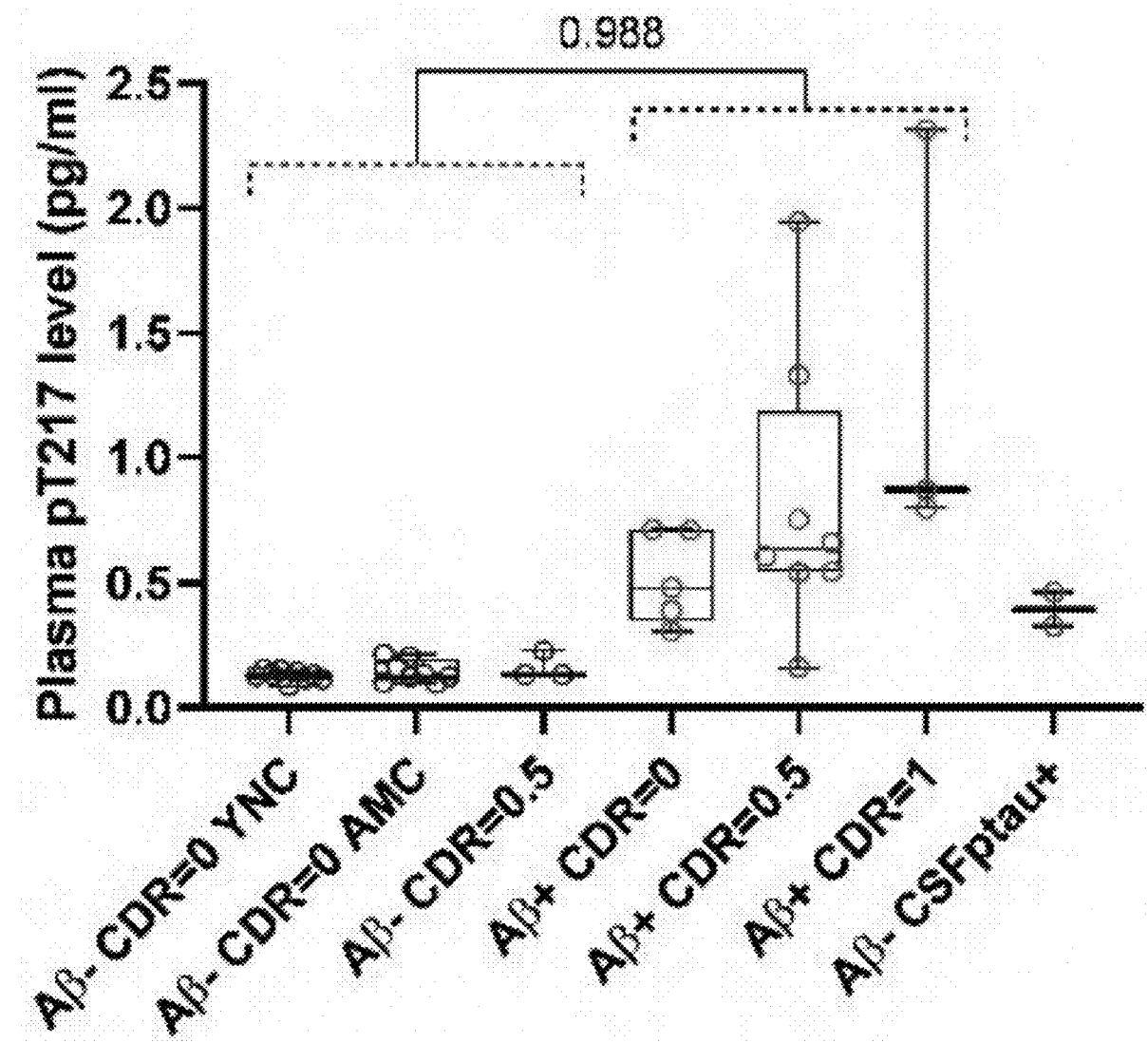
Figure 27D:
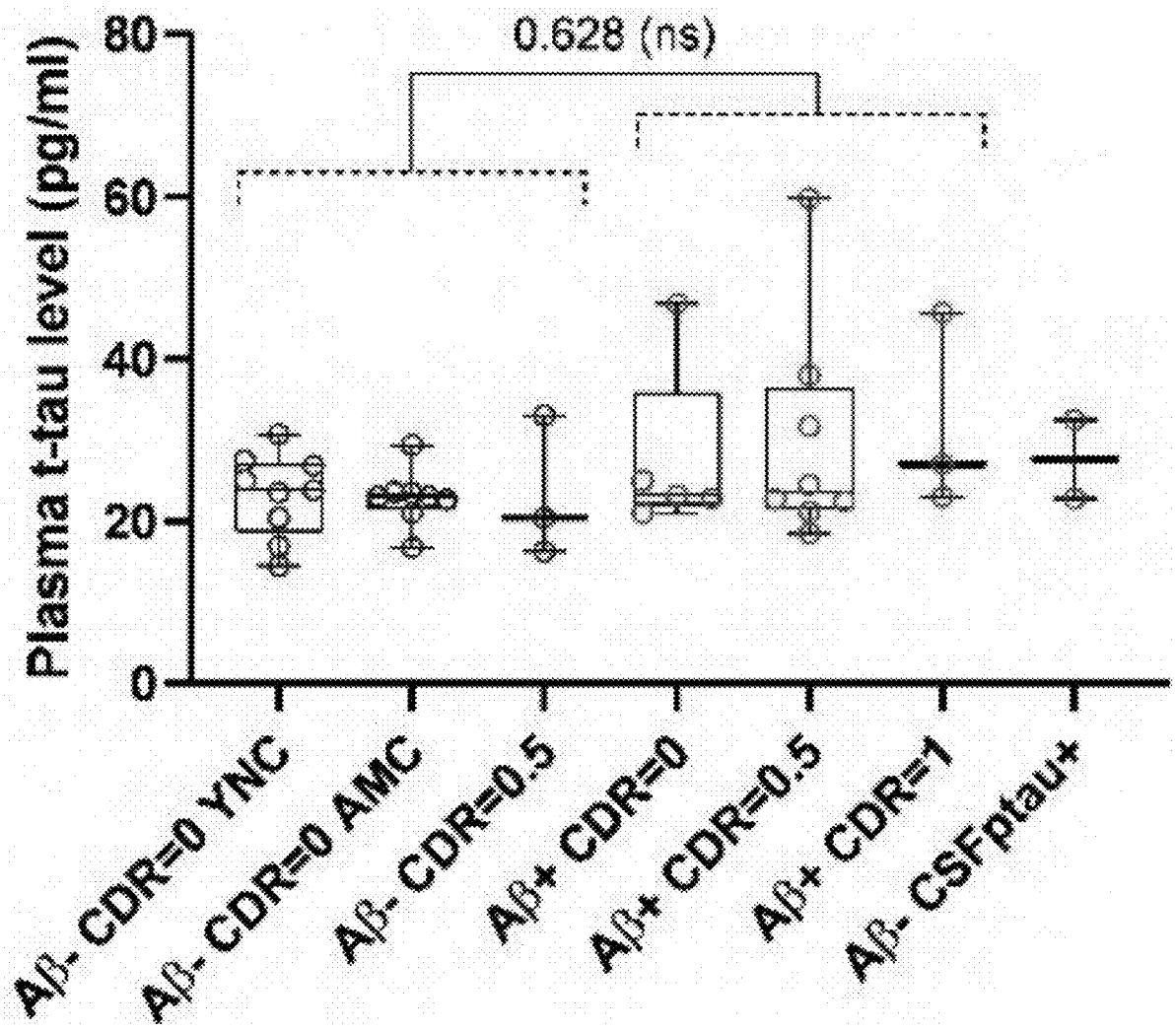
Figure 27E:
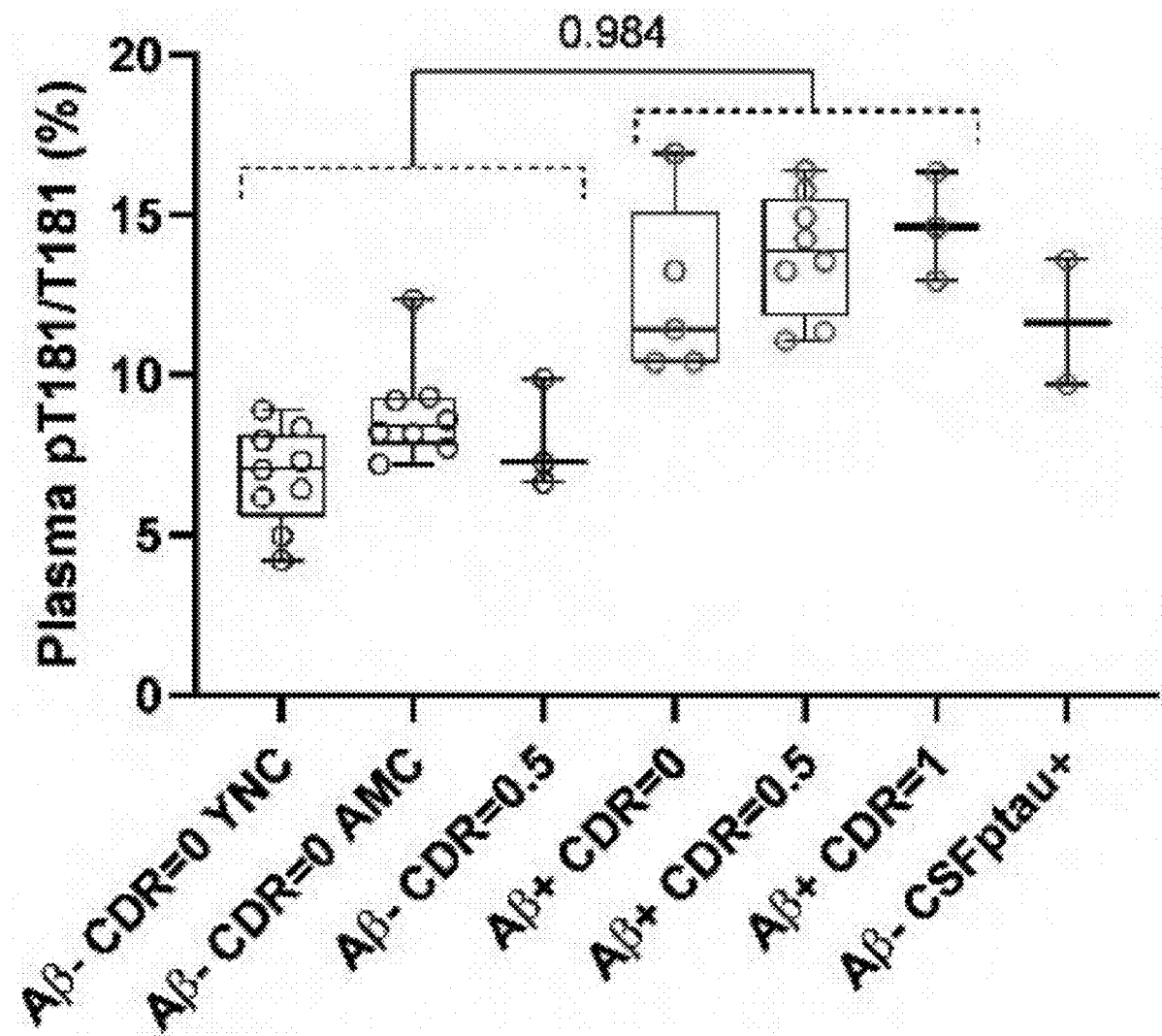
Figure 27F:
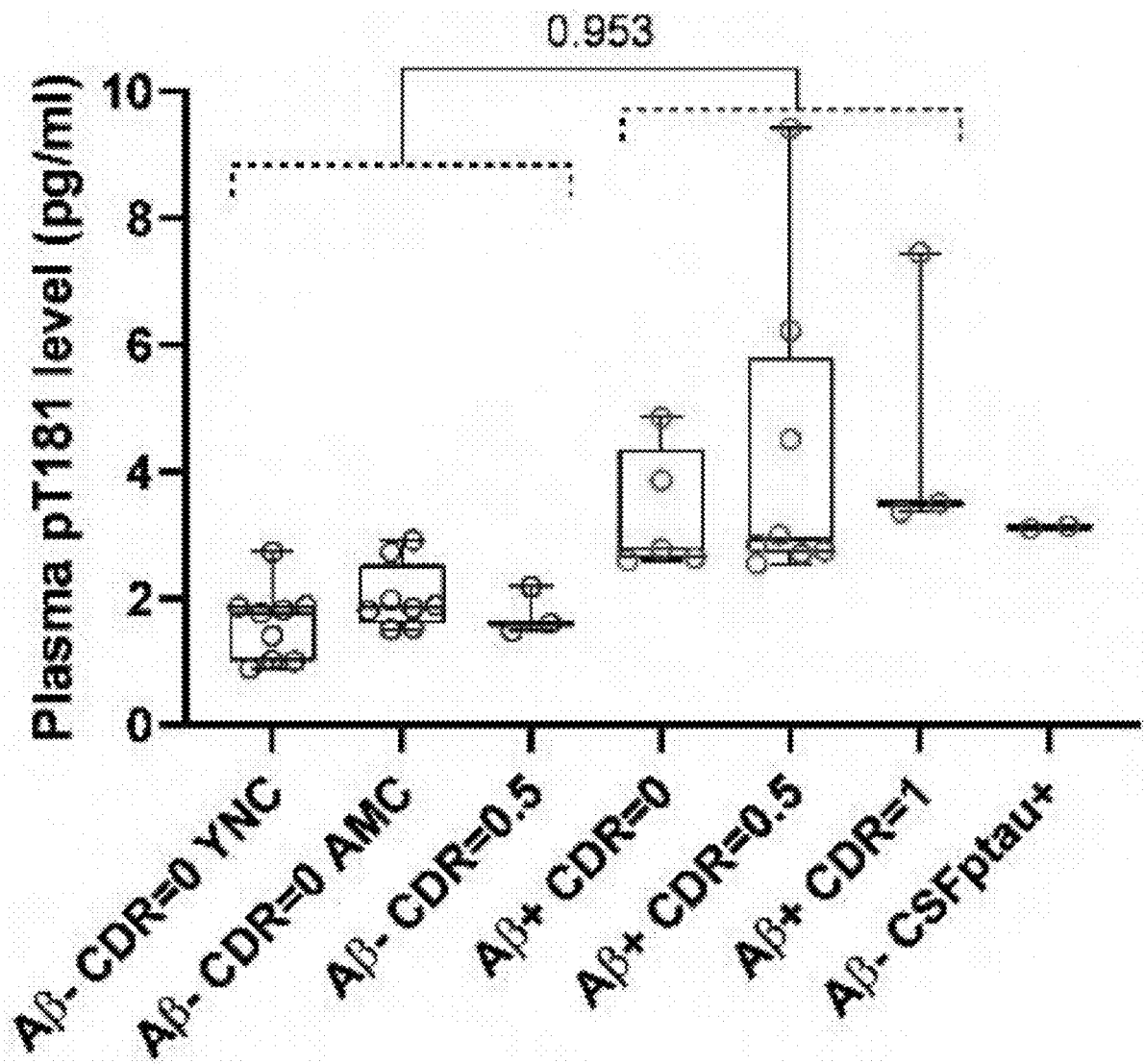

P-tau217 changes more dramatically than p-tau181 in AD CSF and plasma: The magnitude of change between controls and different amyloid clinical groups was calculated (Table 6). In CSF, the highest difference in amplitude between amyloid positive and controls was found for the pT217 level (+800%) group followed by the pT181 level (+250%) group. However, these changes were partially the result of the concomitant contribution of CSF tau isoforms increase as measured for t-tau (+190%). When normalized from tau variation using the ptau/tau ratio, pT217/T217 demonstrated a greater change than pT181/T181 (+220% vs +25%). In plasma, the high magnitude of increase for pT217 levels in amyloid positive group remained higher than pT181 measurements in all of the clinical groups (from +280% to +350% for pT217/T217 and from +60 to +80% for pT181/T181). Importantly, CSF and plasma pT217 (FIG. 27B-C) measures identified amyloid positive, tau PET negative participants from controls. This suggests that phospho-tau biomarkers are changed prior to detectable tau aggregation and reflect abnormal soluble tau metabolism occurring concomitantly with brain Aβ pathology.

Peripheral tau phosphorylation status is different from normal and AD CNS tau: The main origin of plasma t-tau is likely from periphery, not the CNS. This is supported by the absence of correlation between CSF and plasma t-tau levels (Table 2). Plasma t-tau levels seem to reflect CNS tau changes only in patients with acute stroke, brain injury 22-25, brain metastases 26 and likely AD patients with high CNS t-tau release 12,27. Thus, released tau in the CNS would contribute to significant plasma t-tau increases only when its contribution becomes much higher than peripheral tau contribution.

The higher contribution of peripheral tau over CNS tau in plasma is also supported by the difference observed in p-tau/tau ratios between CSF and plasma (Table 2). Both pT217/T217 and pT181/T181 ratios significantly decrease in plasma, supporting the dilution of CNS tau in peripheral tau having much lower pT217 and slightly lower pT181 abundance (Table 6, respectively 4.5 and 1.8 times decreased over CSF in amyloid negative controls). For pS202, the significant increase of pS202/S202 ratio in plasma (1.7 times) supports that peripheral tau is more phosphorylated on this site than in CSF. Consistently, the less the site is phosphorylated in peripheral tau compared to normal CSF, the greater the CNS tau change would impact plasma levels for the corresponding tau isoform. This may explain why CSF and plasma pT217 levels better correlate than pT181 levels and the absence of correlation found for pS202.

Finally, by hypothesizing that peripheral tau does not contain significant amounts of pT217, we estimated CNS tau likely contributes to around 20% of the overall plasma tau level in controls. Assuming CNS tau release could increase by 3 times in AD 28,29, higher CNS AD tau contribution is unlikely to increase AD plasma tau level by more than 40%. Moreover, peripheral tau levels could be affected by different biological factors, potentially interfering with CNS tau contributions to changes in plasma.

Together, these findings support the use of more specific CNS tau isoforms such as pT217 and pT181 over t-tau or pS202 to overcome the contribution of peripheral tau and monitor CNS tau in plasma. Finally, the results suggest that as in CSF, p-tau217 in plasma could be superior to p-tau181 for detecting abnormal CNS tau metabolism.

TABLE 5

Demographics and biomarker values (A)

| Variable | Young controls Aβ−/ptau | Aged controls Aβ−/ptau | Non-AD MCI Aβ−/ptau | Preclinical-AD Aβ+/ptau+ |
|---|---|---|---|---|
| n | 9 | 8 | 3 | 5 |
| Age, years | 44 (12) | 74 (5) | 67 (7) | 75 (5) |
| Gender (F/M, n) | 6/3 | 5/3 | 2/1 | 1/4 |
| CDR | 0 | 0 | 0.5 | 0 |
| CSF42/40 | 0.12 (0.01) | 0.12 (0.02) | 0.12 (0.01) [ns] | 0.07 (0.01)[****] |
| AV45 SUVR | na | 0.95 (0.12)[(7)] | 0.80 (0.00) [(1)] | 1.98 (0.41) [(4)**] |
| PiB MCBP | na | 0.05 (0.04) [(4)] | 0.06 (0.00) [(1)] | 0.44 (0.11) [(4)*] |
| Amyloid status | negative | negative | negative | positive |

TABLE 5-continued

| Demographics and biomarker values | | | | |
|---|---|---|---|---|
| AVI451 SUVR | na | 1.19 (0.09) (6) | 1.30 (0.06) (2) | 1.26 (0.15) (5)ns |
| Tau PET status | na | negative | negative | negative |
| CSF | | | | |
| t-tau (pg/ml) | 339 (112) | 420 (121) | 288 (48) ns | 801 (458)** |
| pT217/T217 (%) | 2.6 (0.2) | 2.7 (0.3) | 2.7 (0.8) ns | 7.0 (1.3)**** |
| pT217 level (pg/ml) | 8.8 (2.9) | 11.0 (2.5) | 8.0 (3.2) ns | 53.9 (29.0)**** |
| pT181/T181 (%) | 13.5 (0.9) | 13.3 (0.8) | 14.2 (1.5) ns | 16.0 (2.0)** |
| pT181 level (pg/ml) | 46 (16) | 56 (17) | 42 (11) ns | 129 (80)*** |
| pS202/S202 (%) | 2.5 (1.2) | 2.0 (0.5) | 3.3 (1.1) ns | 2.1 (0.7) ns |
| pT205/T205 (%) | 0.10 (0.05) | 0.15 (0.04) | 0.17 (0.06) ns | 0.26 (0.08)** |
| Plasma | | | | |
| t-tau (pg/ml) | 23.3 (4.9) | 22.9 (3.3) | 23.3 (7.1) ns | 27.8 (9.6) ns |
| pT217/T217 (%) | 0.6 (0.1) | 0.6 (0.2) | 0.7 (0.1) ns | 2.0(0.7)**** |
| pT217 level (pg/ml) | 0.13 (0.02) | 0.15 (0.04) | 0.16 (0.05) ns | 0.52 (0.17)**** |
| pT181/T181 (%) | 6.8 (1.5) | 8.9 (1.5) | 7.9 (1.4) ns | 12.5 (2.5)*** |
| pT181 level (pg/ml) | 1.6 (0.6) | 2.0 (0.4) | 1.8(0.3) ns | 3.4(0.9)** |
| pS202/S202 (%) | 4.0 (1.0) | 5.3 (1.1) | 4.0 (0.2) ns | 4.8 (1.4) ns |

(B)

| Variable | AD-MCI Aβ+/ptau+ | AD-moderate Aβ+/ptau+ | Non-AD Aβ+/ptau+ |
|---|---|---|---|
| n | 8 | 2□ | 2 |
| Age, years | 81 (7) | 75 (1) | 57 (2) |
| Gender (F/M, n) | 5/3 | 20 | 1/1 |
| CDR | 0.5 | 1 | na |
| CSF42/40 | 0.06 (0.01)**** | 0.06 (0.01)*** | 0.13 (0.005) ns |
| AV45 SUVR | 2.65 (0.38)(5)** | 2.40 (0.29) (2) ns | na |
| PiB MCBP | 0.51 (0.12) (4)* | 0.52 (0.00) (1) | na |
| Amyloid status | positive | positive | negative |
| AVI451 SUVR | 1.79 (0.14) (5)** | 2.36 (0.50) (2)ns | na |
| Tau PET status | positive | positive | na |
| CSF | | | |
| t-tau (pg/ml) | 930 (465)*** | 1966 (1284)* | 842 (296)* |
| pT217/T217 (%) | 8.7 (1.9)**** | 9.61 (0.8)* | 6.6 (0.7)* |
| pT217 level (pg/ml) | 76.8 (31.8)**** | 177.9 (100.6)* | 57.3 (25.3)*** |
| pT181/T181 (%) | 17.5 (1.9)**** | 16.0 (0.2)** | 12.7 (0.1) |
| pT181 level (pg/ml) | 160 (70)**** | 312 (200)* | 106 (37)* |
| pS202/S202 (%) | 1.8 (0.6) ns | 1.8 (0.2) ns | 2.5 (0.3) ns |
| pT205/T205 (%) | 0.28 (0.07)**** | 0.50 (0.04)** | 0.24 (0.10) ns |
| Plasma | | | |
| t-tau (pg/ml) | 29.8 (12.8) ns | 31.9 (9.8) ns | 27.7 (4.8) ns |
| pT217/T217 (%) | 2.7 (1.0)**** | 3.9 (0.9)** | 1.5 (0.5)** |
| pT217 level (pg/ml) | 0.82 (0.52)**** | 1.33 (0.7)** | 0.39 (0.07)* |
| pT181/T181 (%) | 13.8 (1.8)**** | 14.6 (1.4)** | 11.7 (2.0)* |
| pT181 level (pg/ml) | 4.3 (2.3)*** | 4.8 (1.9)** | 3.13 (0.02)* |
| pS202/S202 (%) | 4.4 (1.3) ns | 3.8 (0.5) ns | 4.8 (1.1) ns |

Data are shown as mean (SD).
Na = not available.
**** = p < 0.0001;
*** = p < 0.001;
** = p < 0.01;
* = p < 0.05;
ns = nonsignificant per the Mann-Whitney test against control groups.
□Includes one participant analyzed using 2 plasma replicates (3 samples analyzed in this group).
(7)Indicates the number of available PET scans into the group. Amyloid status was determined by imaging or CSF42/40 measurement.

TABLE 6

Abnormal phosphorylation status detected in AD CSF tau (Aβ+/ptau+) is recapitulated in plasma tau.

| | n | t-tau | pT217/T217 | pT217 level | pT181/T181 | pT181 level | pS202/S202 |
|---|---|---|---|---|---|---|---|
| Area under ROC | | | | | | | |
| CSF Aβ−/ptau− vs Aβ+/ptau+ | 20 vs 15 | 0.95**** [0.88-1.00] | 1.00**** [1.00-1..00] | 1.00**** [1.00-1..00] | 0.95**** [0.89-1.00] | 0.98**** [0.95-1.00] | 0.7* [0.55-0.90] |
| Plasma Aβ−/ptau− vs Aβ+/ptau+ | 20 vs 16 | 0.63 ns | 0.98** ns** [0.95-1.00] | 0.99**** [0.96-1.00] | 0.98**** [0.95-1.00] | 0.95**** [0.89-1.00] | 0.58 ns |

TABLE 6-continued

Abnormal phosphorylation status detected in AD CSF tau
(Aβ+/ptau+) is recapitulated in plasma tau.

|  |  | n | t-tau | pT217/T217 | pT217 level | pT181/T181 | pT181 level | pS202/S202 |
|---|---|---|---|---|---|---|---|---|
| Correlation, Spearman r | | | | | | | | |
| | CSF vs plasm: all | 38 | 0.23 $^{ns}$ | 0.79**** [0.64-0.89] | 0.79**** [0.62-0.88] | 0.59**** [0.32-0.77] | 0.69**** [0.47-0.83] | 0.28 $^{ns}$ |
| | CSF vs plasma: ptau+ | 18 | 0.29 $^{ns}$ | 0.79*** [0.49-0.92] | 0.45 $^{ns}$ [−0.04-0.76] | 0.51* [0.03-0.79] | 0.15 $^{ns}$ | 0.40 $^{ns}$ |
| Magnitude of change (%)$^{(a)}$ | | | | | | | | |
| CSF | All Aβ+ vs Controls | 15 vs 17 | 187 (108) $^{ns}$ | 219 (30) $^{ns}$ | 803 (107)*** | 25 (18) $^{ns}$ | 251 (106) | −15 (57) $^{ns}$ |
| | Aβ+/CDR = 0 vs Controls | 5 vs 17 | 112 (90) $^{ns}$ | 167 (27) $^{ns}$ | 450 (84)** | 19 (19) $^{ns}$ | 154 (97) | −6 (59) $^{ns}$ |
| | Aβ+/CDR = 0.5 vs Controls | 8 vs 17 | 146 (83) $^{ns}$ | 235 (235) $^{ns}$ | 683 (71)** | 30 (18) $^{ns}$ | 213 (79) | −19 (57) $^{ns}$ |
| Plasma | All Aβ+ vs Controls | 16 vs 17 | 28 (57) $^{ns}$ | 350 (67)*** | 506 (93)*** | 74 (39) $^{ns}$ | 126 (79) | −5 (55) $^{ns}$ |
| | Aβ+/CDR = 0 vs Controls | 5 vs 17 | 20 (53) $^{ns}$ | 326 (73)*** | 480 (98)*** | 60 (43) $^{ns}$ | 86 (58) | −5 (55) $^{ns}$ |
| | Aβ+/CDR = 0.5 vs Controls | 5 vs 17 | 29 (61) $^{ns}$ | 282 (73)*** | 379 (93)*** | 78 (36) $^{ns}$ | 136 (85) | −4 (54) $^{ns}$ |
| CSF/Plasma ratio | | | | | | | | |
| | All cohort | 37 | 26 (18) | 4.0 (1.2) | 93 (49) | 1.6 (0.5) | 37 (22) | 0.5 (0.2) |
| | Aβ−/ptau− | 20 | 17 (7) | 4.5 (1.2) | 72 (27) | 1.8 (0.5) | 30 (12) | 0.6 (0.3) |
| | Aβ+/ptau+ | 15 | 37 (21) | 3.6 (1.3) | 138 (125) | 1.3 (0.2) | 47 (29) | 0.5 (0.2) |
| | Aβ−/ptau+ | 2 | 33 (17) | 4.7 (1.1) | 139 (41) | 1.1 (0.2) | 34 (12) | 0.6 (0.2) |

Data are shown as mean (SD) for magnitude of change and ratio and as value (95%. CI) for AUROC and Spearman r.
****p < 0.0001:
***= p < 0.001;
**= p < 0.01;
*= p < 0.05:
$^{ns}$ = non-significant per the Mann-Whitney test against aged and normal control groups.
$^{a}$Statistical significance of the change compared to pT181 level change as reference.

REFERENCES FOR EXAMPLES 11 AND 12

Ref 1: Roberts K F, Elbert D L, Kasten T P, et al. Amyloid-β efflux from the central nervous system into the plasma. Ann Neurol. 2014; 76(6):837-844; doi:10.1002/ana.24270.

Ref 2: Ovod V, Ramsey K N, Mawuenyega K G, et al. Amyloid p concentrations and stable isotope labeling kinetics of human plasma specific to central nervous system amyloidosis. Alzheimers Dement. 2017; 13(8): 841-849; doi:10.1016/j.jalz.2017.06.2266.

Ref 3: Nakamura A, Kaneko N, Villemagne V L, et al. High performance plasma amyloid-β biomarkers for Alzheimer's disease. Nature. 2018; 554(7691):249-254; doi: 10.1038/nature25456.

Ref 4: Schindler S E, Bollinger J G, Ovod V, et al. High-precision plasma β-amyloid 42/40 predicts current and future brain amyloidosis. Neurology. August 2019: 10.1212/WNL.0000000000008081. doi:10.1212/WNL.0000000000008081

Ref 5: Bacioglu M, Maia L F, Preische O, et al. Neurofilament Light Chain in Blood and CSF as Marker of Disease Progression in Mouse Models and in Neurodegenerative Diseases. Neuron. 2016; 91(1):56-66; doi:10.1016/j.neuron.2016.05.018.

Ref 6: Preische O, Schultz S A, Apel A, et al. Serum neurofilament dynamics predicts neurodegeneration and clinical progression in presymptomatic Alzheimer's disease. Nat Med. 2019; 25(2):277-283; doi:10.1038/s41591-018-0304-3.

Ref 7: Bateman R J, Xiong C, Benzinger TLS, et al. Clinical and Biomarker Changes in Dominantly Inherited Alzheimer's Disease. N Engl J Med. 2012; 367(9):795-804; doi:10.1056/NEJMoa1202753.

Ref 8: Fagan A M, Xiong C, Jasielec M S, et al. Longitudinal Change in CSF Biomarkers in Autosomal-Dominant Alzheimer's Disease. Sci Transl Med. 2014; 6(226): 226ra30-226ra30; doi:10.1126/scitranslmed.3007901.

Ref 9: Zetterberg H, Wilson D, Andreasson U, et al. Plasma tau levels in Alzheimer's disease. Alzheimers Res Ther. 2013; 5(2):9; doi:10.1186/alzrt163.

Ref 10: Mattsson N, Zetterberg H, Janelidze S, et al. Plasma tau in Alzheimer disease. Neurology. 2016; 87(17):1827-1835; dx.doi.org/10.1212/WNL.0000000000003246.

Ref 11: Mielke M M, Hagen C E, Wennberg A M V, et al. Association of Plasma Total Tau Level With Cognitive Decline and Risk of Mild Cognitive Impairment or Dementia in the Mayo Clinic Study on Aging. JAMA Neurol. 2017; 74(9):1073-1080; doi:10.1001/jamaneurol.2017.1359.

Ref 12: Mielke M M, Hagen C E, Xu J, et al. Plasma phospho-tau181 increases with Alzheimer's disease clinical severity and is associated with tau- and amyloid-positron emission tomography. Alzheimers Dement. 2018; 14(8):989-997; doi:10.1016/j.jalz.2018.02.013.

Ref 13: Tatebe H, Kasai T, Ohmichi T, et al. Quantification of plasma phosphorylated tau to use as a biomarker for brain Alzheimer pathology: pilot case-control studies including patients with Alzheimer's disease and down syndrome. Mol Neurodegener. 2017; 12(1):63; doi: 10.1186/s13024-017-0206-8.

Ref 14: Barthélemy N R, Mallipeddi N, Moiseyev P, Sato C, Bateman R J. Tau Phosphorylation Rates Measured by Mass Spectrometry Differ in the Intracellular Brain vs. Extracellular Cerebrospinal Fluid Compartments and Are Differentially Affected by Alzheimer's Disease. Front Aging Neurosci. 2019; 11; doi:10.3389/fnagi.2019.00121.

Ref 15: Barthélemy N, Hirtz C, Schraen S, et al. Mass spectrometry follow-up of t181, s199, s202, t205, and T217 tau phosphorylation in cerebrospinal fluid from patients revealed a specific Alzheimer's disease pattern.

Alzheimers Dement J Alzheimers Assoc. 2015; 11(7): P870; doi:10.1016/j.jalz.2015.08.063.

Ref 16: Barthélemy N R, Bateman R J, Marin P, et al. Tau hyperphosphorylation on T217 in cerebrospinal fluid is specifically associated to amyloid-β pathology. bioRxiv. November 2017:226977; doi:10.1101/226977.

Ref 17: Barthëlemy N R, Li Y, Wang G, et al. MASS SPECTROMETRY-BASED MEASUREMENT OF LONGITUDINAL CSF TAU IDENTIFIES DIFFERENT PHOSPHORYLATED SITES THAT TRACK DISTINCT STAGES OF PRESYMPTOMATIC DOMINANTLY INHERITED AD. Alzheimers Dement J Alzheimers Assoc. 2018; 14(7):P273-P274; doi:10.1016/j.jalz.2018.06.024.

Ref 18: Sato C, Barthélemy N R, Mawuenyega K G, et al. Tau Kinetics in Neurons and the Human Central Nervous System. Neuron. 2018; 97(6):1284-1298.e7; doi:10.1016/j.neuron.2018.02.015.

Ref 19: Geyer P E, Holdt L M, Teupser D, Mann M. Revisiting biomarker discovery by plasma proteomics. Mol Syst Biol. 2017; doi.org/10.15252/msb.20156297.

Ref 20: Barthélemy N R, Fenaille F, Hirtz C, et al. Tau Protein Quantification in Human Cerebrospinal Fluid by Targeted Mass Spectrometry at High Sequence Coverage Provides Insights into Its Primary Structure Heterogeneity. J Proteome Res. 2016; 15(2):667-676; doi:10.1021/acs.jproteome.5b01001.

Ref 21: Cicognola C, Brinkmalm G, Wahlgren J, et al. Novel tau fragments in cerebrospinal fluid: relation to tangle pathology and cognitive decline in Alzheimer's disease. Acta Neuropathol (Berl). 2019; 137(2):279-296; doi: 10.1007/s00401-018-1948-2.

Ref 22: Neselius S, Zetterberg H, Blennow K, et al. Olympic boxing is associated with elevated levels of the neuronal protein tau in plasma. Brain Inj. 2013; 27(4):425-433; doi:10.3109/02699052.2012.750752.

Ref 23: Bogoslovsky T, Wilson D, Chen Y, et al. Increases of Plasma Levels of Glial Fibrillary Acidic Protein, Tau, and Amyloid 3 up to 90 Days after Traumatic Brain Injury. J Neurotrauma. 2016; 34(1):66-73; doi:10.1089/neu.2015.4333.

Ref 24: Bulut M, Koksal O, Dogan S, et al. Tau protein as a serum marker of brain damage in mild traumatic brain injury: Preliminary results. Adv Ther. 2006; 23(1):12-22; doi:10.1007/BF02850342.

Ref 25: Rubenstein R, Chang B, Yue J K, et al. Comparing Plasma Phospho Tau, Total Tau, and Phospho Tau-Total Tau Ratio as Acute and Chronic Traumatic Brain Injury Biomarkers. JAMA Neurol. 2017; 74(9):1063-1072; doi: 10.1001/jamaneurol.2017.0655.

Ref 26: Darlix A, Hirtz C, Thezenas S, et al. The prognostic value of the Tau protein serum level in metastatic breast cancer patients and its correlation with brain metastases. BMC Cancer. 2019; 19(1):110; doi:10.1186/s12885-019-5287-z Ref 27: Kasai T, Tatebe H, Kondo M, et al. Increased levels of plasma total tau in adult Down syndrome. PLOS ONE. 2017; 12(11):e0188802; doi:10.1371/journal.pone.0188802.

Ref 28: Fagan A M, Roe C M, Xiong C, Mintun M A, Morris J C, Holtzman D M. Cerebrospinal Fluid tau/3-Amyloid42 Ratio as a Prediction of Cognitive Decline in Nondemented Older Adults. Arch Neurol. 2007; 64(3): 343-349; doi:10.1001/archneur.64.3.noc60123.

Ref 29: Zetterberg H. Review: Tau in biofluids—relation to pathology, imaging and clinical features. Neuropathol Appl Neurobiol. 2017; 43(3):194-199; doi:10.1111/nan.12378.

Ref 30: Potter R, Patterson B W, Elbert D L, et al. Increased in Vivo Amyloid-342 Production, Exchange, and Loss in Presenilin Mutation Carriers. Sci Transl Med. 2013; 5(189):189ra77-189ra77; doi:10.1126/scitranslmed.3005615.

Ref 31: Patterson B W, Elbert D L, Mawuenyega K G, et al. Age and amyloid effects on human central nervous system amyloid-beta kinetics. Ann Neurol. 2015; 78(3):439-453; doi:10.1002/ana.24454.

What is claimed is:

1. A method for selecting a therapeutic agent for a subject in need thereof, the method comprising
   (a) providing an isolated tau sample obtained from the subject and measuring, in the isolated tau sample, tau phosphorylation at T205 and T181, at T205 and T217, or at T205, T181, and T217; and
   (b) administering to the subject a therapeutic agent, wherein:
      (i) the isolated tau sample obtained from the subject contains tau phosphorylation at T181 and/or tau phosphorylation at T217 that significantly deviates from the mean of a control population without brain amyloid plaques as measured by PET imaging and/or Aβ42/40 measurement in CSF, and tau phosphorylation at T205 that does not significantly deviate from the mean of a control population without brain amyloid plaques as measured by PET imaging and/or Aβ42/40 measurement in CSF, and the therapeutic agent prevents amyloid deposition from increasing or reduces a subject's existing plaque load, or
      (ii) the isolated tau sample obtained from the subject contains tau phosphorylation at T181 and/or tau phosphorylation at T217 that significantly deviates from the mean of a control population without brain amyloid plaques as measured by PET imaging and/or Aβ42/40 measurement in CSF, and tau phosphorylation at T205 that significantly deviates from the mean of a control population without brain amyloid plaques as measured by PET imaging and/or Aβ42/40 measurement in CSF, and the therapeutic agent prevents amyloid deposition from increasing, or reduces a subject's existing plaque load, or prevents tau aggregation, or targets neurofibrillary tangles.

2. The method of claim 1, the method further comprising administering a diagnostic test to the subject.

3. The method of claim 2, wherein the diagnostic test is PET imaging.

4. The method of claim 1, wherein the isolated tau sample obtained from the subject contains tau phosphorylation at T217 that is at least 1.5σ above the mean of the control population and tau phosphorylation at T205 that is below 1.5σ above the mean of the control population.

5. The method of claim 1, wherein the isolated tau sample obtained from the subject contains tau phosphorylation at T181 that is at least 1.5σ above the mean of the control population and tau phosphorylation at T205 that is below 1.5σ above the mean of a control population.

6. The method of claim 1, wherein the isolated tau sample obtained from the subject contains tau phosphorylation at T181 and T217 that is at least 1.5σ above the mean of the control population and tau phosphorylation at T205 that is below 1.5σ above the mean of the control population.

7. The method of claim 1, wherein the isolated tau sample obtained from the subject contains tau phosphorylation at T217 and T205 that is at least 1.5σ above the mean of the control population.

8. The method of claim 1, wherein the isolated tau sample obtained from the subject contains tau phosphorylation at T181 and T205 that is at least 1.5σ above the mean of the control population.

9. The method of claim 1, wherein the isolated tau sample obtained from the subject contains tau phosphorylation at T181, T205, and T217 that is at least 1.5σ above the mean of the control population.

10. The method of claim 1, wherein the pharmaceutical composition comprises a cholinesterase inhibitor, an N-methyl D-aspartate (NMDA) antagonist, an antidepressant, a gamma-secretase inhibitor, a beta-secretase inhibitor, an anti-Aβ antibody, an anti-tau antibody, an antagonist of the serotonin receptor 6, a p38alpha MAPK inhibitor, recombinant granulocyte macrophage colony-stimulating factor, a passive immunotherapy, an active vaccine, a tau protein aggregation inhibitor, an anti-inflammatory agent, a phosphodiesterase 9A inhibitor, a sigma-1 receptor agonist, a kinase inhibitor, a phosphatase activator, a phosphatase inhibitor, an angiotensin receptor blocker, a CB1 and/or CB2 endocannabinoid receptor partial agonist, a β-2 adrenergic receptor agonist, a nicotinic acetylcholine receptor agonist, a 5-HT2A inverse agonist, an alpha-2c adrenergic receptor antagonist, a 5-HT 1A and 1D receptor agonist, a glutaminyl-peptide cyclotransferase inhibitor, a selective inhibitor of APP production, a monoamine oxidase B inhibitor, a glutamate receptor antagonist, an AMPA receptor agonist, a nerve growth factor stimulant, a HMG-CoA reductase inhibitor, a neurotrophic agent, a muscarinic M1 receptor agonist, a GABA receptor modulator, a PPAR-gamma agonist, a microtubule protein modulator, a calcium channel blocker, an antihypertensive agent, a statin, or any combination thereof.

11. The method of claim 1, wherein the pharmaceutical composition comprises a kinase inhibitor.

12. The method of claim 1, wherein pharmaceutical composition comprises a phosphatase activator.

13. The method of claim 1, wherein the isolated tau sample is a composition comprising tau, wherein tau has been purified from blood obtained from a human subject.

14. The method of claim 1, wherein the isolated tau sample is a composition comprising tau, wherein tau has been purified from cerebrospinal fluid obtained from a human subject.

15. A method for selecting a therapeutic agent for a subject in need thereof, the method comprising
   (a) providing an isolated tau sample obtained from the subject and measuring, in the isolated tau sample, tau phosphorylation at:
      (i) T205, T181, and at least one site selected from the group consisting of T111, T153, S208, or T231, or
      (ii) T205, T217, and at least one site selected from the group consisting of T111, T153, S208, or T231; and
   (b) administering to the subject a therapeutic agent, wherein:
      (i) the isolated tau sample obtained from the subject contains tau phosphorylation at T181 and/or tau phosphorylation at T217 that significantly deviates from the mean of a control population without brain amyloid plaques as measured by PET imaging and/or Aβ42/40 measurement in CSF, and tau phosphorylation at T205 that does not significantly deviate from the mean of a control population without brain amyloid plaques as measured by PET imaging and/or Aβ42/40 measurement in CSF, and the therapeutic agent prevents amyloid deposition from increasing or reduces a subject's existing plaque load, or (ii) the isolated tau sample obtained from the subject contains tau phosphorylation at T181 and/or tau phosphorylation at T217 that significantly deviates from the mean of a control population without brain amyloid plaques as measured by PET imaging and/or Aβ42/40 measurement in CSF, and tau phosphorylation at T205 that significantly deviates from the mean of a control population without brain amyloid plaques as measured by PET imaging and/or Aβ42/40 measurement in CSF, and the therapeutic agent prevents amyloid deposition from increasing, or reduces a subject's existing plaque load, or prevents tau aggregation, or targets neurofibrillary tangles.

16. The method of claim 15, the method further comprising administering a diagnostic test to the subject.

17. The method of claim 16, wherein the diagnostic test is PET imaging.

18. The method of claim 15, wherein the isolated tau sample obtained from the subject contains tau phosphorylation at T217 that is at least 1.5σ above the mean of the control population and tau phosphorylation at T205 that is below 1.5σ above the mean of the control population.

19. The method of claim 15, wherein the isolated tau sample obtained from the subject contains tau phosphorylation at T181 that is at least 1.5σ above the mean of the control population and tau phosphorylation at T205 that is below 1.5σ above the mean of the control population.

20. The method of claim 15, wherein the isolated tau sample obtained from the subject contains tau phosphorylation at T181 and T217 that is at least 1.5σ above the mean of the control population and tau phosphorylation at T205 that is below 1.5σ above the mean of the control population.

21. The method of claim 15, wherein the isolated tau sample obtained from the subject contains tau phosphorylation at T217 and T205 that is at least 1.5σ above the mean of the control population.

22. The method of claim 15, wherein the isolated tau sample obtained from the subject contains tau phosphorylation at T181 and T205 that is at least 1.5σ above the mean of the control population.

23. The method of claim 15, wherein the isolated tau sample obtained from the subject contains tau phosphorylation at T181, T205, and T217 that is at least 1.5σ above the mean of the control population.

24. The method of claim 15, wherein the pharmaceutical composition comprises a cholinesterase inhibitor, an N-methyl D-aspartate (NMDA) antagonist, an antidepressant, a gamma-secretase inhibitor, a beta-secretase inhibitor, an anti-Aβ antibody, an anti-tau antibody, an antagonist of the serotonin receptor 6, a p38alpha MAPK inhibitor, recombinant granulocyte macrophage colony-stimulating factor, a passive immunotherapy, an active vaccine, a tau protein aggregation inhibitor, an anti-inflammatory agent, a phosphodiesterase 9A inhibitor, a sigma-1 receptor agonist, a kinase inhibitor, a phosphatase activator, a phosphatase inhibitor, an angiotensin receptor blocker, a CB1 and/or CB2 endocannabinoid receptor partial agonist, a β-2 adrenergic receptor agonist, a nicotinic acetylcholine receptor agonist, a 5-HT2A inverse agonist, an alpha-2c adrenergic receptor antagonist, a 5-HT 1A and 1D receptor agonist, a glutaminyl-peptide cyclotransferase inhibitor, a selective inhibitor of APP production, a monoamine oxidase B inhibitor, a glutamate receptor antagonist, an AMPA receptor agonist, a nerve growth factor stimulant, a HMG-CoA reductase inhibitor, a neurotrophic agent, a muscarinic M1 receptor agonist, a GABA receptor modulator, a PPAR-gamma agonist, a microtubule protein modulator, a calcium channel blocker, an antihypertensive agent, a statin, or any combination thereof.

25. The method of claim 15, wherein the pharmaceutical composition comprises a kinase inhibitor.

26. The method of claim 15, wherein pharmaceutical composition comprises a phosphatase activator.

27. The method of claim 15, wherein the isolated tau sample is a composition comprising tau, wherein tau has been purified from blood obtained from a human subject.

28. The method of claim 15, wherein the isolated tau sample is a composition comprising tau, wherein tau has been purified from cerebrospinal fluid obtained from a human subject.

29. A method for selecting a therapeutic agent for a subject in need thereof, the method comprising
(a) providing an isolated tau sample obtained from the subject and measuring, in the isolated tau sample, tau phosphorylation at T205, and at least one site selected from the group consisting of T217, T181, T111, T153, S208, or T231,
(b) administering to the subject a therapeutic agent, wherein:
(i) the isolated tau sample obtained from the subject contains tau phosphorylation at T205 that does not significantly deviate from the mean of a control population without brain amyloid plaques as measured by PET imaging and/or Aβ42/40 measurement in CSF, and the therapeutic agent prevents amyloid deposition from increasing or reduces a subject's existing plaque load, or
(ii) the isolated tau sample obtained from the subject contains tau phosphorylation at T205 that significantly deviates from the mean of a control population without brain amyloid plaques as measured by PET imaging and/or Aβ42/40 measurement in CSF, and the therapeutic agent prevents amyloid deposition from increasing, or reduces a subject's existing plaque load, or prevents tau aggregation, or targets neurofibrillary tangles.

30. The method of claim 29, the method further comprising administering a diagnostic test to the subject.

* * * * *